(12) United States Patent
Rule

(10) Patent No.: US 9,302,045 B2
(45) Date of Patent: *Apr. 5, 2016

(54) FLUID COMPONENT ANALYSIS SYSTEM AND METHOD FOR GLUCOSE MONITORING AND CONTROL

(71) Applicant: OPTISCAN BIOMEDICAL CORPORATION, Hayward, CA (US)

(72) Inventor: Peter Rule, Los Altos Hills, CA (US)

(73) Assignee: OptiScan Biomedical Corporation, Hayward, CA (US)

(*) Notice: Subject to any disclaimer, the term of this patent is extended or adjusted under 35 U.S.C. 154(b) by 136 days.

This patent is subject to a terminal disclaimer.

(21) Appl. No.: 13/857,949

(22) Filed: Apr. 5, 2013

(65) Prior Publication Data

US 2014/0066844 A1 Mar. 6, 2014

Related U.S. Application Data

(63) Continuation of application No. 12/559,328, filed on Sep. 14, 2009, now Pat. No. 8,417,311.

(60) Provisional application No. 61/096,461, filed on Sep. 12, 2008, provisional application No. 61/099,491, filed on Sep. 23, 2008, provisional application No. 61/149,307, filed on Feb. 2, 2009, provisional application No. 61/162,627, filed on Mar. 23, 2009.

(51) Int. Cl.
*A61B 5/00* (2006.01)
*A61M 31/00* (2006.01)
(Continued)

(52) U.S. Cl.
CPC .......... *A61M 5/1723* (2013.01); *A61B 5/1427* (2013.01); *A61B 5/14532* (2013.01);
(Continued)

(58) Field of Classification Search
CPC .............. A61B 5/145; A61B 5/14503; A61B 5/14532; A61B 5/1468; A61B 5/1473
See application file for complete search history.

(56) References Cited

U.S. PATENT DOCUMENTS 2,797,149 A 6/1957 Skeggs
3,634,039 A 1/1972 Broady
(Continued)

FOREIGN PATENT DOCUMENTS

DE 197 56 872 A1 7/1999
EP 0 549 341 A1 6/1993
(Continued)

OTHER PUBLICATIONS

International Search Report and Written Opinion in PCT/US2008/079641 dated Feb. 25, 2009.
(Continued)

*Primary Examiner* — Patricia Mallari
*Assistant Examiner* — Tiffany Weston
(74) *Attorney, Agent, or Firm* — Knobbe, Martens, Olson & Bear, LLP

(57) ABSTRACT

Disclosed are methods and apparatuses for determining analyte concentration in a sample such as bodily fluid. Systems and methods disclosed herein can also include a treatment dosing system to infuse or inject a treatment dose (e.g. insulin, dextrose, etc.) and provide glycemic control. The dose of the treatment drug may be based on the patient's calculated sensitivity to treatment dosing, for example. The dose of the treatment drug may be based on the concentration of the analyte or the average value for the concentration of the analyte and/or the rate of change of the value of the concentration of the analyte. Delivery of the treatment drug can be cut off if the determined analyte concentration indicates that continued delivery would be harmful to the patient.

37 Claims, 62 Drawing Sheets

(51) Int. Cl.
*A61M 5/172* (2006.01)
*A61B 5/155* (2006.01)
*A61B 5/145* (2006.01)
*A61B 5/1455* (2006.01)
*G06F 19/00* (2011.01)
*A61M 5/168* (2006.01)
*A61M 5/14* (2006.01)
*A61M 5/142* (2006.01)

(52) U.S. Cl.
CPC ......... *A61B 5/14535* (2013.01); *A61B 5/14546* (2013.01); *A61B 5/14557* (2013.01); *A61B 5/155* (2013.01); *A61B 5/412* (2013.01); *A61B 5/4839* (2013.01); *A61B 5/7475* (2013.01); *G06F 19/3468* (2013.01); *A61M 5/16827* (2013.01); *A61M 2005/1404* (2013.01); *A61M 2005/14208* (2013.01); *A61M 2005/1726* (2013.01); *A61M 2205/12* (2013.01); *A61M 2230/201* (2013.01)

(56) References Cited

U.S. PATENT DOCUMENTS

| | | |
|---|---|---|
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,403,984 A | 9/1983 | Ash et al. |
| 4,464,170 A | 8/1984 | Clemens et al. |
| 4,526,568 A | 7/1985 | Clemens et al. |
| 4,526,569 A | 7/1985 | Bernardi |
| 4,573,968 A | 3/1986 | Parker |
| 4,633,878 A | 1/1987 | Bombardieri |
| 4,657,529 A | 4/1987 | Prince et al. |
| 4,854,170 A | 8/1989 | Brimhall et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,976,720 A | 12/1990 | Machold et al. |
| 4,981,140 A | 1/1991 | Wyatt |
| 5,097,834 A | 3/1992 | Skrabal |
| 5,102,406 A | 4/1992 | Arnold |
| 5,109,850 A | 5/1992 | Blanco et al. |
| 5,134,079 A | 7/1992 | Cusack et al. |
| 5,165,406 A * | 11/1992 | Wong ............................ 600/345 |
| 5,207,642 A | 5/1993 | Orkin et al. |
| 5,237,993 A | 8/1993 | Skrabal |
| 5,273,517 A | 12/1993 | Barone et al. |
| 5,299,571 A | 4/1994 | Mastrototaro |
| 5,380,665 A | 1/1995 | Cusack et al. |
| 5,385,539 A | 1/1995 | Maynard |
| 5,505,828 A | 4/1996 | Wong et al. |
| 5,558,640 A | 9/1996 | Pfeiler et al. |
| 5,569,186 A | 10/1996 | Lord et al. |
| 5,609,572 A | 3/1997 | Lang |
| 5,665,065 A | 9/1997 | Colman et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,722,397 A | 3/1998 | Eppstein |
| 5,746,217 A | 5/1998 | Erickson et al. |
| 5,758,643 A | 6/1998 | Wong et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,879,310 A | 3/1999 | Sopp et al. |
| 5,902,253 A | 5/1999 | Pfeiffer et al. |
| 5,932,175 A | 8/1999 | Knute et al. |
| 5,947,911 A | 9/1999 | Wong et al. |
| 5,971,941 A | 10/1999 | Simons et al. |
| 6,017,318 A | 1/2000 | Gauthier et al. |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,058,934 A | 5/2000 | Sullivan |
| 6,066,103 A | 5/2000 | Duchon et al. |
| 6,072,180 A | 6/2000 | Kramer et al. |
| 6,077,055 A | 6/2000 | Vilks |
| 6,101,406 A | 8/2000 | Hacker et al. |
| 6,102,872 A | 8/2000 | Doneen et al. |
| 6,123,827 A | 9/2000 | Wong et al. |
| 6,124,134 A | 9/2000 | Stark |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,200,287 B1 | 3/2001 | Keller et al. |
| 6,214,629 B1 | 4/2001 | Freitag et al. |
| 6,226,082 B1 | 5/2001 | Roe |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,285,448 B1 | 9/2001 | Kuenstner |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 * | 4/2002 | Worthington et al. ......... 600/309 |
| 6,402,689 B1 | 6/2002 | Scarantino et al. |
| 6,484,044 B1 | 11/2002 | Lilienfeld-Toal |
| 6,491,656 B1 | 12/2002 | Morris |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,016,713 B2 | 3/2006 | Gardner et al. |
| 7,025,743 B2 | 4/2006 | Mann et al. |
| 7,027,848 B2 | 4/2006 | Robinson et al. |
| 7,043,288 B2 | 5/2006 | Davis, III et al. |
| 7,060,059 B2 | 6/2006 | Keith et al. |

(56) References Cited

U.S. PATENT DOCUMENTS

| | | | |
|---|---|---|---|
| 7,061,593 B2 | 6/2006 | Braig et al. | |
| 7,115,205 B2 | 10/2006 | Robinson et al. | |
| 7,139,598 B2 | 11/2006 | Hull et al. | |
| 7,171,252 B1 | 1/2007 | Scarantino et al. | |
| 7,190,988 B2 | 3/2007 | Say et al. | |
| 7,204,823 B2 | 4/2007 | Estes et al. | |
| 7,248,912 B2 | 7/2007 | Gough et al. | |
| 7,267,665 B2 | 9/2007 | Steil et al. | |
| 7,278,983 B2 | 10/2007 | Ireland et al. | |
| 7,291,107 B2 | 11/2007 | Hellwig et al. | |
| 7,291,497 B2 | 11/2007 | Holmes et al. | |
| 7,303,922 B2 | 12/2007 | Jeng et al. | |
| 7,354,420 B2 | 4/2008 | Steil et al. | |
| 7,388,202 B2 | 6/2008 | Sterling et al. | |
| 7,402,153 B2 | 7/2008 | Steil et al. | |
| 7,404,796 B2 | 7/2008 | Ginsberg | |
| 7,429,255 B2 | 9/2008 | Thompson | |
| 7,460,130 B2 | 12/2008 | Salganicoff | |
| 7,481,787 B2 | 1/2009 | Gable et al. | |
| 7,491,187 B2 | 2/2009 | Van Den Berghe et al. | |
| 7,500,949 B2 | 3/2009 | Gottlieb et al. | |
| 7,509,156 B2 | 3/2009 | Flanders | |
| 7,547,281 B2 | 6/2009 | Hayes et al. | |
| 7,569,030 B2 | 8/2009 | Lebel et al. | |
| 7,608,042 B2 | 10/2009 | Goldberger et al. | |
| 7,680,529 B2 | 3/2010 | Kroll | |
| 7,734,323 B2 | 6/2010 | Blomquist et al. | |
| 7,766,829 B2 | 8/2010 | Sloan et al. | |
| 7,785,258 B2 | 8/2010 | Braig et al. | |
| 7,806,854 B2 | 10/2010 | Damiano et al. | |
| 7,806,886 B2 | 10/2010 | Kanderian, Jr. et al. | |
| 7,946,985 B2 | 5/2011 | Mastrototaro et al. | |
| 7,972,296 B2 | 7/2011 | Braig et al. | |
| 8,251,907 B2 | 8/2012 | Sterling et al. | |
| 8,417,311 B2 | 4/2013 | Rule | |
| 8,449,524 B2 | 5/2013 | Braig et al. | |
| 2001/0051377 A1 | 12/2001 | Hammer et al. | |
| 2002/0128543 A1 | 9/2002 | Leonhardt | |
| 2002/0147423 A1 | 10/2002 | Burbank et al. | |
| 2003/0086074 A1 | 5/2003 | Braig et al. | |
| 2003/0086075 A1 | 5/2003 | Braig et al. | |
| 2003/0090649 A1 | 5/2003 | Sterling et al. | |
| 2003/0130616 A1 | 7/2003 | Steil et al. | |
| 2003/0144582 A1 | 7/2003 | Cohen et al. | |
| 2003/0195404 A1 | 10/2003 | Knobbe et al. | |
| 2003/0208113 A1 | 11/2003 | Mault et al. | |
| 2003/0208154 A1 | 11/2003 | Close et al. | |
| 2004/0034295 A1 | 2/2004 | Salganicoff | |
| 2004/0045879 A1 | 3/2004 | Shults et al. | |
| 2004/0097796 A1 | 5/2004 | Berman et al. | |
| 2004/0122353 A1 | 6/2004 | Shahmirian et al. | |
| 2004/0147034 A1 | 7/2004 | Gore et al. | |
| 2004/0215492 A1 | 10/2004 | Choi | |
| 2004/0220517 A1 | 11/2004 | Starkweather et al. | |
| 2004/0241736 A1 | 12/2004 | Hendee et al. | |
| 2004/0249308 A1 | 12/2004 | Forssell | |
| 2005/0003470 A1 | 1/2005 | Nelson et al. | |
| 2005/0022274 A1 | 1/2005 | Campbell et al. | |
| 2005/0033148 A1 | 2/2005 | Haueter et al. | |
| 2005/0049179 A1 | 3/2005 | Davidson et al. | |
| 2005/0065464 A1 | 3/2005 | Talbot et al. | |
| 2005/0065465 A1 | 3/2005 | Lebel et al. | |
| 2005/0105095 A1 | 5/2005 | Pesach et al. | |
| 2005/0137573 A1 | 6/2005 | McLaughlin | |
| 2005/0171503 A1 | 8/2005 | Van Den Berghe et al. | |
| 2005/0182306 A1 | 8/2005 | Sloan | |
| 2005/0192494 A1* | 9/2005 | Ginsberg | 600/365 |
| 2005/0192557 A1 | 9/2005 | Brauker et al. | |
| 2005/0197621 A1 | 9/2005 | Poulsen et al. | |
| 2005/0203360 A1 | 9/2005 | Brauker et al. | |
| 2005/0261660 A1 | 11/2005 | Choi | |
| 2005/0272640 A1 | 12/2005 | Doyle et al. | |
| 2006/0009727 A1 | 1/2006 | O'Mahony et al. | |
| 2006/0079809 A1 | 4/2006 | Goldberger et al. | |
| 2006/0100494 A1 | 5/2006 | Kroll | |
| 2006/0189925 A1* | 8/2006 | Gable et al. | 604/66 |
| 2006/0189926 A1 | 8/2006 | Hall et al. | |
| 2006/0197015 A1 | 9/2006 | Sterling et al. | |
| 2006/0200070 A1 | 9/2006 | Callicoat et al. | |
| 2006/0229531 A1 | 10/2006 | Goldberger et al. | |
| 2006/0264895 A1 | 11/2006 | Flanders | |
| 2006/0276771 A1 | 12/2006 | Galley et al. | |
| 2007/0016127 A1 | 1/2007 | Staib et al. | |
| 2007/0060796 A1 | 3/2007 | Kim | |
| 2007/0060869 A1 | 3/2007 | Tolle et al. | |
| 2007/0060872 A1 | 3/2007 | Hall et al. | |
| 2007/0083160 A1 | 4/2007 | Hall et al. | |
| 2007/0106135 A1 | 5/2007 | Sloan et al. | |
| 2007/0116601 A1 | 5/2007 | Patton | |
| 2007/0142720 A1 | 6/2007 | Ridder et al. | |
| 2007/0173761 A1 | 7/2007 | Kanderian et al. | |
| 2007/0191716 A1 | 8/2007 | Goldberger et al. | |
| 2007/0225675 A1 | 9/2007 | Robinson et al. | |
| 2007/0287985 A1 | 12/2007 | Estes et al. | |
| 2007/0293843 A1 | 12/2007 | Ireland et al. | |
| 2008/0051764 A1 | 2/2008 | Dent et al. | |
| 2008/0058625 A1 | 3/2008 | McGarraugh et al. | |
| 2008/0071157 A1 | 3/2008 | McGarraugh et al. | |
| 2008/0071158 A1 | 3/2008 | McGarraugh et al. | |
| 2008/0097289 A1 | 4/2008 | Steil et al. | |
| 2008/0161664 A1 | 7/2008 | Mastrototaro et al. | |
| 2008/0177165 A1 | 7/2008 | Blomquist et al. | |
| 2008/0183060 A1 | 7/2008 | Steil et al. | |
| 2008/0188796 A1 | 8/2008 | Steil et al. | |
| 2008/0200838 A1 | 8/2008 | Goldberger et al. | |
| 2008/0208113 A1 | 8/2008 | Damiano et al. | |
| 2008/0214919 A1 | 9/2008 | Harmon et al. | |
| 2008/0228056 A1 | 9/2008 | Blomquist et al. | |
| 2008/0249386 A1 | 10/2008 | Besterman et al. | |
| 2008/0269585 A1 | 10/2008 | Ginsberg | |
| 2009/0006061 A1 | 1/2009 | Thukral et al. | |
| 2009/0030398 A1* | 1/2009 | Yodfat et al. | 604/504 |
| 2009/0069743 A1 | 3/2009 | Krishnamoorthy et al. | |
| 2009/0156922 A1 | 6/2009 | Goldberger et al. | |
| 2009/0228214 A1 | 9/2009 | Say et al. | |
| 2009/0326343 A1 | 12/2009 | Gable et al. | |
| 2010/0174228 A1 | 7/2010 | Buckingham et al. | |
| 2011/0264071 A1 | 10/2011 | Braig et al. | |
| 2013/0165900 A1 | 6/2013 | Braig et al. | |

FOREIGN PATENT DOCUMENTS

| | | |
|---|---|---|
| EP | 1 491 144 | 12/2004 |
| WO | WO 00/32258 A | 6/2000 |
| WO | WO 02/43866 | 6/2002 |
| WO | WO 02/082990 A1 | 10/2002 |
| WO | WO 03/016882 | 2/2003 |
| WO | WO 03/039362 | 5/2003 |
| WO | WO 03/045233 A1 | 6/2003 |
| WO | WO 2004/043250 A1 | 5/2004 |
| WO | WO 2004/092715 A1 | 10/2004 |
| WO | WO 2005/051170 | 6/2005 |
| WO | WO 2005/110601 A1 | 11/2005 |
| WO | WO 2009/049252 A1 | 4/2009 |

OTHER PUBLICATIONS

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration." Analytical Chemistry, vol. 70, No. 3m pp. 623-627, Feb. 1, 1998.

Billman et. al., "Clinical Performance of an in line Ex-Vivo Point of Care Monitor: A Multicenter Study," Clinical Chemistry 48:11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICE Setting"; retrieved from http://www.chestjournal.org; CHEST/127/5/May 2005.

(56) References Cited

OTHER PUBLICATIONS

Glucon Critical Care Blood Glucose Monitor; Glucon; retrieved from http://www.glucon.com.

Fogt, et al., "Development and Evaluation of Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

International Searching Authority, Invitation to Pay Additional Fees, International Application No. PCT/US2006/004929, mailed Jul. 27, 2006.

Farkas et al., "Single-Versus Triple-Lumen Central Catheter-Related Sepsis: A Prospective Randomized Study in a Critically Ill Population" The American Journal of Medicine Sep. 1992 vol. 93 p. 277-282.

Davidson, Paul C., et al., A computer-directed intravenous insulin system shown to be safe, simple, and effectice in 120,618 h of operation, *Diabetes Care*, vol. 28, No. 10, Oct. 2005, pp. 2418-2423.

Davidson, Paul C., et al., Glucommander: A Computer-Directed IV Insulin System Shown to be Safe, Simple, and Effective in 120,618 Hours of Operation, Atlanta Diabetes Associates presentation.

Gorke, A. "Microbial Contamination of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, *The New England Journal of Medicine*, vol. 345, No. 19, Nov. 8, 2001, pp. 1359-1367.

Templeton et al., "Multiumen Central Venous Catheters Increase Risk for Catheter-Related Bloodstream Infection: Prospective Surveillance Study".

Wilson, George S., et al., Progress toward the Development of an Implantable Sensor for Glucose, *Clin. Chem.*, vol. 38, No. 9, 1992, pp. 1613-1617.

Yeung et al., "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley, James S., "Severe hypoglycemia in critically ill patients: Risk factors and outcomes," Critical Care Med, vol. 35, No. 10, pp. 1-6, 2007.

Unger, Jeff, et al., "Glucose Control in the Hospitalized Patient," Emerg Med 36(9): Sep. 12-18, 2004.

Glucommander FAQ, download Mar. 16, 2009 from http://adaendo.com/GlucommanderFAQ.html.

"Normoglycaemia in Intensive Care Evaluation and Survival Using Glucose Algorithm Regulation—Nice-Sugar," downloaded Mar. 23, 2009.

Letters to the Editor regarding "Glucose Control in Critically Ill Patients," N Engl J Med 361:1, Jul. 2, 2009.

"Medtronic is Leading a Highly Attractive Growth Market," Jun. 2, 2009.

Muniyappa et al., "Current Approaches for assessing insulin sensitivity and resistance in vivo: advantages limitations, and appropriate usage," AJP-Endocrinol Metab, vol. 294, E15-E26, first published Oct. 23, 2007.

* cited by examiner

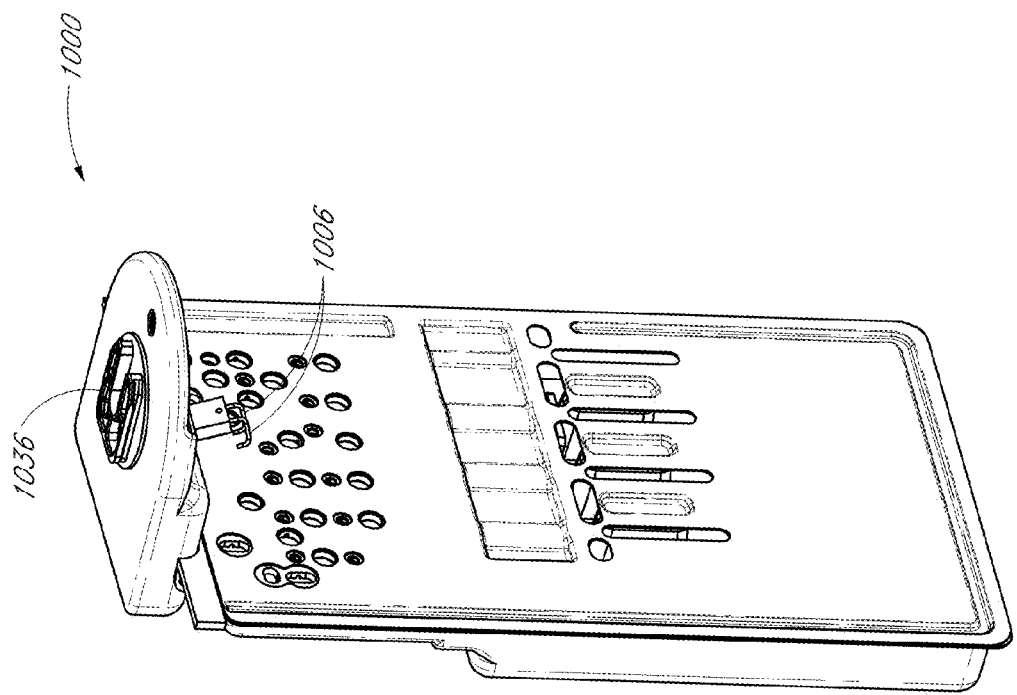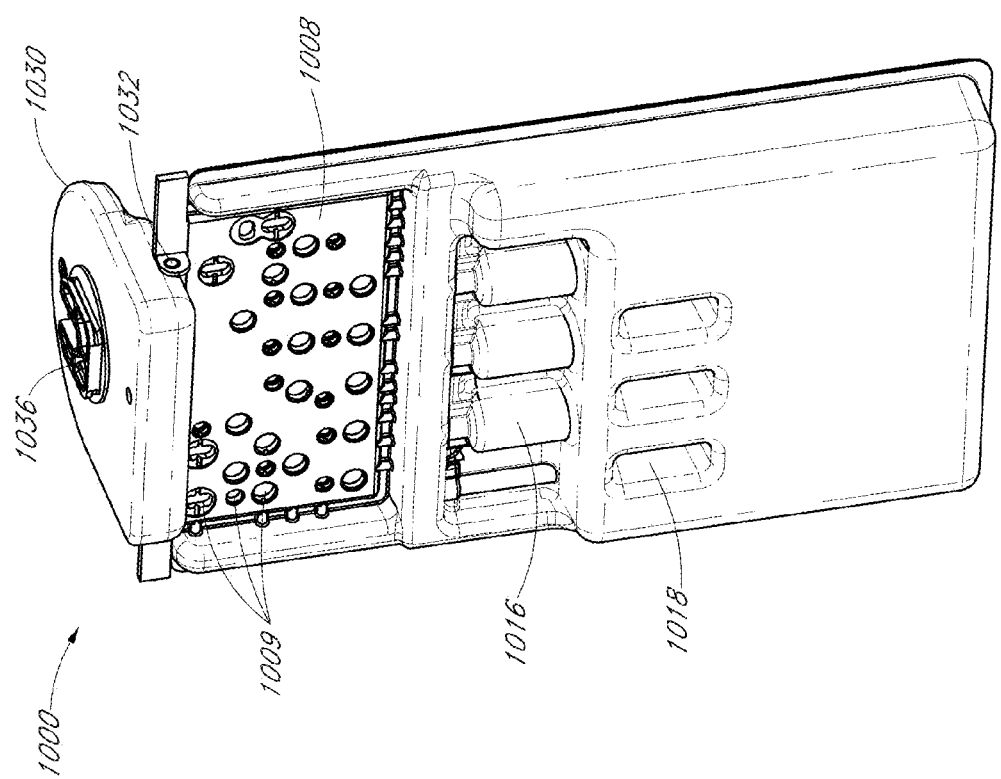
FIG. 10

FLUID COMPONENT ANALYSIS SYSTEM AND METHOD FOR GLUCOSE MONITORING AND CONTROL

CROSS-REFERENCE TO RELATED APPLICATIONS

This application is a continuation of U.S. patent application Ser. No. 12/559,328, titled FLUID COMPONENT ANALYSIS SYSTEM AND METHOD FOR GLUCOSE MONITORING AND CONTROL, filed Sep. 14, 2009, which claims the benefit under 35 U.S.C. §119(e) of U.S. Provisional Patent Application No. 61/096,461, titled ANALYTE MONITORING SYSTEM AND TREATMENT DOSING PROTOCOL, filed Sep. 12, 2008; U.S. Provisional Patent Application No. 61/099,491, titled ANALYTE MONITORING SYSTEM INCLUDING A TREATMENT DOSING ASSISTANT, filed Sep. 23, 2008; U.S. Provisional Patent Application No. 61/149,307, entitled FLUID COMPONENT ANALYSIS SYSTEM AND METHOD FOR GLUCOSE MONITORING AND CONTROL, filed Feb. 2, 2009; U.S. Provisional Patent Application No. 61/162,627, entitled FLUID COMPONENT ANALYSIS SYSTEM AND METHODS FOR SENSITIVITY MONITORING AND DOSAGE CONTROL, filed Mar. 23, 2009. Each of the foregoing applications is hereby incorporated by reference in its entirety and made part of this specification.

BACKGROUND

1. Field

Some embodiments of the disclosure relate generally to methods and devices for determining a concentration of an analyte in a sample, such as an analyte in a sample of bodily fluid, as well as methods and devices which can be used to support the making of such determinations. This disclosure also relates generally to a user interface for use with such apparatus. Some embodiments of this disclosure also relate generally to bolus injection and basal infusion systems and related apparatus. Some embodiments in this disclosure also relate to an analyte detection system configured to provide glycemic control and/or Tight Glycemic Control (TGC). Some aspects of this disclosure relate to an analyte detection system that is configured to determine a dosing protocol based on one or more measurements of the concentration of an analyte. Some aspects of this disclosure relate to a system and method that provides feedback to a healthcare provider regarding the treatment dose being administered to the patient. Some aspects of this disclosure also relate generally to systems and methods for calibrating analyte concentration when dilution of the sample has occurred.

2. Description of Related Art

It is advantageous to measure the levels of certain analytes, such as glucose, in a bodily fluid, such as blood). This can be done, for example, in a hospital or clinical setting when there is a risk that the levels of certain analytes may move outside a desired range, which in turn can jeopardize the health of a patient. Systems for measuring analyte levels may include a user interface (UI) that permits a user such as, for example, a patient, a health care provider, and so forth, to interact with the system. Currently known systems for analyte monitoring in a hospital or clinical setting may suffer from various drawbacks.

SUMMARY

Example embodiments described herein have several features, no single one of which is indispensible or solely responsible for their desirable attributes. Without limiting the scope of the claims, some of the advantageous features will now be summarized.

A patient treatment and analysis system is disclosed. The patient treatment and analysis system can include a body fluid analyzer configured to measure a concentration of an analyte in a bodily fluid, and access an analyte history database and store the measured concentration of the analyte in the analyte history database. The patient treatment and analysis system can include a treatment dosing system in communication with the body fluid analyzer. The treatment dosing system can include a source of a treatment substance and a treatment dosing algorithm stored in a computer memory. The treatment dosing system can be configured to use the treatment dosing algorithm to calculate an estimated treatment sensitivity for the patient by accessing the analyte history database and a dosage history database and comparing portions of the analyte history database to portions of the dosage history database. The treatment dosing system can use the treatment dosing algorithm to calculate a recommended treatment dosage for the patient based at least in part on the estimated treatment sensitivity, administer a dose of the treatment substance to the patient, and access a dosage history database and store a record of the administered dose therein.

The patient treatment and analysis system can further include a communication interface configured to communicate with an external infusion pump. The communication interface can be configured to receive infusion information from the external infusion pump, and the treatment dosing algorithm can be configured to calculate the estimated treatment sensitivity based at least in part on the infusion information received from the external infusion pump.

In some embodiments, the analyte can be glucose and the treatment substance can be insulin. The treatment substance can be IV insulin. The features and activities described above can make up a measurement cycle, and the system can be configured to perform the measurement cycle more frequently than once per hour.

The patient treatment and analysis system can further include a fluid network that is configured to draw a sample of bodily fluid through a catheter connected to the patient and transport at least a portion of the sample of bodily fluid to the body fluid analyzer. The fluid network can be further configured to deliver the treatment dose to the patient using the same catheter used to draw samples of bodily fluid.

The dose of the treatment fluid administered to the patient can be the recommended treatment dosage calculated by the treatment dosing system. The patient treatment and analysis system can further include a user interface configured to display the recommended treatment dosage to a user and to receive input from the user, and the dose of the treatment fluid administered to the patient can be determined at least in part by the input received from the user via the user interface. The source of the treatment substance can be a non-dedicated reservoir.

A patient monitoring and dosing system is disclosed. The patient monitoring and dosing system can include a body fluid analyzer configured to measure a concentration of an analyte in a sample of bodily fluid from a patient and a treatment dosing system in communication with the body fluid analyzer. The treatment dosing system can include a treatment dosing algorithm stored in a computer memory. The treatment dosing algorithm can be configured to automatically calculate an estimated treatment sensitivity for the patient based at least in part on the measured concentration of the analyte, and a recommended treatment dosage for the patient. The automatic calculation of the recommended treatment dosage can be based at least in part on the estimated treatment sensitivity.

The treatment dosing system can further include a source of treatment fluid, and the treatment dosing system can be configured to automatically deliver the recommended treatment dosage to the patient. The body fluid analyzer can be configured to periodically measure samples of bodily fluid, and the treatment dosing system can be configured to deliver the recommended treatment dosage to the patient at least in part as a basal infusion. The treatment dosing system can be configured to adjust a basal infusion rate to deliver the recommended treatment dosage to the patient. In some embodiments, the basal infusion can be halted at least five minutes before the next measurement is taken. The body fluid analyzer can be configured to periodically measure samples of bodily fluid, and the treatment dosing system can be configured to deliver the recommended treatment dosage to the patient at least in part as a bolus injection delivered at least five minutes before the next measurement is taken.

The patient monitoring and dosing system can further include a database in communication with the body fluid analyzer, and the database can be configured to store a history of measured concentrations of the analyte. The treatment dosing algorithm can be configured to access the database and calculate the estimated treatment sensitivity based at least in part on the history of measured concentrations of the analyte. The database can be configured to store a history of treatment doses delivered to the patient, and the treatment dosing algorithm can be configured to calculate the estimated treatment sensitivity based at least in part on the history of treatment doses. The history of treatment doses can include a plurality of active dose amounts delivered to the patient at different times, and the treatment dosing algorithm can be configured to calculate an amount remaining for each of the plurality of active dose amounts based at least in part on a treatment fluid half-life. The treatment dosing algorithm can be configured to calculate the estimated treatment sensitivity based at least in part on the amount remaining for each of the plurality of active dose amounts. The treatment dosing algorithm can be configured to calculate the estimated treatment sensitivity based at least in part on a comparison of at least a portion of the history of measured concentrations of the analyte to at least a portion of the history of treatment doses.

The treatment dosing algorithm can be configured to calculate a predicted accuracy of the estimated treatment sensitivity, and the treatment dosing algorithm can be configured to calculate the recommended treatment dosage based at least in part on the predicted accuracy of the estimated treatment sensitivity. The treatment dosing algorithm can be configured to apply a first dosing protocol if the predicted accuracy is above a predetermined level and apply a second dosing protocol if the predicted accuracy is below the predetermined level, and the second dosing protocol can be more conservative than the first dosing protocol. The treatment dosing algorithm can include a sliding scale dosing protocol having a varying level of aggressiveness that is based at least in part on the predicted accuracy, such that the aggressiveness of the sliding scale dosing protocol increases as the predicted accuracy increases.

The treatment dosing algorithm can be configured to calculate an expected analyte concentration range based at least in part on the estimated treatment sensitivity, and the treatment dosing algorithm can be configured to trigger an alert if the measured analyte concentration falls outside the expected analyte concentration range. The treatment dosing algorithm can be configured to calculate the estimated treatment sensitivity based at least in part on additional patient data including patient feeding information, patient medication information, or patient exercise information. The body fluid analyzer can be configured for glucose control solution calibration no more than once per day. The body fluid analyzer can be configured for glucose control solution calibration no more than once each week.

A method of providing analysis and control of blood chemistry is disclosed. The method can include: drawing a sample of bodily fluid from a patient; measuring a concentration of an analyte in the sample of bodily fluid; accessing an analyte concentration history and a treatment dosage history; calculating an estimated treatment sensitivity for the patient based at least in part on the measured concentration of the analyte, at least a portion of the analyte concentration history, and at least a portion of the treatment dosage history; calculating a recommended treatment dosage based at least in part on the estimated treatment sensitivity; providing the recommended treatment dosage to the patient; and updating the analyte concentration history and the treatment dosage history.

An infusion control system is disclosed. The infusion control system can include an external infusion pump configured to infuse an infusion fluid into a patient. The external infusion pump can include a memory containing an identity of the infusion fluid. The infusion control system can also include a patient monitoring device configured to measure the concentration of an analyte in a sample of bodily fluid drawn from the patient. The patient monitoring device can include a communication interface providing a communication link to the external infusion pump. The communication interface can be configured to query the external infusion pump and to receive the identity of the infusion fluid. The patient monitoring system can be configured to determine whether the infusion fluid affects the concentration of the analyte.

The memory can also contain the identity of the patient connected to the external infusion pump, and the communication interface can be configured to query the external infusion pump, to receive the identity of the patient connected to the external infusion pump, and to determine whether the external infusion pump is connected to the same patient as the patient monitoring device. The communication interface can be configured to query the external infusion pump and receive an infusion rate at which the infusion fluid is being infused into the patient.

The communication interface can be configured to send a command to the external infusion pump. The command can be to change the infusion rate at which the infusion fluid is infused into the patient. The command can be to stop infusion of the infusion fluid. The external infusion pump can be configured to query the patient monitoring system in response to receiving the command, to receive an identity of the analyte, to determine whether the infusion fluid affects the concentration of the analyte, and to refuse the command if the infusion fluid does not affect the concentration of the analyte. The external infusion pump can be configured to query the patient monitoring system in response to receiving the command, to receive an identity of the patient associated with the monitoring device, to determine whether the external infusion pump is connected to the same patient, and to refuse the command if the external infusion pump is not connected to the same patient. The communication link can be a wireless communication link.

A patient monitoring system is disclosed. The patient monitoring system can include a fluid network connected to a patient, and a body fluid analyzer connected to the fluid network. The fluid network can be configured to draw a sample of bodily fluid from the patient and transport at least a portion of the sample of bodily fluid to the body fluid analyzer. The body fluid analyzer can be configured to measure a concentration of an analyte in the at least a portion of the sample of bodily fluid. The patient monitoring system can include a first infusion fluid connected the patient, and an infusion control system positioned between the first infusion fluid and the patient. The infusion control system can be configured to operate in an infusion mode in which the first infusion fluid is allowed to infuse into the patient and a cutoff mode in which the first infusion fluid is stopped from infusing into the patient. The infusion control system can be configured to determine whether to automatically change from the infusion mode to the cutoff mode based at least in part on the concentration of the analyte.

A method of preventing hypoglycemia is disclosed. The method can include: connecting a fluid network to a patient; connecting a first infusion fluid to the patient; and providing an infusion control system positioned between the first infusion fluid and the patient. The infusion control system can be configured to operate in an infusion mode in which the first infusion fluid is allowed to infuse into the patient and a cutoff mode in which the first infusion fluid is stopped from infusing into the patient. The method can include operating the infusion control system in the infusion mode, thereby infusing the first infusion fluid into the patient; drawing a sample of bodily fluid from the patient; and transporting at least a portion of the sample of bodily fluid through the fluid network to a body fluid analyzer. The method can include using the body fluid analyzer to measure a parameter of the at least a portion of the sample of bodily fluid and determining a concentration of an analyte in the at least a portion of the sample of bodily fluid from the measured parameter. The method can include automatically changing the infusion control system to the cutoff mode in response to determining the concentration of the analyte, thereby stopping infusion of the first infusion fluid.

BRIEF DESCRIPTION OF THE DRAWINGS

The following drawings and the associated descriptions are provided to illustrate embodiments of the present disclosure and do not limit the scope of the claims.

FIG. 10 illustrates an embodiment of a removable cartridge that can interface with a monitoring device.

Figure 1:
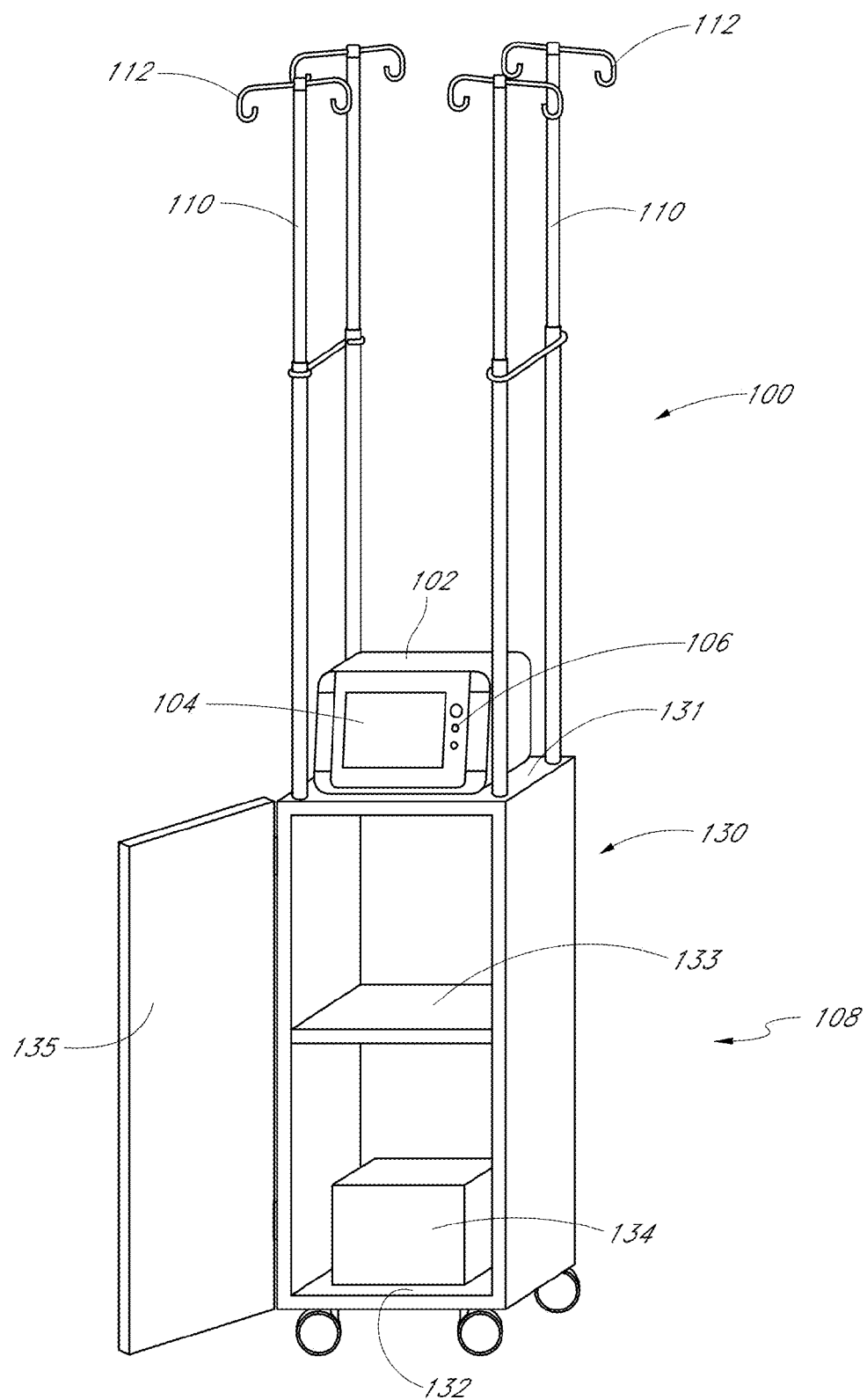
FIG. 1 shows an embodiment of an apparatus for withdrawing and analyzing fluid samples.

These and other features will now be described with reference to the drawings summarized above. The drawings and the associated descriptions are provided to illustrate embodiments and not to limit the scope of any claim. Throughout the drawings, reference numbers may be reused to indicate correspondence between referenced elements. In addition, where applicable, the first one or two digits of a reference numeral for an element can frequently indicate the figure number in which the element first appears.

DETAILED DESCRIPTION OF PREFERRED EMBODIMENTS

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The systems and methods discussed herein can be used anywhere, including, for example, in laboratories, hospitals, healthcare facilities, intensive care units (ICUs), or residences. Moreover, the systems and methods discussed herein can be used for invasive techniques, as well as non-invasive techniques or techniques that do not involve a body or a patient such as, for example, in vitro techniques.

Analyte Monitoring Apparatus

FIG. 1 shows an embodiment of an apparatus 100 for withdrawing and analyzing fluid samples. The apparatus 100 includes a monitoring device 102. In some embodiments, the monitoring device 102 can be an "OptiScanner®" monitor available from OptiScan Biomedical Corporation of Hayward, Calif. In some embodiments, the device 102 can measure one or more physiological parameters, such as the concentration of one or more substance(s) in a sample fluid. The sample fluid can be, for example, whole blood from a patient 302 (see, e.g., FIG. 3) and/or a component of whole blood such as, e.g., blood plasma. In some embodiments, the device 100 can also deliver an infusion fluid to a patient.

In the illustrated embodiment, the monitoring device 102 includes a display 104 such as, for example, a touch-sensitive liquid crystal display. The display 104 can provide an interface that includes alerts, indicators, charts, and/or soft buttons. The device 102 also can include one or more inputs and/or outputs 106 that provide connectivity and/or permit user interactivity.

In the embodiment shown in FIG. 1, the device 102 is mounted on a stand 108. The stand 108 may comprise a cart such as, for example, a wheeled cart 130 as shown in FIG. 1. In some embodiments, the stand 108 is configured to roll on a wheeled pedestal 240 (shown in FIG. 2). The stand 108 advantageously can be easily moved and includes one or more poles 110 and/or hooks 112. The poles 110 and hooks 112 can be configured to accommodate other medical devices and/or implements, including, for example, infusion pumps, saline bags, arterial pressure sensors, other monitors and medical devices, and so forth. Some stands or carts may become unstable if intravenous (IV) bags, IV pumps, and other medical devices are hung too high on the stand or cart. In some embodiments, the apparatus 100 can be configured to have a low center of gravity, which may overcome possible instability. For example, the stand 108 can be weighted at the bottom to at least partially offset the weight of IV bags, IV pumps and medical devices that may be attached to the hooks 112 that are placed above the monitoring device 102. Adding weight toward the bottom (e.g., near the wheels) may help prevent the apparatus 100 from tipping over.

In some embodiments, the apparatus 100 includes the cart 130, which has an upper shelf 131 on which the monitoring device 102 may be placed (or attached) and a bottom shelf 132 on which a battery 134 may be placed (or attached). The battery 134 may be used as a main or backup power supply for the monitoring device 102 (which may additionally or alternatively accept electrical power from a wall socket). Two or more batteries are used in certain embodiments. The apparatus 100 may be configured so that the upper and lower shelves 131, 132 are close to ground level, and the battery provides counterweight. Other types of counterweights may be used. For example, in some embodiments, portions of the cart 130 near the floor (e.g., a lower shelf) are weighted, formed from a substantial quantity of material (e.g., thick sheets of metal), and/or formed from a relatively high-density metal (e.g., lead). In some embodiments the bottom shelf 132 is approximately 6 inches to 1 foot above ground level, and the upper shelf 131 is approximately 2 feet to 4 feet above ground level. In some embodiments the upper shelf 131 may be configured to support approximately 40 pounds (lbs), and the bottom shelf 132 may be configured to support approximately 20 lbs. One possible advantage of embodiments having such a configuration is that IV pumps, bags containing saline, blood and/or drugs, and other medical equipment weighing approximately 60 lbs, collectively, can be hung on the hooks 112 above the shelves without making the apparatus 100 unstable. The apparatus 100 may be moved by applying a horizontal force on the apparatus 100, for example, by pushing and/or pulling the poles 110. In many cases, a user may exert force on an upper portion of the apparatus 100, for example, close to shoulder-height. By counterbalancing the weight as described above, the apparatus 100 may be moved in a reasonably stable manner.

In the illustrated embodiment, the cart 130 includes the bottom shelf 132 and an intermediate shelf 133, which are enclosed on three sides by walls and on a fourth side by a door 135. The door 135 can be opened (as shown in FIG. 1) to provide access to the shelves 132, 133. In other embodiments, the fourth side is not enclosed (e.g., the door 135 is not used). Many cart variations are possible. In some embodiments the battery 134 can be placed on the bottom shelf 134 or the intermediate shelf 133.

Figure 2:
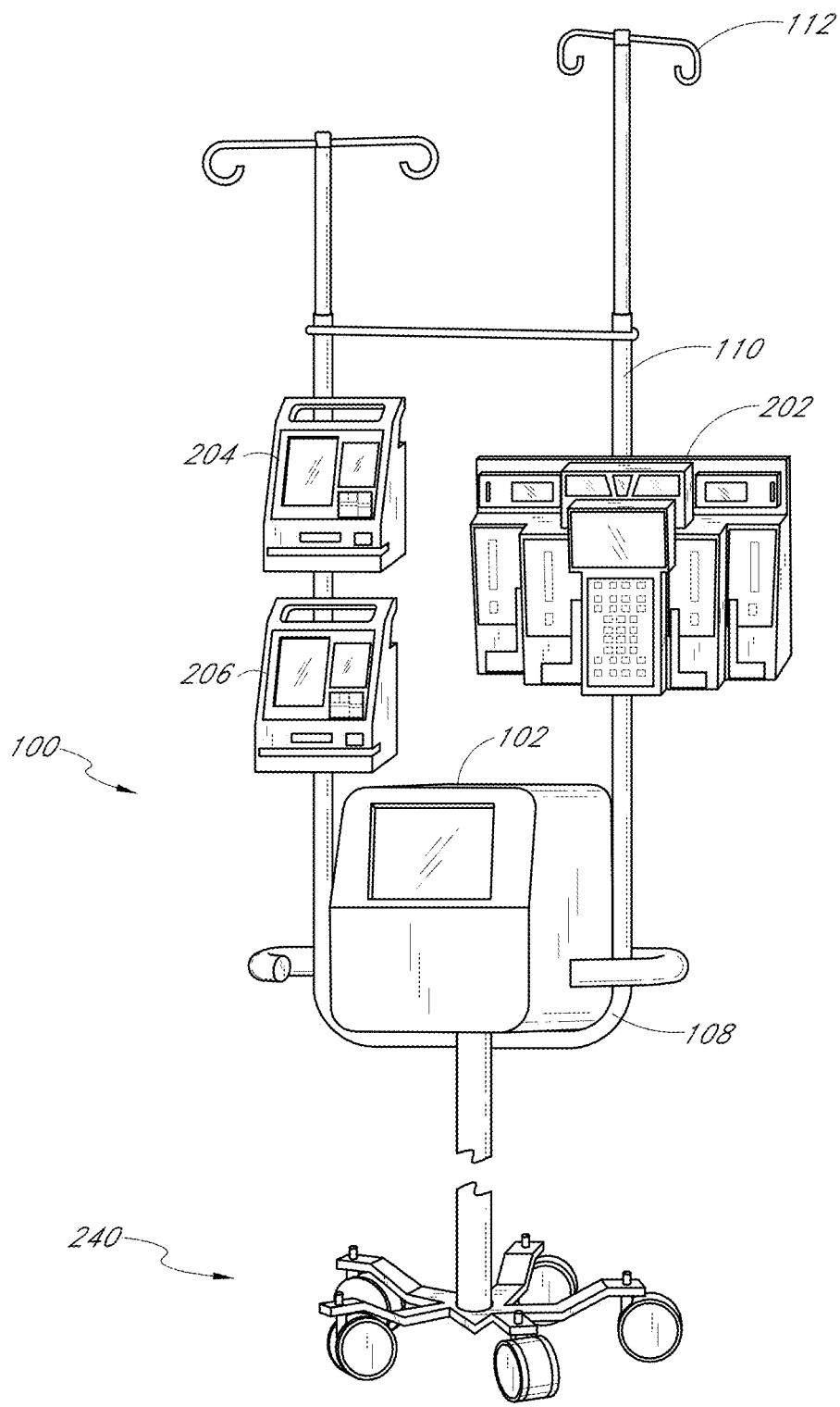
FIG. 2 illustrates how various other devices can be supported on or near an embodiment of apparatus illustrated in FIG. 1.

FIG. 2 illustrates how various other devices can be supported on or near the apparatus 100 illustrated in FIG. 1. For example, the poles 110 of the stand 108 can be configured (e.g., of sufficient size and strength) to accommodate multiple devices 202, 204, 206. In some embodiments, one or more COLLEAGUE® volumetric infusion pumps available from Baxter International Inc. of Deerfield, Ill. can be accommodated. In some embodiments, one or more Alaris® PC units available from Cardinal Health, Inc. of Dublin, Ohio can be accommodated. Furthermore, various other medical devices (including the two examples mentioned here), can be integrated with the disclosed monitoring device 102 such that multiple devices function in concert for the benefit of one or multiple patients without the devices interfering with each other.

Figure 3:
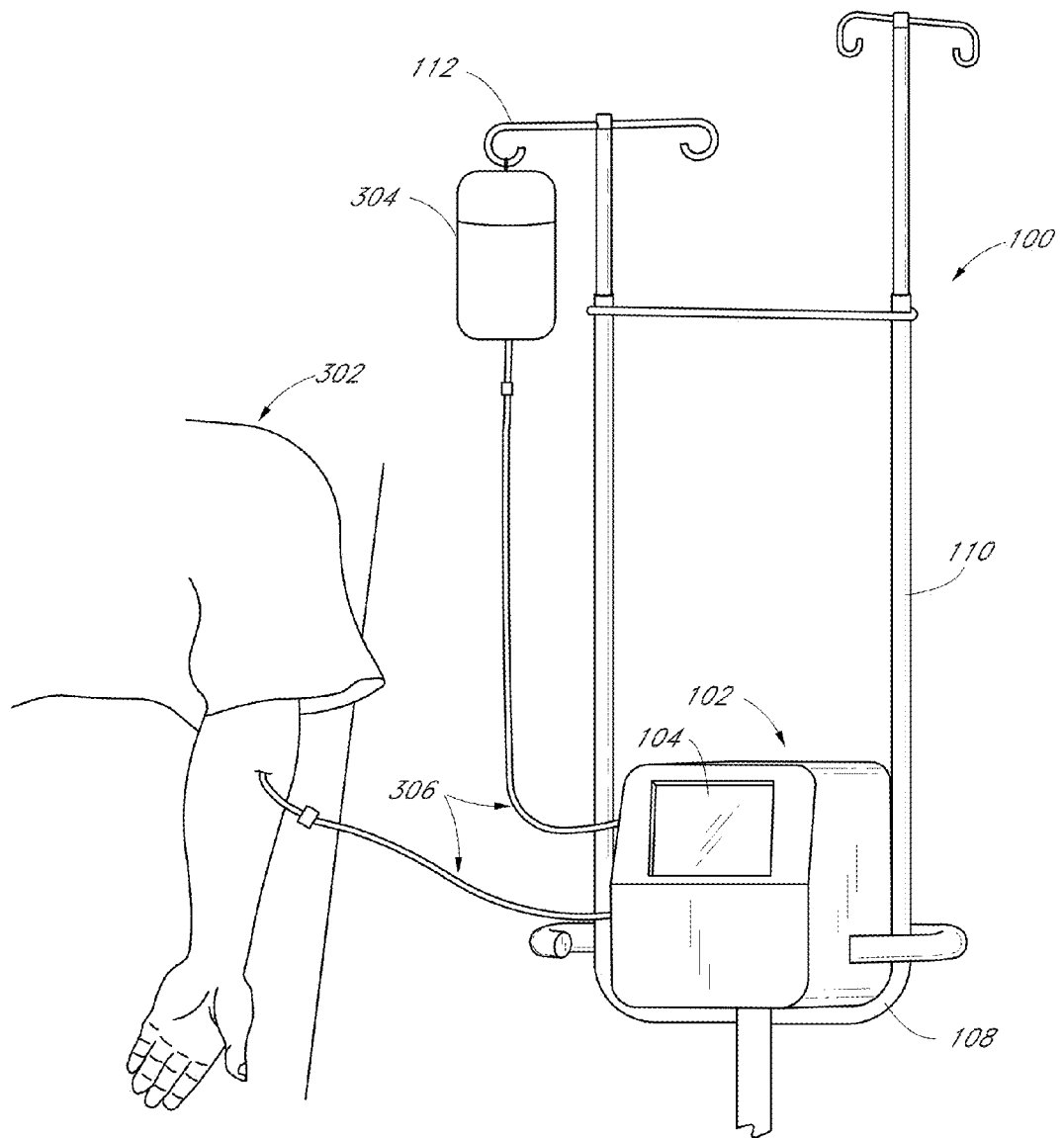
FIG. 3 illustrates an embodiment of the apparatus in FIG. 1 configured to be connected to a patient.
Figure 3A:
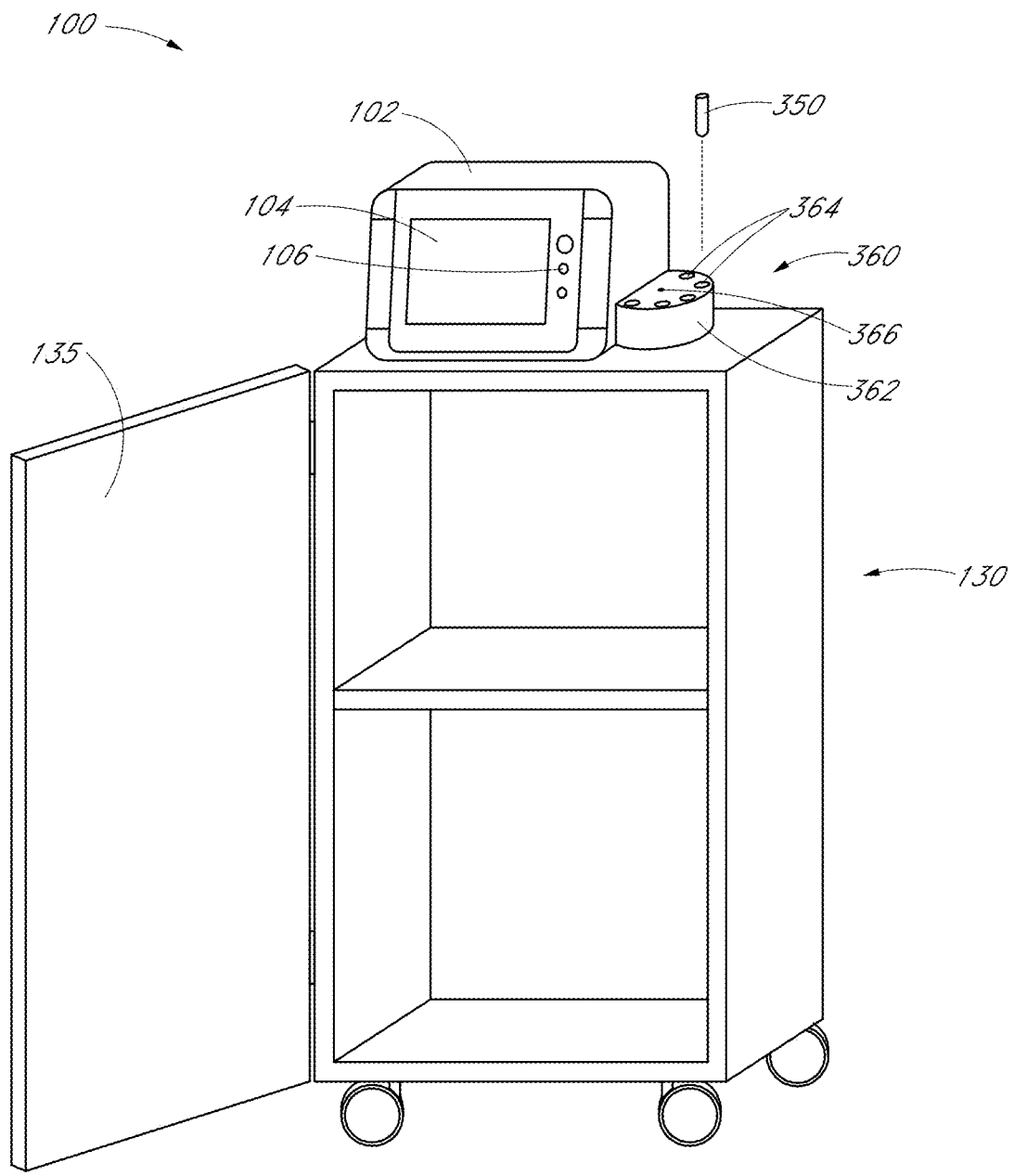
FIG. 3A illustrates an embodiment of the apparatus in FIG. 1 that is not configured to be connected to a patient but which receives a fluid sample from an extracorporeal fluid container such as, for example, a test tube. This embodiment of the apparatus can advantageously provide in vitro analysis of a fluid sample.

FIG. 3 illustrates the apparatus 100 of FIG. 1 as it can be connected to a patient 302. The monitoring device 102 can be used to determine the concentration of one or more substances in a sample fluid. The sample fluid can come can come from the patient 302, as illustrated in FIG. 3, or the sample fluid can come from a fluid container, as illustrated in FIG. 3A. In some preferred embodiments, the sample fluid is whole blood.

In some embodiments (see, e.g., FIG. 3), the monitoring device 102 can also deliver an infusion fluid to the patient 302. An infusion fluid container 304 (e.g., a saline bag), which can contain infusion fluid (e.g., saline and/or medication), can be supported by the hook 112. The monitoring device 102 can be in fluid communication with both the container 304 and the sample fluid source (e.g., the patient 302), through tubes 306. The infusion fluid can comprise any combination of fluids and/or chemicals. Some advantageous examples include (but are not limited to): water, saline, dextrose, lactated Ringer's solution, drugs, and insulin.

The example monitoring device 102 schematically illustrated in FIG. 3 allows the infusion fluid to pass to the patient 302 and/or uses the infusion fluid itself (e.g., as a flushing fluid or a standard with known optical properties, as discussed further below). In some embodiments, the monitoring device 102 may not employ infusion fluid. The monitoring device 102 may thus draw samples without delivering any additional fluid to the patient 302. The monitoring device 102 can include, but is not limited to, fluid handling and analysis apparatuses, connectors, passageways, catheters, tubing, fluid control elements, valves, pumps, fluid sensors, pressure sensors, temperature sensors, hematocrit sensors, hemoglobin sensors, colorimetric sensors, gas (e.g., "bubble") sensors, fluid conditioning elements, gas injectors, gas filters, blood plasma separators, and/or communication devices (e.g., wireless devices) to permit the transfer of information within the monitoring device 102 or between the monitoring device 102 and a network.

In some embodiments, the apparatus 100 is not connected to a patient and may receive fluid samples from a container such as a decanter, flask, beaker, tube, cartridge, test strip, etc., or any other extracorporeal fluid source. The container may include a biological fluid sample such as, e.g., a body fluid sample. For example, FIG. 3A schematically illustrates an embodiment of the monitoring device 102 that is configured to receive a fluid sample from one or more test tubes 350. This embodiment of the monitoring device 102 is configured to perform in vitro analysis of a fluid (or a fluid component) in the test tube 350. The test tube 350 may comprise a tube, vial, bottle, or other suitable container or vessel. The test tube 350 may include an opening disposed at one end of the tube through which the fluid sample may be added prior to delivery of the test tube to the monitoring device 102. In some embodiments, the test tubes 350 may also include a cover adapted to seal the opening of the tube. The cover may include an aperture configured to permit a tube, nozzle, needle, pipette, or syringe to dispense the fluid sample into the test tube 350. The test tubes 350 may comprise a material such as, for example, glass, polyethylene, or polymeric compounds. In various embodiments, the test tubes 350 may be re-usable units or may be disposable, single-use units. In certain embodiments, the test tubes 350 may comprise commercially available low pressure/vacuum sample bottles, test bottles, or test tubes.

In the embodiment shown in FIG. 3A, the monitoring device 102 comprises a fluid delivery system 360 configured to receive a container (e.g., the test tube 350) containing a fluid sample and deliver the fluid sample to a fluid handling system (such as, e.g., fluid handling system 404 described below). In some embodiments, the fluid handling system delivers a portion of the fluid sample to an analyte detection system for in vitro measurement of one or more physiological parameters (e.g., an analyte concentration). Prior to measurement, the fluid handling system may, in some embodiments, separate the fluid sample into components, and a measurement may be performed on one or more of the components. For example, the fluid sample in the test tube 350 may comprise whole blood, and the fluid handling system may separate blood plasma from the sample (e.g., by filtering and/or centrifuging).

In the embodiment illustrated in FIG. 3A, the fluid delivery system 360 comprises a carousel 362 having one or more openings 364 adapted to receive the test tube 350. The carousel 362 may comprise one, two, four, six, twelve, or more openings 364. In the illustrated embodiment, the carousel 362 is configured to rotate around a central axis or spindle 366 so that a test tube 350 inserted into one of the openings 364 is delivered to the monitoring device 102. In certain embodiments, the fluid handling system of the monitoring device 102 comprises a sampling probe that is configured to collect a portion of the fluid sample from the test tube 350 (e.g., by suction or aspiration). The collected portion may then be transported in the device 102 as further described below (see, e.g., FIGS. 4-7). For example, in one embodiment suitable for use with whole blood, the collected portion of the whole blood sample is transported to a centrifuge for separation into blood plasma, a portion of the blood plasma is transported to an infrared spectroscope for measurement of one or more analytes (e.g., glucose), and the measured blood plasma is then transported to a waste container for disposal.

In other embodiments of the apparatus 100 shown in FIG. 3A, the fluid delivery system 360 may comprise a turntable, rack, or caddy adapted to receive the test tube 350. In yet other embodiments, the monitoring device 102 may comprise an inlet port adapted to receive the test tube 350. Additionally, in other embodiments, the fluid sample may be delivered to the apparatus 100 using a test cartridge, a test strip, or other suitable container. Many variations are possible.

In some embodiments, one or more components of the apparatus 100 can be located at another facility, room, or other suitable remote location. One or more components of the monitoring device 102 can communicate with one or more other components of the monitoring device 102 (or with other devices) by communication interface(s) such as, but not limited to, optical interfaces, electrical interfaces, and/or wireless interfaces. These interfaces can be part of a local network, internet, wireless network, or other suitable networks.

System Overview

Figure 4:
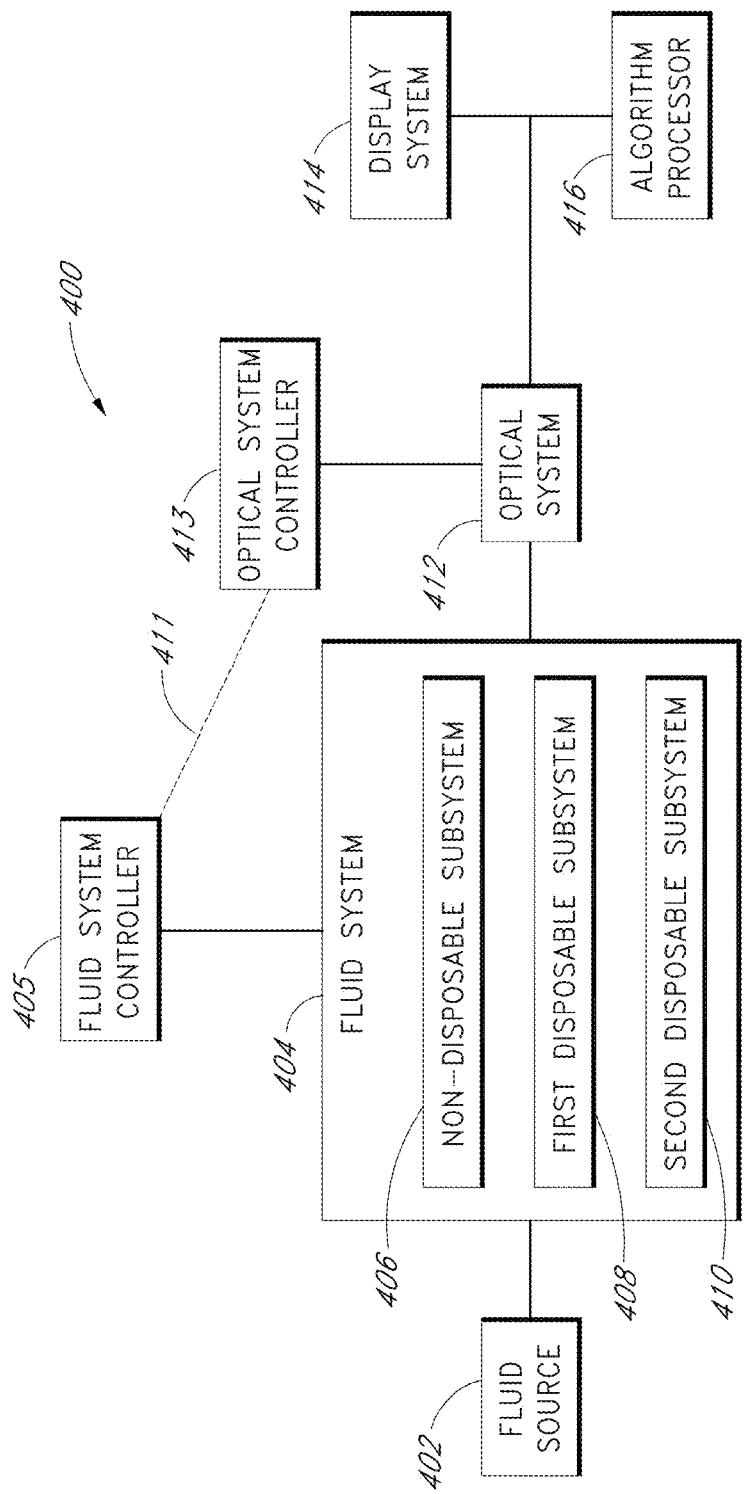
FIG. 4 is a block diagram of an embodiment of a system for withdrawing and analyzing fluid samples.

FIG. 4 is a block diagram of a system 400 for sampling and analyzing fluid samples. The monitoring device 102 can comprise such a system. The system 400 can include a fluid source 402 connected to a fluid-handling system 404. The fluid-handling system 404 includes fluid passageways and other components that direct fluid samples. Samples can be withdrawn from the fluid source 402 and analyzed by an optical system 412. The fluid-handling system 404 can be controlled by a fluid system controller 405, and the optical system 412 can be controlled by an optical system controller 413. The sampling and analysis system 400 can also include a display system 414 and an algorithm processor 416 that assist in fluid sample analysis and presentation of data.

In some embodiments, the sampling and analysis system 400 is a mobile point-of-care apparatus that monitors physiological parameters such as, for example, blood glucose concentration. Components within the system 400 that may contact fluid and/or a patient, such as tubes and connectors, can be coated with an antibacterial coating to reduce the risk of infection. Connectors between at least some components of the system 400 can include a self-sealing valve, such as a spring valve, in order to reduce the risk of contact between port openings and fluids, and to guard against fluid escaping from the system. Other components can also be included in a system for sampling and analyzing fluid in accordance with the described embodiments.

The sampling and analysis system 400 can include a fluid source 402 (or more than one fluid source) that contain(s) fluid to be sampled. The fluid-handling system 404 of the sampling and analysis system 400 is connected to, and can draw fluid from, the fluid source 402. The fluid source 402 can be, for example, a blood vessel such as a vein or an artery, a container such as a decanter, flask, beaker, tube, cartridge, test strip, etc., or any other corporeal or extracorporeal fluid source. For example, in some embodiments, the fluid source 402 may be a vein or artery in the patient 302 (see, e.g., FIG. 3). In other embodiments, the fluid source 402 may comprise an extracorporeal container 350 of fluid delivered to the system 400 for analysis (see, e.g., FIG. 3B). The fluid to be sampled can be, for example, blood, plasma, interstitial fluid, lymphatic fluid, or another fluid. In some embodiments, more than one fluid source can be present, and more than one fluid and/or type of fluid can be provided.

In some embodiments, the fluid-handling system 404 withdraws a sample of fluid from the fluid source 402 for analysis, centrifuges at least a portion of the sample, and prepares at least a portion of the sample for analysis by an optical sensor such as a spectrophotometer (which can be part of an optical system 412, for example). These functions can be controlled by a fluid system controller 405, which can also be integrated into the fluid-handling system 404. The fluid system controller 405 can also control the additional functions described below.

In some embodiments, at least a portion of the sample is returned to the fluid source 402. At least some of the sample, such as portions of the sample that are mixed with other materials or portions that are otherwise altered during the sampling and analysis process, or portions that, for any reason, are not to be returned to the fluid source 402, can also be placed in a waste bladder (not shown in FIG. 4). The waste bladder can be integrated into the fluid-handling system 404 or supplied by a user of the system 400. The fluid-handling system 404 can also be connected to a saline source, a detergent source, and/or an anticoagulant source, each of which can be supplied by a user, attached to the fluid-handling system 404 as additional fluid sources, and/or integrated into the fluid-handling system 404.

Components of the fluid-handling system 404 can be modularized into one or more non-disposable, disposable, and/or replaceable subsystems. In the embodiment shown in FIG. 4, components of the fluid-handling system 404 are separated into a non-disposable subsystem 406, a first disposable subsystem 408, and a second disposable subsystem 410.

The non-disposable subsystem 406 can include components that, while they may be replaceable or adjustable, do not generally require regular replacement during the useful lifetime of the system 400. In some embodiments, the non-disposable subsystem 406 of the fluid-handling system 404 includes one or more reusable valves and sensors. For example, the non-disposable subsystem 406 can include one or more valves (or non-disposable portions thereof), (e.g., pinch-valves, rotary valves, etc.), sensors (e.g., ultrasonic bubble sensors, non-contact pressure sensors, optical blood dilution sensors, etc). The non-disposable subsystem 406 can also include one or more pumps (or non-disposable portions thereof). For example, some embodiments can include pumps available from Hospira. In some embodiments, the components of the non-disposable subsystem 406 are not directly exposed to fluids and/or are not readily susceptible to contamination.

The first and second disposable subsystems 408, 410 can include components that are regularly replaced under certain circumstances in order to facilitate the operation of the system 400. For example, the first disposable subsystem 408 can be replaced after a certain period of use, such as a few days, has elapsed. Replacement may be necessary, for example, when a bladder within the first disposable subsystem 408 is filled to capacity. Such replacement may mitigate fluid system performance degradation associated with and/or contamination wear on system components.

In some embodiments, the first disposable subsystem 408 includes components that may contact fluids such as patient blood, saline, flushing solutions, anticoagulants, and/or detergent solutions. For example, the first disposable subsystem 408 can include one or more tubes, fittings, cleaner pouches and/or waste bladders. The components of the first disposable subsystem 408 can be sterilized in order to decrease the risk of infection and can be configured to be easily replaceable.

In some embodiments, the second disposable subsystem 410 can be designed to be replaced under certain circumstances. For example, the second disposable subsystem 410 can be replaced when the patient being monitored by the system 400 is changed. The components of the second disposable subsystem 410 may not need replacement at the same intervals as the components of the first disposable subsystem 408. For example, the second disposable subsystem 410 can include a sample holder and/or at least some components of a centrifuge, components that may not become filled or quickly worn during operation of the system 400. Replacement of the second disposable subsystem 410 can decrease or eliminate the risk of transferring fluids from one patient to another during operation of the system 400, enhance the measurement performance of system 400, and/or reduce the risk of contamination or infection.

In some embodiments, the sample holder of the second disposable subsystem 410 receives the sample obtained from the fluid source 402 via fluid passageways of the first disposable subsystem 408. The sample holder is a container that can hold fluid for the centrifuge and can include a window to the sample for analysis by a spectrometer. In some embodiments, the sample holder includes windows that are made of a material that is substantially transparent to electromagnetic radiation in the mid-infrared range of the spectrum. For example, the sample holder windows can be made of calcium fluoride.

An injector can provide a fluid connection between the first disposable subsystem 408 and the sample holder of the second disposable subsystem 410. In some embodiments, the injector can be removed from the sample holder to allow for free spinning of the sample holder during centrifugation.

In some embodiments, the components of the sample are separated by centrifuging for a period of time before measurements are performed by the optical system 412. For example, a fluid sample (e.g., a blood sample) can be centrifuged at a relatively high speed. The sample can be spun at a certain number of revolutions per minute (RPM) for a given length of time to separate blood plasma for spectral analysis. In some embodiments, the fluid sample is spun at about 7200 RPM. In some embodiments, the sample is spun at about 5000 RPM. In some embodiments, the fluid sample is spun at about 4500 RPM. In some embodiments, the fluid sample is spun at more than one rate for successive time periods. The length of time can be approximately 5 minutes. In some embodiments, the length of time is approximately 2 minutes. Separation of a sample into the components can permit measurement of solute (e.g., glucose) concentration in plasma, for example, without interference from other blood components. This kind of post-separation measurement, (sometimes referred to as a "direct measurement") has advantages over a solute measurement taken from whole blood because the proportions of plasma to other components need not be known or estimated in order to infer plasma glucose concentration. In some embodiments, the separated plasma can be analyzed electrically using one or more electrodes instead of, or in addition to, being analyzed optically. This analysis may occur within the same device, or within a different device. For example, in certain embodiments, an optical analysis device can separate blood into components, analyze the components, and then allow the components to be transported to another analysis device that can further analyze the components (e.g., using electrical and/or electrochemical measurements).

An anticoagulant, such as, for example, heparin can be added to the sample before centrifugation to prevent clotting. The fluid-handling system 404 can be used with a variety of anticoagulants, including anticoagulants supplied by a hospital or other user of the monitoring system 400. A detergent solution formed by mixing detergent powder from a pouch connected to the fluid-handling system 404 with saline can be used to periodically clean residual protein and other sample remnants from one or more components of the fluid-handling system 404, such as the sample holder. Sample fluid to which anticoagulant has been added and used detergent solution can be transferred into the waste bladder.

The system 400 shown in FIG. 4 includes an optical system 412 that can measure optical properties (e.g., transmission) of a fluid sample (or a portion thereof). In some embodiments, the optical system 412 measures transmission in the mid-infrared range of the spectrum. In some embodiments, the optical system 412 includes a spectrometer that measures the transmission of broadband infrared light through a portion of a sample holder filled with fluid. The spectrometer need not come into direct contact with the sample. As used herein, the term "sample holder" is a broad term that carries its ordinary meaning as an object that can provide a place for fluid. The fluid can enter the sample holder by flowing.

In some embodiments, the optical system 412 includes a filter wheel that contains one or more filters. In some embodiments, more than ten filters can be included, for example twelve or fifteen filters. In some embodiments, more than 20 filters (e.g., twenty-five filters) are mounted on the filter wheel. The optical system 412 includes a light source that passes light through a filter and the sample holder to a detector. In some embodiments, a stepper motor moves the filter wheel in order to position a selected filter in the path of the light. An optical encoder can also be used to finely position one or more filters. In some embodiments, one or more tunable filters may be used to filter light into multiple wavelengths. The one or more tunable filters may provide the multiple wavelengths of light at the same time or at different times (e.g., sequentially). The light source included in the optical system 412 may emit radiation in the ultraviolet, visible, near-infrared, mid-infrared, and/or far-infrared regions of the electromagnetic spectrum. In some embodiments, the light source can be a broadband source that emits radiation in a broad spectral region (e.g., from about 1500 nm to about 6000 nm). In other embodiments, the light source may emit radiation at certain specific wavelengths. The light source may comprise one or more light emitting diodes (LEDs) emitting radiation at one or more wavelengths in the radiation regions described herein. In other embodiments, the light source may comprise one or more laser modules emitting radiation at one or more wavelengths. The laser modules may comprise a solid state laser (e.g., a Nd:YAG laser), a semiconductor based laser (e.g., a GaAs and/or InGaAsP laser), and/or a gas laser (e.g., an Ar-ion laser). In some embodiments, the laser modules may comprise a fiber laser. The laser modules may emit radiation at certain fixed wavelengths. In some embodiments, the emission wavelength of the laser module(s) may be tunable over a wide spectral range (e.g., about 30 nm to about 100 nm). In some embodiments, the light source included in the optical system 412 may be a thermal infrared emitter. The light source can comprise a resistive heating element, which, in some embodiments, may be integrated on a thin dielectric membrane on a micromachined silicon structure. In one embodiment the light source is generally similar to the electrical modulated thermal infrared radiation source, IRSource™, available from the Axetris Microsystems division of Leister Technologies, LLC (Itasca, Ill.).

The optical system 412 can be controlled by an optical system controller 413. The optical system controller can, in some embodiments, be integrated into the optical system 412. In some embodiments, the fluid system controller 405 and the optical system controller 413 can communicate with each other as indicated by the line 411. In some embodiments, the function of these two controllers can be integrated and a single controller can control both the fluid-handling system 404 and the optical system 412. Such an integrated control can be advantageous because the two systems are preferably integrated, and the optical system 412 is preferably configured to analyze the very same fluid handled by the fluid-handling system 404. Indeed, portions of the fluid-handling system 404 (e.g., the sample holder described above with respect to the second disposable subsystem 410 and/or at least some components of a centrifuge) can also be components of the optical system 412. Accordingly, the fluid-handling system 404 can be controlled to obtain a fluid sample for analysis by optical system 412, when the fluid sample arrives, the optical system 412 can be controlled to analyze the sample, and when the analysis is complete (or before), the fluid-handling system 404 can be controlled to return some of the sample to the fluid source 402 and/or discard some of the sample, as appropriate.

Figure 24:
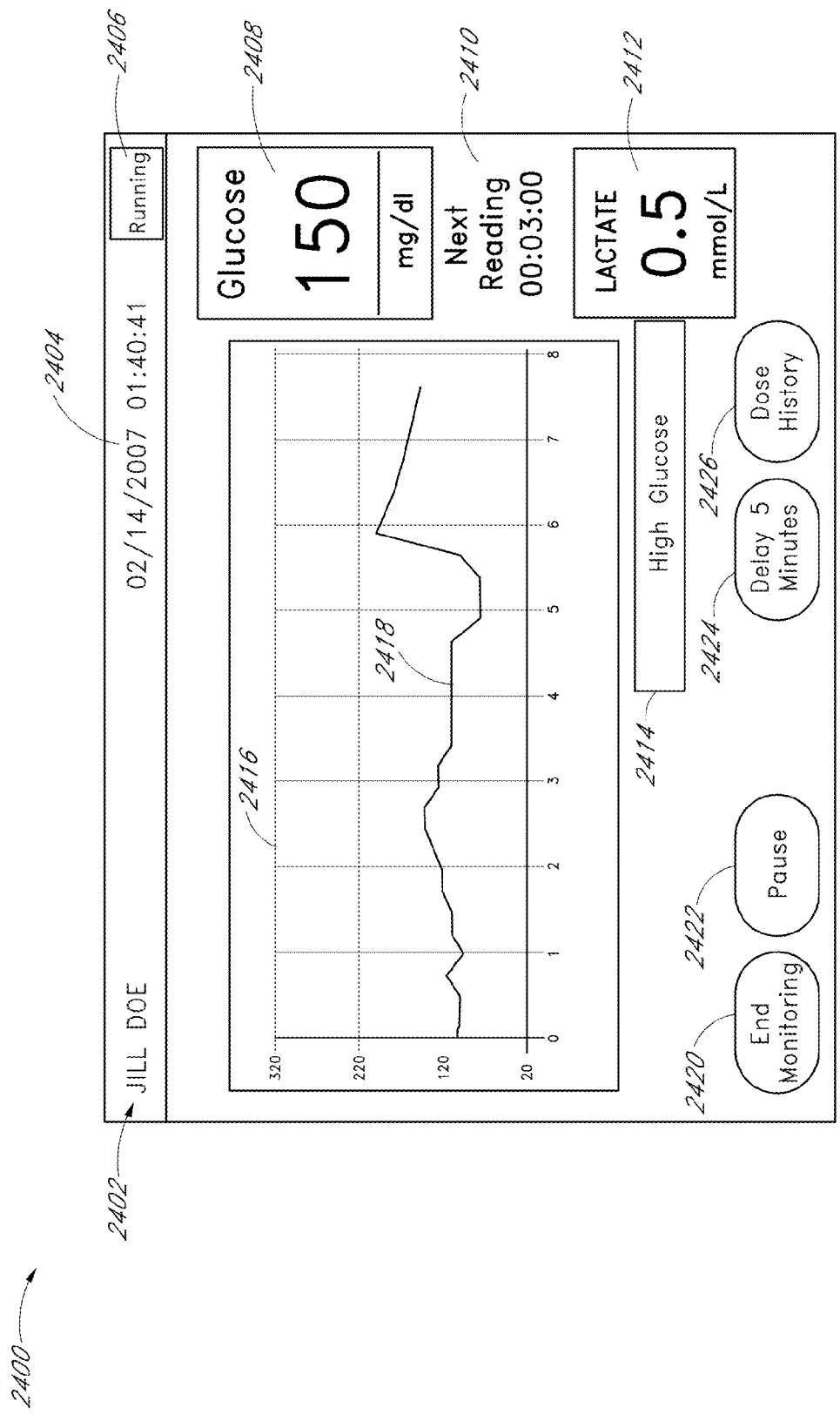
FIGS. 24 and 25 schematically illustrate the visual appearance of embodiments of a user interface for a system for withdrawing and analyzing fluid samples.
Figure 25:
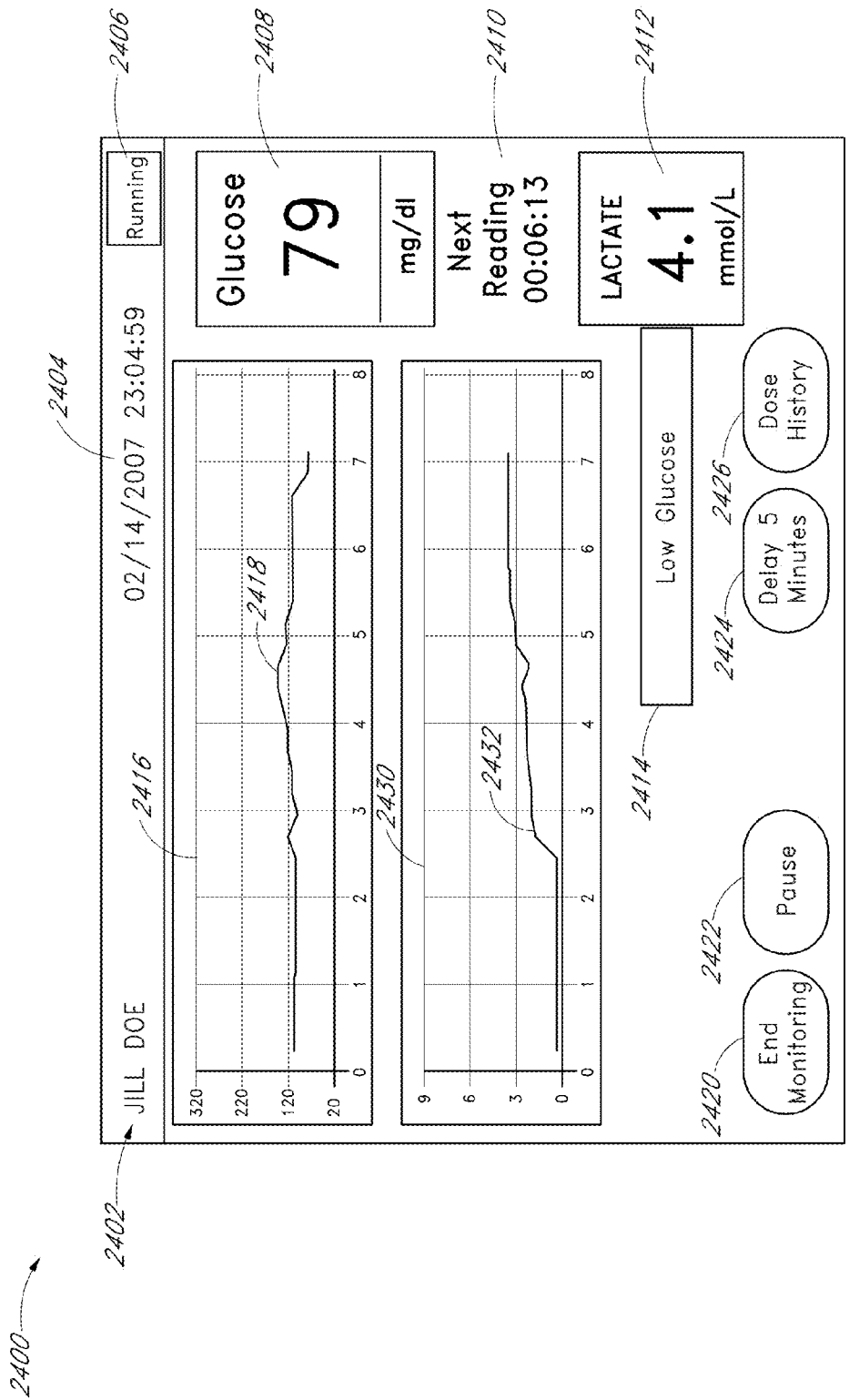

The system 400 shown in FIG. 4 includes a display system 414 that provides for communication of information to a user of the system 400. In some embodiments, the display 414 can be replaced by or supplemented with other communication devices that communicate in non-visual ways. The display system 414 can include a display processor that controls or produces an interface to communicate information to the user. The display system 414 can include a display screen. One or more parameters such as, for example, blood glucose concentration, system 400 operating parameters, and/or other operating parameters can be displayed on a monitor (not shown) associated with the system 400. An example of one way such information can be displayed is shown in FIGS. 24 and 25. In some embodiments, the display system 414 can communicate measured physiological parameters and/or operating parameters to a computer system over a communications connection.

The system 400 shown in FIG. 4 includes an algorithm processor 416 that can receive spectral information, such as optical density (OD) values (or other analog or digital optical data) from the optical system 412 and or the optical system controller 413. In some embodiments, the algorithm processor 416 calculates one or more physiological parameters and can analyze the spectral information. Thus, for example and without limitation, a model can be used that determines, based on the spectral information, physiological parameters of fluid from the fluid source 402. The algorithm processor 416, a controller that may be part of the display system 414, and any embedded controllers within the system 400 can be connected to one another with a communications bus.

Some embodiments of the systems described herein (e.g., the system 400), as well as some embodiments of each method described herein, can include a computer program accessible to and/or executable by a processing system, e.g., a one or more processors and memories that are part of an embedded system. Indeed, the controllers may comprise one or more computers and/or may use software. Thus, as will be appreciated by those skilled in the art, various embodiments may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various embodiments may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Fluid Handling System

Figure 5:
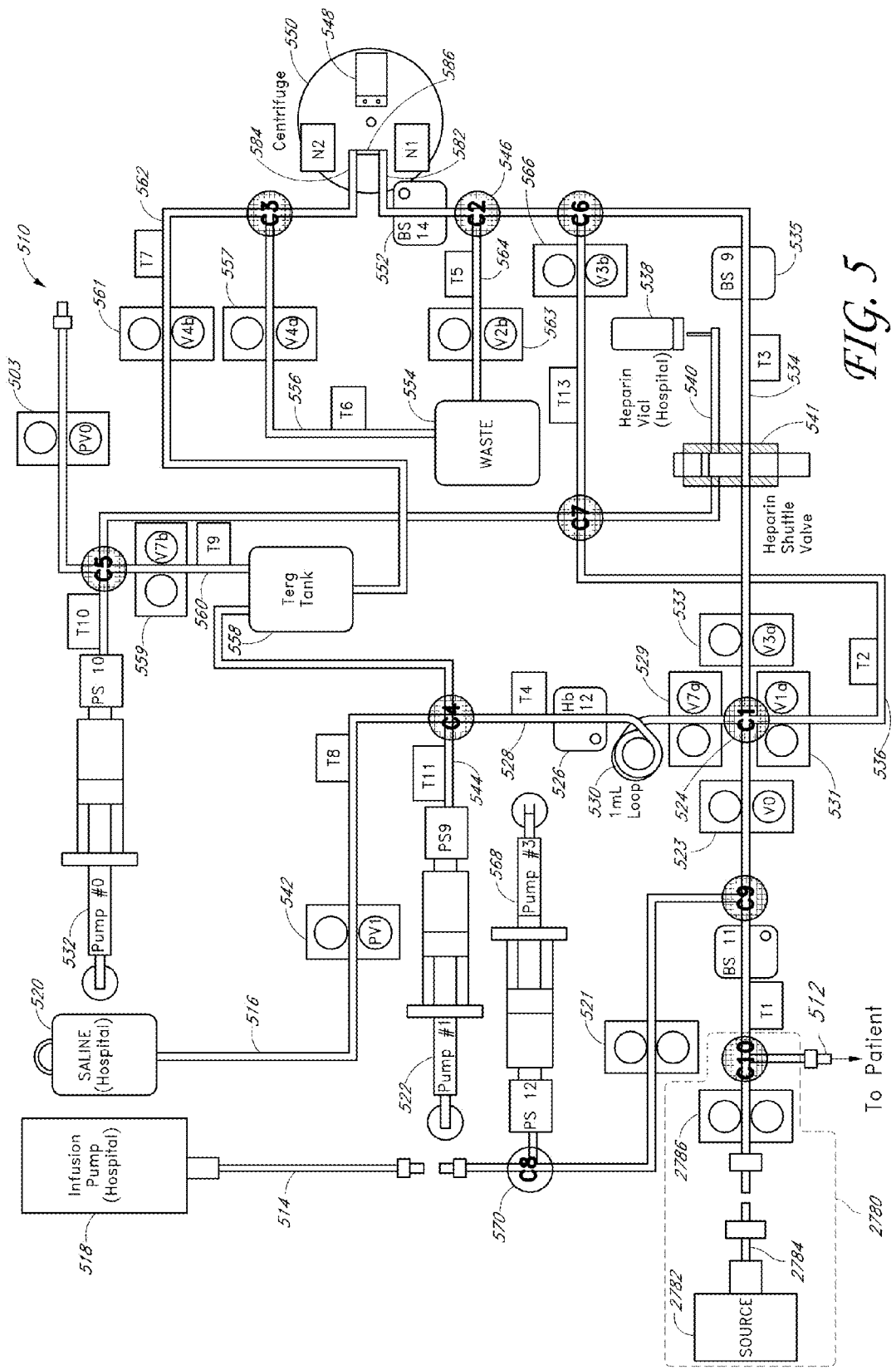
FIG. 5 schematically illustrates an embodiment of a fluid system that can be part of a system for withdrawing and analyzing fluid samples.

The generalized fluid-handling system 404 can have various configurations. In this context, FIG. 5 schematically illustrates the layout of an example embodiment of a fluid system 510. In this schematic representation, various components are depicted that may be part of a non-disposable subsystem 406, a first disposable subsystem 408, a second disposable subsystem 410, and/or an optical system 412. The fluid system 510 is described practically to show an example cycle as fluid is drawn and analyzed.

In addition to the reference numerals used below, the various portions of the illustrated fluid system 510 are labeled for convenience with letters to suggest their roles as follows: T# indicates a section of tubing. C# indicates a connector that joins multiple tubing sections. V# indicates a valve. BS# indicates a bubble sensor or ultrasonic air detector. N# indicates a needle (e.g., a needle that injects sample into a sample holder). PS# indicates a pressure sensor (e.g., a reusable pressure sensor). Pump# indicates a fluid pump (e.g., a syringe pump with a disposable body and reusable drive).

"Hb 12" indicates a sensor for hemoglobin (e.g., a dilution sensor that can detect hemoglobin optically).

The term "valve" as used herein is a broad term and is used, in accordance with its ordinary meaning, to refer to any flow regulating device. For example, the term "valve" can include, without limitation, any device or system that can controllably allow, prevent, or inhibit the flow of fluid through a fluid passageway. The term "valve" can include some or all of the following, alone or in combination: pinch valves, rotary valves, stop cocks, pressure valves, shuttle valves, mechanical valves, electrical valves, electro-mechanical flow regulators, etc. In some embodiments, a valve can regulate flow using gravitational methods or by applying electrical voltages or by both.

The term "pump" as used herein is a broad term and is used, in accordance with its ordinary meaning, to refer to any device that can urge fluid flow. For example, the term "pump" can include any combination of the following: syringe pumps, peristaltic pumps, vacuum pumps, electrical pumps, mechanical pumps, hydraulic pumps, etc. Pumps and/or pump components that are suitable for use with some embodiments can be obtained, for example, from or through Hospira.

The function of the valves, pumps, actuators, drivers, motors (e.g., the centrifuge motor), etc. described below is controlled by one or more controllers (e.g., the fluid system controller 405, the optical system controller 413, etc.) The controllers can include software, computer memory, electrical and mechanical connections to the controlled components, etc.

At the start of a measurement cycle, most lines, including a patient tube 512 (T1), an Arrival sensor tube 528 (T4), an anticoagulant valve tube 534 (T3), and a sample cell 548 can be filled with saline that can be introduced into the system through the infusion tube 514 and the saline tube 516, and which can come from an infusion pump 518 and/or a saline bag 520. The infusion pump 518 and the saline bag 520 can be provided separately from the system 510. For example, a hospital can use existing saline bags and infusion pumps to interface with the described system. The infusion valve 521 can be open to allow saline to flow into the tube 512 (T1).

Before drawing a sample, the saline in part of the system 510 can be replaced with air. Thus, for example, the following valves can be closed: air valve 503 (PV0), the detergent tank valve 559 (V7b), 566 (V3b), 523 (V0), 529 (V7a), and 563 (V2b). At the same time, the following valves can be open: valves 531 (Via), 533 (V3a) and 577 (V4a). Simultaneously, a second pump 532 (pump #0) pumps air through the system 510 (including tube 534 (T3), sample cell 548, and tube 556 (T6)), pushing saline through tube 534 (T3) and sample cell 548 into a waste bladder 554.

Next, a sample can be drawn. With the valves 542 (PV1), 559 (V7b), and 561 (V4b) closed, a first pump 522 (pump #1) is actuated to draw sample fluid to be analyzed (e.g. blood) from a fluid source (e.g., a laboratory sample container, a living patient, etc.) up into the patient tube 512 (T1), through the tube past the two flanking portions of the open pinch-valve 523 (V0), through the first connector 524 (C1), into the looped tube 530, past the arrival sensor 526 (Hb12), and into the arrival sensor tube 528 (T4). The arrival sensor 526 may be used to detect the presence of blood in the tube 528 (T4). For example, in some embodiments, the arrival sensor 526 may comprise a hemoglobin sensor. In some other embodiments, the arrival sensor 526 may comprise a color sensor that detects the color of fluid flowing through the tube 528 (T4). During this process, the valve 529 (V7a) and 523 (V0) are open to fluid flow, and the valves 531 (Via), 533 (V3a), 542 (PV1), 559 (V7b), and 561 (V4b) can be closed and therefore block (or substantially block) fluid flow by pinching the tube.

Before drawing the sample, the tubes 512 (T1) and 528 (T4) are filled with saline and the hemoglobin (Hb) level is zero. The tubes that are filled with saline are in fluid communication with the sample source (e.g., the fluid source 402). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually nondiluted sample fluid. In the example illustrated here, the sample fluid is blood.

The arrival sensor 526 (Hb12) can detect and/or verify the presence of blood in the tubes. For example, in some embodiments, the arrival sensor 526 can determine the color of the fluid in the tubes. In some embodiments, the arrival sensor 526 (Hb12) can detect the level of Hemoglobin in the sample fluid. As blood starts to arrive at the arrival sensor 526 (Hb12), the sensed hemoglobin level rises. A hemoglobin level can be selected, and the system can be pre-set to determine when that level is reached. A controller such as the fluid system controller 405 of FIG. 4 can be used to set and react to the pre-set value, for example. In some embodiments, when the sensed hemoglobin level reaches the pre-set value, substantially undiluted sample is present at the first connector 524 (C1). The preset value can depend, in part, on the length and diameter of any tubes and/or passages traversed by the sample. In some embodiments, the pre-set value can be reached after approximately 2 mL of fluid (e.g., blood) has been drawn from a fluid source. A nondiluted sample can be, for example, a blood sample that is not diluted with saline solution, but instead has the characteristics of the rest of the blood flowing through a patient's body. A loop of tubing 530 (e.g., a 1-mL loop) can be advantageously positioned as illustrated to help insure that undiluted fluid (e.g., undiluted blood) is present at the first connector 524 (C1) when the arrival sensor 526 registers that the preset Hb threshold is crossed. The loop of tubing 530 provides additional length to the Arrival sensor tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1).

In some embodiments, when nondiluted blood is present at the first connector 524 (C1), a sample is mixed with an anticoagulant and is directed toward the sample cell 548. An amount of anticoagulant (e.g., heparin) can be introduced into the tube 534 (T3), and then the undiluted blood is mixed with the anticoagulant. A heparin vial 538 (e.g., an insertable vial provided independently by the user of the system 510) can be connected to a tube 540. An anticoagulant valve 541 (which can be a shuttle valve, for example) can be configured to connect to both the tube 540 and the anticoagulant valve tube 534 (T3). The valve can open the tube 540 to a suction force (e.g., created by the pump 532), allowing heparin to be drawn from the vial 538 into the valve 541. Then, the anticoagulant valve 541 can slide the heparin over into fluid communication with the anticoagulant valve tube 534 (T3). The anticoagulant valve 541 can then return to its previous position. Thus, heparin can be shuttled from the tube 540 into the anticoagulant valve tube 534 (T3) to provide a controlled amount of heparin into the tube 534 (T3).

With the valves 542 (PV1), 559 (V7b), 561 (V4b), 523 (V0), 531 (V1a), 566 (V3b), and 563 (V2b) closed, and the valves 529 (V7a) and 553 (V3a) open, first pump 522 (pump #1) pushes the sample from tube 528 (T4) into tube 534 (T3), where the sample mixes with the heparin injected by the anticoagulant valve 541 as it flows through the system 510. As the sample proceeds through the tube 534 (T3), the air that was previously introduced into the tube 534 (T3) is displaced. The sample continues to flow until a bubble sensor 535 (BS9) indicates a change from air to a liquid, and thus the arrival of a sample at the bubble sensor. In some embodiments, the volume of tube 534 (T3) from connector 524 (C1) to bubble sensor 535 (BS9) is a known and/or engineered amount, and may be approximately 500 µL, 200 µL or 100 µL, for example.

When bubble sensor 535 (BS9) indicates the presence of a sample, the remainder of the sampled blood can be returned to its source (e.g., the patient veins or arteries). The first pump 522 (pump #1) pushes the blood out of the Arrival sensor tube 528 (T4) and back to the patient by opening the valve 523 (V0), closing the valves 531 (V1a) and 533 (V3a), and keeping the valve 529 (V7a) open. The Arrival sensor tube 528 (T4) is preferably flushed with approximately 2 mL of saline. This can be accomplished by closing the valve 529 (V7a), opening the valve 542 (PV1), drawing saline from the saline source 520 into the tube 544, closing the valve 542 (PV1), opening the valve 529 (V7a), and forcing the saline down the Arrival sensor tube 528 (T4) with the pump 522. In some embodiments, less than two minutes elapse between the time that blood is drawn from the patient and the time that the blood is returned to the patient.

Following return of the unused patient blood sample, the sample is pushed up the anticoagulant valve tube 534 (T3), through the second connector 546 (C2), and into the sample cell 548, which can be located on the centrifuge rotor 550. This fluid movement is facilitated by the coordinated action (either pushing or drawing fluid) of the pump 522 (pump #1), the pump 532 (pump #0), and the various illustrated valves. In particular, valve 531 (V1a) can be opened, and valves 503 (PV0) and 559 (V7b) can be closed. Pump movement and valve position corresponding to each stage of fluid movement can be coordinated by one ore multiple controllers, such as the fluid system controller 405 of FIG. 4.

After the unused sample is returned to the patient, the sample can be divided into separate slugs before being delivered into the sample cell 548. Thus, for example, valve 553 (V3a) is opened, valves 566 (V3b), 523 (V0) and 529 (V7a) are closed, and the pump 532 (pump #0) uses air to push the sample toward sample cell 548. In some embodiments, the sample (for example, 200 µL or 100 µL) is divided into multiple (e.g., more than two, five, or four) "slugs" of sample, each separated by a small amount of air. As used herein, the term "slug" refers to a continuous column of fluid that can be relatively short. Slugs can be separated from one another by small amounts of air (or bubbles) that can be present at intervals in the tube. In some embodiments, the slugs are formed by injecting or drawing air into fluid in the first connector 546 (C2).

In some embodiments, when the leading edge of the sample reaches blood sensor 553 (BS14), a small amount of air (the first "bubble") is injected at a connector C6. This bubble helps define the first "slug" of liquid, which extends from the bubble sensor to the first bubble. In some embodiments, the valves 533 (V3a) and 556 (V3b) are alternately opened and closed to form a bubble at connector C6, and the sample is pushed toward the sample cell 548. Thus, for example, with pump 532 actuated, valve 566 V(3b) is briefly opened and valve 533 (V3a) is briefly closed to inject a first air bubble into the sample.

In some embodiments, the volume of the tube 534 (T3) from the connector 546 (C2) to the bubble sensor 552 (BS14) is less than the volume of tube 534 (T3) from the connector 524 (C1) to the bubble sensor 535 (BS9). Thus, for example and without limitation, the volume of the tube 534 (T3) from the connector 524 (C1) to the bubble sensor 535 (BS9) can be in the range of approximately 80 µL to approximately 120 µL, (e.g., 100 µL) and the volume of the tube 534 (T3) from the connector 546 (C2) to the bubble sensor 552 (BS14) can be in the range of approximately 5 µL to approximately 25 µL (e.g., 15 µL). In some embodiments, multiple blood slugs are created. For example, more than two blood slugs can be created, each having a different volume. In some embodiments, five blood slugs are created, each having approximately the same volume of approximately 20 µL each. In some embodiments, three blood slugs are created, the first two having a volume of 10 µL and the last having a volume of 20 µL. In some embodiments, four blood slugs are created; the first three blood slugs can have a volume of approximately 154, and the fourth can have a volume of approximately 35 µL.

A second slug can be prepared by opening the valve 553 (V3a), closing the valve 566 (V3b), with pump 532 (pump #0) operating to push the first slug through a first sample cell holder interface tube 582 (N1), through the sample cell 548, through a second sample cell holder interface tube 584 (N2), and toward the waste bladder 554. When the first bubble reaches the bubble sensor 552 (BS 14), the open/closed configurations of valves 553 (V3a) and 566 (V3b) are reversed, and a second bubble is injected into the sample, as before. A third slug can be prepared in the same manner as the second (pushing the second bubble to bubble sensor 552 (BS 14) and injecting a third bubble). After the injection of the third air bubble, the sample can be pushed through system 510 until the end of the sample is detected by bubble sensor 552 (BS 14). The system can be designed such that when the end of the sample reaches this point, the last portion of the sample (a fourth slug) is within the sample cell 548, and the pump 532 can stop forcing the fluid column through the anticoagulant valve tube 534 (T3) so that the fourth slug remains within the sample cell 548. Thus, the first three blood slugs can serve to flush any residual saline out the sample cell 548. The three leading slugs can be deposited in the waste bladder 554 by passing through the tube 556 (T6) and past the tube-flanking portions of the open pinch valve 557 (V4a).

In some embodiments, the fourth blood slug is centrifuged for a given length of time (e.g., more than 1 minute, five minutes, or 2 minutes, to take three advantageous examples) at a relatively fast speed (e.g., 7200 RPM, 5000 RPM, or 4500 RPM, to take three examples). Thus, for example, the sample cell holder interface tubes 582 (N1) and 584 (N2) disconnect the sample cell 548 from the tubes 534 (T3) and 562 (T7), permitting the centrifuge rotor 550 and the sample cell 548 to spin together. Spinning separates a sample (e.g., blood) into its components, isolates the plasma, and positions the plasma in the sample cell 548 for measurement. The centrifuge 550 can be stopped with the sample cell 548 in a beam of radiation (not shown) for analysis. The radiation, a detector, and logic can be used to analyze a portion of the sample (e.g., the plasma) spectroscopically (e.g., for glucose, lactate, or other analyte concentration). In some embodiments, some or all of the separated components (e.g., the isolated plasma) may be transported to a different analysis chamber. For example, another analysis chamber can have one or more electrodes in electrical communication with the chamber's contents, and the separated components may be analyzed electrically. At any suitable point, one or more of the separated components can be transported to the waste bladder 554 when no longer needed. In some chemical analysis systems and apparatus, the separated components are analyzed electrically. Analysis devices may be connected serially, for example, so that the analyzed substance from an optical analysis system (e.g., an "OptiScanner®" fluid analyzer) can be transferred to an independent analysis device (e.g., a chemical analysis device) for subsequent analysis. In certain embodiments, the analysis devices are integrated into a single system. Many variations are possible.

In some embodiments, portions of the system 510 that contain blood after the sample cell 548 has been provided with a sample are cleaned to prevent blood from clotting. Accordingly, the centrifuge rotor 550 can include two passageways for fluid that may be connected to the sample cell holder interface tubes 582 (N1) and 584 (N2). One passageway is sample cell 548, and a second passageway is a shunt 586. An embodiment of the shunt 586 is illustrated in more detail in FIG. 16 (see reference numeral 1586).

The shunt 586 can allow cleaner (e.g., a detergent such as tergazyme A) to flow through and clean the sample cell holder interface tubes without flowing through the sample cell 548. After the sample cell 548 is provided with a sample, the interface tubes 582 (N1) and 584 (N2) are disconnected from the sample cell 548, the centrifuge rotor 550 is rotated to align the shunt 586 with the interface tubes 582 (N1) and 584 (N2), and the interface tubes are connected with the shunt. With the shunt in place, the detergent tank 559 is pressurized by the second pump 532 (pump #0) with valves 561 (V4b) and 563 (V2b) open and valves 557 (V4a) and 533 (V3a) closed to flush the cleaning solution back through the interface tubes 582 (N1) and 584 (N2) and into the waste bladder 554. Subsequently, saline can be drawn from the saline bag 520 for a saline flush. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

Following analysis, the second pump 532 (pump #0) flushes the sample cell 548 and sends the flushed contents to the waste bladder 554. This flush can be done with a cleaning solution from the detergent tank 558. In some embodiments, the detergent tank valve 559 (V7b) is open, providing fluid communication between the second pump 532 and the detergent tank 558. The second pump 532 forces cleaning solution from the detergent tank 558 between the tube-flanking portions of the open pinch valve 561 and through the tube 562 (T7). The cleaning flush can pass through the sample cell 548, through the second connector 546, through the tube 564 (T5) and the open valve 563 (V2b), and into the waste bladder 554.

Subsequently, the first pump 522 (pump #1) can flush the cleaning solution out of the sample cell 548 using saline in drawn from the saline bag 520. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

When the fluid source is a living entity such as a patient, a low flow of saline (e.g., 1-5 mL/hr) is preferably moved through the patient tube 512 (T1) and into the patient to keep the patient's vessel open (e.g., to establish a keep vessel open, or "KVO" flow). This KVO flow can be temporarily interrupted when fluid is drawn into the fluid system 510. The source of this KVO flow can be the infusion pump 518, the third pump 568 (pump #3), or the first pump 522 (pump #1). In some embodiments, the infusion pump 518 can run continuously throughout the measurement cycle described above. This continuous flow can advantageously avoid any alarms that may be triggered if the infusion pump 518 senses that the flow has stopped or changed in some other way. In some embodiments, when the infusion valve 521 closes to allow pump 522 (pump #1) to withdraw fluid from a fluid source (e.g., a patient), the third pump 568 (pump #3) can withdraw fluid through the connector 570, thus allowing the infusion pump 518 to continue pumping normally as if the fluid path was not blocked by the infusion valve 521. If the measurement cycle is about two minutes long, this withdrawal by the third pump 568 can continue for approximately two minutes. Once the infusion valve 521 is open again, the third pump 568 (pump #3) can reverse and insert the saline back into the system at a low flow rate. Preferably, the time between measurement cycles is longer than the measurement cycle itself (for example, the time interval can be longer than ten minutes, shorter than ten minutes, shorter than five minutes, longer than two minutes, longer than one minute, etc.). Accordingly, the third pump 568 can insert fluid back into the system at a lower rate than it withdrew that fluid. This can help prevent an alarm by the infusion pump.

Figure 6:
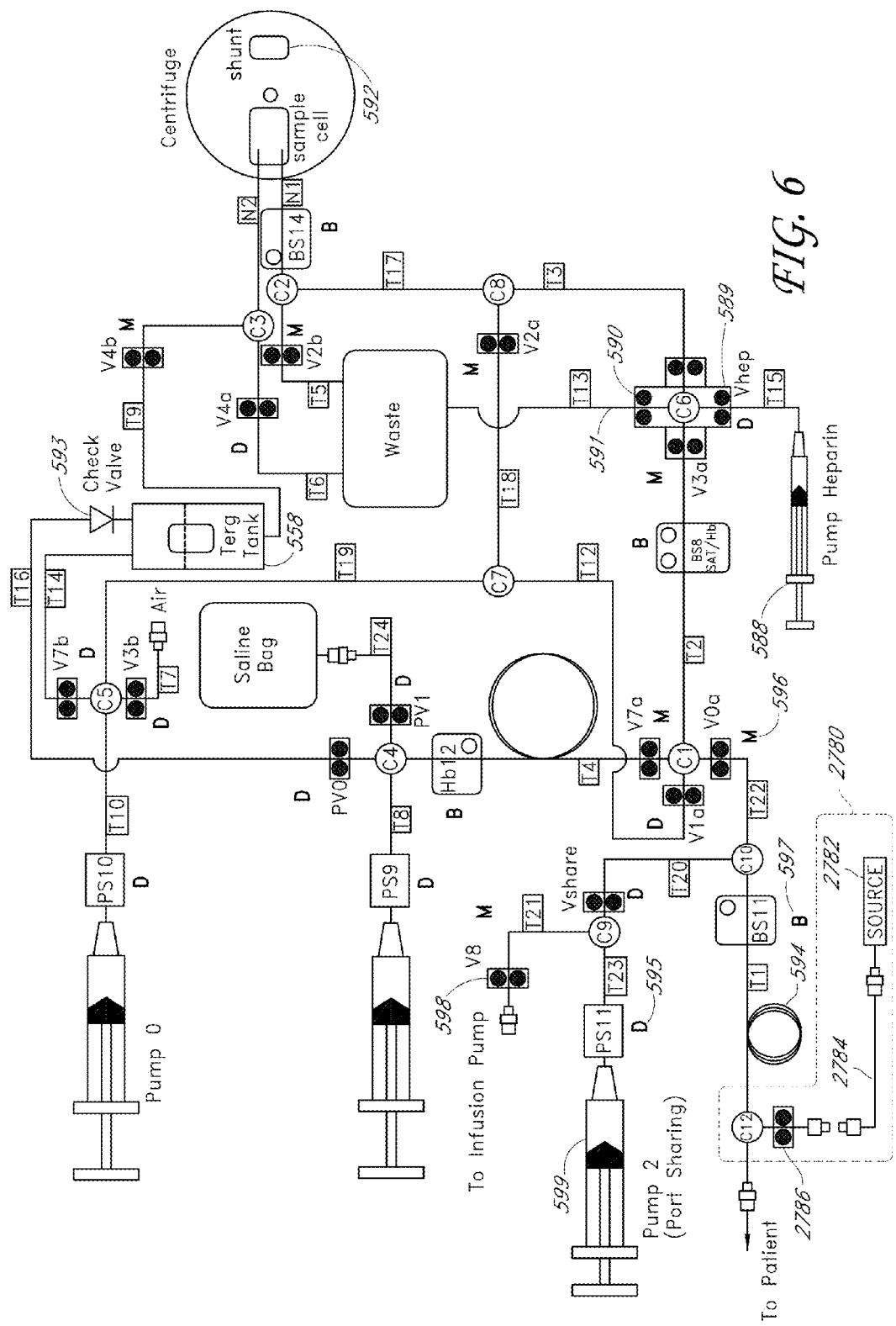
FIG. 6 schematically illustrates another embodiment of a fluid system that can be part of a system for withdrawing and analyzing fluid samples.

FIG. 6 schematically illustrates another embodiment of a fluid system that can be part of a system for withdrawing and analyzing fluid samples. In this embodiment, the anticoagulant valve 541 has been replaced with a syringe-style pump 588 (Pump Heparin) and a series of pinch valves around a junction between tubes. For example, a heparin pinch valve 589 (Vhep) can be closed to prevent flow from or to the pump 588, and a heparin waste pinch valve 590 can be closed to prevent flow from or to the waste container from this junction through the heparin waste tube 591. This embodiment also illustrates the shunt 592 schematically. Other differences from FIG. 5 include the check valve 593 located near the detergent tank 558 and the patient loop 594. The reference letters D, for example, the one indicated at 595, refer to components that are advantageously located on the door. The reference letters M, for example, the one indicated at 596, refer to components that are advantageously located on the monitor. The reference letters B, for example, the one indicated at 597, refer to components that can be advantageously located on both the door and the monitor.

In some embodiments, the system 400 (see FIG. 4), the apparatus 100 (see FIG. 1), or even the monitoring device 102 (see FIG. 1) itself can also actively function not only to monitor analyte levels (e.g., glucose), but also to change and/or control analyte levels. Thus, the monitoring device 102 can be both a monitoring and an infusing device. In some embodiments, the fluid handling system 510 can include an optional analyte control subsystem 2780 that will be further described below (see discussion of analyte control).

In certain embodiments, analyte levels in a patient can be adjusted directly (e.g., by infusing or extracting glucose) or indirectly (e.g., by infusing or extracting insulin). FIG. 6 illustrates one way of providing this function. The infusion pinch valve 598 (V8) can allow the port sharing pump 599 (compare to the third pump 568 (pump #3) in FIG. 5) to serve two roles. In the first role, it can serve as a "port sharing" pump. The port sharing function is described with respect to the third pump 568 (pump #3) of FIG. 5, where the third pump 568 (pump #3) can withdraw fluid through the connector 570, thus allowing the infusion pump 518 to continue pumping normally as if the fluid path was not blocked by the infusion valve 521. In the second role, the port sharing pump 599 can serve as an infusion pump. The infusion pump role allows the port sharing pump 599 to draw a substance (e.g., glucose, saline, etc.) from another source when the infusion pinch valve 598 is open, and then to infuse that substance into the system or the patient when the infusion pinch valve 598 is closed. This can occur, for example, in order to change the level of a substance in a patient in response to a reading by the monitor that the substance is too low. In some embodiments, one or more of the pumps may comprise a reversible infusion pump configured to interrupt the flow of the infusion fluid and draw a sample of blood for analysis.

Mechanical/Fluid System Interface

Figure 7:
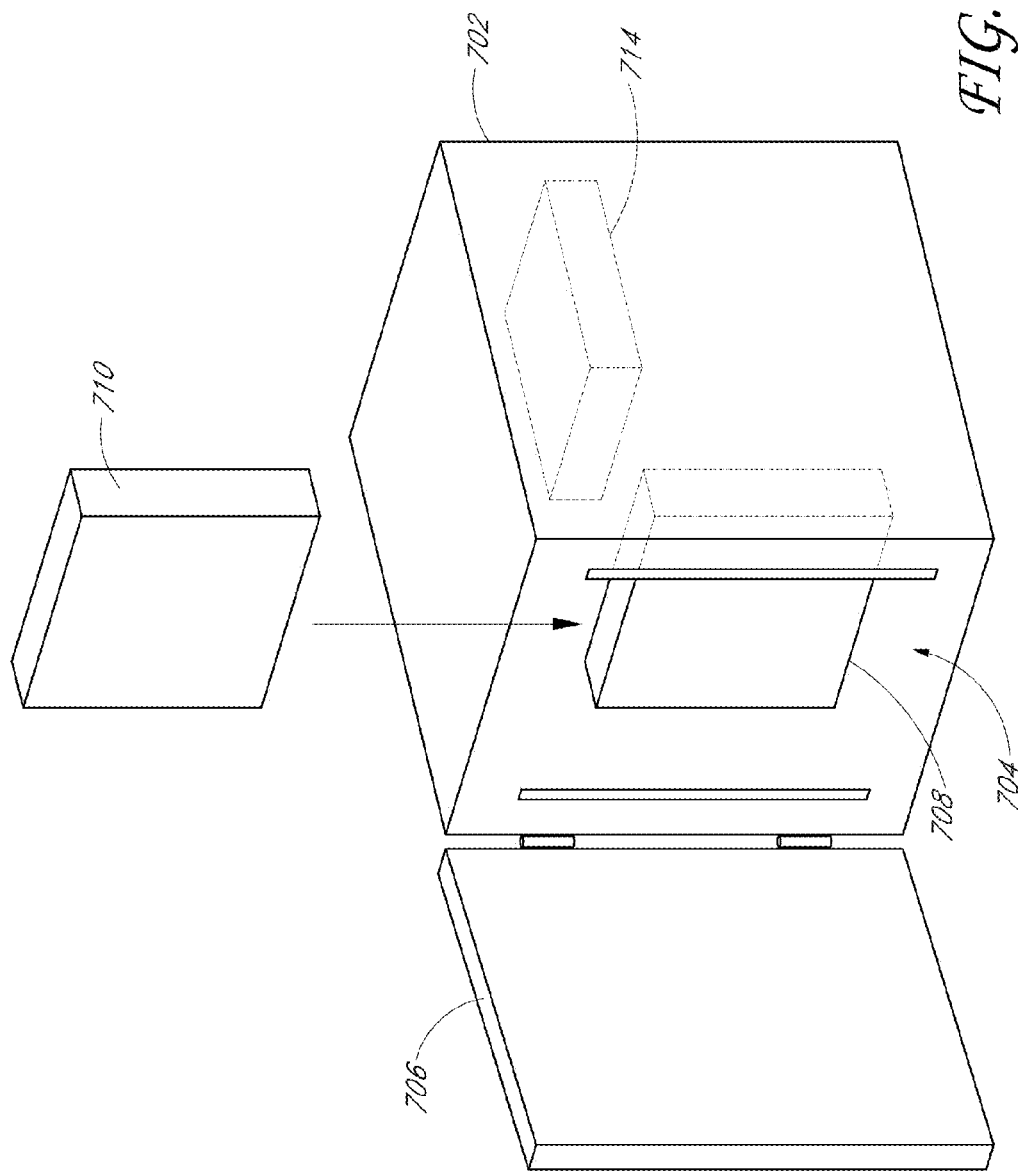
FIG. 7 is an oblique schematic depiction of an embodiment of a monitoring device.

FIG. 7 is an oblique schematic depiction of a modular monitoring device 700, which can correspond to the monitoring device 102. The modular monitoring device 700 includes a body portion 702 having a receptacle 704, which can be accessed by moving a movable portion 706. The receptacle 704 can include connectors (e.g., rails, slots, protrusions, resting surfaces, etc.) with which a removable portion 710 can interface. In some embodiments, portions of a fluidic system that directly contact fluid are incorporated into one or more removable portions (e.g., one or more disposable cassettes, sample holders, tubing cards, etc.). For example, a removable portion 710 can house at least a portion of the fluid system 510 described previously, including portions that contact sample fluids, saline, detergent solution, and/or anticoagulant.

In some embodiments, a non-disposable fluid-handling subsystem 708 is disposed within the body portion 702 of the monitoring device 700. The first removable portion 710 can include one or more openings that allow portions of the non-disposable fluid-handling subsystem 708 to interface with the removable portion 710. For example, the non-disposable fluid-handling subsystem 708 can include one or more pinch valves that are designed to extend through such openings to engage one or more sections of tubing. When the first removable portion 710 is present in a corresponding first receptacle 704, actuation of the pinch valves can selectively close sections of tubing within the removable portion. The non-disposable fluid-handling subsystem 708 can also include one or more sensors that interface with connectors, tubing sections, or pumps located within the first removable portion 710. The non-disposable fluid-handling subsystem 708 can also include one or more actuators (e.g., motors) that can actuate moveable portions (e.g., the plunger of a syringe) that may be located in the removable portion F10. A portion of the non-disposable fluid-handling subsystem 708 can be located on or in the moveable portion F06 (which can be a door having a slide or a hinge, a detachable face portion, etc.).

In the embodiment shown in FIG. 7, the monitoring device 700 includes an optical system 714 disposed within the body portion 702. The optical system 714 can include a light source and a detector that are adapted to perform measurements on fluids within a sample holder (not shown). The light source may comprise a fixed wavelength light source and/or a tunable light source. The light source may comprise one or more sources including, for example, broadband sources, LEDs, and lasers. In some embodiments, the sample holder comprises a removable portion, which can be associated with or disassociated from the removable portion F10. The sample holder can include an optical window through which the optical system 714 can emit radiation for measuring properties of a fluid in the sample holder. The optical system 714 can include other components such as, for example, a power supply, a centrifuge motor, a filter wheel, and/or a beam splitter.

In some embodiments, the removable portion 710 and the sample holder are adapted to be in fluid communication with each other. For example, the removable portion 710 can include a retractable injector that injects fluids into a sample holder. In some embodiments, the sample holder can comprise or be disposed in a second removable portion (not shown). In some embodiments, the injector can be retracted to allow the centrifuge to rotate the sample holder freely.

The body portion 702 of the monitoring device 700 can also include one or more connectors for an external battery (not shown). The external battery can serve as a backup emergency power source in the event that a primary emergency power source such as, for example, an internal battery (not shown) is exhausted.

FIG. 7 shows an embodiment of a system having subcomponents illustrated schematically. By way of a more detailed (but nevertheless non-limiting) example, FIG. 8 and FIG. 9 show more details of the shape and physical configuration of a sample embodiment.

Figure 8:
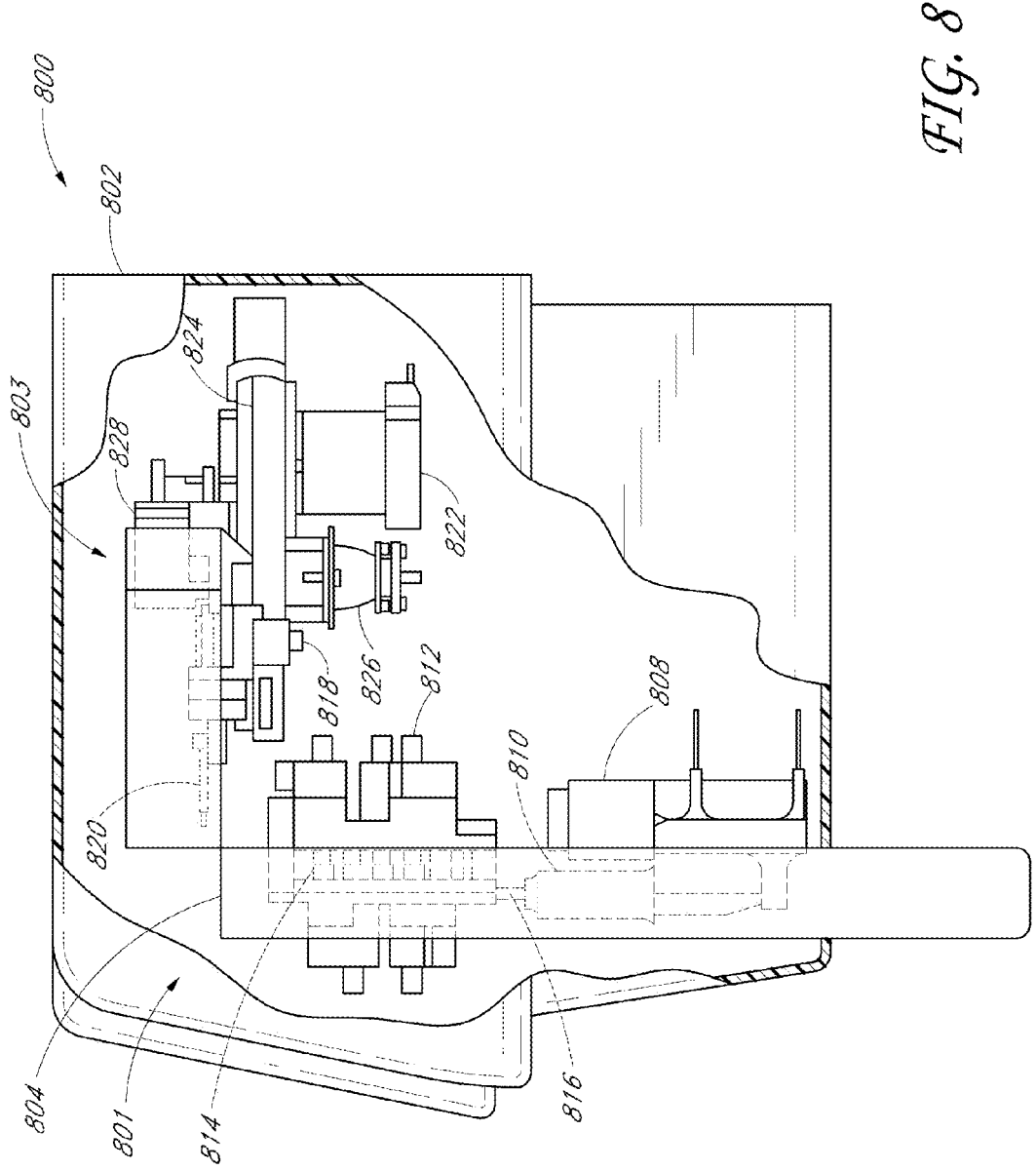
FIG. 8 shows a cut-away side view of an embodiment of a monitoring device.
Figure 9:
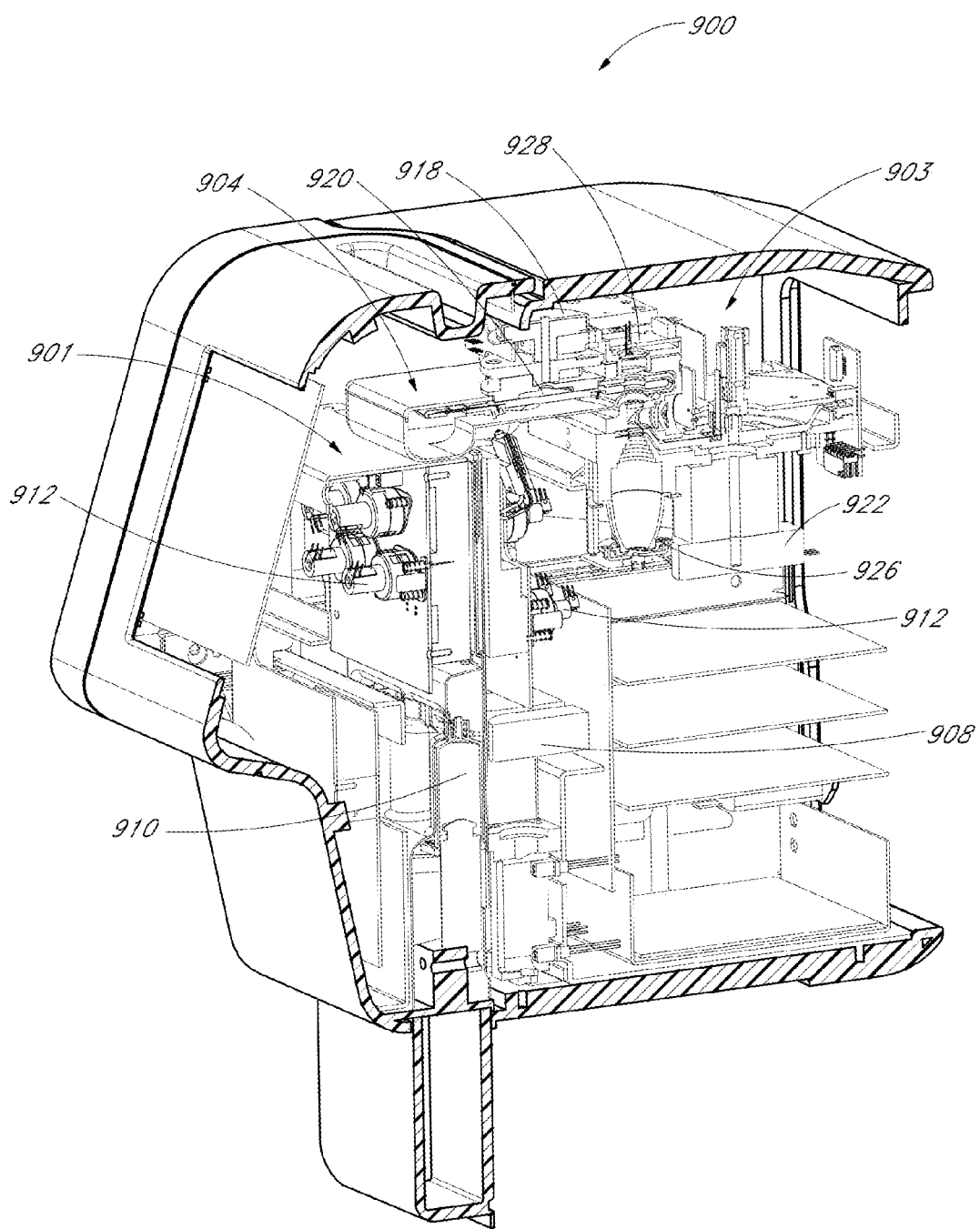
FIG. 9 shows a cut-away perspective view of an embodiment of a monitoring device.

FIG. 8 shows a cut-away side view of a monitoring device 800 (which can correspond, for example, to the device 102 shown in FIG. 1). The device 800 includes a casing 802. The monitoring device 800 can have a fluid system. For example, the fluid system can have subsystems, and a portion or portions thereof can be disposable, as schematically depicted in FIG. 4. As depicted in FIG. 8, the fluid system is generally located at the left-hand portion of the casing 802, as indicated by the reference 801. The monitoring device 800 can also have an optical system. In the illustrated embodiment, the optical system is generally located in the upper portion of the casing 802, as indicated by the reference 803. Advantageously, however, the fluid system 801 and the optical system 803 can both be integrated together such that fluid flows generally through a portion of the optical system 803, and such that radiation flows generally through a portion of the fluid system 801.

Depicted in FIG. 8 are examples of ways in which components of the device 800 mounted within the casing 802 can interface with components of the device 800 that comprise disposable portions. Not all components of the device 800 are shown in FIG. 8. A disposable portion 804 having a variety of components is shown in the casing 802. In some embodiments, one or more actuators 808 housed within the casing 802, operate syringe bodies 810 located within a disposable portion 804. The syringe bodies 810 are connected to sections of tubing 816 that move fluid among various components of the system. The movement of fluid is at least partially controlled by the action of one or more pinch valves 812 positioned within the casing 802. The pinch valves 812 have arms 814 that extend within the disposable portion 804. Movement of the arms 814 can constrict a section of tubing 816.

In some embodiments, a sample cell holder 820 can engage a centrifuge motor 818 mounted within the casing 802 of the device 800. A filter wheel motor 822 disposed within the housing 802 rotates a filter wheel 824, and in some embodiments, aligns one or more filters with an optical path. An optical path can originate at a source 826 within the housing 802 that can be configured to emit a beam of radiation (e.g., infrared radiation, visible radiation, ultraviolet radiation, etc.) through the filter and the sample cell holder 820 and to a detector 828. A detector 828 can measure the optical density of the light when it reaches the detector.

FIG. 9 shows a cut-away perspective view of an alternative embodiment of a monitoring device 900. Many features similar to those illustrated in FIG. 8 are depicted in this illustration of an alternative embodiment. A fluid system 901 can be partially seen. The disposable portion 904 is shown in an operative position within the device. One of the actuators 808 can be seen next to a syringe body 910 that is located within the disposable portion 904. Some pinch valves 912 are shown next to a fluid-handling portion of the disposable portion 904. In this figure, an optical system 903 can also be partially seen. The sample holder 920 is located underneath the centrifuge motor 918. The filter wheel motor 922 is positioned near the radiation source 926, and the detector 928 is also illustrated.

FIG. 10 illustrates two views of a cartridge 1000 that can interface with a fluid system such as the fluid system 510 of FIG. 5. The cartridge 1000 can be configured for insertion into a receptacle of the device 800 of FIG. 8 and/or the device 900 shown in FIG. 9. In some embodiments, the cartridge 1000 can comprise a portion that is disposable and a portion that is reusable. In some embodiments, the cartridge 1000 can be disposable. The cartridge 1000 can fill the role of the removable portion 710 of FIG. 7, for example. In some embodiments, the cartridge 1000 can be used for a system having only one disposable subsystem, making it a simple matter for a health care provider to replace and/or track usage time of the disposable portion. In some embodiments, the cartridge 1000 includes one or more features that facilitate insertion of the cartridge 1000 into a corresponding receptacle. For example, the cartridge 1000 can be shaped so as to promote insertion of the cartridge 1000 in the correct orientation. The cartridge 1000 can also include labeling or coloring affixed to or integrated with the cartridge's exterior casing that help a handler insert the cartridge 1000 into a receptacle properly.

The cartridge 1000 can include one or more ports for connecting to material sources or receptacles. Such ports can be provided to connect to, for example, a saline source, an infusion pump, a sample source, and/or a source of gas (e.g., air, nitrogen, etc.). The ports can be connected to sections of tubing within the cartridge 1000. In some embodiments, the sections of tubing are opaque or covered so that fluids within the tubing cannot be seen, and in some embodiments, sections of tubing are transparent to allow interior contents (e.g., fluid) to be seen from outside.

Figure 15:
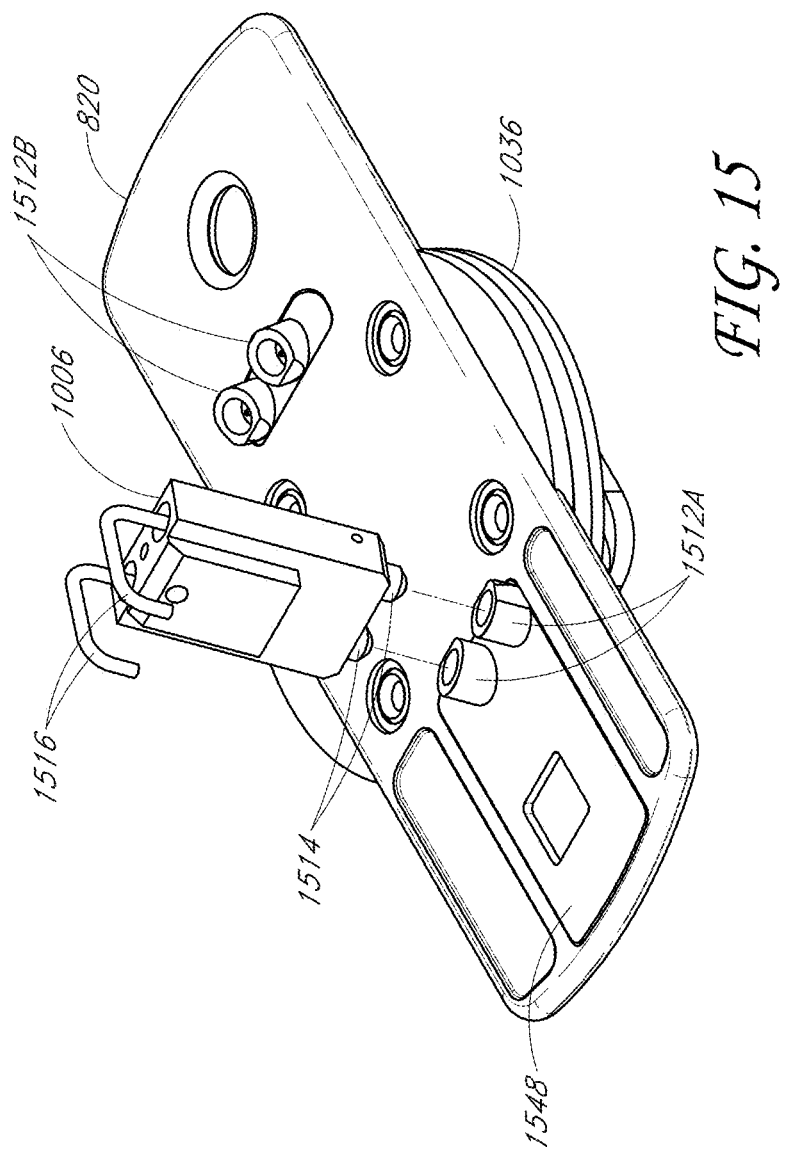
FIG. 15 shows an underneath perspective view of a sample cell holder attached to a centrifuge interface, with a view of an interface with a sample injector.

The cartridge 1000 shown in FIG. 10 can include a sample injector 1006. The sample injector 1006 can be configured to inject at least a portion of a sample into a sample holder (see, e.g., the sample cell 548), which can also be incorporated into the cartridge 1000. The sample injector 1006 can include, for example, the sample cell holder interface tubes 582 (N1) and 584 (N2) of FIG. 5, embodiments of which are also illustrated in FIG. 15.

The housing of the cartridge 1000 can include a tubing portion 1008 containing within it a card having one or more sections of tubing. In some embodiments, the body of the cartridge 1000 includes one or more apertures 1009 through which various components, such as, for example, pinch valves and sensors, can interface with the fluid-handling portion contained in the cartridge 1000. The sections of tubing found in the tubing portion 1008 can be aligned with the apertures 1009 in order to implement at least some of the functionality shown in the fluid system 510 of FIG. 5.

The cartridge 1000 can include a pouch space (not shown) that can comprise one or more components of the fluid system 510. For example, one or more pouches and/or bladders can be disposed in the pouch space (not shown). In some embodiments, a cleaner pouch and/or a waste bladder can be housed in a pouch space. The waste bladder can be placed under the cleaner pouch such that, as detergent is removed from the cleaner pouch, the waste bladder has more room to fill. The components placed in the pouch space (not shown) can also be placed side-by-side or in any other suitable configuration.

The cartridge 1000 can include one or more pumps 1016 that facilitate movement of fluid within the fluid system 510. Each of the pump housings 1016 can contain, for example, a syringe pump having a plunger. The plunger can be configured to interface with an actuator outside the cartridge 1000. For example, a portion of the pump that interfaces with an actuator can be exposed to the exterior of the cartridge 1000 housing by one or more apertures 1018 in the housing.

The cartridge 1000 can have an optical interface portion 1030 that is configured to interface with (or comprise a portion of) an optical system. In the illustrated embodiment, the optical interface portion 1030 can pivot around a pivot structure 1032. The optical interface portion 1030 can house a sample holder (not shown) in a chamber that can allow the sample holder to rotate. The sample holder can be held by a centrifuge interface 1036 that can be configured to engage a centrifuge motor (not shown). When the cartridge 1000 is being inserted into a system, the orientation of the optical interface portion 1030 can be different than when it is functioning within the system.

In some embodiments, the cartridge 1000 is designed for single patient use. The cartridge 1000 may also be disposable and/or designed for replacement after a period of operation. For example, in some embodiments, if the cartridge 1000 is installed in a continuously operating monitoring device that performs four measurements per hour, the waste bladder may become filled or the detergent in the cleaner pouch depleted after about three days. The cartridge 1000 can be replaced before the detergent and waste bladder are exhausted. In some embodiments, a portion of the cartridge 1000 can be disposable while another portion of the cartridge 1000 is disposable, but lasts longer before being discarded. In some embodiments, a portion of the cartridge 1000 may not be disposable at all. For example, a portion thereof may be configured to be cleaned thoroughly and reused for different patients. Various combinations of disposable and less- or non-disposable portions are possible.

The cartridge 1000 can be configured for easy replacement. For example, in some embodiments, the cartridge 1000 is designed to have an installation time of only minutes. For example, the cartridge can be designed to be installed in less than about five minutes, or less than two minutes. During installation, various fluid lines contained in the cartridge 1000 can be primed by automatically filling the fluid lines with saline. The saline can be mixed with detergent powder from the cleaner pouch in order to create a cleaning solution.

The cartridge 1000 can also be designed to have a relatively brief shut down time. For example, the shut down process can be configured to take less than about fifteen minutes, or less than about ten minutes, or less than about five minutes. The shut down process can include flushing the patient line; sealing off the insulin pump connection, the saline source connection, and the sample source connection; and taking other steps to decrease the risk that fluids within the used cartridge 1000 will leak after disconnection from the monitoring device.

Some embodiments of the cartridge 1000 can comprise a flat package to facilitate packaging, shipping, sterilizing, etc. Advantageously, however, some embodiments can further comprise a hinge or other pivot structure. Thus, as illustrated, an optical interface portion 1030 can be pivoted around a pivot structure 1032 to generally align with the other portions of the cartridge 1000. The cartridge can be provided to a medical provider sealed in a removable wrapper, for example.

In some embodiments, the cartridge 1000 is designed to fit within standard waste containers found in a hospital, such as a standard biohazard container. For example, the cartridge 1000 can be less than one foot long, less than one foot wide, and less than two inches thick. In some embodiments, the cartridge 1000 is designed to withstand a substantial impact, such as that caused by hitting the ground after a four foot drop, without damage to the housing or internal components. In some embodiments, the cartridge 1000 is designed to withstand significant clamping force applied to its casing. For example, the cartridge 1000 can be built to withstand five pounds per square inch of force without damage. In some embodiments, the cartridge 1000 can be designed to be less sturdy and more biodegradable. In some embodiments, the cartridge 1000 can be formed and configured to withstand more or less than five pounds of force per square inch without damage. In some embodiments, the cartridge 1000 is non pyrogenic and/or latex free.

Figure 11:
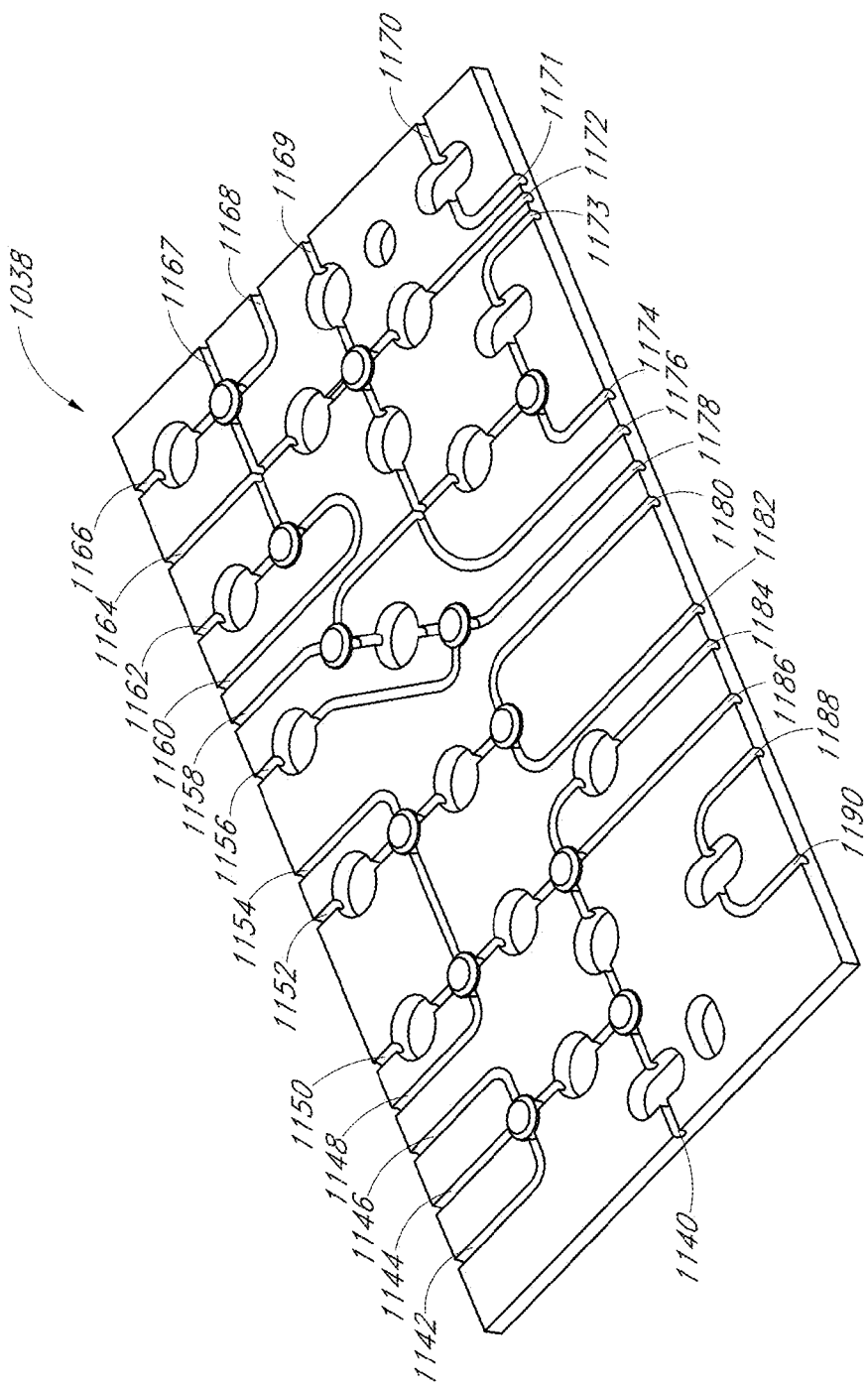
FIG. 11 illustrates an embodiment of a fluid routing card that can be part of the removable cartridge of FIG. 10.

FIG. 11 illustrates an embodiment of a fluid-routing card 1038 that can be part of the removable cartridge of FIG. 10. For example, the fluid-routing card 1038 can be located generally within the tubing portion 1008 of the cartridge 1000. The fluid-routing card 1038 can contain various passages and/or tubes through which fluid can flow as described with respect to FIG. 5 and/or FIG. 6, for example. Thus, the illustrated tube opening openings can be in fluid communication with the following fluidic components, for example:

| Tube Opening Reference Numeral | Can Be In Fluid Communication With |
| --- | --- |
| 1142 | third pump 568 (pump #3) |
| 1144 | infusion pump 518 |
| 1146 | Presx |
| 1148 | air pump |
| 1150 | Vent |
| 1152 | detergent (e.g., tergazyme) source or waste tube |
| 1154 | Presx |
| 1156 | detergent (e.g., tergazyme) source or waste tube |
| 1158 | waste receptacle |
| 1160 | first pump 522 (pump #1) (e.g., a saline pump) |
| 1162 | saline source or waste tube |
| 1164 | anticoagulant (e.g., heparin) pump (see FIG. 6) and/or shuttle valve |
| 1166 | detergent (e.g., tergazyme) source or waste tube |
| 1167 | Presx |
| 1168 | Arrival sensor tube 528 (T4) |
| 1169 | tube 536 (T2) |
| 1170 | Arrival sensor tube 528 (T4) |
| 1171 | Arrival sensor tube 528 (T4) |
| 1172 | anticoagulant (e.g., heparin) pump |
| 1173 | T17 (see FIG. 6) |
| 1174 | Sample cell holder interface tube 582 (N1) |
| 1176 | anticoagulant valve tube 534 (T3) |
| 1178 | Sample cell holder interface tube 584 (N2) |
| 1180 | T17 (see FIG. 6) |
| 1182 | anticoagulant valve tube 534 (T3) |
| 1184 | Arrival sensor tube 528 (T4) |
| 1186 | tube 536 (T2) |
| 1188 | anticoagulant valve tube 534 (T3) |
| 1190 | anticoagulant valve tube 534 (T3) |

The depicted fluid-routing card 1038 can have additional openings that allow operative portions of actuators and/or valves to protrude through the fluid-routing card 1038 and interface with the tubes.

Figure 12:
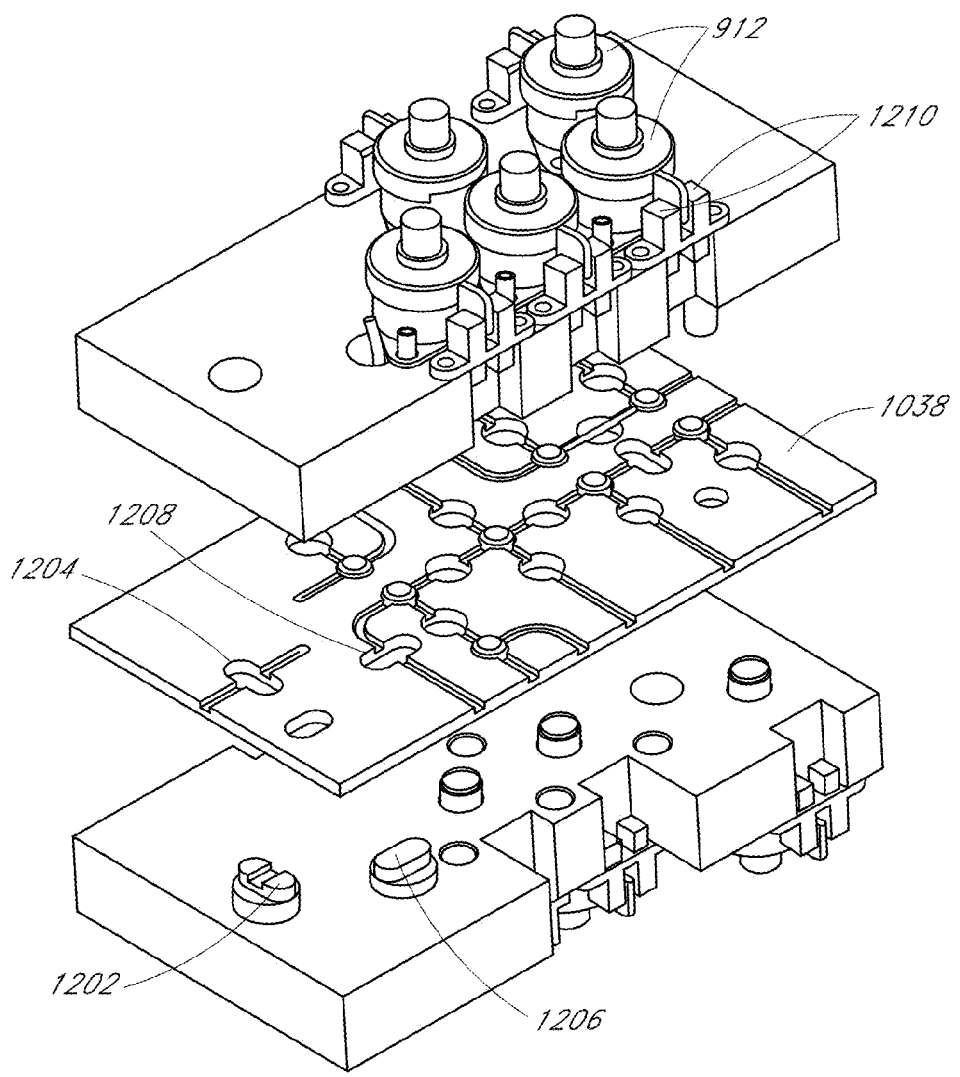
FIG. 12 illustrates how non-disposable actuators can interface with the fluid routing card of FIG. 11.

FIG. 12 illustrates how actuators, which can sandwich the fluid-routing card 1038 between them, can interface with the fluid-routing card 1038 of FIG. 11. Pinch valves 812 can have an actuator portion that protrudes away from the fluid-routing card 1038 containing a motor. Each motor can correspond to a pinch platen 1202, which can be inserted into a pinch platen receiving hole 1204. Similarly, sensors, such as a bubble sensor 1206 can be inserted into receiving holes (e.g., the bubble sensor receiving hole 1208). Movement of the pinch valves 812 can be detected by the position sensors 1210.

Figure 13:
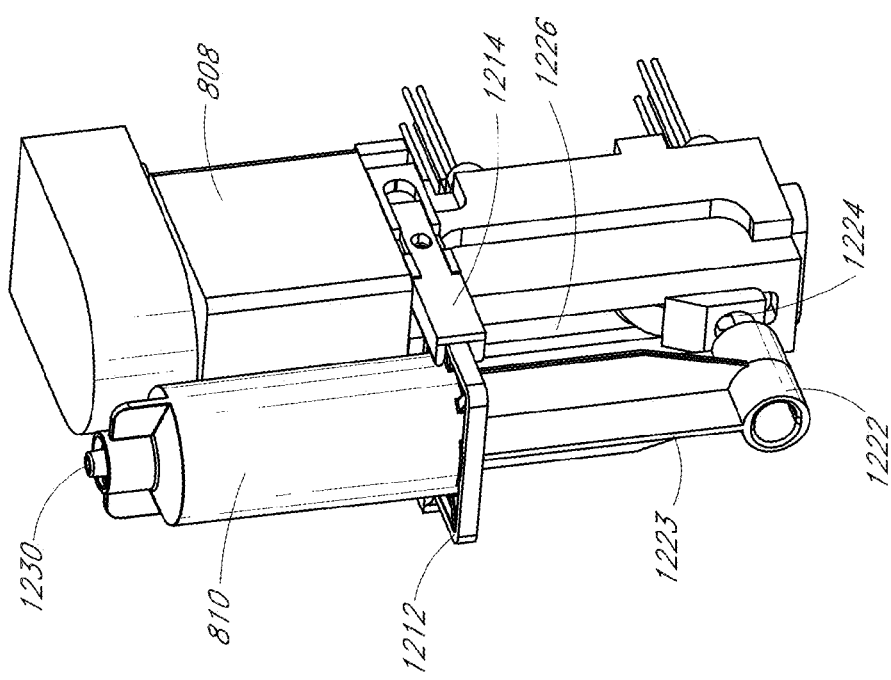
FIG. 13 illustrates a modular pump actuator connected to a syringe housing that can form a portion of a removable cartridge.

FIG. 13 illustrates an actuator 808 that is connected to a corresponding syringe body 810. The actuator 808 is an example of one of the actuators 808 that is illustrated in FIG. 8 and in FIG. 9, and the syringe body 810 is an example of one of the syringe bodies 810 that are visible in FIG. 8 and in FIG. 9. A ledge portion 1212 of the syringe body 810 can be engaged (e.g., slid into) a corresponding receiving portion 1214 in the actuator 808. In some embodiments, the receiving portion 1214 can slide outward to engage the stationary ledge portion 1212 after the disposable cartridge 804 is in place. Similarly, a receiving tube 1222 in the syringe plunger 1223 can be slide onto (or can receive) a protruding portion 1224 of the actuator 808. The protruding portion 1224 can slide along a track 1226 under the influence of a motor inside the actuator 808, thus actuating the syringe plunger 1223 and causing fluid to flow into or out of the syringe tip 1230.

Figure 14:
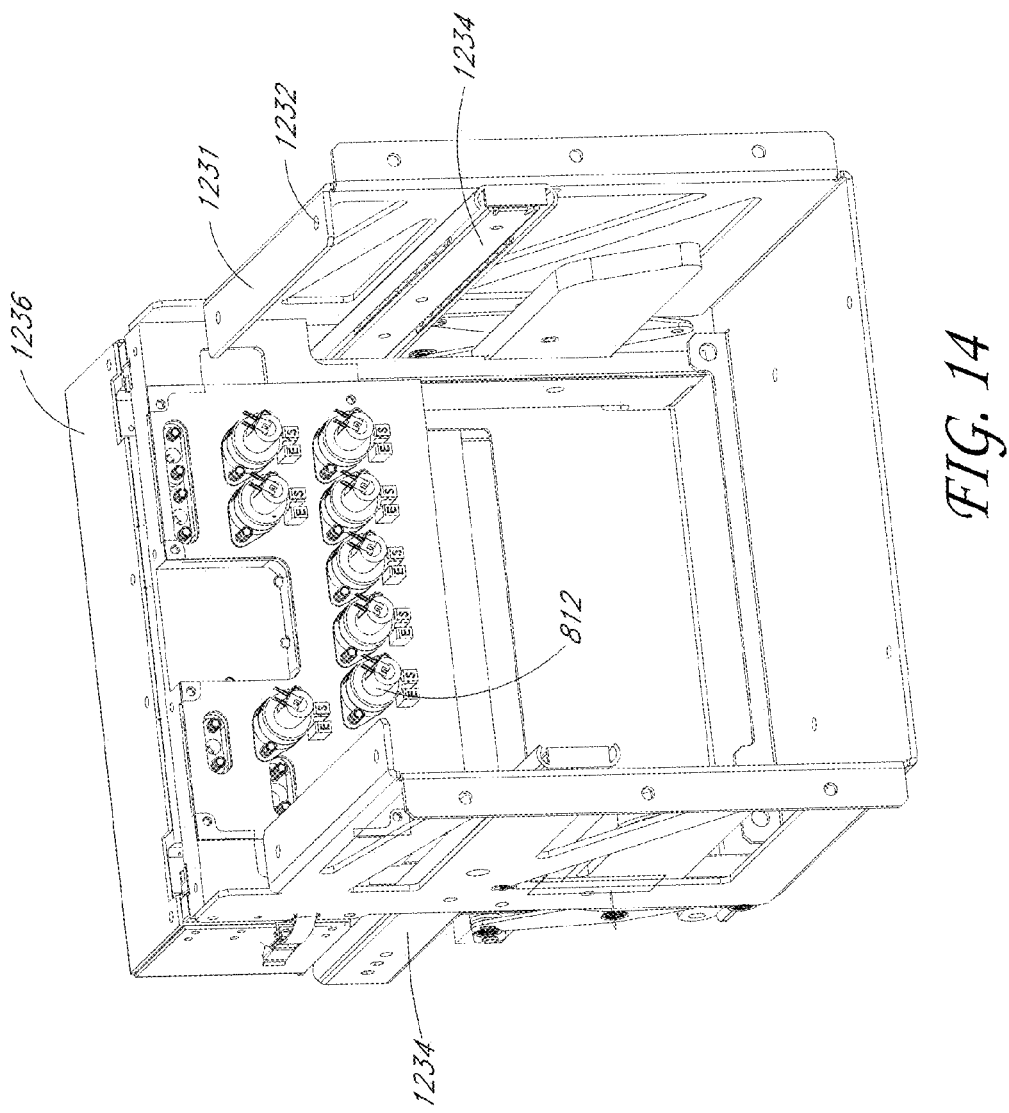
FIG. 14 shows a rear perspective view of internal scaffolding and some pinch valve pump bodies.

FIG. 14 shows a rear perspective view of internal scaffolding 1231 and the protruding bodies of some pinch valves 812. The internal scaffolding 1231 can be formed from metal and can provide structural rigidity and support for other components. The scaffolding 1231 can have holes 1232 into which screws can be screwed or other connectors can be inserted. In some embodiments, a pair of sliding rails 1234 can allow relative movement between portions of an analyzer. For example, a slidable portion 1236 (which can correspond to the movable portion 706, for example) can be temporarily slid away from the scaffolding 1231 of a main unit in order to allow an insertable portion (e.g., the cartridge 804) to be inserted.

FIG. 15 shows an underneath perspective view of the sample cell holder 820, which is attached to the centrifuge interface 1036. The sample cell holder 820 can have an opposite side (see FIG. 17) that allows it to slide into a receiving portion of the centrifuge interface 1036. The sample cell holder 820 can also have receiving nubs 1512A that provide a pathway into a sample cell 1548 held by the sample cell holder 820. Receiving nubs 1512B can provide access to a shunt 1586 (see FIG. 16) inside the sample cell holder 820. The receiving nubs 1512A and 1512B can receive and or dock with fluid nipples 1514. The fluid nipples 1514 can protrude at an angle from the sample injector 1006, which can in turn protrude from the cartridge 1000 (see FIG. 10). The tubes 1516 shown protruding from the other end of the sample injector 1006 can be in fluid communication with the sample cell holder interface tubes 582 (N1) and 584 (N2) (see FIG. 5 and FIG. 6), as well as 1074 and 1078 (see FIG. 11).

Figure 16:
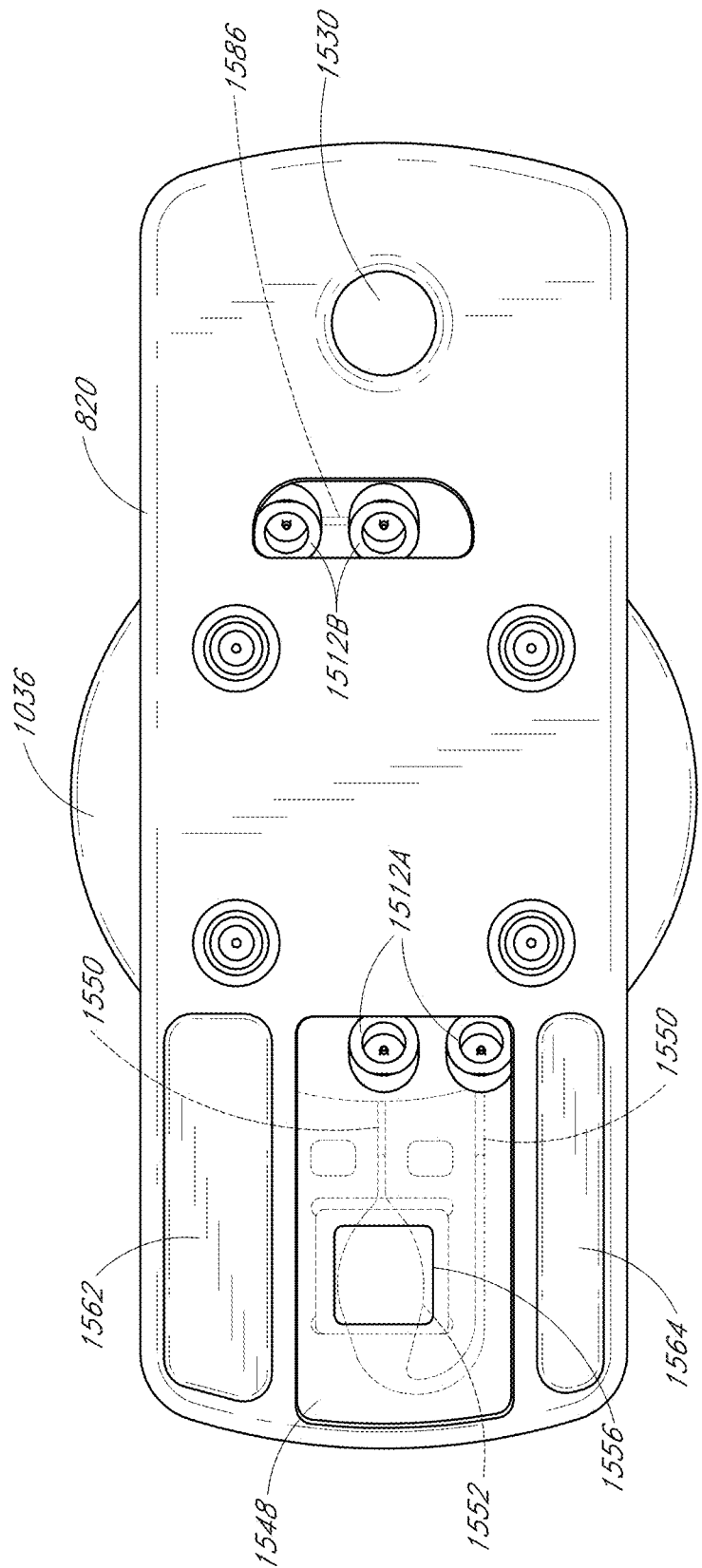
FIG. 16 shows a plan view of a sample cell holder with hidden and/or non-surface portions illustrated using dashed lines.

FIG. 16 shows a plan view of the sample cell holder 820 with hidden and/or non-surface portions illustrated using dashed lines. The receiving nubs 1512A communicate with passages 1550 inside the sample cell 1548 (which can correspond, for example to the sample cell 548 of FIG. 5). The passages widen out into a wider portion 1552 that corresponds to a window 1556. The window 1556 and the wider portion 1552 can be configured to house the sample when radiation is emitted along a pathlength that is generally non-parallel to the sample cell 1548. The window 1556 can allow calibration of the instrument with the sample cell 1548 in place, even before a sample has arrived in the wider portion 1552.

An opposite opening 1530 can provide an alternative optical pathway between radiation source and a radiation detector (e.g., the radiation source 826 of FIG. 18) and may be used, for example, for obtaining a calibration measurement of the source and detector without an intervening window or sample. Thus, the opposite opening 1530 can be located generally at the same radial distance from the axis of rotation as the window 1556.

The receiving nubs 1512B communicate with a shunt passage 1586 inside the sample cell holder 820 (which can correspond, for example to the shunt 586 of FIG. 5).

Other features of the sample cell holder 820 can provide balancing properties for even rotation of the sample cell holder 820. For example, the wide trough 1562 and the narrower trough 1564 can be sized or otherwise configured so that the weight and/or mass of the sample cell holder 820 is evenly distributed from left to right in the view of FIG. 16, and/or from top to bottom in this view of FIG. 16.

Figure 17:
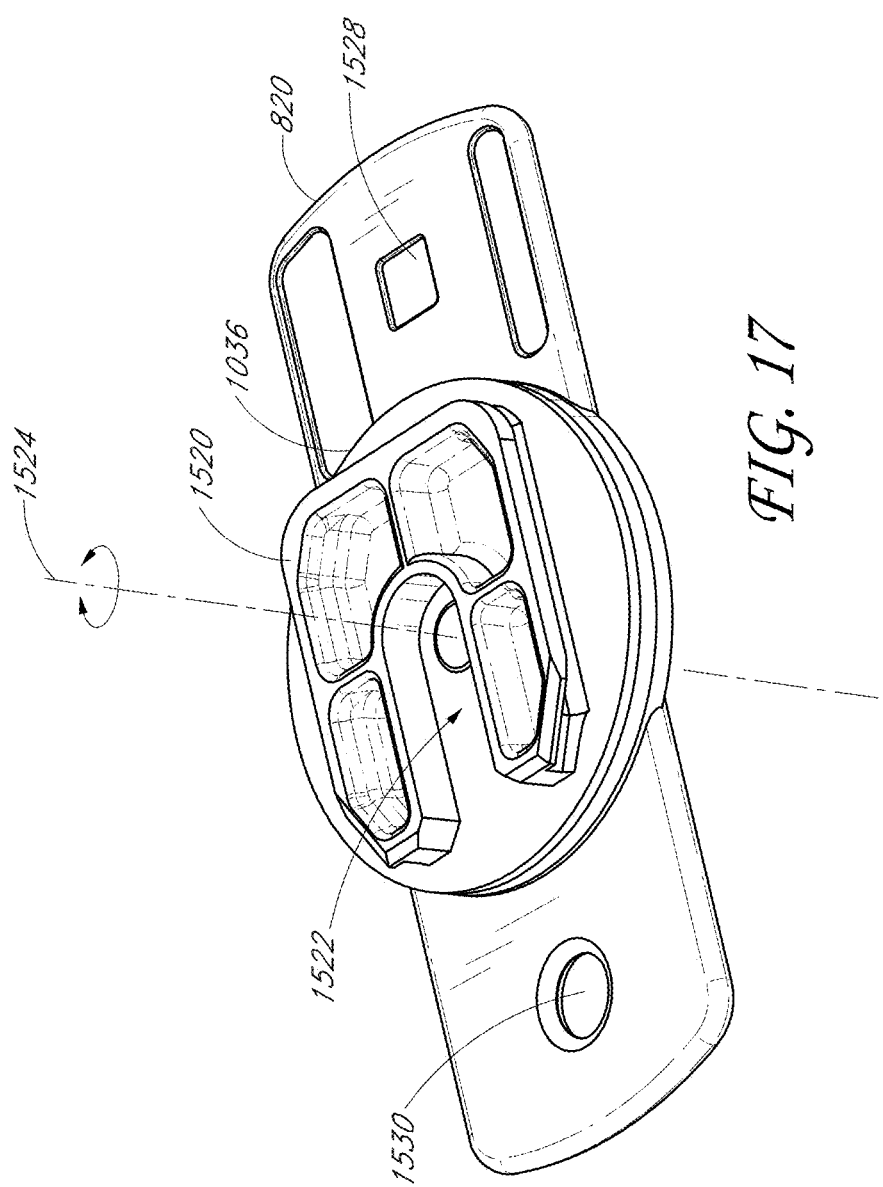
FIG. 17 shows a top perspective view of the centrifuge interface connected to the sample holder.

FIG. 17 shows a top perspective view of the centrifuge interface 1036 connected to the sample cell holder 820. The centrifuge interface 1036 can have a bulkhead 1520 with a rounded slot 1522 into which an actuating portion of a centrifuge can be slid from the side. The centrifuge interface 1036 can thus be spun about an axis 1524, along with the sample cell holder 820, causing fluid (e.g., whole blood) within the sample cell 1548 to separate into concentric strata, according to relative density of the fluid components (e.g., plasma, red blood cells, buffy coat, etc.), within the sample cell 1548. The sample cell holder 820 can be transparent, or it can at least have transparent portions (e.g., the window 1556 and/or the opposite opening 1530) through which radiation can pass, and which can be aligned with an optical pathway between a radiation source and a radiation detector (see, e.g., FIG. 20). In addition, a round opening 1530 through centrifuge rotor 1520 provides an optical pathway between the radiation source and radiation detector and may be used, for example, for obtaining a calibration measurement of the source and detector without an intervening window or sample.

Figure 18:
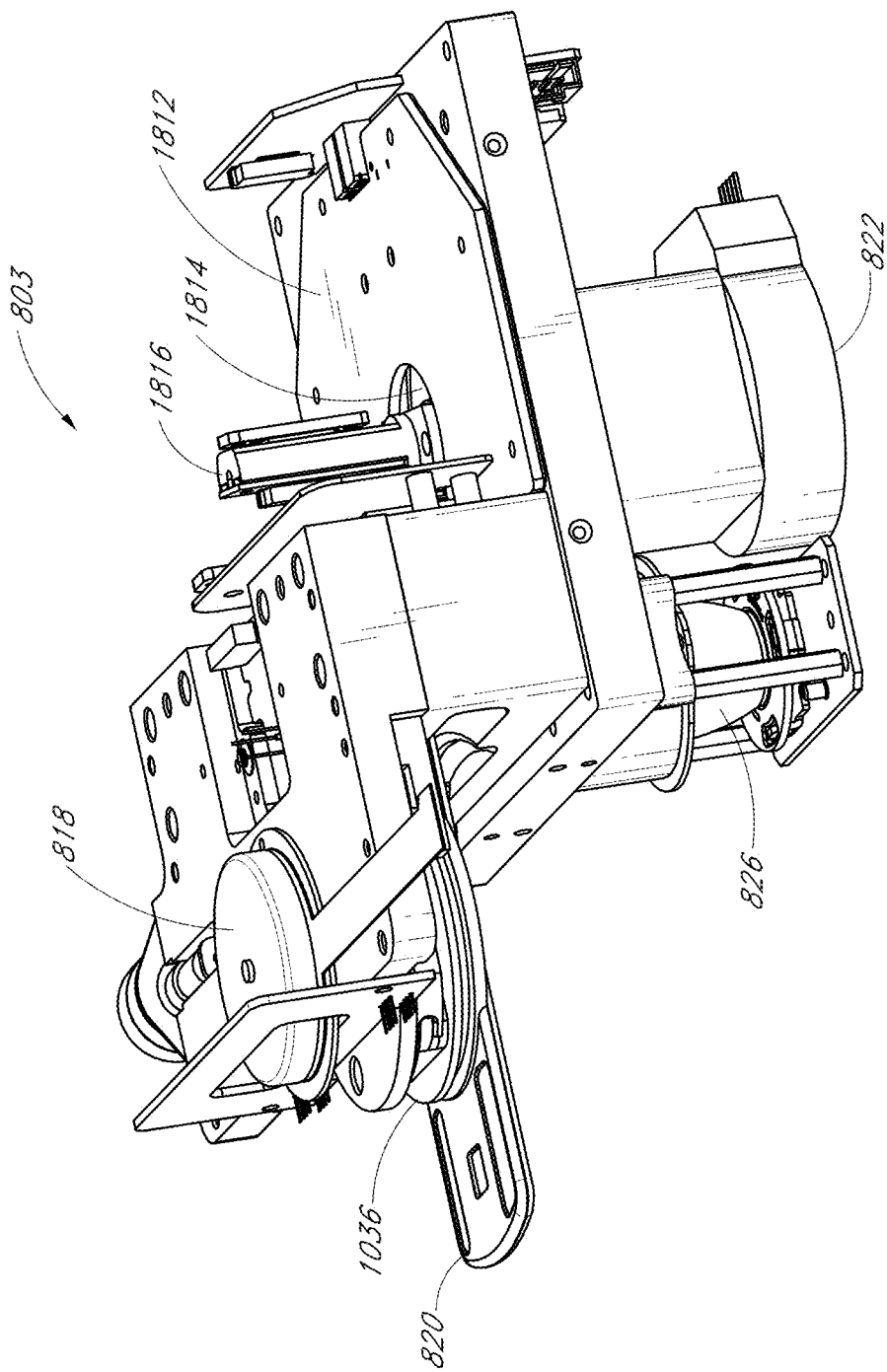
FIG. 18 shows a perspective view of an example optical system.

FIG. 18 shows a perspective view of an example optical system 803. Such a system can be integrated with other systems as shown in FIG. 9, for example. The optical system 803 can fill the role of the optical system 412, and it can be integrated with and/or adjacent to a fluid system (e.g., the fluid-handling system 404 or the fluid system 801). The sample cell holder 820 can be seen attached to the centrifuge interface 1036, which is in turn connected to, and rotatable by the centrifuge motor 818. A filter wheel housing 1812 is attached to the filter wheel motor 822 and encloses a filter wheel 1814. A protruding shaft assembly 1816 can be connected to the filter wheel 1814. The filter wheel 1814 can have multiple filters (see FIG. 19). The radiation source 826 is aligned to transmit radiation through a filter in the filter wheel 1814 and then through a portion of the sample cell holder 820. Transmitted and/or reflected and/or scattered radiation can then be detected by a radiation detector.

Figure 19:
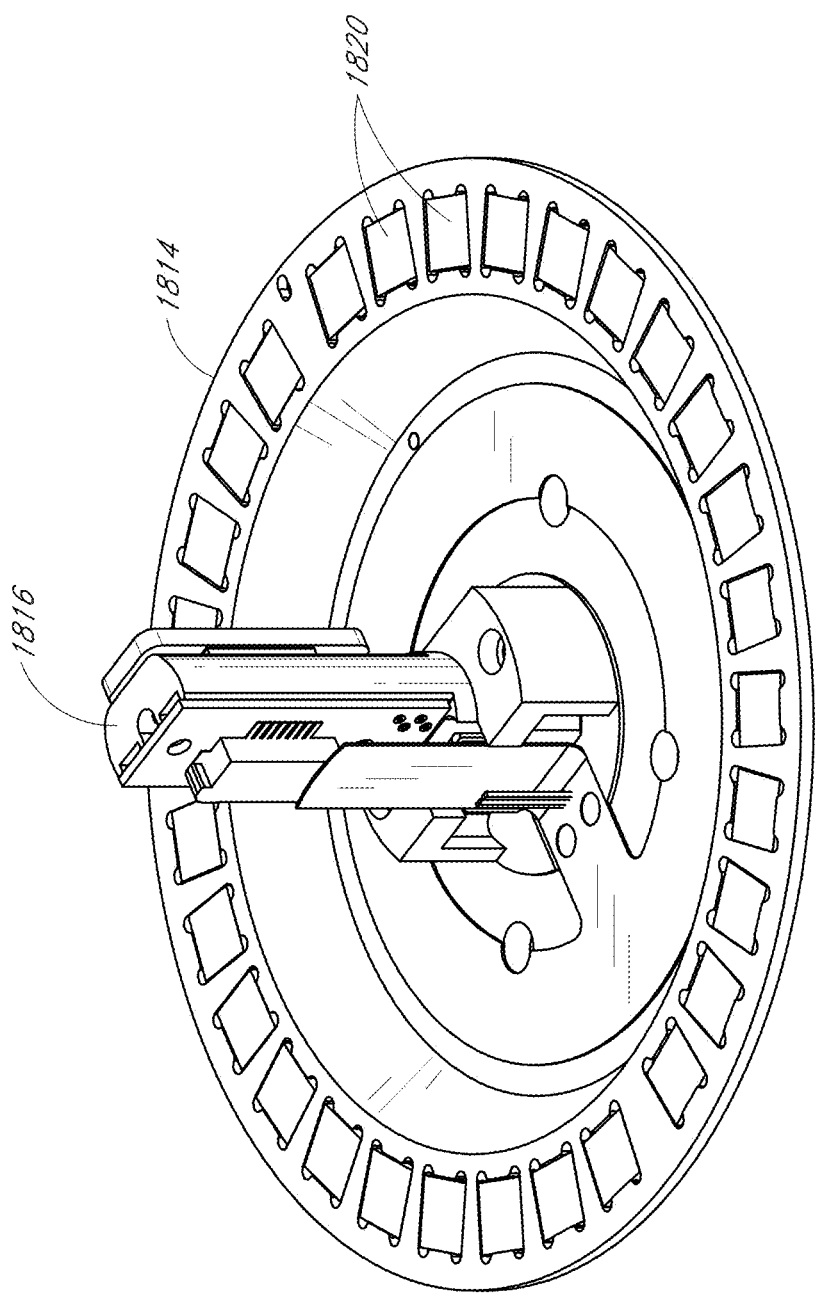
FIG. 19 shows a filter wheel that can be part of the optical system of FIG. 18.

FIG. 19 shows a view of the filter wheel 1814 when it is not located within the filter wheel housing 1812 of the optical system 803. Additional features of the protruding shaft assembly 1816 can be seen, along with multiple filters 1820. In some embodiments, the filters 1820 can be removably and/or replaceably inserted into the filter wheel 1814.

Spectroscopic System

As described above with reference to FIG. 4, the system 400 comprises the optical system 412 for analysis of a fluid sample. In various embodiments, the optical system 412 comprises one or more optical components including, for example, a spectrometer, a photometer, a reflectometer, or any other suitable device for measuring optical properties of the fluid sample. The optical system 412 may perform one or more optical measurements on the fluid sample including, for example, measurements of transmittance, absorbance, reflectance, scattering, and/or polarization. The optical measurements may be performed in one or more wavelength ranges including, for example, infrared (IR) and/or optical wavelengths. As described with reference to FIG. 4 (and further described below), the measurements from the optical system 412 are communicated to the algorithm processor 416 for analysis. For example, in some embodiments the algorithm processor 416 computes concentration of analyte(s) (and/or interferent(s)) of interest in the fluid sample. Analytes of interest can include, for example, glucose and/or lactate in whole blood and/or in blood plasma. In some embodiments the algorithm processor 416 can advantageously calibrate a measured analyte concentration for some or all of the effects of sample dilution. In some embodiments, the algorithm processor 416 may correct a measured analyte concentration for dilution to provide an estimate of analyte concentration that is more representative of the concentration in the patient's body than would otherwise be the case without correcting for dilution.

Figure 20:
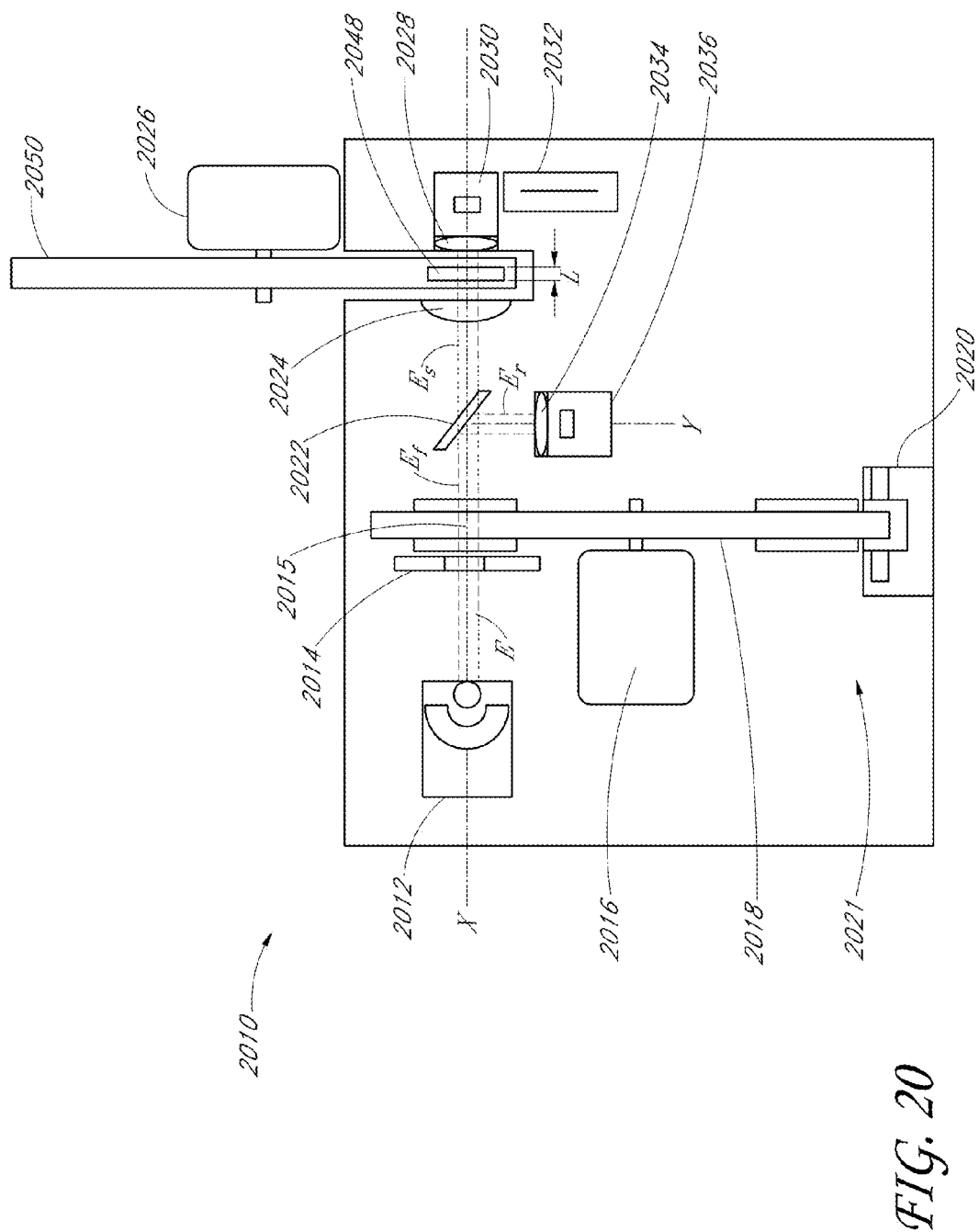
FIG. 20 schematically illustrates an embodiment of an optical system that comprises a spectroscopic analyzer adapted to measure spectra of a fluid sample.

FIG. 20 schematically illustrates an embodiment of the optical system 412 that comprises a spectroscopic analyzer 2010 adapted to measure spectra of a fluid sample such as, for example, blood or blood plasma. The analyzer 2010 comprises an energy source 2012 disposed along an optical axis X of the analyzer 2010. When activated, the energy source 2012 generates an electromagnetic energy beam E, which advances from the energy source 2012 along the optical axis X. In some embodiments, the energy source 2012 comprises an infrared energy source, and the energy beam E comprises an infrared beam. In some embodiments, the infrared energy beam E comprises a mid-infrared energy beam or a near-infrared energy beam. In some embodiments, the energy beam E can include optical and/or radio frequency wavelengths.

The energy source 2012 may comprise a broad-band and/or a narrow-band source of electromagnetic energy. In some embodiments, the energy source 2012 comprises optical elements such as, e.g., filters, collimators, lenses, mirrors, etc., that are adapted to produce a desired energy beam E. For example, in some embodiments, the energy beam E is an infrared beam in a wavelength range between about 2 µm and 20 µm. In some embodiments, the energy beam E comprises an infrared beam in a wavelength range between about 4 µm and 10 µm. In the infrared wavelength range, water generally is the main contributor to the total absorption together with features from absorption of other blood components, particularly in the 6 µm-10 µm range. The 4 µm to 10 µm wavelength band has been found to be advantageous for determining glucose concentration, because glucose has a strong absorption peak structure from about 8.5 µm to 10 µm, whereas most other blood components have a relatively low and flat absorption spectrum in the 8.5 µm to 10 µm range. Two exceptions are water and hemoglobin, which are interferents in this range.

The energy beam E may be temporally modulated to provide increased signal-to-noise ratio (S/N) of the measurements provided by the analyzer 2010 as further described below. For example, in some embodiments, the beam E is modulated at a frequency of about 10 Hz or in a range from about 1 Hz to about 30 Hz. A suitable energy source 2012 may be an electrically modulated thin-film thermoresistive element such as the HawkEye IR-50 available from Hawkeye Technologies of Milford, Conn.

As depicted in FIG. 20, the energy beam E propagates along the optical axis X and passes through an aperture 2014 and a filter 2015 thereby providing a filtered energy beam $E_f$.

The aperture 2014 helps collimate the energy beam E and can include one or more filters adapted to reduce the filtering burden of the filter 2015. For example, the aperture 2014 may comprise a broadband filter that substantially attenuates beam energy outside a wavelength band between about 4 µm to about 10 µm. The filter 2015 may comprise a narrow-band filter that substantially attenuates beam energy having wavelengths outside of a filter passband (which may be tunable or user-selectable in some embodiments). The filter passband may be specified by a half-power bandwidth ("HPBW"). In some embodiments, the filter 2015 may have an HPBW in a range from about 0.1 µm to about 2 µm, or 0.01 µm to about 1 µm. In some embodiments, the bandwidths are in a range from about 0.2 µm to 0.5 µm, or 0.1 µm to 0.35 µm. Other filter bandwidths may be used. The filter 2015 may comprise a varying-passband filter, an electronically tunable filter, a liquid crystal filter, an interference filter, and/or a gradient filter. In some embodiments, the filter 2015 comprises one or a combination of a grating, a prism, a monochrometer, a Fabry-Perot etalon, and/or a polarizer. Other optical elements may be utilized as well.

In the embodiment shown in FIG. 20, the analyzer 2010 comprises a filter wheel assembly 2021 configured to dispose one or more filters 2015 along the optical axis X. The filter wheel assembly 2021 comprises a filter wheel 2018, a filter wheel motor 2016, and a position sensor 2020. The filter wheel 2018 may be substantially circular and have one or more filters 2015 or other optical elements (e.g., apertures, gratings, polarizers, mirrors, etc.) disposed around the circumference of the wheel 2018. In some embodiments, the number of filters 2015 in the filter wheel 2016 may be, for example, 1, 2, 5, 10, 15, 20, 25, 29, or more. In some particularly advantageous embodiments, the number of filters is 29. The motor 2016 is configured to rotate the filter wheel 2018 to dispose a desired filter 2015 (or other optical element) in the energy beam E so as to produce the filtered beam $E_f$. In some embodiments, the motor 2016 comprises a stepper motor. The position sensor 2020 determines the angular position of the filter wheel 2016, and communicates a corresponding filter wheel position signal to the algorithm processor 416, thereby indicating which filter 2015 is in position on the optical axis X. In various embodiments, the position sensor 2020 may be a mechanical, optical, and/or magnetic encoder. An alternative to the filter wheel 2018 is a linear filter translated by a motor. The linear filter can include an array of separate filters or a single filter with properties that change along a linear dimension.

The filter wheel motor 2016 rotates the filter wheel 2018 to position the filters 2015 in the energy beam E to sequentially vary the wavelengths or the wavelength bands used to analyze the fluid sample. In some embodiments, each individual filter 2015 is disposed in the energy beam E for a dwell time during which optical properties in the passband of the filter are measured for the sample. The filter wheel motor 2016 then rotates the filter wheel 2018 to position another filter 2015 in the beam E. In some embodiments, 25 narrow-band filters are used in the filter wheel 2018, and the dwell time is about 2 seconds for each filter 2015. A set of optical measurements for all the filters can be taken in about 2 minutes, including sampling time and filter wheel movement. In some embodiments, the dwell time may be different for different filters 2015, for example, to provide a substantially similar S/N ratio for each filter measurement. Accordingly, the filter wheel assembly 2021 functions as a varying-passband filter that allows optical properties of the sample to be analyzed at a number of wavelengths or wavelength bands in a sequential manner.

In some embodiments of the analyzer 2010, the filter wheel 2018 includes 25 finite-bandwidth infrared filters having a Gaussian transmission profile and full-width half-maximum (FWHM) bandwidth of 28 $cm^{-1}$ corresponding to a bandwidth that varies from 0.14 µm at 7.08 µm to 0.28 µm at 10 µm. The central wavelength of the filters are, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990.

With further reference to FIG. 20, the filtered energy beam $E_f$ propagates to a beamsplitter 2022 disposed along the optical axis X. The beamsplitter 2022 separates the filtered energy beam $E_f$ into a sample beam $E_s$ and a reference beam $E_r$. The reference beam $E_r$ propagates along a minor optical axis Y, which in this embodiment is substantially orthogonal to the optical axis X. The energies in the sample beam $E_s$ and the reference beam $E_r$ may comprise any suitable fraction of the energy in the filtered beam $E_f$. For example, in some embodiments, the sample beam $E_s$ comprises about 80%, and the reference beam $E_r$ comprises about 20%, of the filtered beam energy $E_f$. A reference detector 2036 is positioned along the minor optical axis Y. An optical element 2034, such as a lens, may be used to focus or collimate the reference beam $E_r$ onto the reference detector 2036. The reference detector 2036 provides a reference signal, which can be used to monitor fluctuations in the intensity of the energy beam E emitted by the source 2012. Such fluctuations may be due to drift effects, aging, wear, or other imperfections in the source 2012. The algorithm processor 416 may utilize the reference signal to identify changes in properties of the sample beam $E_s$, that are attributable to changes in the emission from the source 2012 and not to the properties of the fluid sample. By so doing, the analyzer 2010 may advantageously reduce possible sources of error in the calculated properties of the fluid sample (e.g., concentration). In other embodiments of the analyzer 2010, the beamsplitter 2022 is not used, and substantially all of the filtered energy beam $E_f$ propagates to the fluid sample.

As illustrated in FIG. 20, the sample beam $E_s$ propagates along the optical axis X and a relay lens 2024 transmits the sample beam $E_s$ into a sample cell 2048 so that at least a fraction of the sample beam $E_s$, is transmitted through at least a portion of the fluid sample in the sample cell 2048. A sample detector 2030 is positioned along the optical axis X to measure the sample beam $E_s$ that has passed through the portion of the fluid sample. An optical element 2028, such as a lens, may be used to focus or collimate the sample beam $E_s$ onto the sample detector 2030. The sample detector 2030 provides a sample signal that can be used by the algorithm processor 416 as part of the sample analysis.

In the embodiment of the analyzer 2010 shown in FIG. 20, the sample cell 2048 is located toward the outer circumference of the centrifuge wheel 2050 (which can correspond, for example, to the sample cell holder 820 described herein). The sample cell 2048 preferably comprises windows that are substantially transmissive to energy in the sample beam E. For example, in implementations using mid-infrared energy, the windows may comprise calcium fluoride. As described herein with reference to FIG. 5, the sample cell 2048 is in fluid communication with an injector system that permits filling the sample cell 2048 with a fluid sample (e.g., whole blood) and flushing the sample cell 2048 (e.g., with saline or a detergent). The injector system may disconnect after filling the sample cell 2048 with the fluid sample to permit free spinning of the centrifuge wheel 2050.

The centrifuge wheel 2050 can be spun by a centrifuge motor 2026. In some embodiments of the analyzer 2010, the fluid sample (e.g., a whole blood sample) is spun at a certain number of revolutions per minute (RPM) for a given length of time to separate blood plasma for spectral analysis. In some embodiments, the fluid sample is spun at about 7200 RPM. In some embodiments, the fluid sample is spun at about 5000 RPM or 4500 RPM. In some embodiments, the fluid sample is spun at more than one rate for successive time periods. The length of time can be approximately 5 minutes. In some embodiments, the length of time is approximately 2 minutes. In some embodiments, an anti-clotting agent such as heparin may be added to the fluid sample before centrifuging to reduce clotting. With reference to FIG. 20, the centrifuge wheel 2050 is rotated to a position where the sample cell 2048 intercepts the sample beam $E_s$, allowing energy to pass through the sample cell 2048 to the sample detector 2030.

The embodiment of the analyzer 2010 illustrated in FIG. 20 advantageously permits direct measurement of the concentration of analytes in the plasma sample rather than by inference of the concentration from measurements of a whole blood sample. An additional advantage is that relatively small volumes of fluid may be spectroscopically analyzed. For example, in some embodiments the fluid sample volume is between about 1 μL and 80 μL and is about 25 μL in some embodiments. In some embodiments, the sample cell 2048 is disposable and is intended for use with a single patient or for a single measurement.

In some embodiments, the reference detector 2036 and the sample detector 2030 comprise broadband pyroelectric detectors. As known in the art, some pyroelectric detectors are sensitive to vibrations. Thus, for example, the output of a pyroelectric infrared detector is the sum of the exposure to infrared radiation and to vibrations of the detector. The sensitivity to vibrations, also known as "microphonics," can introduce a noise component to the measurement of the reference and sample energy beams $E_r$, $E_s$ using some pyroelectric infrared detectors. Because it may be desirable for the analyzer 2010 to provide high signal-to-noise ratio measurements, such as, e.g., S/N in excess of 100 dB, some embodiments of the analyzer 2010 utilize one or more vibrational noise reduction apparatus or methods. For example, the analyzer 2010 may be mechanically isolated so that high S/N spectroscopic measurements can be obtained for vibrations below an acceleration of about 1.5 G.

In some embodiments of the analyzer 2010, vibrational noise can be reduced by using a temporally modulated energy source 2012 combined with an output filter. In some embodiments, the energy source 2012 is modulated at a known source frequency, and measurements made by the detectors 2036 and 2030 are filtered using a narrowband filter centered at the source frequency. For example, in some embodiments, the energy output of the source 2012 is sinusoidally modulated at 10 Hz, and outputs of the detectors 2036 and 2030 are filtered using a narrow bandpass filter of less than about 1 Hz centered at 10 Hz. Accordingly, microphonic signals that are not at 10 Hz are significantly attenuated. In some embodiments, the modulation depth of the energy beam E may be greater than 50% such as, for example, 80%. The duty cycle of the beam may be between about 30% and 70%. The temporal modulation may be sinusoidal or any other waveform. In embodiments utilizing temporally modulated energy sources, detector output may be filtered using a synchronous demodulator and digital filter. The demodulator and filter are software components that may be digitally implemented in a processor such as the algorithm processor 416. Synchronous demodulators, coupled with low pass filters, are often referred to as "lock in amplifiers."

The analyzer 2010 may also include a vibration sensor 2032 (e.g., one or more accelerometers) disposed near one (or both) of the detectors 2036 and 2030. The output of the vibration sensor 2032 is monitored, and suitable actions are taken if the measured vibration exceeds a vibration threshold. For example, in some embodiments, if the vibration sensor 2032 detects above-threshold vibrations, the system discards any ongoing measurement and "holds off" on performing further measurements until the vibrations drop below the threshold. Discarded measurements may be repeated after the vibrations drop below the vibration threshold. In some embodiments, if the duration of the "hold off" is sufficiently long, the fluid in the sample cell 2030 is flushed, and a new fluid sample is delivered to the cell 2030 for measurement. The vibration threshold may be selected so that the error in analyte measurement is at an acceptable level for vibrations below the threshold. In some embodiments, the threshold corresponds to an error in glucose concentration of 5 mg/dL. The vibration threshold may be determined individually for each filter 2015.

Certain embodiments of the analyzer 2010 include a temperature system (not shown in FIG. 20) for monitoring and/or regulating the temperature of system components (such as the detectors 2036, 2030) and/or the fluid sample. Such a temperature system can include temperature sensors, thermoelectrical heat pumps (e.g., a Peltier device), and/or thermistors, as well as a control system for monitoring and/or regulating temperature. In some embodiments, the control system comprises a proportional-plus-integral-plus-derivative (PID) control. For example, in some embodiments, the temperature system is used to regulate the temperature of the detectors 2030, 2036 to a desired operating temperature, such as 35 degrees Celsius.

Optical Measurement

The analyzer 2010 illustrated in FIG. 20 can be used to determine optical properties of a substance in the sample cell 2048. The substance can include whole blood, plasma, saline, water, air or other substances. In some embodiments, the optical properties include measurements of an absorbance, transmittance, and/or optical density in the wavelength passbands of some or all of the filters 2015 disposed in the filter wheel 2018. As described above, a measurement cycle comprises disposing one or more filters 2015 in the energy beam E for a dwell time and measuring a reference signal with the reference detector 2036 and a sample signal with the sample detector 2030. The number of filters 2015 used in the measurement cycle will be denoted by N, and each filter 2015 passes energy in a passband around a center wavelength $\lambda_i$, where i is an index ranging over the number of filters (e.g., from 1 to N). The set of optical measurements from the sample detector 2036 in the passbands of the N filters 2015 provide a wavelength-dependent spectrum of the substance in the sample cell 2048. The spectrum will be denoted by $C_s(\lambda_i)$, where $C_s$ may be a transmittance, absorbance, optical density, or some other measure of an optical property of the substance. In some embodiments, the spectrum is normalized with respect to one or more of the reference signals measured by the reference detector 2030 and/or with respect to spectra of a reference substance (e.g., air or saline). The measured spectra are communicated to the algorithm processor 416 for calculation of the concentration of the analyte(s) of interest in the fluid sample.

In some embodiments, the analyzer 2010 performs spectroscopic measurements on the fluid sample (known as a "wet" reading) and on one or more reference samples. For example, an "air" reading occurs when the sample detector 2036 measures the sample signal without the sample cell 2048 in place along the optical axis X. (This can occur, for example, when the opposite opening 1530 is aligned with the optical axis X). A "water" or "saline" reading occurs when the sample cell 2048 is filled with water or saline, respectively. The algorithm processor 416 may be programmed to calculate analyte concentration using a combination of these spectral measurements. In some embodiments, an advantage of combining the "wet reading" with at least the "water" or "saline" reading is to calibrate a measured analyte concentration for some or all of the effects of dilution.

In some embodiments, a pathlength corrected spectrum is calculated using wet, air, and reference readings. For example, the transmittance at wavelength $\lambda_i$, denoted by $T_i$, may be calculated according to $T_i=(S_i(\text{wet})/R_i(\text{wet}))/(S_i(\text{air})/R_i(\text{air}))$, where $S_i$ denotes the sample signal from the sample detector 2036 and $R_i$ denotes the corresponding reference signal from the reference detector 2030. In some embodiments, the algorithm processor 416 calculates the optical density, $OD_i$, as a logarithm of the transmittance, e.g., according to $OD_i=-\text{Log}(T_i)$. In one implementation, the analyzer 2010 takes a set of wet readings in each of the N filter passbands and then takes a set of air readings in each of the N filter passbands. In other embodiments, the analyzer 2010 may take an air reading before (or after) the corresponding wet reading.

The optical density $OD_i$ is the product of the absorption coefficient at wavelength $\lambda_i$, $\alpha_i$, times the pathlength L over which the sample energy beam $E_s$ interacts with the substance in the sample cell 2048, e.g., $OD_i=\alpha_i L$. The absorption coefficient $\alpha_i$ of a substance may be written as the product of an absorptivity per mole times a molar concentration of the substance. FIG. 20 schematically illustrates the pathlength L of the sample cell 2048. The pathlength L may be determined from spectral measurements made when the sample cell 2048 is filled with a reference substance. For example, because the absorption coefficient for water (or saline) is known, one or more water (or saline) readings can be used to determine the pathlength L from measurements of the transmittance (or optical density) through the cell 2048. In some embodiments, several readings are taken in different wavelength passbands, and a curve-fitting procedure is used to estimate a best-fit pathlength L. The pathlength L may be estimated using other methods including, for example, measuring interference fringes of light passing through an empty sample cell 2048.

The pathlength L may be used to determine the absorption coefficients of the fluid sample at each wavelength. Molar concentration of an analyte of interest can be determined from the absorption coefficient and the known molar absorptivity of the analyte. In some embodiments, a sample measurement cycle comprises a saline reading (at one or more wavelengths), a set of N wet readings (taken, for example, through a sample cell 2048 containing saline solution), followed by a set of N air readings (taken, for example, through the opposite opening 1530). As discussed above, the sample measurement cycle can be performed in a given length of time that may depend, at least in part, on filter dwell times. For example, the measurement cycle may take five minutes when the filter dwell times are about five seconds. In some embodiments, the measurement cycle may take about two minutes when the filter dwell times are about two seconds. After the sample measurement cycle is completed, a detergent cleaner may be flushed through the sample cell 2048 to reduce buildup of organic matter (e.g., proteins) on the windows of the sample cell 2048. The detergent is then flushed to a waste bladder.

In some embodiments, the system stores information related to the spectral measurements so that the information is readily available for recall by a user. The stored information can include wavelength-dependent spectral measurements (including fluid sample, air, and/or saline readings), computed analyte values, system temperatures and electrical properties (e.g., voltages and currents), and any other data related to use of the system (e.g., system alerts, vibration readings, S/N ratios, etc.). The stored information may be retained in the system for a time period such as, for example, 30 days. After this time period, the stored information may be communicated to an archival data storage system and then deleted from the system. In some embodiments, the stored information is communicated to the archival data storage system via wired or wireless methods, e.g., over a hospital information system (HIS).

Analyte Analysis

The algorithm processor 416 (FIG. 4) (or any other suitable processor or processors) may be configured to receive from the analyzer 2010 the wavelength-dependent optical measurements $Cs(\lambda_i)$ of the fluid sample. In some embodiments, the optical measurements comprise spectra such as, for example, optical densities $OD_i$ measured in each of the N filter passbands centered around wavelengths $\lambda_i$. The optical measurements $Cs(\lambda_i)$ are communicated to the processor 416, which analyzes the optical measurements to detect and quantify one or more analytes in the presence of interferents. In some embodiments, one or more poor quality optical measurements $Cs(\lambda_i)$ are rejected (e.g., as having a S/N ratio that is too low), and the analysis performed on the remaining, sufficiently high-quality measurements. In another embodiment, additional optical measurements of the fluid sample are taken by the analyzer 2010 to replace one or more of the poor quality measurements.

Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte, in at least a portion of the wavelength range of the measurements. The presence of such an interferent can introduce errors in the quantification of the analyte. More specifically, the presence of one or more interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As an example of these classes of interferents, consider the analysis of a blood sample (or a blood component sample or a blood plasma sample) for the analyte glucose. Endogenous interferents include those blood components having origins within the body that affect the quantification of glucose, and can include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly, but not necessarily, present in the sample type under analysis. In the example of analyzing samples of blood or blood plasma drawn from patients who are receiving medical treatment, a medicament such as acetaminophen is possibly, but not necessarily, present in this sample type. In contrast, water is necessarily present in such blood or plasma samples.

Certain disclosed analysis methods are particularly effective if each analyte and interferent has a characteristic signature in the measurement (e.g., a characteristic spectroscopic feature), and if the measurement is approximately affine (e.g., includes a linear term and an offset) with respect to the concentration of each analyte and interferent. In such methods, a calibration process is used to determine a set of one or more calibration coefficients and a set of one or more optional offset values that permit the quantitative estimation of an analyte. For example, the calibration coefficients and the offsets may be used to calculate an analyte concentration from spectroscopic measurements of a material sample (e.g., the concentration of glucose in blood plasma). In some of these methods, the concentration of the analyte is estimated by multiplying the calibration coefficient by a measurement value (e.g., an optical density) to estimate the concentration of the analyte. Both the calibration coefficient and measurement can comprise arrays of numbers. For example, in some embodiments, the measurement comprises spectra $C_s(\lambda_i)$ measured at the wavelengths $\lambda_i$, and the calibration coefficient and optional offset comprise an array of values corresponding to each wavelength $\lambda_i$. In some embodiments, as further described below, a hybrid linear analysis (HLA) technique is used to estimate analyte concentration in the presence of a set of interferents, while retaining a high degree of sensitivity to the desired analyte. The data used to accommodate the set of possible interferents can include (a) signatures of each of the members of the family of potential additional substances and (b) a typical quantitative level at which each additional substance, if present, is likely to appear. In some embodiments, the calibration coefficient (and optional offset) are adjusted to minimize or reduce the sensitivity of the calibration to the presence of interferents that are identified as possibly being present in the fluid sample.

In some embodiments, the analyte analysis method uses a set of training spectra each having known analyte concentration and produces a calibration that minimizes the variation in estimated analyte concentration with interferent concentration. The resulting calibration coefficient indicates sensitivity of the measurement to analyte concentration. The training spectra need not include a spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the analyte analysis process. The term "Sample Population" is a broad term and includes, without limitation, a large number of samples having measurements that are used in the computation of calibration values (e.g., calibration coefficients and optional offsets). In some embodiments, the term Sample Population comprises measurements (such as, e.g., spectra) from individuals and may comprise one or more analyte measurements determined from those same individuals. Additional demographic information may be available for the individuals whose sample measurements are included in the Sample Population. For an embodiment involving the spectroscopic determination of glucose concentration, the Sample Population measurements may include a spectrum (measurement) and a glucose concentration (analyte measurement).

Various embodiments of Sample Populations may be used in various embodiments of the systems and methods described herein. Several examples of Sample Populations will now be described. These examples are intended to illustrate certain aspects of possible Sample Population embodiments but are not intended to limit the types of Sample Populations that may be generated. In certain embodiments, a Sample Population may include samples from one or more of the example Sample Populations described below.

In some embodiments of the systems and methods described herein, one or more Sample Populations are included in a "Population Database." The Population Database may be implemented and/or stored on a computer-readable medium. In certain embodiments, the systems and methods may access the Population Database using wired and/or wireless techniques. Certain embodiments may utilize several different Population Databases that are accessible locally and/or remotely. In some embodiments, the Population Database includes one or more of the example Sample Populations described below. In some embodiments, two or more databases can be combined into a single database, and in other embodiments, any one database can be divided into multiple databases.

An example Sample Population may comprise samples from individuals belonging to one or more demographic groups including, for example, ethnicity, nationality, gender, age, etc. Demographic groups may be established for any suitable set of one or more distinctive factors for the group including, for example, medical, cultural, behavioral, biological, geographical, religious, and genealogical traits. For example, in certain embodiments, a Sample Population includes samples from individuals from a specific ethnic group (e.g., Caucasians, Hispanics, Asians, African Americans, etc.). In another embodiment, a Sample Population includes samples from individuals of a specific gender or a specific race. In some embodiments, a Sample Population includes samples from individuals belonging to more than one demographic group (e.g., samples from Caucasian women).

Another example Sample Population can comprise samples from individuals having one or more medical conditions. For example, a Sample Population may include samples from individuals who are healthy and unmedicated (sometimes referred to as a Normal Population). In some embodiments, the Sample Population includes samples from individuals having one or more health conditions (e.g., diabetes). In some embodiments, the Sample Population includes samples from individuals taking one or more medications. In certain embodiments, Sample Population includes samples from individuals diagnosed to have a certain medical condition or from individuals being treated for certain medical conditions or some combination thereof. The Sample Population may include samples from individuals such as, for example, ICU patients, maternity patients, and so forth.

An example Sample Population may comprise samples that have the same interferent or the same type of interferents. In some embodiments, a Sample Population can comprise multiple samples, all lacking an interferent or a type of interferent. For example, a Sample Population may comprise samples that have no exogenous interferents, that have one or more exogenous interferents of either known or unknown concentration, and so forth. The number of interferents in a sample depends on the measurement and analyte(s) of interest, and may number, in general, from zero to a very large number (e.g., greater than 300). All of the interferents typically are not expected to be present in a particular material sample, and in many cases, a smaller number of interferents (e.g., 0, 1, 2, 5, 10, 15, 20, or 25) may be used in an analysis.

In certain embodiments, the number of interferents used in the analysis is less than or equal to the number of wavelength-dependent measurements N in the spectrum $Cs(\lambda_i)$.

Certain embodiments of the systems and methods described herein are capable of analyzing a material sample using one or more Sample Populations (e.g., accessed from the Population Database). Certain such embodiments may use information regarding some or all of the interferents which may or may not be present in the material sample. In some embodiments, a list of one or more possible interferents, referred to herein as forming a "Library of Interferents," can be compiled. Each interferent in the Library can be referred to as a "Library Interferent." The Library Interferents may include exogenous interferents and endogenous interferents that may be present in a material sample. For example, an interferent may be present due to a medical condition causing abnormally high concentrations of the exogenous and endogenous interferents. In some embodiments, the Library of Interferents may not include one or more interferents that are known to be present in all samples. Thus, for example, water, which is a glucose interferent for many spectroscopic measurements, may not be included in the Library of Interferents. In certain embodiments, the systems and methods use samples in the Sample Population to train calibration methods.

The material sample being measured, for example a fluid sample in the sample cell 2048, may also include one or more Library Interferents which may include, but is not limited to, an exogenous interferent or an endogenous interferent. Examples of exogenous interferent can include medications, and examples of endogenous interferents can include urea in persons suffering from renal failure. In addition to components naturally found in the blood, the ingestion or injection of some medicines or illicit drugs can result in very high and rapidly changing concentrations of exogenous interferents.

In some embodiments, measurements of a material sample (e.g., a bodily fluid sample), samples in a Sample Population, and the Library Interferents comprise spectra (e.g., infrared spectra). The spectra obtained from a sample and/or an interferent may be temperature dependent. In some embodiments, it may be beneficial to calibrate for temperatures of the individual samples in the Sample Population or the interferents in the Library of Interferents. In some embodiments, a temperature calibration procedure is used to generate a temperature calibration factor that substantially accounts for the sample temperature. For example, the sample temperature can be measured, and the temperature calibration factor can be applied to the Sample Population and/or the Library Interferent spectral data. In some embodiments, a water or saline spectrum is subtracted from the sample spectrum to account for temperature effects of water in the sample.

In other embodiments, temperature calibration may not be used. For example, if Library Interferent spectra, Sample Population spectra, and sample spectra are obtained at approximately the same temperature, an error in a predicted analyte concentration may be within an acceptable tolerance. If the temperature at which a material sample spectrum is measured is within, or near, a temperature range (e.g., several degrees Celsius) at which the plurality of Sample Population spectra are obtained, then some analysis methods may be relatively insensitive to temperature variations. Temperature calibration may optionally be used in such analysis methods.

Figure 21:
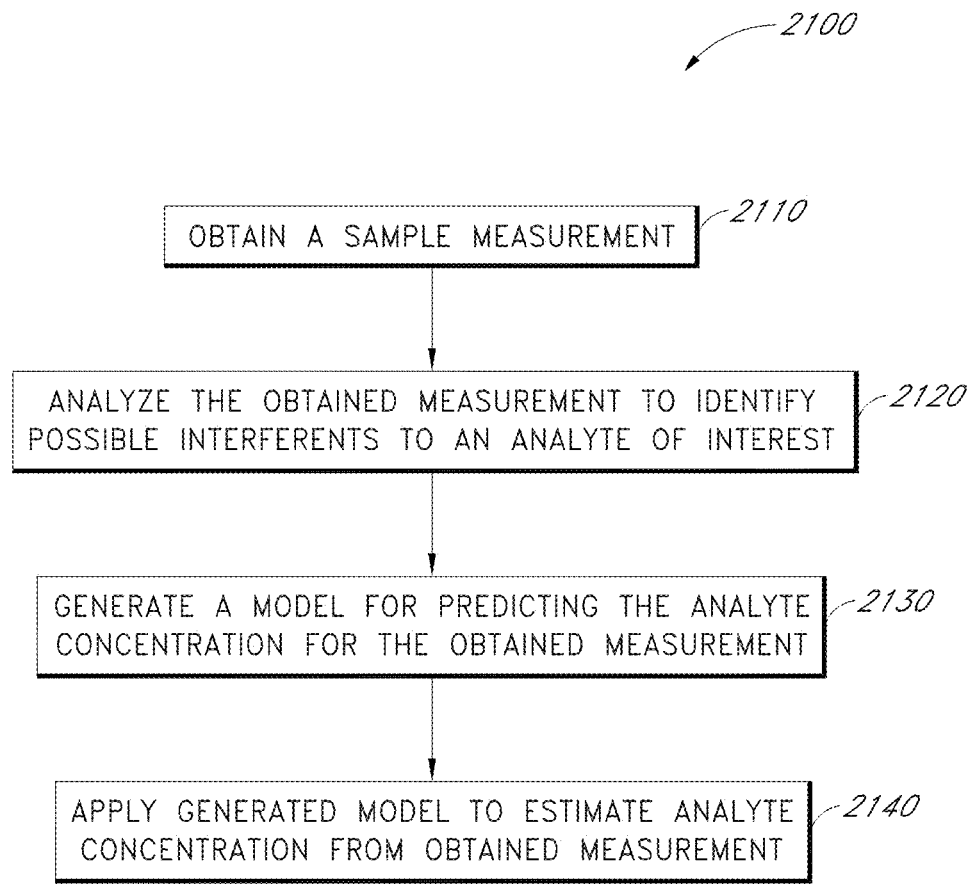
FIG. 21 is a flowchart that schematically illustrates an embodiment of a method for estimating the concentration of an analyte in the presence of interferents.

Systems and Methods for Estimating Analyte Concentration in the Presence of Interferents FIG. 21 is a flowchart that schematically illustrates an embodiment of a method 2100 for estimating the concentration of an analyte in the presence of interferents. In block 2110, a measurement of a sample is obtained, and in block 2120 data relating to the obtained measurement is analyzed to identify possible interferents to the analyte. In block 2130, a model is generated for predicting the analyte concentration in the presence of the identified possible interferents, and in block 2140 the model is used to estimate the analyte concentration in the sample from the measurement. In certain embodiments of the method 2100, the model generated in block 2130 is selected to reduce or minimize the effect of identified interferents that are not present in a general population of which the sample is a member.

An example embodiment of the method 2100 of FIG. 21 for the determination of an analyte (e.g., glucose) in a blood sample will now be described. This example embodiment is intended to illustrate various aspects of the method 2100 but is not intended as a limitation on the scope of the method 2100 or on the range of possible analytes. In this example, the sample measurement in block 2110 is an absorption spectrum, $Cs(X)$, of a measurement sample S that has, in general, one analyte of interest, glucose, and one or more interferents.

In block 2120, a statistical comparison of the absorption spectrum of the sample S with a spectrum of the Sample Population and combinations of individual Library Interferent spectra is performed. The statistical comparison provides a list of Library Interferents that are possibly contained in sample S and can include either no Library Interferents or one or more Library Interferents. In this example, in block 2130, one or more sets of spectra are generated from spectra of the Sample Population and their respective known analyte concentrations and known spectra of the Library Interferents identified in block 2120. In block 2130, the generated spectra are used to calculate a model for predicting the analyte concentration from the obtained measurement. In some embodiments, the model comprises one or more calibration coefficients $\kappa(\lambda_i)$ that can be used with the sample measurements $Cs(\lambda_i)$ to provide an estimate of the analyte concentration, $g_{est}$. In block 2140, the estimated analyte concentration is determined form the model generated in block 2130. For example, in some embodiments of HLA, the estimated analyte concentration is calculated according to a linear formula: $g_{est} = \kappa(\lambda_i) \cdot C_s(\lambda_i)$. Because the absorption measurements and calibration coefficients may represent arrays of numbers, the multiplication operation indicated in the preceding formula may comprise a sum of the products of the measurements and coefficients (e.g., an inner product or a matrix product). In some embodiments, the calibration coefficient is determined so as to have reduced or minimal sensitivity to the presence of the identified Library Interferents.

Figure 22:
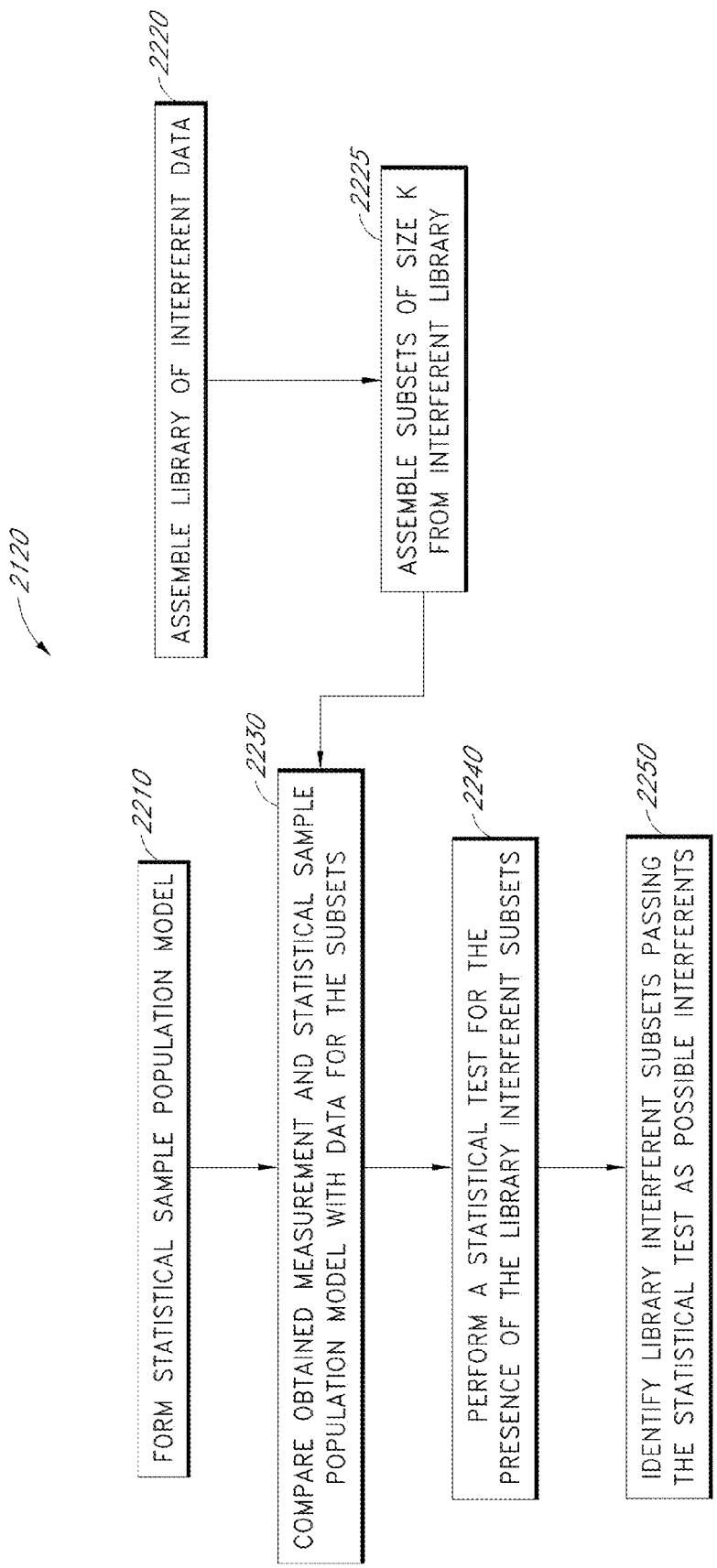
FIG. 22 is a flowchart that schematically illustrates an embodiment of a method for performing a statistical comparison of the absorption spectrum of a sample with the spectrum of a sample population and combinations of individual library interferent spectra.

An example embodiment of block 2120 of the method 2100 will now be described with reference to FIG. 22. In this example, block 2120 includes forming a statistical Sample Population model (block 2210), assembling a library of interferent data (block 2220), assembling all subsets of size K of the library interferents (block 2225), comparing the obtained measurement and statistical Sample Population model with data for each set of interferents from an interferent library (block 2230), performing a statistical test for the presence of each interferent from the interferent library (block 2240), and identifying possible interferents that pass the statistical test (block 2250). The size K of the subsets may be an integer such as, for example, 1, 2, 3, 4, 5, 6, 10, 16, or more. The acts of block 2220 can be performed once or can be updated as necessary. In certain embodiments, the acts of blocks 2230, 2240, and 2250 are performed sequentially for all subsets of Library Interferents that pass the statistical test (block 2240). In this example, in block 2210, a Sample Population Database is formed that includes a statistically large Sample Population of individual spectra taken over the same wavelength range as the sample spectrum, $C_s(\lambda_i)$. The Database also includes an analyte concentration corresponding to each spectrum. For example, if there are P Sample Population spectra, then the spectra in the Database can be represented as $C=\{C_1, C_2, \ldots, C_P\}$, and the analyte concentration corresponding to each spectrum can be represented as $g=\{g_1, g_2, \ldots, g_P\}$. In some embodiments, the Sample Population does not have any of the Library Interferents present, and the material sample has interferents contained in the Sample Population and one or more of the Library Interferents.

In some embodiments of block 2210, the statistical sample model comprises a mean spectrum and a covariance matrix calculated for the Sample Population. For example, if each spectrum measured at N wavelengths $\lambda_i$ is represented by an N×1 array, C, then the mean spectrum, $\mu$, is an N×1 array having values at each wavelength averaged over the range of spectra in the Sample Population. The covariance matrix, V, is calculated as the expected value of the deviation between C and $\mu$ and can be written as $V=E((C-\mu)(C-\mu)^T)$ where $E(\bullet)$ represents the expected value and the superscript T denotes transpose. In other embodiments, additional statistical parameters may be included in the statistical model of the Sample Population spectra.

Additionally, a Library of Interferents may be assembled in block 2220. A number of possible interferents can be identified, for example, as a list of possible medications or foods that might be ingested by the population of patients at issue. Spectra of these interferents can be obtained, and a range of expected interferent concentrations in the blood, or other expected sample material, can be estimated. In certain embodiments, the Library of Interferents includes, for each of "M" interferents, the absorption spectrum normalized to unit interferent concentration of each interferent, $IF=\{IF_1, IF_2, \ldots, IF_M\}$, and a range of concentrations for each interferent from $Tmax=\{Tmax_1, Tmax_2, \ldots, Tmax_M\}$ to $Tmin=\{Tmin_1, Tmin_2, \ldots, Tmin_M\}$. Information in the Library may be assembled once and accessed as needed. For example, the Library and the statistical model of the Sample Population may be stored in a storage device associated with the algorithm processor 416 (see, FIG. 4).

Continuing in block 2225, the algorithm processor 416 assembles one or more subsets comprising a number K of spectra taken from the Library of Interferents. The number K may be an integer such as, for example, 1, 2, 3, 4, 5, 6, 10, 16, or more. In some embodiments, the subsets comprise all combinations of the M Library spectra taken K at a time. In these embodiments, the number of subsets having K spectra is M!/(K!(M−K)!), where ! represents the factorial function.

Continuing in block 2230, the obtained measurement data (e.g., the sample spectrum) and the statistical Sample Population model (e.g., the mean spectrum and the covariance matrix) are compared with data for each subset of interferents determined in block 2225 in order to determine the presence of possible interferents in the sample (block 2240). In some embodiments, the statistical test for the presence of an interferent subset in block 2240 comprises determining the concentrations of each subset of interferences that minimize a statistical measure of "distance" between a modified spectrum of the material sample and the statistical model of the Sample Population (e.g., the mean $\mu$ and the covariance V). The term "concentration" used in this context refers to a computed value, and, in some embodiments, that computed value may not correspond to an actual concentration. The concentrations may be calculated numerically. In some embodiments, the concentrations are calculated by algebraically solving a set of linear equations. The statistical measure of distance may comprise the well-known Mahalanobis distance (or square of the Mahalanobis distance) and/or some other suitable statistical distance metric (e.g., Hotelling's T-square statistic). In certain implementations, the modified spectrum is given by $C'_s(T)=C_s-IF\cdot T$ where $T=(T_1, T_2, \ldots T_K)^T$ is a K-dimensional column vector of interferent concentrations and $IF=\{IF_1, IF_2, \ldots IF_K\}$ represents the K interferent absorption spectra of the subset. In some embodiments, concentration of the $i^{th}$ interferent is assumed to be in a range from a minimum value, $Tmin_i$, to a maximum value, $Tmax_i$. The value of $Tmin_i$ may be zero, or may be a value between zero and $Tmax_i$, such as a fraction of $Tmax_i$, or may be a negative value. Negative values represent interferent concentrations that are smaller than baseline interferent values in the Sample Population.

In block 2250, a list of a number $N_S$ of possible interferent subsets $\xi$ may be identified as the particular subsets that pass one or more statistical tests (in block 2240) for being present in the material sample. One or more statistical tests may be used, alone or in combination, to identify the possible interferents. For example, if a statistical test indicates that an $i^{th}$ interferent is present in a concentration outside the range $Tmin_i$ to $Tmax_i$, then this result may be used to exclude the $i^{th}$ interferent from the list of possible interferents. In some embodiments, only the single most probable interferent subset is included on the list, for example, the subset having the smallest statistical distance (e.g., Mahalanobis distance). In an embodiment, the list includes the subsets $\xi$ having statistical distances smaller than a threshold value. In certain embodiments, the list includes a number $N_S$ of subsets having the smallest statistical distances, e.g., the list comprises the "best" candidate subsets. The number $N_S$ may be any suitable integer such as 10, 20, 50, 100, 200, or more. An advantage of selecting the "best" $N_S$ subsets is reduced computational burden on the algorithm processor 416. In some embodiments, the list includes all the Library Interferents. In certain such embodiments, the list is selected to comprise combinations of the $N_S$ subsets taken L at a time. For example, in some embodiments, pairs of subsets are taken (e.g., L=2). An advantage of selecting pairs of subsets is that pairing captures the most likely combinations of interferents and the "best" candidates are included multiple times in the list of possible interferents. In embodiments in which combinations of L subsets are selected, the number of combinations of subsets in the list of possible interferent subsets is $N_S!/(L!(N_S-L)!)$.

In other embodiments, the list of possible interferent subsets $\xi$ is determined using a combination of some or all of the above criteria. In another embodiment, the list of possible interferent subsets $\xi$ includes each of the subsets assembled in block 2225. Many selection criteria are possible for the list of possible interferent subsets $\xi$.

Figure 23:
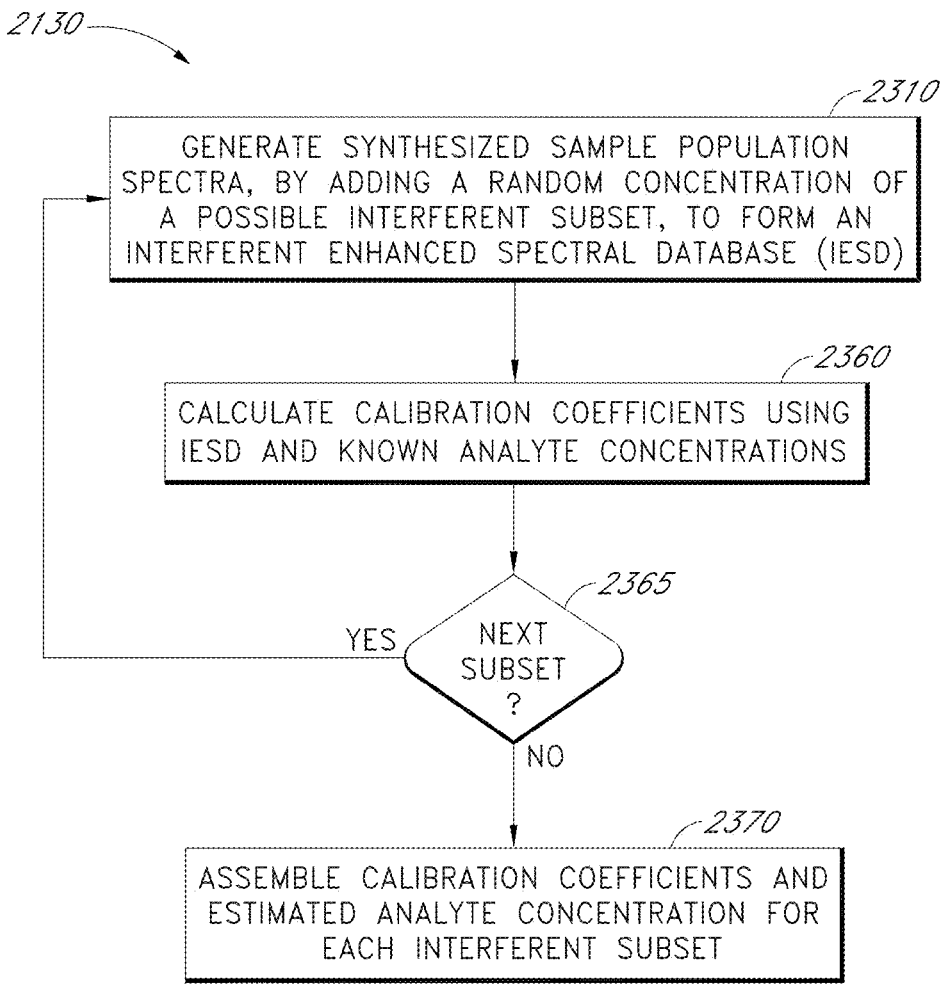
FIG. 23 is a flowchart that schematically illustrates an example embodiment of a method for estimating analyte concentration in the presence of the possible interferents.

Returning to FIG. 21, the method 2100 continues in block 2130 where analyte concentration is estimated in the presence of the possible interferent subsets $\xi$ determined in block 2250. FIG. 23 is a flowchart that schematically illustrates an example embodiment of the acts of block 2130. In block 2310, synthesized Sample Population measurements are generated to form an Interferent Enhanced Spectral Database (IESD). In block 2360, the IESD and known analyte concentrations are used to generate calibration coefficients for the selected interferent subset. As indicated in block 2365, blocks 2310 and 2360 may be repeated for each interferent subset $\xi$ identified in the list of possible interferent subsets (e.g., in block 2250 of FIG. 22). In this example embodiment, when all the interferent subsets $\xi$ have been processed, the method continues in block 2370, wherein an average calibration coefficient is applied to the measured spectra to determine a set of analyte concentrations.

In one example embodiment for block 2310, synthesized Sample Population spectra are generated by adding random concentrations of each interferent in one of the possible interferent subsets $\xi$. These spectra are referred to herein as an Interferent-Enhanced Spectral Database or IESD. In one example method, the IESD is formed as follows. A plurality of Randomly-Scaled Single Interferent Spectra (RSIS) are formed for each interferent in the interferent subset $\xi$. Each RSIS is formed by combinations of the interferent having spectrum IF multiplied by the maximum concentration Tmax, which is scaled by a random factor between zero and one. In certain embodiments, the scaling places the maximum concentration at the $95^{th}$ percentile of a log-normal distribution in order to generate a wide range of concentrations. In some embodiments, the log-normal distribution has a standard deviation equal to half of its mean value.

In this example method, individual RSIS are then combined independently and in random combinations to form a large family of Combination Interferent Spectra (CIS), with each spectrum in the CIS comprising a random combination of RSIS, selected from the full set of identified Library Interferents. An advantage of this method of selecting the CIS is that it produces adequate variability with respect to each interferent, independently across separate interferents.

The CIS and replicates of the Sample Population spectra are combined to form the IESD. Since the interferent spectra and the Sample Population spectra may have been obtained from measurements having different optical pathlengths, the CIS may be scaled to the same pathlength as the Sample Population spectra. The Sample Population Database is then replicated R times, where R depends on factors including the size of the Database and the number of interferents. The IESD includes R copies of each of the Sample Population spectra, where one copy is the original Sample Population Data, and the remaining R-1 copies each have one randomly chosen CIS spectra added. Accordingly, each of the IESD spectra has an associated analyte concentration from the Sample Population spectra used to form the particular IESD spectrum. In some embodiments, a 10-fold replication of the Sample Population Database is used for 130 Sample Population spectra obtained from 58 different individuals and 18 Library Interferents. A smaller replication factor may be used if there is greater spectral variety among the Library Interferent spectra, and a larger replication factor may be used if there is a greater number of Library Interferents.

After the IESD is generated in block 2310, in block 2360, the IESD spectra and the known, random concentrations of the subset interferents are used to generate a calibration coefficient for estimating the analyte concentration from a sample measurement. The calibration coefficient is calculated in some embodiments using a hybrid linear analysis (HLA) technique. In certain embodiments, the HLA technique uses a reference analyte spectrum to construct a set of spectra that are free of the desired analyte, projecting the analyte's spectrum orthogonally away from the space spanned by the analyte-free calibration spectra, and normalizing the result to produce a unit response. Further description of embodiments of HLA techniques may be found in, for example, "Measurement of Analytes in Human Serum and Whole Blood Samples by Near-Infrared Raman Spectroscopy," Chapter 4, Andrew J. Berger, Ph. D. thesis, Massachusetts Institute of Technology, 1998, and "An Enhanced Algorithm for Linear Multivariate Calibration," by Andrew J. Berger, et al., Analytical Chemistry, Vol. 70, No. 3, Feb. 1, 1998, pp. 623-627, the entirety of each of which is hereby incorporated by reference herein. In other embodiments, the calibration coefficients may be calculated using other techniques including, for example, regression techniques such as, for example, ordinary least squares (OLS), partial least squares (PLS), and/or principal component analysis.

In block 2365, the processor 416 determines whether additional interferent subsets $\xi$ remain in the list of possible interferent subsets. If another subset is present in the list, the acts in blocks 2310-2360 are repeated for the next subset of interferents using different random concentrations. In some embodiments, blocks 2310-2360 are performed for only the most probable subset on the list.

The calibration coefficient determined in block 2360 corresponds to a single interferent subset $\xi$ from the list of possible interferent subsets and is denoted herein as a single-interferent-subset calibration coefficient $\kappa_{avg}(\xi)$. In this example method, after all subsets $\xi$ have been processed, the method continues in block 2370, in which the single-interferent-subset calibration coefficient is applied to the measured spectra $C_s$ to determine an estimated, single-interferent-subset analyte concentration, $g(\xi)=\kappa_{avg}(\xi) \cdot C_s$, for the interferent subset $\xi$. The set of the estimated, single-interferent-subset analyte concentrations $g(\xi)$ for all subsets in the list may be assembled into an array of single-interferent-subset concentrations. As noted above, in some embodiments the blocks 2310-2370 are performed once for the most probable single-interferent-subset on the list (e.g., the array of single-interferent analyte concentrations has a single member).

Returning to block 2140 of FIG. 21, the array of single-interferent-subset concentrations, $g(\xi)$, is combined to determine an estimated analyte concentration, $g_{est}$, for the material sample. In certain embodiments, a weighting function $p(\xi)$ is determined for each of the interferent subsets $\xi$ on the list of possible interferent subsets. The weighting functions may be normalized such that $\Sigma p(\xi)=1$, where the sum is over all subsets $\xi$ that have been processed from the list of possible interferent subsets. In some embodiments, the weighting functions can be related to the minimum Mahalanobis distance or an optimal concentration. In certain embodiments, the weighting function $p(\xi)$, for each subset $\xi$, is selected to be a constant, e.g., $1/N_S$ where $N_S$ is the number of subsets processed from the list of possible interferent subsets. In other embodiments, other weighting functions $p(\xi)$ can be selected.

In certain embodiments, the estimated analyte concentration, $g_{est}$, is determined (in block 2140) by combining the single-interferent-subset estimates, $g(\xi)$, and the weighting functions, $p(\xi)$, to generate an average analyte concentration. The average concentration may be computed according to $g_{est}=\Sigma g(\xi) p(\xi)$, where the sum is over the interferent subsets processed from the list of possible interferent subsets. In some embodiments, the weighting function $p(\xi)$ is a constant value for each subset (e.g., a standard arithmetic average is used for determining average analyte concentration). By testing the above described example method on simulated data, it has been found that the average analyte concentration advantageously has errors that may be reduced in comparison to other methods (e.g., methods using only a single most probable interferent).

Although the flowchart in FIG. 21 schematically illustrates an embodiment of the method 2100 performed with reference to the blocks 2110-2140 described herein, in other embodiments, the method 2100 can be performed differently. For example, some or all of the blocks 2110-2140 can be combined, performed in a different order than shown, and/or the functions of particular blocks may be reallocated to other blocks and/or to different blocks. Embodiments of the method 2100 may utilize different blocks than are shown in FIG. 21.

For example, in some embodiments of the method 2100, the calibration coefficient is computed without synthesizing spectra and/or partitioning the data into calibration sets and test sets. Such embodiments are referred to herein as "Parameter-Free Interferent Rejection" (PFIR) methods. In one example embodiment using PFIR, for each of the possible interferent subsets $\xi$, the following calculations may be performed to compute an estimate of a calibration coefficient for each subset $\xi$. An average concentration may be estimated according to $g_{est} = \Sigma g(\xi) p(\xi)$, where the sum is over the interferent subsets processed from the list of possible interferent subsets.

An example of an alternative embodiment of block 2130 includes the following steps and calculations.

Step 1: For a subset's $N_{IF}$ interferents, form a scaled interferent spectra matrix. In certain embodiments, the scaled interferent spectra matrix is the product of an interferent spectral matrix, IF, multiplied by an interferent concentration matrix, $T_{max}$, and can be written as: IF $T_{max}$. In certain such embodiments, the interferent concentration matrix $T_{max}$ is a diagonal matrix having entries given by the maximum plasma concentrations for the various interferents.

Step 2: Calculate a covariance for the interferent component. If X denotes the IESD, the covariance of X, cov(X), is defined as the expectation $E((X-\text{mean}(X))(X-\text{mean}(X))^T)$ and is $$\text{cov}(X) \approx X X^T/(N-1) - \text{mean}(X)\text{mean}(X)^T.$$

As described above, the IESD (e.g., X) is obtained as a combination of Sample Population Spectra, C, with Combination Interferent Spectra (CIS): $X_j = C_j + IF_j \xi_j$ therefore the covariance is:

$$\text{cov}(X) \approx C C^T/(N-1) + IF \Xi\Xi^T IF^T/(N-1) - \text{mean}(X)\text{mean}(X)^T,$$

which can be written as, $$\text{cov}(X) \approx \text{cov}(C) + IF\, \text{cov}(\Xi) IF^T.$$

If the weights in the weighting matrix $\Xi$ are independent and identically distributed, the covariance of $\Xi$, cov($\Xi$), is a diagonal matrix having along the diagonal the variance, v, of the samples in $\Xi$. The last equation may be written as $$\text{cov}(X) \approx V_0 + v\Phi,$$

where $V_0$ is the covariance of the original sample population and $\Phi$ is the covariance of the IF spectral set.

Step 3: The group's covariance may be at least partially corrected for the presence of a single replicate of the Sample Population spectra with the IESD as formed from $N_{IF}$ replicates of the Sample Population Spectra with Combined Interferent Spectra. This partial correction may be achieved by multiplying the second term in the covariance formula given above by a correction factor $\rho$:

$$V = V_0 + \rho v\Phi,$$

where $\rho$ is a scalar weighting function that depends on the number of interferents in the group. In some embodiments, the scalar weighting function is $\rho = N_{IF}/(N_{IF}+1)$. In certain embodiments, the variance v of the weights is assumed to be the variance of a log-normal random variable having a 95th percentile at a value of 1.0, and a standard deviation equal to half of the mean value.

Step 4: The eigenvectors and the corresponding eigenvalues of the covariance matrix V are determined using any suitable linear algebraic methods. The number of eigenvectors (and eigenvalues) is equal to the number of wavelengths L in the spectral measurements. The eigenvectors may be sorted based on decreasing order of their corresponding eigenvalues.

Step 5: The matrix of eigenvectors is decomposed so as to provide an orthogonal matrix Q. For example, in some embodiments, a QR-decomposition is performed, thereby yielding the matrix Q having orthonormal columns and rows.

Step 6: The following matrix operations are performed on the orthogonal matrix Q. For n=2 to L−1, the product $P^{\|}_n = Q(:,1:n) Q(:,1:n)^T$ is calculated, where $Q(:,1:n)$ denotes the submatrix comprising the first n columns of the full matrix Q. The orthogonal projection, $P^{\perp}_n$, away from the space spanned by $Q(:,1:n)$ is determined by subtracting $P^{\|}_n$ from the L×L identity matrix I. The $n^{th}$ calibration vector is then determined from $\kappa_n = P^{\perp}_n \alpha_X / \alpha_X^T P^{\perp}_n \alpha_X$, and the $n^{th}$ error variance $E_n$ is determined as the projection of the full covariance V onto the subspace spanned by $\kappa_n$ as follows: $E_n = \kappa_n^T V \kappa_n$.

The steps 4-6 of this example are an embodiment of the HLA technique.

In some embodiments, the calibration coefficient $\kappa$ is selected as the calibration vector corresponding to the minimum error variance $E_n$. Thus, for example, the average group calibration coefficient $\kappa$ may be found by searching among all the error variances for the error variance $E_n$ that has the minimum value. The calibration coefficient is then selected as the $n^{th}$ calibration vector $\kappa_n$ corresponding to the minimum error variance $E_n$. In other embodiments, the calibration coefficient is determined by averaging some or all of the calibration vectors $\kappa_n$.

Examples of Algorithm Results and Effects of Sample Population

Embodiments of the above-described methods have been used to estimate blood plasma glucose concentrations in humans. Four example experiments will now be described. The population of individuals from whom samples were obtained for analysis (estimation of glucose concentration) will be referred to as the "target population." Infrared spectra obtained from the target population will be referred to as the "target spectra." In the four example experiments, the target population included 41 intensive care unit (ICU) patients. Fifty-five samples were obtained from the target population.

Example Experiment 1

In this example experiment, a partial least squares (PLS) regression method was applied to the infrared target spectra of the target patients' blood plasma to obtain the glucose estimates. In example experiment 1, estimated glucose concentration was not corrected for effects of interferents. The Sample Population used for the analysis included infrared spectra and independently measured glucose concentrations for 92 individuals selected from the general population. This Sample Population will be referred to as a "Normal Population."

Figure 23A:
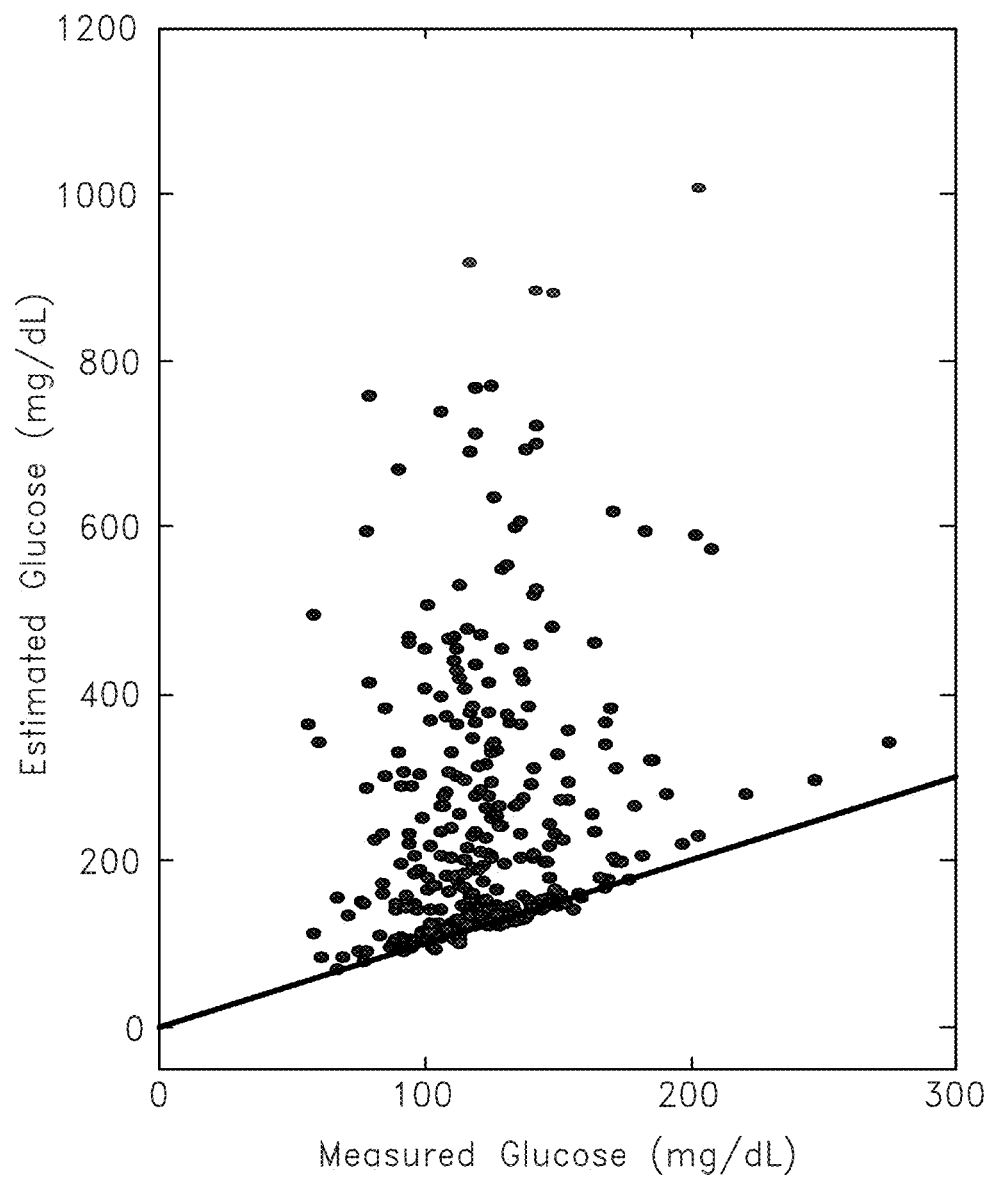
FIGS. 23A through 23D illustrate different examples of the results obtained by using various algorithms to estimate the concentration of an analyte in a sample.

FIG. 23A plots predicted versus measured glucose measurements for 55 measurements taken from 41 intensive care unit (ICU) patients. PLS regression method was applied to the infrared spectra of the patients' blood plasma to obtain the glucose measurements. In the example depicted in FIG. 23A, the Sample Population measurements include infrared spectra measurements and independently measured glucose concentrations for 92 individuals selected from the general population. This Sample Population is referred to herein, without limitation, as a "Normal Population." Some embodiments of a method can calculate the calibration constants that correspond to the infrared spectra of the Normal Population to obtain the predicted value of the glucose concentration. The population whose infrared spectra are intended to be analyzed by the analysis device and whose glucose concentration is intended to be predicted therefrom will be referred to herein as a "target population." The infrared spectra of that target population is referred to herein as the "target spectra".

From FIG. 23A it is observed that the estimated glucose values in the blood plasma of ICU patients do not always correspond to the measured glucose values. If the estimated glucose values matched the measured glucose values then all the dots would lie on the straight line 2380. The estimated or predicted glucose values have an average prediction error of 126 mg/dl and a standard deviation of prediction error of 164 mg/dl. Possible reasons for the high average prediction error and high standard deviation of prediction error could be a result of using a Sample Population that includes only the Normal Population and the fact that the predicted values were not corrected for possible interferents.

Example Experiment 2

Figure 23B:
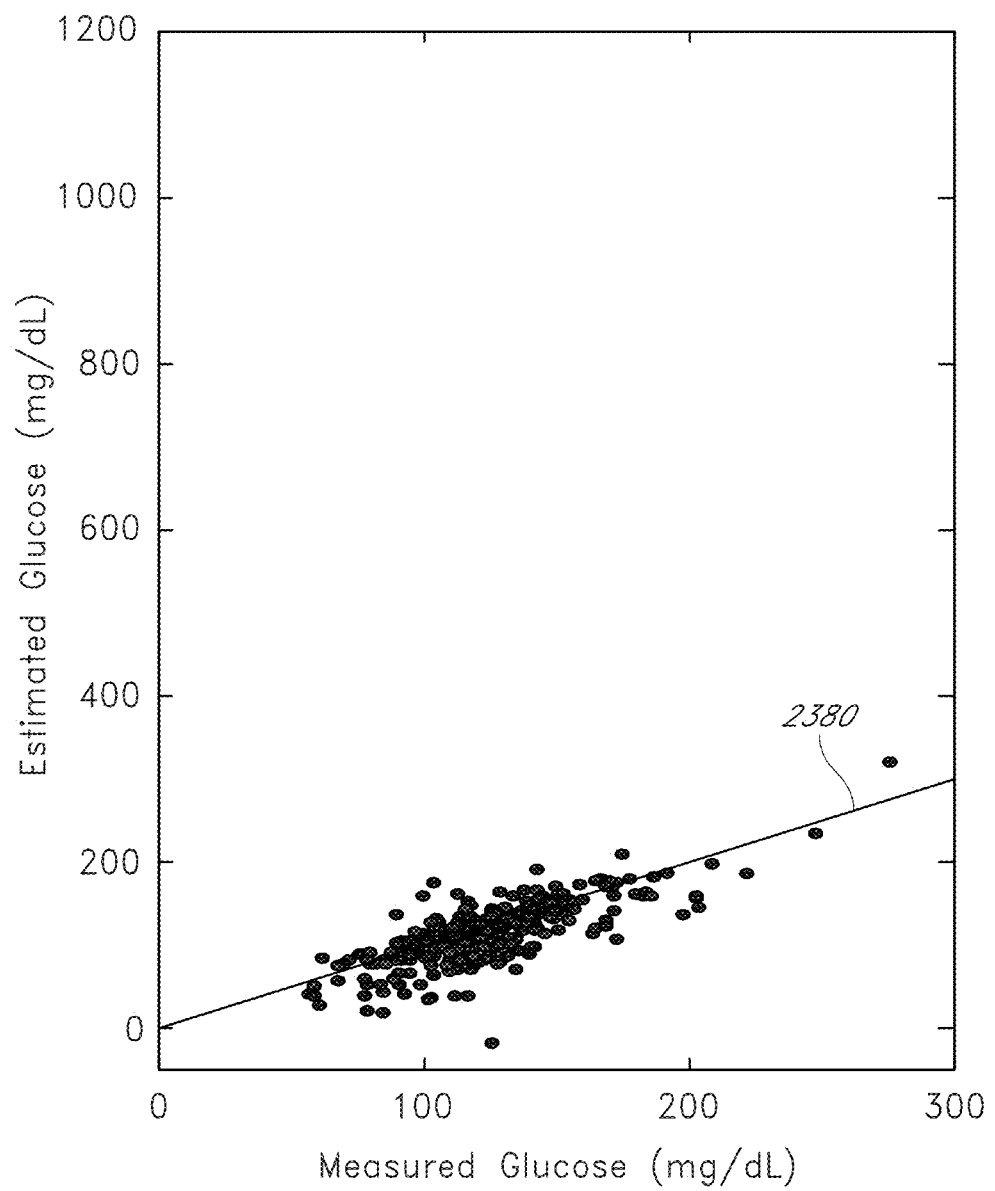

In example experiment 2, an embodiment of the Parameter-Free Interferent Rejection (PFIR) method was used to estimate glucose concentration for the same target population of patients in example experiment 1. To achieve better correlation between the predicted glucose value and the measured glucose value, a PFIR method can be applied to infrared spectra of the patient's blood plasma and the prediction can be corrected for interfering substances (e.g., those present in a library of interferents). FIG. 23B plots the predicted versus independently measured glucose values for the same patients as those of FIG. 23A, except that this time, the predicted glucose values are obtained using a PFIR method, and the prediction is corrected for interfering substances. The Sample Population was the Normal Population. In this example, calibration for Library Interferents was applied to the measured target spectra. The Library of Interferents included spectra of the 59 substances listed below:

| | | |
|---|---|---|
| Acetylsalicylic Acid | Hetastarch | Pyruvate Sodium |
| Ampicillin Sulbactam | Human Albumin | Pyruvic Acid |
| Azithromycin | Hydroxy Butyric Acid | Salicylate Sodium |
| Aztreonam | Imipenem Cilastatin | Sodium Acetate |
| Bacitracin | Iohexol | Sodium Bicarbonate |
| Benzyl Alcohol | L_Arginine | Sodium Chloride |
| Calcium Chloride | Lactate Sodium | Sodium Citrate |
| Calcium Gluconate | Magnesium Sulfate | Sodium Thiosulfate |
| Cefazolin | Maltose | Sulfadiazine |
| Cefoparazone | Mannitol | Urea |
| Cefotaxime Sodium | Meropenem | Uric Acid |
| Ceftazidime | Oxylate Potassium | Voriconazole |
| Ceftriaxone | Phenytoin | Xylitol |
| D_Sorbitol | Phosphates Potassium | Xylose |
| Dextran | Piperacillin | PC 1 of Saline covariance |
| Ertapenem | Piperacillin Tazobactam | PC 2 of Saline covariance |
| Ethanol | PlasmaLyteA | PC 3 of Saline covariance |
| Ethosuximide | Procaine HCl | PC 4 of Saline covariance |
| Glycerol | Propylene Glycol | ICU/Normal difference spectrum |
| Heparin | Pyrazinamide | |

In some embodiments, the calibration data set is determined according to two criteria: the calibration method itself (e.g., HLA, PLS, OLS, PFIR) and the intended application of the method. The calibration data set may comprise spectra and corresponding analyte levels derived from a set of plasma samples from the Sample Population. In some embodiments, e.g., those where an HLA calibration method is used, the calibration data set may also include spectra of the analyte of interest.

From FIG. 23B it is observed that by including the spectral effects of the interferents in the above table, the predicted glucose values are closer to the measured glucose values. The average prediction error in this case is approximately −6.8 mg/dL and the standard deviation of the prediction error is approximately 23.2 mg/dL. The difference in the average prediction error and the standard deviation of prediction error between FIG. 23A and FIG. 23B illustrates that the prediction is greatly improved when the model includes the effects of possible interferents.

In the example experiments 1 and 2, the Sample Population was the Normal Population. Thus, samples were drawn from a population of normal individuals who did not have identifiable medical conditions that might affect the spectra of their plasma samples. For example, the sample plasma spectra typically did not show effects of high levels of medications or other substances (e.g., ethanol), or effects of chemicals that are indicative of kidney or liver malfunction. Similarly, in the data presented in FIGS. 23A and 23B, the Sample Population samples are drawn from a population of normal individuals. These individuals do not have identifiable medical conditions that might affect the spectra of their plasma, for example, the spectra of their plasma may not exhibit high plasma levels of medications or other substances such as ethanol, or other chemicals that are indicative of kidney or liver malfunction.

In some embodiments, an analysis method may calibrate for deviations from the distribution defined by the calibration plasma spectra by identifying a "base" set of interferent spectra likely to be responsible for the deviation. The analysis method may then recalibrate with respect to an enhanced spectral data set. In some embodiments, the enhancement can be achieved by including the identified interferent spectra into the calibration plasma spectra. When it is anticipated that the target population may have been administered significant amounts of substances not present in the samples of the calibration set, or when the target population have many distinct interferents, estimation of the interferents present in the target spectrum may be subject to a large degree of uncertainty. In some cases, this may cause analyte estimation to be subject to errors.

Accordingly, in certain embodiments, the calibration data set may be enhanced beyond the base of "normal" samples to include a population of samples intended to be more representative of the target population. The enhancement of the calibration set may be generated, in some embodiments, by including samples from a sufficiently diverse range of individuals in order to represent the range of likely interferents (both in type and in concentration) and/or the normal variability in underlying plasma characteristics. The enhancement may, additionally or alternatively, be generated by synthesizing interferent spectra having a range of concentrations as described above (see, e.g., discussion of block 2310 in FIG. 23). Using the enhanced calibration set may reduce the error in estimating the analyte concentration in the target spectra.

Example Experiments 3 and 4

Example experiments 3 and 4 use the analysis methods of example experiments 1 and 2, respectively (PLS without interferent correction and PFIR with interferent correction). However, example experiments 3 and 4 use a Sample Population having blood plasma spectral characteristics different from the Normal Population used in example experiments 1 and 2. In example experiments 3 and 4, the Sample Population was modified to include spectra of both the Normal Population and spectra of an additional population of 55 ICU patients. These spectra will be referred to as the "Normal+Target Spectra." In experiments 3 and 4, the ICU patients included Surgical ICU patients, Medical ICU patients as well as victims of severe trauma, including a large proportion of patients who had suffered major blood loss. Major blood loss may necessitate replacement of the patient's total blood volume multiple times during a single day and subsequent treatment of the patient via electrolyte and/or fluid replacement therapies. Major blood loss may also require administration of plasma-expanding medications. Major blood loss may lead to significant deviations from the blood plasma spectra representative of a Normal Population. The population of 55 ICU patients (who provided the Target Spectra) has some similarities to the individuals for whom the analyses in experiments 1-4 were performed (e.g., all were ICU patients), but in these experiments, target spectra from individuals in the target population were not included in the Target Spectra.

Figure 23C:
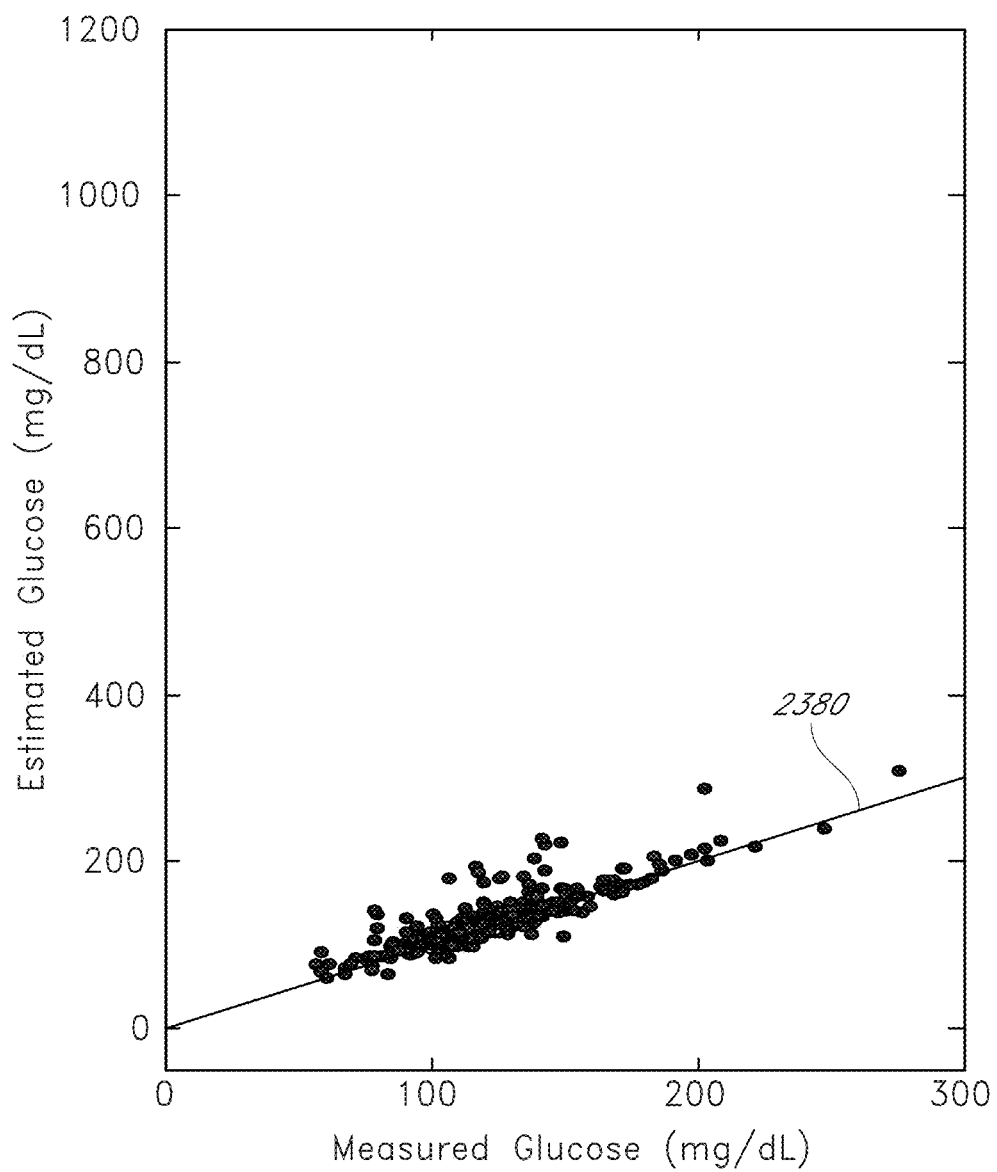
Figure 23D:
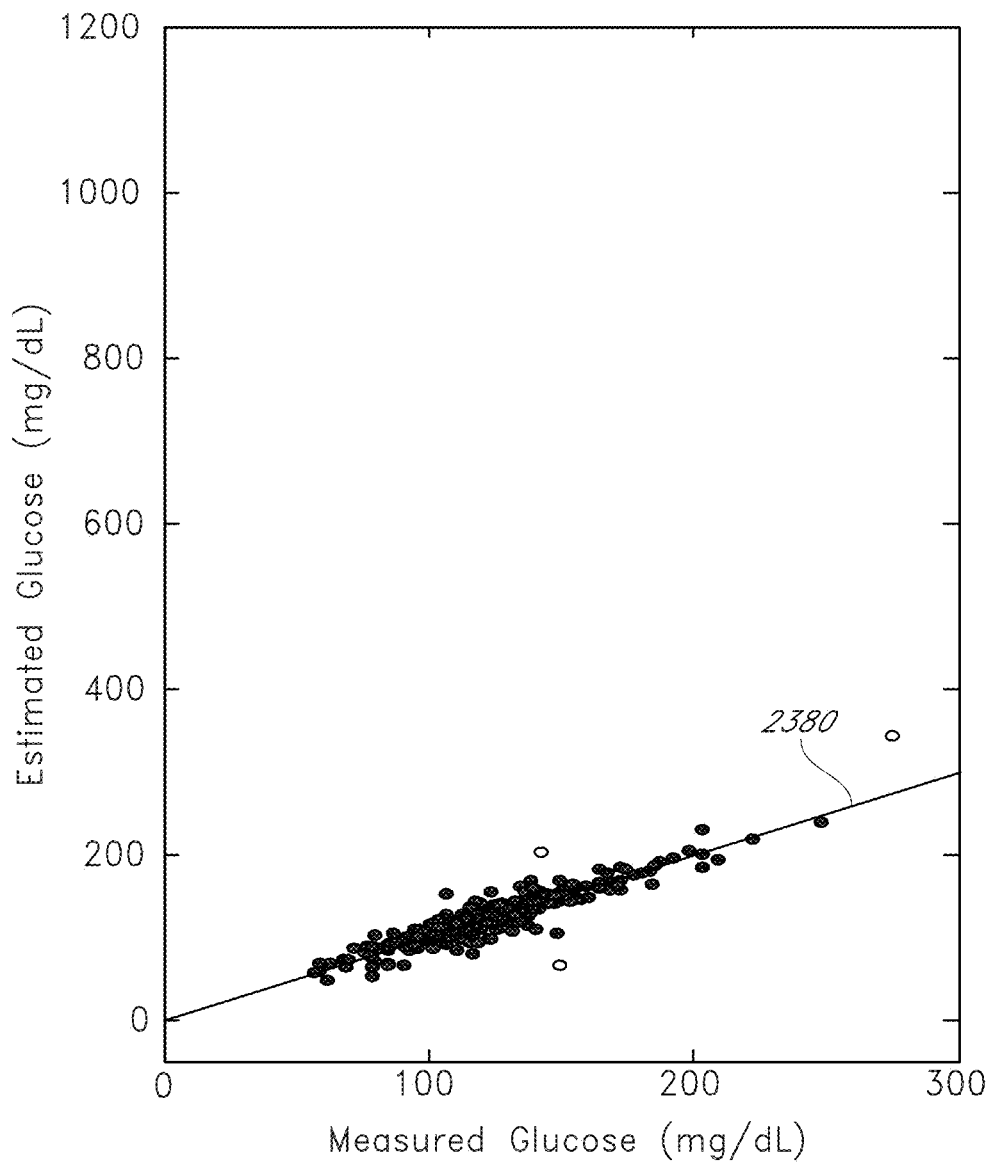

FIG. 23C and FIG. 23D illustrate the principles discussed with respect to Experiments 3 and 4. Specifically, to obtain the data presented in FIG. 23C, the method used to obtain the data of FIG. 23A is modified to include spectra of both Normal Population members and spectra of 55 ICU patients. (The target population, for such a method, can advantageously comprise ICU patients. For example, the spectra obtained from a target population of ICU patients can be similar in many ways to the spectra obtained from the 55 ICU patients.) This combined set of Spectra is referred to herein as the "Normal+Target Spectra." In this particular study, the ICU was a major trauma center, and the ICU patients were all victims of severe trauma, including a large proportion of patients who had suffered major blood loss. In such cases, researchers generally agree that this degree of blood loss—which may necessitate replacement of the patient's total blood volume multiple times during a single day and subsequent treatment of the patient via electrolyte/fluid replacement and the administration of plasma-expanding medications—can lead to significant spectral deviations from the blood plasma spectra of a Normal Population. A comparison of FIG. 23A and FIG. 23C shows that the predicted glucose values match the measured glucose values to a greater extent in FIG. 23C than in FIG. 23A. Statistical analysis of the data presented in FIG. 23C shows that the average prediction error of the predicted glucose value is approximately 8.2 mg/dl and the standard deviation of the prediction error is approximately 16.9 mg/dl. It should be noted that in predicting the glucose value in FIG. 23C, the presence of interferents was not taken into account.

The data shown in FIG. 23D, is obtained by modifying the method used to obtain the data for FIG. 23B (which included correction for possible interferents) to include spectra of the "Normal+Target Spectra." A comparison of FIG. 23B and FIG. 23D shows that the predicted glucose values match the measured glucose values to a greater extent in FIG. 23D than in FIG. 23B. Statistical analysis of the data presented in FIG. 23D shows that in this example, the average prediction error of the predicted glucose value is approximately 1.32 mg/dl and the standard deviation of the prediction error is approximately 12.6 mg/dl. It can be concluded from this example that determining calibration constants from a population that includes both normal spectra and spectra derived from individuals similar to those of the target population, and also correcting for possible interferents, provides a good match between the estimated value and the measured value.

Results of example experiments 1-4 are shown in the following table. The glucose concentrations estimated from the analysis method were compared to independently determined glucose measurements to provide an average prediction error and a standard deviation of the average prediction error. The table demonstrates that independent of the Sample Population used (e.g., either the Normal Population or the Normal+Target Population), calibrating for interferents reduces both the average prediction error and the standard deviation (e.g., compare the results for experiment 2 to the results for experiment 1 and compare the results for experiment 4 to the results for experiment 3). The table further demonstrates that independent of the analysis method used (e.g., either PLS or PFIR), using a Sample Population with more similarity to the target population (e.g., the Normal+Target Population) reduces both the average prediction error and the standard deviation (e.g., compare the results for experiment 3 to the results for experiment 1 and compare the results for experiment 4 to the results for experiment 2).

| Example Experiment No. | Interferent Calibration | Sample Population | Average Prediction Error (mg/dL) | Standard Deviation (mg/dL) |
| --- | --- | --- | --- | --- |
| 1 | NO | Normal | 126 | 164 |
| 2 | YES | Normal | −6.8 | 23.2 |
| 3 | NO | Normal + Target | 8.2 | 16.9 |
| 4 | YES | Normal + Target | 1.32 | 12.6 |

Accordingly, embodiments of analysis methods that use a Sample Population that includes both normal spectra and spectra from individuals similar to those of the target population and that calibrate for possible interferents provide a good match between the estimated glucose concentration and the measured glucose concentration. As discussed above, a suitable Sample Population may be assembled from the Population Database in order to include normal spectra plus suitable target spectra from individuals that match a desired target population including, for example, ICU patients, trauma patients, a particular demographic group, a group having a common medical condition (e.g., diabetes), and so forth.

User Interface

The system 400 can include a display system 414, for example, as depicted in FIG. 4. The display system 414 may comprise an input device including, for example, a keypad or a keyboard, a mouse, a touchscreen display, and/or any other suitable device for inputting commands and/or information. The display system 414 may also include an output device including, for example, an LCD monitor, a CRT monitor, a touchscreen display, a printer, and/or any other suitable device for outputting text, graphics, images, videos, etc. In some embodiments, a touchscreen display is advantageously used for both input and output.

The display system 414 can include a user interface 2400 by which users can conveniently and efficiently interact with the system 400. The user interface 2400 may be displayed on the output device of the system 400 (e.g., the touchscreen display). In some embodiments, the user interface 2400 is implemented and/or stored as one or more code modules, which may be embodied in hardware, firmware, and/or software.

FIGS. 24 and 25 schematically illustrate the visual appearance of embodiments of the user interface 2400. The user interface 2400 may show patient identification information 2402, which can include patient name and/or a patient ID number. The user interface 2400 also can include the current date and time 2404. An operating graphic 2406 shows the operating status of the system 400. For example, as shown in FIGS. 24 and 25, the operating status is "Running," which indicates that the system 400 is fluidly connected to the patient ("Jill Doe") and performing normal system functions such as infusing fluid and/or drawing blood. The user interface 2400 can include one or more analyte concentration graphics 2408, 2412, which may show the name of the analyte and its last measured concentration. For example, the graphic 2408 in FIG. 24 shows "Glucose" concentration of 150 mg/dL, while the graphic 2412 shows "Lactate" concentration of 0.5 mmol/L. The particular analytes displayed and their measurement units (e.g., mg/dL, mmol/L, or other suitable unit) may be selected by the user. The size of the graphics 2408, 2412 may be selected to be easily readable out to a distance such as, e.g., 30 feet. The user interface 2400 may also include a next-reading graphic 2410 that indicates the time until the next analyte measurement is to be taken. In FIG. 24, the time until next reading is 3 minutes, whereas in FIG. 25, the time is 6 minutes, 13 seconds.

The user interface 2400 can include an analyte concentration status graphic 2414 that indicates status of the patient's current analyte concentration compared with a reference standard. For example, the analyte may be glucose, and the reference standard may be a hospital ICU's tight glycemic control (TGC). In FIG. 24, the status graphic 2414 displays "High Glucose," because the glucose concentration (150 mg/dL) exceeds the maximum value of the reference standard. In FIG. 25, the status graphic 2414 displays "Low Glucose," because the current glucose concentration (79 mg/dL) is below the minimum reference standard. If the analyte concentration is within bounds of the reference standard, the status graphic 2414 may indicate normal (e.g., "Normal Glucose"), or it may not be displayed at all. The status graphic 2414 may have a background color (e.g., red) when the analyte concentration exceeds the acceptable bounds of the reference standard.

The user interface 2400 can include one or more trend indicators 2416 that provide a graphic indicating the time history of the concentration of an analyte of interest. In FIGS. 24 and 25, the trend indicator 2416 comprises a graph of the glucose concentration (in mg/dL) versus elapsed time (in hours) since the measurements started. The graph includes a trend line 2418 indicating the time-dependent glucose concentration. In other embodiments, the trend line 2418 can include measurement error bars and may be displayed as a series of individual data points. In FIG. 25, the glucose trend indicator 2416 is shown as well as a trend indicator 2430 and trend line 2432 for the lactate concentration. In some embodiments, a user may select whether none, one, or both trend indicators 2416, 2418 are displayed. In some embodiments, one or both of the trend indicators 2416, 2418 may appear only when the corresponding analyte is in a range of interest such as, for example, above or below the bounds of a reference standard.

The user interface 2400 can include one or more buttons 2420-2426 that can be actuated by a user to provide additional functionality or to bring up suitable context-sensitive menus and/or screens. For example, in the embodiments shown in FIG. 24 and FIG. 25, four buttons 2420-2426 are shown, although fewer or more buttons are used in other embodiments. The button 2420 ("End Monitoring") may be pressed when one or more removable portions (see, e.g., 710 of FIG. 7) are to be removed. In many embodiments, because the removable portions 710, 712 are not reusable, a confirmation window appears when the button 2420 is pressed. If the user is certain that monitoring should stop, the user can confirm this by actuating an affirmative button in the confirmation window. If the button 2420 were pushed by mistake, the user can select a negative button in the confirmation window. If "End Monitoring" is confirmed, the system 400 performs appropriate actions to cease fluid infusion and blood draw and to permit ejection of a removable portion (e.g., the removable portion 710).

The button 2422 ("Pause") may be actuated by the user if patient monitoring is to be interrupted but is not intended to end. For example, the "Pause" button 2422 may be actuated if the patient is to be temporarily disconnected from the system 400 (e.g., by disconnecting the tubes 306). After the patient is reconnected, the button 2422 may be pressed again to resume monitoring. In some embodiments, after the "Pause" button 2422 has been pressed, the button 2422 displays "Resume."

The button 2424 ("Delay 5 Minutes") causes the system 400 to delay the next measurement by a delay time period (e.g., 5 minutes in the depicted embodiments). Actuating the delay button 2424 may be advantageous if taking a reading would be temporarily inconvenient, for example, because a health care professional is attending to other needs of the patient. The delay button 2424 may be pressed repeatedly to provide longer delays. In some embodiments, pressing the delay button 2424 is ineffective if the accumulated delay exceeds a maximum threshold. The next-reading graphic 2410 automatically increases the displayed time until the next reading for every actuation of the delay button 2424 (up to the maximum delay).

The button 2426 ("Dose History") may be actuated to bring up a dosing history window that displays patient dosing history for an analyte or medicament of interest. For example, in some embodiments, the dosing history window displays insulin dosing history of the patient and/or appropriate hospital dosing protocols. A nurse attending the patient can actuate the dosing history button 2426 to determine the time when the patient last received an insulin dose, the last dose amount, and/or the time and amount of the next dose. The system 400 may receive the patient dosing history via wired or wireless communications from a hospital information system.

In other embodiments, the user interface 2400 can include additional and/or different buttons, menus, screens, graphics, etc. that are used to implement additional and/or different functionalities.

Related Components

Figure 26:
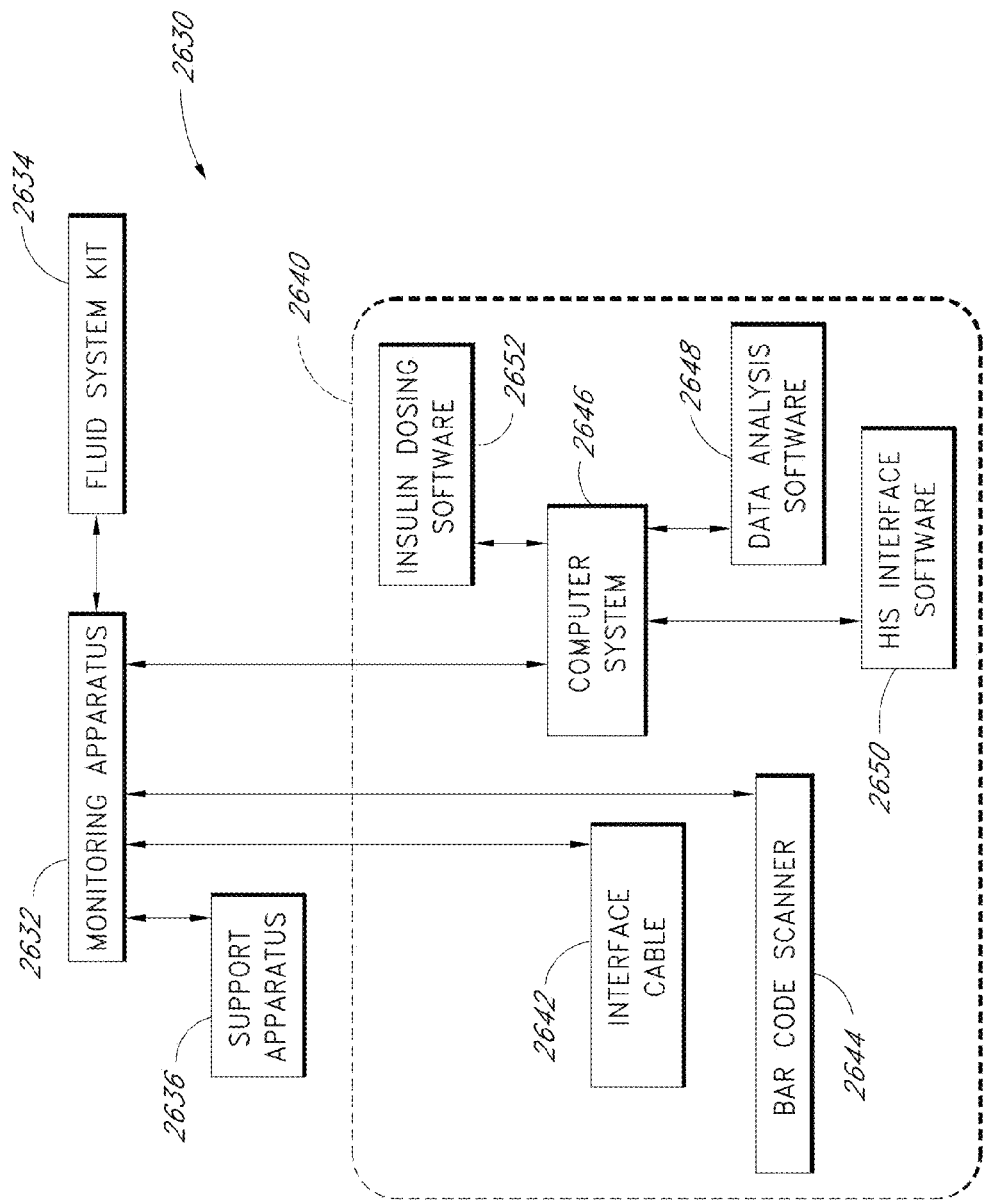
FIG. 26 schematically depicts various components and/or aspects of a patient monitoring system and the relationships among the components and/or aspects.

FIG. 26 schematically depicts various components and/or aspects of a patient monitoring system 2630 and how those components and/or aspects relate to each other. In some embodiments, the monitoring system 2630 can be the apparatus 100 for withdrawing and analyzing fluid samples. Some of the depicted components can be included in a kit containing a plurality of components. Some of the depicted components, including, for example, the components represented within the dashed rounded rectangle 2640 of FIG. 26, are optional and/or can be sold separately from other components.

The patient monitoring system 2630 shown in FIG. 26 includes a monitoring apparatus 2632. The monitoring apparatus 2632 can be the monitoring device 102, shown in FIG. 1 and/or the system 400 of FIG. 4. The monitoring apparatus 2632 can provide monitoring of physiological parameters of a patient. In some embodiments, the monitoring apparatus 2632 measures glucose and/or lactate concentrations in the patient's blood. In some embodiments, the measurement of such physiological parameters is substantially continuous. The monitoring apparatus 2632 may also measure other physiological parameters of the patient. In some embodiments, the monitoring apparatus 2632 is used in an intensive care unit (ICU) environment. In some embodiments, one monitoring apparatus 2632 is allocated to each patient room in an ICU.

The patient monitoring system 2630 can include an optional interface cable 2642. In some embodiments, the interface cable 2642 connects the monitoring apparatus 2632 to a patient monitor (not shown). The interface cable 2642 can be used to transfer data from the monitoring apparatus 2632 to the patient monitor for display. In some embodiments, the patient monitor is a bedside cardiac monitor having a display that is located in the patient room (see, e.g., the user interface 2400 shown in FIG. 24 and FIG. 25.) In some embodiments, the interface cable 2642 transfers data from the monitoring apparatus 2632 to a central station monitor and/or to a hospital information system (HIS). The ability to transfer data to a central station monitor and/or to a HIS may depend on the capabilities of the patient monitor system.

In the embodiment shown in FIG. 26, an optional bar code scanner 2644 is connected to the monitoring apparatus 2632. In some embodiments, the bar code scanner 2644 is used to enter patient identification codes, nurse identification codes, and/or other identifiers into the monitoring apparatus 2632. In some embodiments, the bar code scanner 2644 contains no moving parts. The bar code scanner 2644 can be operated by manually sweeping the scanner 2644 across a printed bar code or by any other suitable means. In some embodiments, the bar code scanner 2644 includes an elongated housing in the shape of a wand.

The patient monitoring system 2630 includes a fluid system kit 2634 connected to the monitoring apparatus 2632. In some embodiments, the fluid system kit 2634 includes fluidic tubes that connect a fluid source to an analytic subsystem. For example, the fluidic tubes can facilitate fluid communication between a blood source or a saline source and an assembly including a sample holder and/or a centrifuge. In some embodiments, the fluid system kit 2634 includes many of the components that enable operation of the monitoring apparatus 2632. In some embodiments, the fluid system kit 2634 can be used with anti-clotting agents (such as heparin), saline, a saline infusion set, a patient catheter, a port sharing IV infusion pump, and/or an infusion set for an IV infusion pump, any or all of which may be made by a variety of manufacturers. In some embodiments, the fluid system kit 2634 includes a monolithic housing that is sterile and disposable. In some embodiments, at least a portion of the fluid system kit 2634 is designed for single patient use. For example, the fluid system kit 2634 can be constructed such that it can be economically discarded and replaced with a new fluid system kit 2634 for every new patient to which the patient monitoring system 2630 is connected. In addition, at least a portion of the fluid system kit 2634 can be designed to be discarded after a certain period of use, such as a day, several days, several hours, three days, a combination of hours and days such as, for example, three days and two hours, or some other period of time. Limiting the period of use of the fluid system kit 2634 may decrease the risk of malfunction, infection, or other conditions that can result from use of a medical apparatus for an extended period of time.

In some embodiments, the fluid system kit 2634 includes a connector with a luer fitting for connection to a saline source. The connector may be, for example, a three-inch pigtail connector. In some embodiments, the fluid system kit 2634 can be used with a variety of spikes and/or IV sets used to connect to a saline bag. In some embodiments, the fluid system kit 2634 also includes a three-inch pigtail connector with a luer fitting for connection to one or more IV pumps. In some embodiments, the fluid system kit 2634 can be used with one or more IV sets made by a variety of manufacturers, including IV sets obtained by a user of the fluid system kit 2634 for use with an infusion pump. In some embodiments, the fluid system kit 2634 includes a tube with a low dead volume luer connector for attachment to a patient vascular access point. For example, the tube can be approximately seven feet in length and can be configured to connect to a proximal port of a cardiovascular catheter. In some embodiments, the fluid system kit 2634 can be used with a variety of cardiovascular catheters, which can be supplied, for example, by a user of the fluid system kit 2634.

As shown in FIG. 26, the monitoring apparatus 2632 is connected to a support apparatus 2636, such as an IV pole. The support apparatus 2636 can be customized for use with the monitoring apparatus 2632. A vendor of the monitoring apparatus 2632 may choose to bundle the monitoring apparatus 2632 with a custom support apparatus 2636. In some embodiments, the support apparatus 2636 includes a mounting platform for the monitoring apparatus 2632. The mounting platform can include mounts that are adapted to engage threaded inserts in the monitoring apparatus 2632. The support apparatus 2636 can also include one or more cylindrical sections having a diameter of a standard IV pole, for example, so that other medical devices, such as IV pumps, can be mounted to the support apparatus. The support apparatus 2636 can also include a clamp adapted to secure the apparatus to a hospital bed, an ICU bed, or another variety of patient conveyance device.

In the embodiment shown in FIG. 26, the monitoring apparatus 2632 is electrically connected to an optional computer system 2646. The computer system 2646 can comprise one or multiple computers, and it can be used to communicate with one or more monitoring devices. In an ICU environment, the computer system 2646 can be connected to at least some of the monitoring devices in the ICU. The computer system 2646 can be used to control configurations and settings for multiple monitoring devices (for example, the system can be used to keep configurations and settings of a group of monitoring devices common). The computer system 2646 can also run optional software, such as data analysis software 2648, HIS interface software 2650, and insulin dosing software 2652.

In some embodiments, the computer system 2646 runs optional data analysis software 2648 that organizes and presents information obtained from one or more monitoring devices. In some embodiments, the data analysis software 2648 collects and analyzes data from the monitoring devices in an ICU. The data analysis software 2648 can also present charts, graphs, and statistics to a user of the computer system 2646.

In some embodiments, the computer system 2646 runs optional hospital information system (HIS) interface software 2650 that provides an interface point between one or more monitoring devices and an HIS. The HIS interface software 2650 may also be capable of communicating data between one or more monitoring devices and a laboratory information system (LIS).

In some embodiments, the computer system 2646 runs optional insulin dosing software 2652 that provides a platform for implementation of an insulin dosing regimen. In some embodiments, the hospital tight glycemic control protocol is included in the software. The protocol allows computation of proper insulin doses for a patient connected to a monitoring device 2646. The insulin dosing software 2652 can communicate with the monitoring device 2646 to ensure (or at least improve the likelihood) that proper insulin doses are calculated. For example, the insulin dosing software 2652 can communicate with the computer system 2646 to perform the dosing calculations. The user interface 2400 can be used to communicate relevant information such as, for example, rate of dose and/or infusion, type of dose and/or infusion (e.g., bolus injection, basal infusion, steady state dose, treatment dose, etc.), to a health care practitioner so that the infusion rate and type of dose can be provided to the patient. The insulin dosing software 2652 and user interface can be implemented with the monitoring system 102 (FIG. 1), the system 400 (FIG. 4), or any other suitable patient monitoring system.

Analyte Control and Monitoring

In some embodiments, it can be advantageous to control a level of an analyte (e.g., glucose) in a patient using an embodiment of an analyte detection system described herein. Although certain examples of glucose control are described below, embodiments of the systems and methods disclosed herein can be used to monitor and/or control other analytes (e.g., lactate).

For example, diabetic individuals control their glucose levels by administration of insulin. If a diabetic patient is admitted to a hospital or ICU, the patient may be in a condition in which he or she cannot self-administer insulin. Advantageously, embodiments of the analyte detection systems disclosed herein can be used to control the level of glucose in the patient. Additionally, it has been found that a majority of patients admitted to the ICU exhibit hyperglycemia without having diabetes. In such patients it may be beneficial to monitor and control their blood glucose level to be within a particular range of values. Further, it has been shown that tightly controlling blood glucose levels to be within a stringent range may be beneficial to patients undergoing surgical procedures.

A patient admitted to the ICU or undergoing surgery can be administered a variety of drugs and fluids such as Hetastarch, intravenous antibiotics, intravenous glucose, intravenous insulin, intravenous fluids such as saline, etc., which may act as interferents and make it difficult to determine the blood glucose level. Moreover, the presence of additional drugs and fluids in the blood stream may require different methods for measuring and controlling blood glucose level. Also, the patient may exhibit significant changes in hematocrit levels due to blood loss or internal hemorrhage, and there can be unexpected changes in the blood gas level or a rise in the level of bilirubin and ammonia levels in the event of an organ failure. Embodiments of the systems and methods disclosed herein advantageously can be used to monitor and control blood glucose (and/or other analytes) in the presence of possible interferents to estimation of glucose and for patients experiencing health problems.

In some environments, Tight Glycemic Control (TGC) can include: (1) substantially continuous monitoring (which can include periodic monitoring, at relatively frequent intervals of every 15, 30, 45, 60, 76, and/or 90 minutes, for example) of glucose levels; (2) determination of substances that tend to increase glucose levels (e.g., sugars such as dextrose) and/or decrease glucose levels (e.g., insulin); and/or (3) responsive delivery of one or more of such substances, if appropriate under the controlling TGC protocol. For example, one possible TGC protocol can be achieved by controlling glucose within a relatively narrow range (for example between 70 mg/dL to 110 mg/dL). As will be further described, in some embodiments, TGC can be achieved by using an analyte monitoring system to make continuous and/or periodic but frequent measurements of glucose levels.

In some embodiments, the analyte detection system schematically illustrated in FIGS. 4, 5, and 6 can be used to regulate the concentration of one or more analytes in the sample in addition to determining and monitoring the concentration of the one or more analytes. In some cases, the analyte detection system can be used in an ICU to monitor (and/or control) analytes that may be present in patients experiencing trauma. In some implementations, the concentration of the analytes is regulated to be within a certain range. The range can be predetermined (e.g., according to a hospital protocol or a physician's recommendation), or the range can be adjusted as conditions change.

In an example of glycemic control, a system can be used to determine and monitor the concentration of glucose in the sample. If the concentration of glucose falls below a lower threshold, glucose from an external source can be supplied and/or delivery of insulin can be scaled back or halted altogether. Although some embodiments disclosed herein discuss using glucose in connection with providing glycemic control, it should be understood that other substances (e.g., dextrose or other sugars) can be used in place of glucose. If the concentration of glucose exceeds an upper threshold, insulin from an external source can be supplied and/or delivery of glucose can be scaled back or halted altogether. Although some embodiments disclosed herein discuss using insulin in connection with providing glycemic control, it should be understood that other substances (e.g., GLP-1 or other "insulin sensitizers") can be used in place of insulin. A treatment dose of glucose and/or insulin can be infused into a patient continuously over a certain time interval or can be injected in a relatively large quantity at once (referred to as "bolus injection"). Moreover, a steady-state or baseline (as opposed to a treatment) can be achieved as glucose and/or insulin can be infused into a patient relatively continuously at a low delivery rate (referred to as "basal infusion") to maintain the concentration of one or more analytes within a predetermined range. For example, in some cases a basal infusion can comprise a series of discrete doses designed to maintain a concentration of one or more analytes in a patient (e.g., concentration of glucose in a patient's blood stream). Such a serial infusion of discrete packets or doses can be referred to as "pulsatile" infusion. In some cases, instead of a series of discrete doses, a steady stream of infusion substance can be provided. The automatic and/or recommended basal infusion rate of glucose or insulin can be determined on the basis of one or more factors. For example, body weight, medical condition, medical history, presence or absence of other drugs and chemicals in the patient, etc. can all be factors that contribute to such a determination. Without contradicting the use of the term "basal" set forth above, the "basal infusion rate" can also refer to the rate of insulin needed to cover the "basal" metabolic functions (e.g. breathing, maintaining heart rate and other metabolic processes).

Various dosing protocols can be used to determine a dose of a treatment substance (e.g., a drug, glucose, dextrose, insulin, etc.). For example, in some embodiments, the dosing protocol used by personnel at a hospital is integrated into the glucose monitoring system to automatically determine the delivery rate of the treatment drug. In some embodiments, the system and method for recommending insulin bolus quantities to an insulin user disclosed in U.S. Pat. No. 7,291,107 B2 titled "INSULIN BOLUS RECOMMENDATION SYSTEM", by Hellwig et. al. can be used with the above described glucose monitoring system to determine the bolus dose of insulin to be delivered to the patient in the event of hyperglycemia or hypoglycemia. The entire content of U.S. Pat. No. 7,291,107 B2 is hereby incorporated by reference herein and is made a part of this specification. Additional details regarding determining a suitable dose of a treatment substance are provided in U.S. Patent Publication No. 2007/0083090, filed Dec. 21, 2005, and entitled "SYSTEM AND METHOD FOR DETERMINING A TREATMENT DOSE FOR A PATIENT," the entire disclosure of which is hereby incorporated by reference herein.

In some embodiments, a hospital dosing protocol can be integrated into a glucose monitoring and control system. For example, the protocol instructions for a nurse can be accomplished automatically by the system rather than by the nurse. In some embodiments, a hospital or other health care provider can use its own protocol and program a monitoring system to incorporate the specific protocol. The procedure outline and corresponding tables below are an example of such a dosing protocol (the example provided can be referred to as the "Atlanta Protocol" and related information publically available at the following web address: "http://www.gha.org/pha/health/diabetes/Toolkit/guidelines/IVins80110/80-110chart_ col1-16.pdf"). The following protocol can also be modified and incorporated into a monitoring system:

---

START infusion using the drip rate (ml/hr) shown in Column 2 for the current Blood Glucose Range.
To determine the new drip rate for each hourly measurement, compare the latest BG Range to the previous BG Range
If latest BG Range has decreased:
Stay in the same column
If latest BG Range has not changed or increased:
Move 1 column to the right
When hourly BG 80-110, stay in the same column to determine the new drip rate. (Do Not Change Columns)
When BG <80, move one column to the left and treat for hypoglycemia

---

| Blood Glucose Ranges | 1 (ml/hr) | 2 (ml/hr) START | 3 (ml/hr) | 4 (ml/hr) | 5 (ml/hr) | 6 (ml/hr) | 7 (ml/hr) | 8 (ml/hr) | 9 (ml/hr) | 10 (ml/hr) |
|---|---|---|---|---|---|---|---|---|---|---|
| >450 | 4.4 | 8.8 | 13.2 | 17.6 | 22.0 | 26.4 | 30.8 | 35.2 | 39.6 | 44.0 |
| 385-450 | 3.6 | 7.2 | 10.8 | 14.4 | 18.0 | 21.6 | 25.2 | 28.8 | 32.4 | 36.0 |
| 326-384 | 3.0 | 6.0 | 9.0 | 12.0 | 15.0 | 18.0 | 21.0 | 24.0 | 27.0 | 30.0 |
| 290-333 | 2.5 | 5.0 | 7.5 | 10.0 | 12.5 | 15.0 | 17.5 | 20.0 | 22.5 | 25.0 |
| 251-289 | 2.1 | 4.2 | 6.3 | 8.4 | 10.5 | 12.6 | 14.7 | 16.8 | 18.9 | 21.0 |
| 217-250 | 1.7 | 3.4 | 5.1 | 7.2 | 8.5 | 10.2 | 11.9 | 13.6 | 15.3 | 17.0 |
| 188-216 | 1.4 | 2.8 | 4.2 | 5.6 | 7.0 | 8.4 | 9.8 | 11.2 | 12.6 | 14.0 |
| 163-187 | 1.2 | 2.4 | 3.6 | 4.8 | 6.0 | 7.2 | 8.4 | 9.6 | 10.8 | 12.0 |
| 141-162 | 1.0 | 2.0 | 3.0 | 4.0 | 5.0 | 6.0 | 7.0 | 8.0 | 9.0 | 10.0 |
| 119-140 | 0.8 | 1.6 | 2.4 | 3.2 | 4.0 | 4.8 | 5.6 | 6.4 | 7.2 | 8.0 |
| 111-120 | 0.6 | 1.2 | 1.8 | 2.4 | 3.0 | 3.6 | 4.2 | 4.8 | 5.4 | 6.0 |
| 106-110 | 0.5 | 1.0 | 1.5 | 2.0 | 2.5 | 3.0 | 3.5 | 4.0 | 4.5 | 5.0 |
| 101-105 | 0.4 | 0.9 | 1.3 | 1.8 | 2.2 | 2.7 | 3.1 | 3.6 | 4.0 | 4.5 |
| 96-100 | 0.4 | 0.8 | 1.2 | 1.6 | 2.0 | 2.4 | 2.8 | 3.2 | 3.6 | 4.0 |
| 91-95 | 0.3 | 0.7 | 1.0 | 1.4 | 1.7 | 2.1 | 2.4 | 2.8 | 3.2 | 3.5 |
| 86-90 | 0.3 | 0.6 | 0.9 | 1.2 | 1.5 | 1.8 | 2.1 | 2.4 | 2.7 | 3.0 |
| 80-85 | 0.2 | 0.5 | 0.7 | 1.0 | 1.2 | 1.5 | 1.7 | 2.0 | 2.3 | 2.5 |
| 75-79 | 0.2 | 0.4 | 0.6 | 0.8 | 1.0 | 1.2 | 1.4 | 1.6 | 1.8 | 2.0 |
| 70-74 | 0.1 | 0.3 | 0.4 | 0.6 | 0.7 | 0.9 | 1.0 | 1.2 | 1.3 | 1.5 |
| 60-70 | 0.1 | 0.2 | 0.3 | 0.4 | 0.5 | 0.6 | 0.7 | 0.8 | 0.9 | 1.0 |
| <60 | 0 | 0 | 0 | 0 | 0 | 0 | 0 | 0 | 0 | 0 |

| BG | D50W | ACTION |
|---|---|---|
| 70-79 | 10.0 ml IV push | Move 1 column to the left |
| 60-69 | 15.0 ml IV push | Recheck BG in 15 minutes Repeat as necessary |
| 50-59 | 20.0 ml IV push | Move 1 column to the left |
| 30-49 | 25.0 ml IV push | Recheck BG in 15 minutes |
| <30 | 30.0 ml IV push | Repeat as necessary Contact Physician if BG <60 for 2 consecutive BG measurements |

| Notify Physician If: |
|---|
| BG is less <60 for 2 consecutive BG measurements |
| BG reverts to >200 for 2 consecutive BG measurements |
| Insulin requirement exceeds 24 units/hour |
| If the K+ level drops to <4 |
| If drip rate (ml/hr) is 0.5 or less |
| If continuous enteral feeding, TPN, or IV insulin infusion is stopped or interrupted |

In some embodiments, a glycemic control system is capable of delivering glucose, dextrose, glycogen, and/or glucagon from an external source relatively quickly in the event of hypoglycemia. As discussed herein, embodiments of the glycemic control system are capable of delivering insulin from an external source relatively quickly in the event of hyperglycemia.

Returning to FIGS. 5 and 6, these figures schematically illustrate embodiments of a fluid handling system that comprise optional analyte control subsystems 2780. The analyte control subsystem 2780 can be used for providing control of an analyte such as, e.g., glucose, and may provide delivery of the analyte and/or related substances (e.g., dextrose solution and/or insulin in the case of glucose). The analyte control subsystem 2780 comprises a source 2782 such as, for example, the analyte (or a suitable compound related to the analyte) dissolved in water or saline. For example, if the analyte is glucose, the source 2782 may comprise a bag of dextrose solution (e.g., Dextrose or Dextrose 50%). The source 2782 can be coupled to an infusion pump (not shown).

The source 2782 and the infusion pump can be provided separately from the analyte control subsystem 2780. For example, a hospital advantageously can use existing dextrose bags and infusion pumps with the subsystem 2780.

As schematically illustrated in FIGS. 5 and 6, the source 2782 is in fluid communication with the patient tube 512 via a tube 2784 and suitable connectors. A pinch valve 2786 can be disposed adjacent the tube 2784 to regulate the flow of fluid from the source 2782. A patient injection port can be located at a short distance from the proximal port of the central venous catheter or some other catheter connected to the patient.

In an example implementation for glycemic control, if the analyte detection system determines that the level of glucose has fallen below a lower threshold value (e.g., the patient is hypoglycemic), a control system (e.g., the fluid system controller 405 in some embodiments) controlling an infusion delivery system may close the pinch valves 521 and/or 542 to prevent infusion of insulin and/or saline into the patient. The control system may open the pinch valve 2786 and dextrose solution from the source 2782 can be infused (or alternatively injected as a bolus) into the patient. After a suitable amount of dextrose solution has been infused to the patient, the pinch valve 2786 can be closed, and the pinch valves 521 and/or 542 can be opened to allow flow of insulin and/or saline. In some systems, the amount of dextrose solution to be delivered as a basal infusion or as a bolus injection can be calculated based on one or more detected concentration levels of glucose. The source 2782 advantageously can be located at a short enough fluidic distance from the patient such that dextrose can be delivered to the patient within a time period of about one to about ten minutes of receiving an instruction (e.g. from a control system or a health care provider). In other embodiments, the source 2782 can be located at the site where the patient tube 512 interfaces with the patient so that dextrose can be delivered within about one minute of receiving an instruction (e.g. from a control system or a health care provider).

If the analyte detection system determines that the level of glucose has increased above an upper threshold value (e.g., the patient is hyperglycemic), the control system may close the pinch valves 542 and/or 2786 to prevent infusion of saline and/or dextrose into the patient. The control system may open the pinch valve 521, and insulin can be infused at a basal infusion rate (and/or injected as a bolus) into the patient. After a suitable amount of insulin has been infused (or bolus injected) to the patient, the control system can close the pinch valve 521 and open the pinch valves 542 and/or 2786 to allow flow of saline and/or glucose. The suitable amount of insulin can be calculated based on one or more detected concentration levels of glucose in the patient. In some embodiments, the insulin source can be connected to the infusion pump 518 which advantageously can be located at a short enough fluidic distance from the patient such that insulin can be delivered to the patient rapidly, e.g., within about one to about ten minutes. In some embodiments, the insulin source can be located at the site where the patient tube 512 interfaces with the patient so that insulin can be delivered to the patient rapidly, e.g., within about one minute.

In some embodiments, sampling bodily fluid from a patient and providing medication to the patient can be achieved through the same lines of the fluid handling system. For example, in some embodiments, a port to a patient can be shared by alternately drawing samples and medicating through the same line. In some embodiments, insulin can be provided to the patient at regular intervals (in the same or different lines). For example, insulin can be provided to a patient after meals. In some embodiments, the medication can be delivered to the patient continuously at a basal infusion rate combined with intermittent bolus injections (e.g. after meals). In some embodiments, the medication can be delivered through a fluid passageway connected to the patient (e.g. patient tube 512 of FIG. 5). Intermittent injections can be provided to the patient by the same fluid passageway (e.g. patient tube 512 of FIG. 5). In some embodiments, a separate delivery system comprising a delivery pump can be used to provide the medication. In some embodiments comprising a shared line, medication can be delivered when returning part of a body fluid sample back to the patient. In some implementations, medication is delivered midway between samples (e.g., every 7.5 minutes if samples are drawn every 15 minutes). In some embodiments, a dual lumen tube can be used, wherein one lumen is used for the sample and the other lumen to medicate. In some embodiments, an analyte detection system (e.g., an "OptiScanner®" monitor) may provide suitable commands to a separate insulin pump (on a shared port or different line) to provide the recommended dose of insulin. Additional details regarding the delivery of insulin (or other medicaments) through the same port used to draw samples are provided in U.S. Patent Publication No. 2008/0161723, filed Sep. 6, 2007, and entitled "INFUSION FLOW INTERRUPTION METHOD AND APPARATUS," the entire disclosure of which is hereby incorporated by reference herein.

Example Method for Glycemic Control

Figure 27:
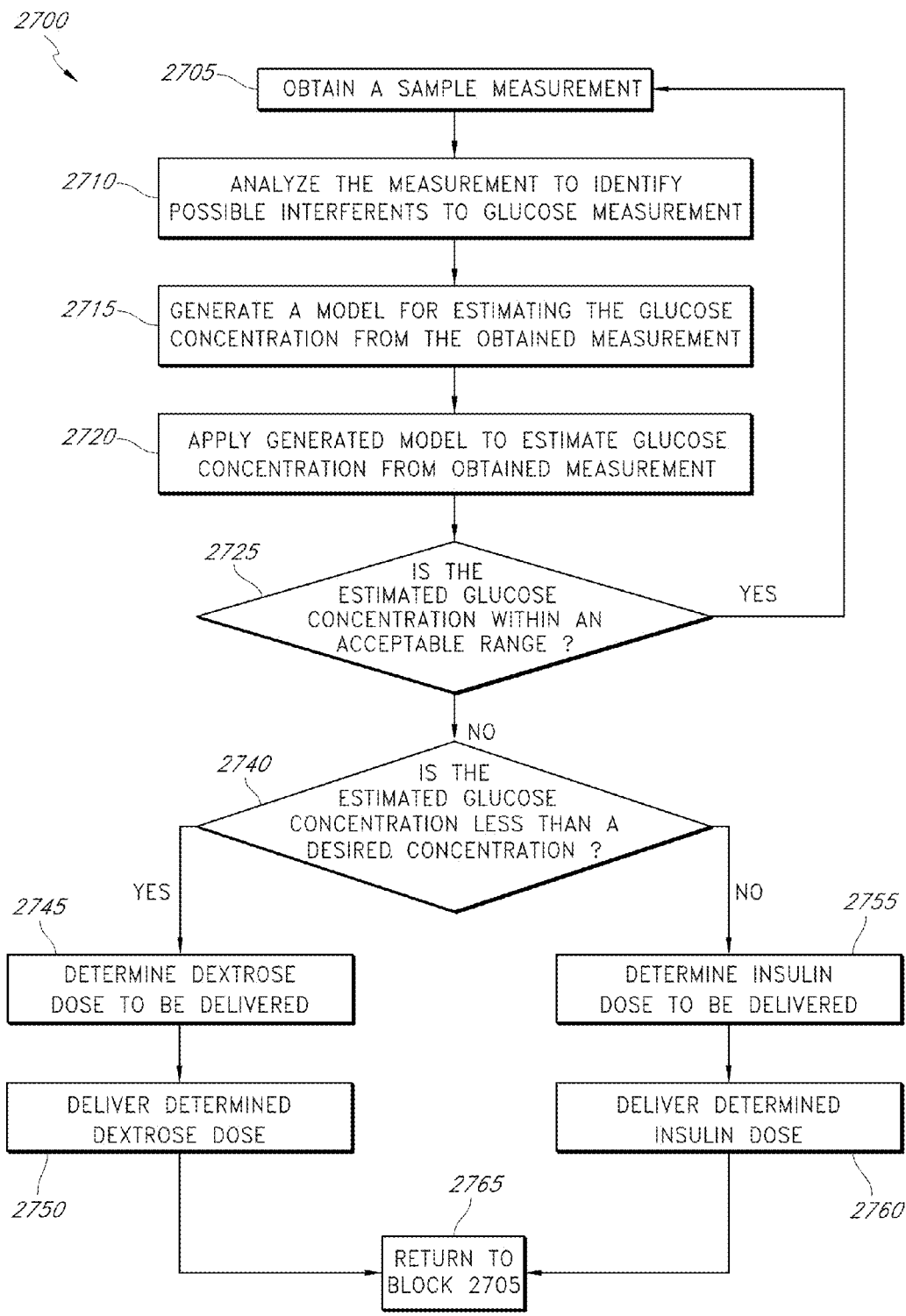
FIG. 27 is a flowchart that schematically illustrates an embodiment of a method of providing glycemic control.

FIG. 27 is a flowchart that schematically illustrates an example embodiment of a method 2700 of providing analyte control. The example embodiment is directed toward one possible implementation for glycemic control (including but not limited to tight glycemic control) and is intended to illustrate certain aspects of the method 2700 and is not intended to limit the scope of possible analyte control methods. In block 2705, a glucose monitoring apparatus (e.g., the monitoring apparatus 2632 of FIG. 26) draws a sample (e.g., a blood or blood plasma sample) from a sample source (e.g., a patient) and obtains a measurement from the sample (e.g., a portion of the drawn sample). The measurement may comprise an optical measurement such as, for example, an infrared spectrum of the sample. In block 2710, the measurement sample is analyzed to identify possible interferents to an estimation of the glucose concentration in the measurement sample. In block 2715, a model is generated for estimating the glucose concentration from the obtained measurement. In some embodiments, models developed from the algorithms describe above with reference to FIGS. 21-23 are used. The generated model may reduce or minimize effects of the identified interferents on the estimated glucose concentration, in certain embodiments. In block 2720, an estimated glucose concentration is determined from the model and the obtained measurement. In block 2725, the estimated glucose concentration in the sample is compared to an acceptable range of concentrations. The acceptable range can be determined according to a suitable glycemic control protocol such as, for example, a TGC protocol. For example, in certain TGC protocols the acceptable range can be a glucose concentration in a range from about 70 mg/dL to about 110 mg/dL. If the estimated glucose concentration lies within the acceptable range, the method 2700 returns to block 2705 to obtain the next sample measurement, which can be made after a relatively short or a relatively long time period has elapsed since the last measurement. For example, the next measurement can be taken within about one minute. In another example, the succeeding measurement can be taken after about one hour. In other examples, measurements are taken every fifteen minutes or less, every thirty minutes or less, ever forty-five minutes or less, etc. In some embodiments, a treatment substance (e.g. insulin or glucose) or drug can be continuously infused through the patient even if the estimated glucose concentration is already within the predetermined range. This can be advantageous when it is determined, for example, that without such a basal injection, the glucose concentration may drift outside the range, or when it is predicted that the glucose concentration would preferably be within another range.

In block 2725, if the estimated glucose concentration is outside the acceptable range of concentrations, then the method 2700 proceeds to block 2740 in which the estimated glucose concentration is compared with a desired glucose concentration. The desired glucose concentration can be based on, for example, the acceptable range of glucose concentrations, the parameters of the particular glycemic protocol, the patient's estimated glucose concentration, and so forth. If the estimated glucose concentration is below the desired concentration (e.g., the patient is hypoglycemic), a dose of dextrose to be delivered to the patient is calculated in block 2745. In some embodiments, this dose of dextrose can be delivered in addition to a low dose of the treatment substance (e.g. a drug, insulin, glucose, etc.) being delivered to the patient continuously at a steady rate. The calculation of the dose of dextrose may take into account various factors including, for example, one or more estimated glucose concentrations, presence of additional drugs in the patient's system, time taken for dextrose to be assimilated by the patient, and the delivery method (e.g., continuous infusion or bolus injection). In block 2750, a fluid delivery system (e.g., a system such as the optional subsystem 2780 shown in FIGS. 5 and 6) delivers the calculated dose of dextrose to the patient.

In block 2740, if the estimated glucose concentration is greater than the desired concentration (e.g., the patient is hyperglycemic), a dose of insulin to be delivered is calculated in block 2755. In some embodiments, this dose of insulin can be delivered in addition to a low dose of the treatment substance (e.g. a drug, insulin, glucose, etc.) being delivered to the patient continuously at a steady rate. The calculation of the dose of insulin may depend on various factors including, for example, one or more estimated glucose concentrations in the patient, presence of other drugs, type of insulin used, time taken for insulin to be assimilated by the patient, method of delivery (e.g., continuous infusion or bolus injection), etc. In block 2750, a fluid delivery system (e.g., the optional subsystem 2780 shown in FIGS. 5 and 6) delivers the calculated dose of insulin to the patient.

In block 2765, the method 2700 returns to block 2705 to await the start of the next measurement cycle, which can be within about one minute to about one hour (e.g., every fifteen minutes or less, every 30 minutes or less, every 45 minutes or less, etc.). In some embodiments, the next measurement cycle begins at a different time than normally scheduled in cases in which the estimated glucose concentration lies outside the acceptable range of concentrations under the glycemic protocol. Such embodiments advantageously allow the system to monitor response of the patient to the delivered dose of dextrose (or insulin). In some such embodiments, the time between measurement cycles is reduced so the system can more accurately monitor analyte levels in the patient.

Examples of Some Possible Additional or Alternative Analytes

Although examples of control and/or monitoring has been described in the illustrative context of glycemic control, embodiments of the systems and methods can be configured for control and/or monitoring of one or more of many possible analytes, in addition to or instead of glucose. Monitor and/or control of analytes can be particularly helpful in ICUs, which receive trauma patients. For example, another parameter that can be monitored is level of Hemoglobin (Hb). If the Hb level of a patient goes down without an apparent external reason, the patient could be suffering from internal bleeding. Indeed, many ICU patients (some estimate as many as 10%) suffer from what appears to be spontaneous internal bleeding that may not be otherwise detectable until the consequences are too drastic to easily overcome. In some embodiments, level of Hb can be measured indirectly, because its relationship to oxygen in the veins and arteries (at different points in the vasculature with respect to the heart and lungs) is understood.

In some embodiments, the apparatus, systems and methods described herein can be useful for measuring a level of Hb.

Another parameter that can be monitored is lactate level, which can be related to sepsis or toxic shock. Indeed, high levels and/or rapid rise in lactate levels can be correlated to organ failure and oxygenation problems in the blood and organs. However, other direct measures of the biological effects related to lactate level problems can be difficult to measure, for example, only becoming measurable with a delay (e.g., 2-6 hours later). Thus, measurement of lactate level can help provide a valuable early warning of other medical problems. Indeed, if a problem with lactate levels is detected, a nurse or doctor may be able to prevent the correlated problems by providing more fluids.

Another parameter that can be monitored is central venous oxygen saturation (ScvO2). It can be advantageous to try to maintain an ScvO2 of 65-70% or greater in ICU patients (to help avoid sepsis, for example). In some embodiments, the apparatus, systems, and methods described herein can be useful for measuring a level of ScvO2.

Levels of lactate and ScvO2 in a patient can be used together to provide information and/or warnings to a health care provider, which can be especially useful in an ICU setting. For example, if lactate and ScvO2 are both high, a warning can be provided (e.g., automatically using an alarm). If lactate is high, but ScvO2 is low, a patient may benefit from additional fluids. If ScvO2 is high, but lactate is low, a cardiac problem may be indicated. Thus, a system that provides information about both lactate and ScvO2 can be very beneficial to a patient, especially, for example, in the ICU environment. Although lactate and ScvO2 have been used as an illustrative example, in other embodiments different combinations of analytes can be monitored and used to provide information and/or warnings (e.g., to a patient and/or health care provider).

Treatment Dosing System

Some implementations of a hospital's TGC protocol suffer from disadvantages. For example, in some healthcare environments (e.g., an ICU) healthcare providers such as nurses may not have readily available a paper insulin protocol that is sometimes used with IV insulin drips as part of the TGC protocol. As a result, such healthcare providers may have to "estimate" the next required insulin dose adjustment or may have to leave the patient's care in order to find the appropriate protocol. Further, when a new insulin dose is estimated, there is a risk that there may be a transcription error if the healthcare provider incorrectly inputs a new dose rate into an IV delivery pump. In such examples, an "estimated" rate is typically considered to be a deviation from the hospital's TGC protocol. Hospitals refine their insulin protocols and generally seek "high compliance" with the insulin protocol in order, for example, to improve quality of care. Accordingly, in some embodiments, the patient monitoring system (e.g. 2630 of FIG. 26) advantageously is configured to determine insulin doses in compliance with the TGC protocol.

In some embodiments, the insulin dose rate adjustments are determined from one or more previously-made glucose readings and the current glucose reading. One or both glucose readings can be determined by the patient monitoring system (e.g., by the monitoring apparatus 2632 of FIG. 26) and/or can be input to the patient monitoring system (e.g., via the HIS interface software 2650). Possible advantages of determining glucose readings with the system patient monitoring system include increased precision, reduced transcription errors, and near real-time access to the most current patient readings.

In some embodiments, the patient monitoring system may comprise a treatment dosing system including a treatment dosing software (e.g. insulin dosing software 2652 of FIG. 26). In some embodiments, the dosing software is configured to include a treatment dosing protocol (e.g. an insulin protocol and/or TGC protocol). For example, the dosing software may include the hospital's current, approved, local insulin protocol. If an adjustment to a patient's insulin dose should be made because of the patient's current glucose values, the patient monitoring system can be configured to calculate the next recommended (or suggested) treatment dose. The calculation of the next recommended treatment dose can be made at least in part based on the insulin dosing protocol for the particular hospital. In some embodiments, information related to the recommended treatment dose is output on the user interface (e.g., the user interface 2400 and/or a display graphic as shown in FIGS. 28A-F). For example, the user interface may display the current rate of dose and/or infusion, the dose type (e.g., bolus or steady (basal) rate), and the recommended dose. A healthcare provider may use the information output by the user interface to adjust the actual dose value, as needed by a specific patient condition, and may initiate infusion. In some embodiments, the patient monitoring system performs the calculation of recommended dose, makes the adjustments to the actual dose value, and provides this dose value to the patient, for example, by infusion with the fluid system kit 2634 of FIG. 26. In some embodiments, a control system (e.g. fluid system controller 405 of FIG. 4) in communication with the patient monitoring system can be configured to provide instructions to an infusion pump fluidically connected to the source of infusion fluid to start infusion. The control system may also be configured to adjust the pump rate of the infusion fluid to deliver the recommended dose to the patient at a basal rate or as a bolus injection.

Figure 28A:
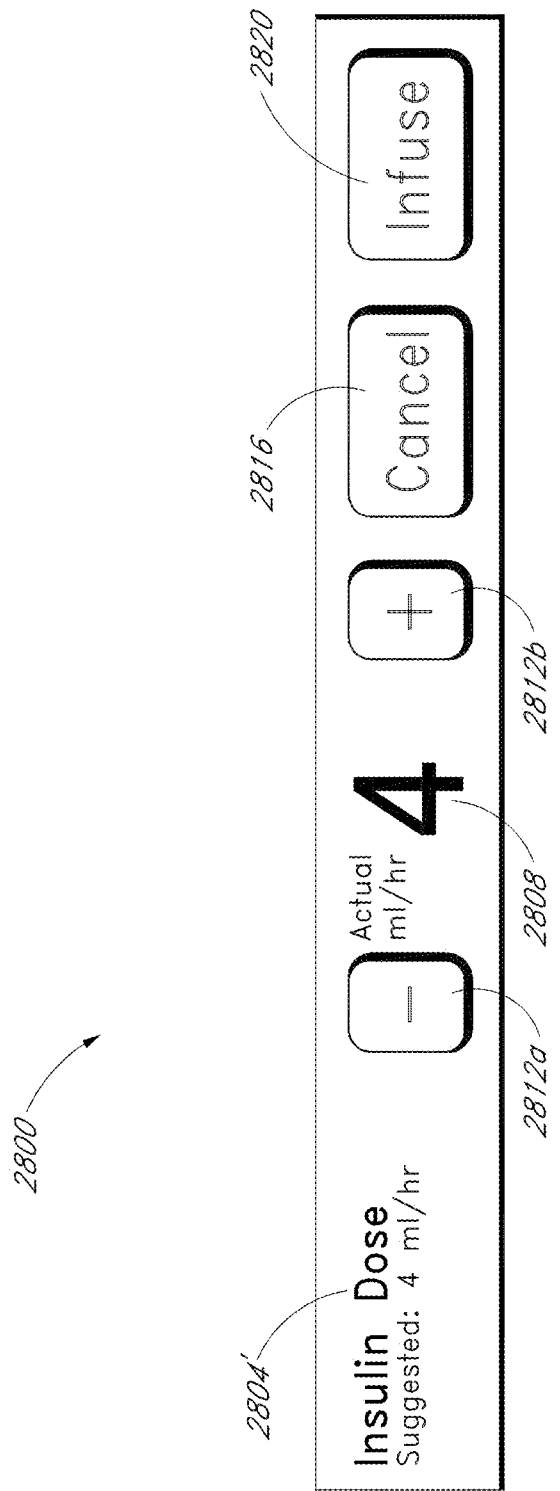
FIG. 28A schematically illustrates the visual appearance of an embodiment of a display graphic for providing information related to suggested and actual insulin dose for a patient.

FIG. 28A schematically illustrates an example of a display graphic 2800 for use with an embodiment of the user interface 2400. The display graphic 2800 can be output by, for example, a touchscreen display device so that a user can view the information on the display graphic 2800 and actuate suitable insulin dosing controls. In other embodiments, buttons, keys, a mouse, or other input device can be used instead of (or in addition to) touchscreen buttons. The embodiment of the display graphic 2800 shown in FIG. 28A includes a suggested dose graphic 2804, an actual dose graphic 2808, dose decrement and increment buttons 2812*a* and 2812*b*, and dosing control buttons 2816, and 2820. In other embodiments, the graphics and buttons schematically illustrated in FIG. 28A can be arranged differently, and the display graphic 2800 may include additional and/or different information and controls.

In this embodiment, the suggested dose graphic 2804 includes a suggested dose rate (e.g., 4 ml/hr) and a title graphic ("Insulin Dose"). As described above, the suggested dose rate can be calculated using the dosing software. The actual dose graphic 2708 includes a graphic representation of the current, actual dose (e.g., 4 ml/hr). In this embodiment, the suggested dose graphic 2808 and the actual dose graphic 2808 use alphanumeric graphics to output dose information. In other embodiments, the graphics 2804, 2808 may output dose information using, for example, trend graphs, bar or pie charts, symbols, and so forth. Advantageously, the values for the suggested and actual doses are displayed in a sufficiently large graphic font that a user can readily read the values, which reduces potential error in dosing the patient. In the example shown in FIG. 28A, a steady (basal) infusion rate (e.g., 4 ml/hr) is shown. In other embodiments, the display graphic 2800 may show a suggested bolus dose in addition to, or instead of, a steady state (basal) dose.

In this illustrative example, the actual dose and the recommended dose are the same (e.g., 4 ml/hr), but this is not a limitation. In a typical implementation, if the actual dose differs from the suggested dose, a user may adjust the actual dose value by actuating (e.g., pressing on a touchscreen) a decrement button 2812*a* and/or an increment button 2812*b* until the actual dose equals the suggested dose. The decrement and increment buttons 2812*a* and 2812*b* can be graduated in any suitable dose fractions (e.g., 0.1 ml/hr or some other amount).

The dosing control buttons include a cancel button 2816 and an infuse button 2820. The cancel button 2816 can be used to stop, and the infuse button 2820 can be used to actuate an infusion pump coupled to the infusion fluid source and start, infusion of the insulin dose. In other embodiments, additional or different infusion control buttons can be used.

In some embodiments, a control system (e.g. fluid system controller 405 of FIG. 4) configured to provide instructions to an infusion pump fluidically connected to a source of infusion fluid may comprise the display graphic 2800. A health care provider or a user may actuate the infusion pump or control the pump rate through the display graphic 2800 and the control system. Moreover, the patient monitoring system can allow a user to control delivery of infusion fluids using controls on a graphic user interface of the monitoring system, even if the infusion fluids are pumped by a separate system that is not contained within the same housing as the patient monitoring system. For example, the monitoring system can have built in wireless connectivity that can locate infusion pumps (e.g., those that have wireless capabilities) in the vicinity and establish communication with them. The monitoring system can allow a user to control those external infusion pumps through its own control interface (e.g., through its display graphic described herein). In some embodiments, the monitoring system can wirelessly search for an infusion pump delivering total parenteral nutrition (TPN), for example, and, with a handshake protocol, query that infusion pump for its hourly rate. This information can affect various outputs from the system (including, for example, a dose or rate suggested by the insulin dosing algorithm). The monitoring system can do the same with an infusion pump that is delivering insulin, and provide remote control of that pump through the monitoring system's graphic user interface, for example.

The display graphic 2800 can be output on to any suitable monitor or output device (e.g., a touchscreen display). For example, in some embodiments, the display graphic 2800 is displayed on the user interface 2400, e.g., adjacent an outer boundary of the example UI graphic shown in FIGS. 24 and 25. In other embodiments, the display graphic 2800 is shown instead of the trend indicators 2816. In yet other embodiments, the display graphic 2800 is output with optional patient identification information. Many variations are possible.

Accordingly, certain embodiments of the patient monitoring system (e.g. system 2630 of FIG. 26) can be used as an infusion pump, actuatable using an embodiment of the display graphic 2800. In certain such embodiments, a healthcare provider advantageously will be able to control insulin delivery through the same patient IV access line. Embodiments of patient monitoring system that are configured to include a treatment dosing protocol (e.g. insulin protocol and/or a TGC protocol), to determine a patient treatment dose based on patient glucose reading(s), and to deliver a recommended treatment dose to the patient via a fluidic system (e.g. the fluid system kit 26134 of FIG. 26 or via an infusion pump, for example, infusion pump 518 of FIG. 5) may have one or more of the following potential benefits: increased compliance with a treatment dosing protocol, reduction in treatment dosing errors, time savings for healthcare providers, and greater IV access efficiency by delivery of some or all TGC-related medicaments through a common IV line (e.g., a proximal port of a central venous catheter or a lumen of a peripherally inserted central catheter).

FIGS. 28B-28F schematically illustrate embodiments of a display graphic comprising a graphic user interface. These figures illustrate how an analyte detection system can be configured to have a numerical display mode (see, e.g., 2822) and a trend display mode (see, e.g., 2824) to display the present and/or historical concentration of one or more analytes (e.g. glucose, ScvO2, lactate, etc.). Similar to the embodiment illustrated in FIG. 28A, the embodiments illustrated in FIGS. 28B-28F can also provide information related to suggested and/or actual insulin dose and enable the user or health care provider to control (e.g., start, cancel, increase, decrease, etc.) delivery of insulin.

Figure 28B:
FIGS. 28B-28F schematically illustrate embodiments of a display graphic comprising a graphic user interface and illustrate examples of numerical display mode, trend display mode, suggested and actual insulin dose information, and controls for delivery of insulin.

FIG. 28B shows an example of an embodiment of the display graphic 2800. In this example, the concentrations of three analytes; glucose, ScvO2 and lactate are displayed on a screen of the display graphic 2800. The concentration can be displayed as a number (see, e.g., 2822) or as a trend line (see, e.g., 2824), or both. In some embodiments, the concentration can be displayed as a trend graph of the concentration versus time. The embodiments illustrated in FIG. 28B can also display the rate at which an infusion substance (e.g. insulin) is being delivered to the patient. For example reference numeral 2808 indicates that the amount of insulin being infused is 0.5 units/hr. In some embodiments, the display can be refreshed periodically to display the most current measured and/or stored values. The display can indicate when the last measurement was taken and/or the last time the display was refreshed (see, e.g., the text "rate confirmation at: 01:35").

The example illustrated in FIG. 28B also illustrates a button 2812 that can be used to modify the rate at which insulin is being infused or otherwise control an analyte level. The display graphic, 2800 of FIG. 28B can comprise additional buttons such as the Menu button 2828, which can provide additional functionalities.

Figure 28C:
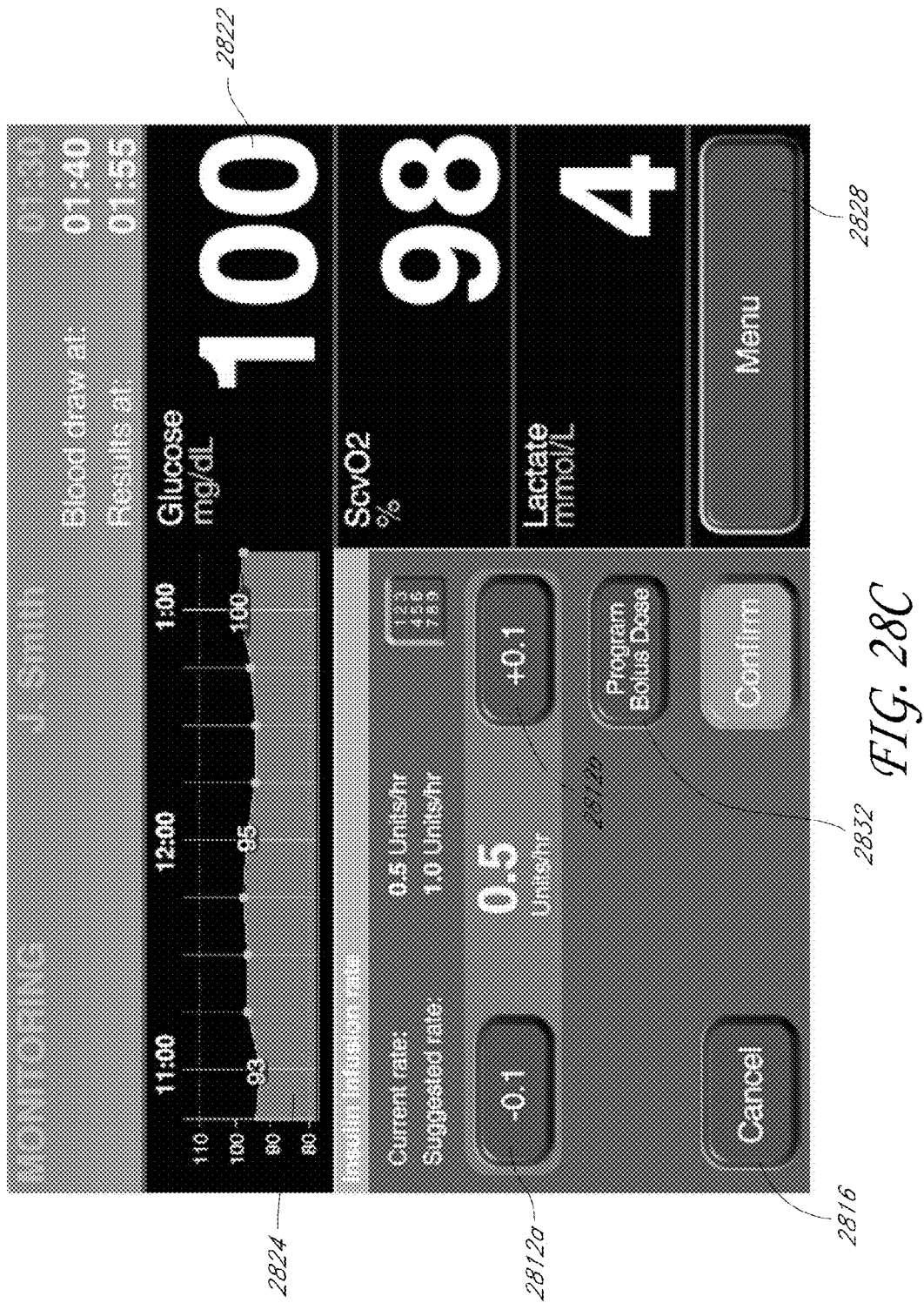
Figure 28D:
Figure 28E:
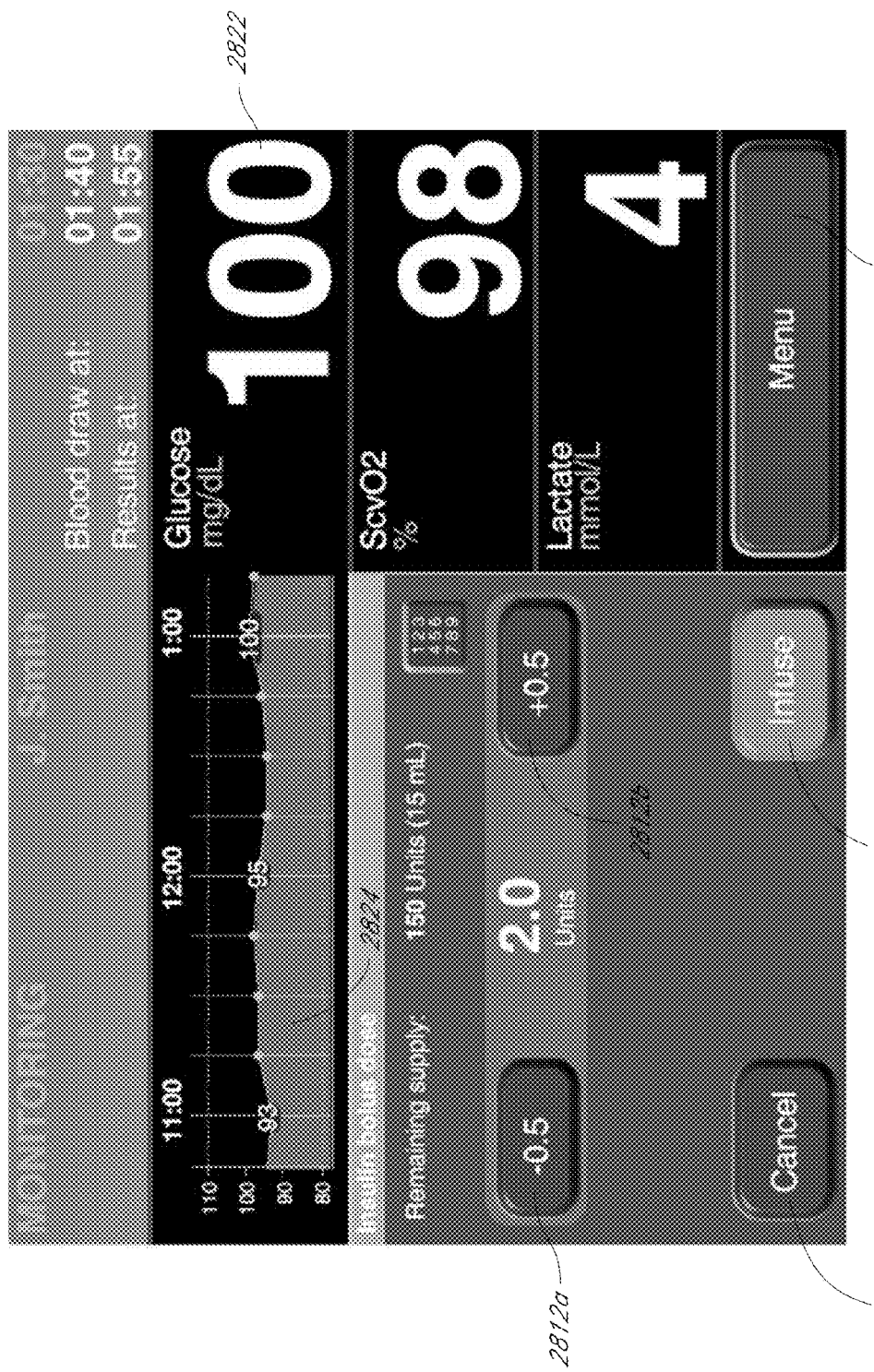
Figure 28F:

A user or a health care provider can activate the button 2812 of FIG. 28B to control infusion (e.g., modify the rate at which insulin or another infusion substance is delivered). In some embodiments, activating the button 2812 can display a secondary screen as illustrated in FIG. 28C. The secondary screen may display the current rate at which insulin is being infused and the suggested rate at which insulin should be infused. The secondary screen may comprise a dose increment button 2812a and a dose decrement button 2812b to increase or decrease the rate at which insulin is being infused. In some embodiments, a keypad may be provided so that the user or health care provider can input the value for the insulin infusion rate. The secondary screen may comprise controls (e.g. cancel button 2816 or confirm button 2836) to cancel or confirm the change in the insulin infusion rate. In the example embodiments illustrated in FIGS. 28C and 28D, a bolus dose button 2832 can be provided to program a bolus dose that can be delivered to the patient. If the user or the health care provider activates the bolus dose button 2832, the display graphic can display a bolus dose screen which displays a value for the bolus dose as illustrated in FIG. 28E. In some embodiments, the bolus dose screen may display the remaining supply of insulin as illustrated in FIG. 28E. The user or the health care provider can change the amount of insulin bolus to be delivered and instruct the system to deliver the bolus amount by activating the button 2820. A confirmation screen 2840 may be displayed on the display graphic 2800 as illustrated in FIG. 28F to confirm that the user or health care provider wished to proceed with the bolus delivery. The embodiments illustrated in FIGS. 28B-28F can comprise a touch screen to accept instructions and input from the user or the health care provider.

Although the insulin dosing software 2652 schematically illustrated in FIG. 26 and the display graphic 2800 schematically illustrated in FIGS. 28A-28F are shown and described with respect to delivery of an insulin dose, this is not a limitation, and in other embodiments, the dosing software 2652 and the display graphic 2800 can be used to provide suitable doses and information related thereto for any suitable item or items administered to a person, such as medicaments, drugs, foods or herbs, whether administered orally, intravenously, topically, etc. The dosing software 2652 of FIG. 26 may calculate a recommended dose based (at least in part) on readings of suitable analyte(s) of interest in the patient (e.g., glucose in the case of insulin dosing). The readings can be performed by the system 2630 (e.g., with the monitoring apparatus 2632) and/or by other analyte detection systems.

Examples of Calculating Treatment Dose

In the method for providing glycemic control schematically illustrated in FIG. 27, the dextrose or insulin dose can be determined by a treatment dosing protocol. In some embodiments, the treatment dosing protocol may determine the amount of dextrose or insulin to be delivered by comparing the currently estimated value of glucose concentration with a target or desired value of glucose concentration. In some embodiments, the treatment dosing protocol may determine the treatment dose based on one or more of the following factors: the patient's medical condition and medical history, the effectiveness of the treatment dose, the presence or absence of other analytes, other drugs being administered, etc.

For example, in some embodiments, different types of insulin, listed in the table below, having different activation properties can be used to control the concentration of glucose in patients with hyperglycemia. Some of the types of insulin listed here are generally delivered to patients subcutaneously. Others, (e.g., "Regular IV insulin" listed at the bottom), are generally delivered intravenously. Additional details are provided below regarding regular IV insulin.

| Name: | Starts working: | Active: |
| --- | --- | --- |
| Quick-acting, such as the insulin analog lispro | 5 to 15 minutes | 3 to 4 hours |
| Short-acting, such as regular insulin | 30 minutes | 5 to 8 hours |
| Intermediate-acting, such as NPH insulin, or lente insulin | 1 to 3 hours | 16 to 24 hours |
| Long-acting, such as ultralente insulin | 4 to 6 hours | 24 to 28 hours |
| Insulin glargine and Insulin detemir | 1 to 2 hours | active, without peaks or dips: 24 hours |
| A mixture of NPH and regular insulin | 30 minutes | 16 to 24 hours |
| Regular IV insulin | 5 minutes | about 30 minutes |

In some embodiments, IV insulin can be infused directly into the patient's vein. Regular IV insulin can take effect quickly (after about 5 minutes), and IV insulin also clears the patient's body quickly (a 90% peak between 20-25 minutes, and inactive after about 30 minutes). Thus, using IV insulin, a patient's blood glucose level can be brought down quickly to prevent or stop hyperglycemia. Moreover, a patient's blood glucose level can be brought up more quickly using IV insulin because it clears the system more quickly. However, because IV insulin is so potent, the risk of harming a patient through incorrect dosage may also increase with the short, five-minute lag time before the insulin begins to have a clinical effect. Because medical personnel can make mistakes and are often too busy to perform the frequent glucose measurements that may be indicated for frequent IV insulin dosing adjustments, the use of IV insulin sometimes causes a patient to become severely hypoglycemic. The system 2630 can frequently (e.g., every 15 minutes) measure the patient's blood glucose concentration, and insulin dosing software 2652 can automatically adjust the insulin delivery rate according to the automatically measured blood glucose concentration. Thus, system 2630 provides for an environment where fast acting IV insulin can be used while reducing risk of harming the patient through potentially incorrect or outdated dosing. This can be especially appropriate and useful in an ICU context to avoid complications (e.g., mortality) that may result from providing too high a dose of insulin for too great a length of time. Accordingly, some embodiments of the system 2630 are able take the pressure off medical practitioners and provide accurate, timely checking of glucose, in addition to the highly valuable function of automatically shutting off insulin, when appropriate.

In these embodiments, the insulin delivery rate can be calculated based on factors such as the type of insulin, the time taken by the insulin to start working, the time it remains active in the body, etc. In some embodiments the amount of treatment dose provided to control the analyte concentration is adjusted no more frequently than once every hour. In these embodiments, determining the treatment dose only on the basis of the comparison of the currently estimated value of glucose concentration with a desired value of glucose concentration and a few other factors may be insufficient to accurately determine the treatment dose required to provide TGC. Thus treatment dosing protocols that determine the treatment dose by taking an average of two or more sequential glucose values or by calculating a rate of change of the glucose concentration over a period of time, or both, may be effective in providing glycemic control.

Figure 29:
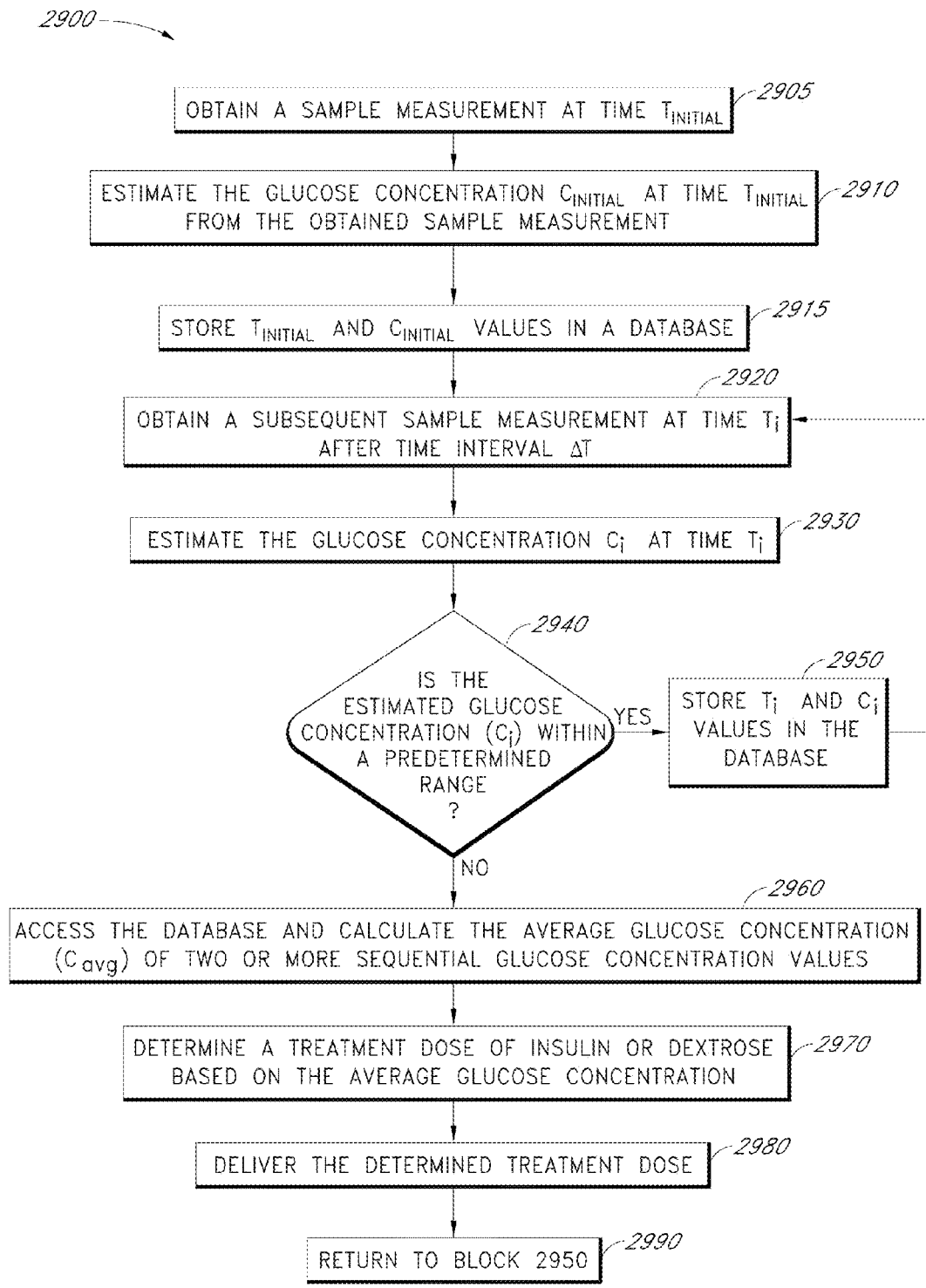
FIG. 29 is a flowchart that schematically illustrates an embodiment of a method of determining a treatment dose based on the average concentration of an analyte.

FIG. 29 is a flowchart that schematically illustrates an embodiment of a method 2900 of determining the treatment dose based on the average concentration of an analyte (e.g. glucose). In block 2905, an analyte monitoring system (e.g., the monitoring apparatus 2632 of FIG. 26) comprising a fluidic system (e.g. the fluid system kit 2634 of FIG. 26) obtains a sample of bodily fluid (e.g., a blood or blood plasma sample) from a source of bodily fluid (e.g., a patient) at an initial time $T_{initial}$. In some embodiments, the analyte monitoring system may further comprise an analyte detection system that spectroscopically analyzes the sample and obtains a measurement from the sample. The measurement may comprise an optical measurement such as, for example, an infrared spectrum of the sample. In block 2910, the initial concentration ($C_{initial}$) of an analyte (e.g. glucose) in the sample is estimated from the measurement by using any of the methods described above. In block 2915, the initial concentration $C_{initial}$ at time $T_{initial}$ is stored in an internal or an external database.

In some embodiments, the database can be located in a processing system (e.g. a computer system 2646 of FIG. 26) in electrical communication with the monitoring system. In some embodiments, the initial concentration $C_{initial}$ at time $T_{initial}$ can be stored in a memory location of a memory device. The memory device can be located in the monitoring system or the processing system. In some embodiments, the memory device can be located external to the monitoring system and be in electrical communication with the monitoring system. In some embodiments, an initial treatment dose $D_{initial}$ can be determined and delivered to the patient if the initial concentration $C_{initial}$ of the analyte is not within a predetermined range. The initial treatment dose $D_{initial}$ may also be stored in the database or the memory location.

At a later time $T_i$, a subsequent sample measurement is obtained as shown in block 2920. The time $T_i$ may occur after a time interval $\Delta T$ from time $T_{i-1}$ when a sample measurement was previously obtained. For example, a first sample measurement can be obtained at a first time $T_1$ which occurs after a time interval $\Delta T$ from the initial time $T_{initial}$ and a second sample measurement can be obtained at a second time $T_2$ which occurs after a time interval $\Delta T$ from the first time $T_1$ and so on. The time interval $\Delta T$ may range anywhere from 5 minutes to 15 minutes. In some embodiments, the time interval $\Delta T$ may be less than 5 minutes or greater than 15 minutes. In block 2930, the concentration $C_i$ of the same analyte at time $T_i$ is estimated from the obtained sample measurement. The method 2900 then proceeds to block 2940 wherein the estimated concentration $C_i$ of the analyte is compared to a predetermined range. The predetermined range can be determined by taking into account various factors such as a patient's medical condition, the medications and drugs being administered to the patient, etc. In some embodiments, the predetermined range is a glucose concentration in a range from about 70 mg/dL to about 110 mg/dL. If in block 2940, the concentration $C_i$ of the analyte is within the predetermined range, then the method 2900 moves to block 2950 where the value of the estimated concentration $C_i$ of the analyte at time $T_i$ is stored in the database or the memory location. The method 2900 then returns to block 2920 to obtain a next sample measurement after a time interval $\Delta T$.

However, if in block 2940, the estimated concentration of the analyte $C_i$ is determined to be not within the predetermined range, then the method 2900 proceeds to block 2960 wherein an average concentration $C_{avg}$ of the analyte is calculated. In some embodiments, the average concentration $C_{avg}$ can be calculated by taking an arithmetic mean of the estimated concentration $C_i$ and one or more previous concentration values stored in the database or the memory location and is given by the equation:

$$C_{avg} = \frac{C_i + \sum_{k=1}^{n} C_{i-k}}{n+1},$$

where n is an integer greater than or equal to 1.

In the above equation, the variable $C_i$ corresponds to the currently estimated concentration value and the variables $C_{i-1}, C_{i-2}, \ldots, C_{i-n}$ correspond to the concentration values previously obtained. In some embodiments, the average concentration $C_{avg}$ can be calculated by taking a weighted average of the estimated concentration $C_i$ and one or more previous concentration values and is given by the equation:

$$C_{avg} = \frac{w_i C_i + \sum_{k=1}^{n} w_{i-k} C_{i-k}}{w_i + \sum_{k=1}^{n} w_{i-k}},$$

where n can be an integer greater than or equal to 1.

The weights $w_i$ and $w_{i-k}$ can be determined in a variety of ways. For example, in some embodiments the weight $w_i$ associated with the current estimated concentration value $C_i$ may be greater than the weights $w_{i-k}$ associated with the previous concentration values. In some embodiments, a greater weight can be assigned to a concentration value that is either abnormally high or abnormally low. In some embodiments, by contrast a smaller weight can be assigned to a concentration value that is either abnormally high or abnormally low.

The method 2900 then proceeds to block 2970 where a treatment dose of dextrose or insulin can be determined according to a glycemic control protocol based at least in part on the calculated average concentration $C_{avg}$. In some embodiments, the treatment dose of dextrose or insulin can be determined according to a glycemic control protocol based on the calculated average concentration $C_{avg}$ and variety of factors such as patient's sensitivity to the treatment drug (e.g. insulin), the treatment dosing history, the effectiveness of the treatment dose, the presence or absence of other analytes, other drugs being administered, etc. In some embodiments, the determined treatment dose can be displayed to a health care provider on a display graphic (e.g. display graphic 2800 of FIGS. 28A-28F). In block 2980 the determined treatment dose can be delivered to the patient by a fluid delivery system or a fluid infusion system (e.g., a system such as the subsystem 2780 shown in FIGS. 5 and 6). In some embodiments, a control system (e.g. fluid system controller 405 of FIG. 4) can be configured to provide instructions to an infusion pump fluidically connected to a source of infusion fluid to start infusion. The control system may also be configured to adjust the pump rate of the infusion fluid to deliver the recommended treatment dose to the patient at a basal rate or as a bolus injection. In some embodiments, the treatment dose can be delivered to the patient in addition to a low dose of the treatment drug (e.g. insulin or glucose) being delivered to the patient continuously at a steady rate. In some embodiments, the healthcare provider may actuate the infusion pump fluidically connected to a source of infusion fluid through a graphic user interface (e.g. display graphic 2800 of FIGS. 28A-28F). In some embodiments, the health care provider may provide instructions regarding the pump rate to the infusion pump through a graphic user interface (e.g. display graphic 2800 of FIGS. 28A-28F). In block 2990 the method 2900 returns to block 2950 where the value of the estimated concentration $C_i$ of the analyte at time $T_i$ is stored in the database or the memory location.

Figure 30:
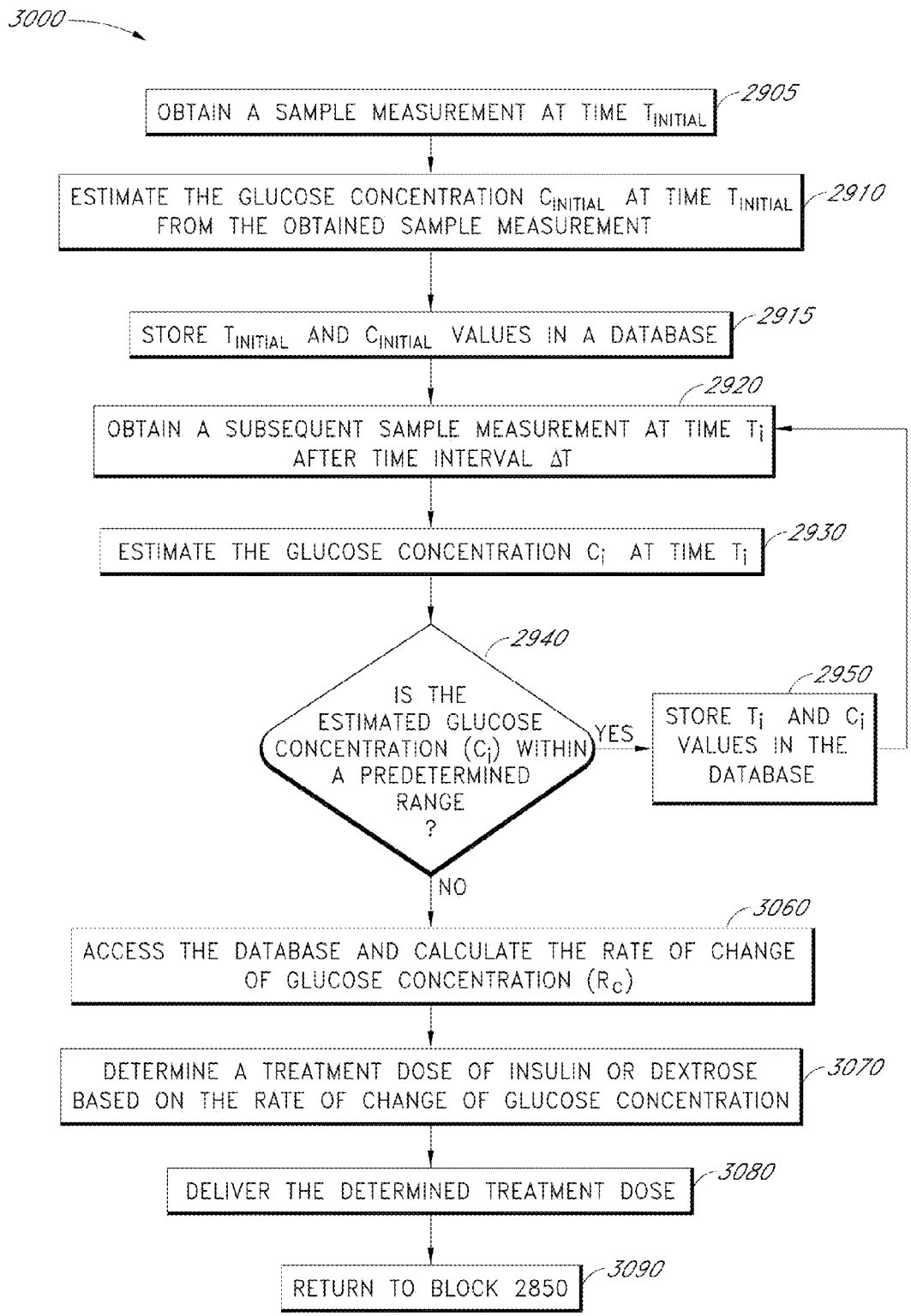
FIG. 30 is a flowchart that schematically illustrates an embodiment of a method of determining a treatment dose based on the rate of change of the concentration of an analyte.

FIG. 30 is a flowchart that schematically illustrates an embodiment of a method 3000 of determining the treatment dose based on the rate of change of the concentration of an analyte (e.g. glucose). The method 3000 differs from the method 2900 in that if in block 2940, the estimated concentration of the analyte $C_i$ is determined to be not within the predetermined range, then the method 3000 proceeds to block 3060 where a rate of change of the concentration $R_c$ of the analyte is calculated. The rate of change of the concentration of the analyte $R_c$ can be calculated in a variety of ways. In some embodiments, the rate $R_c$ can be calculated from the current estimated concentration of the analyte $C_i$ at time $T_i$ and the previously determined concentration of the analyte $C_{i-1}$ at time $T_{i-1}$ stored in the database or memory location and is given by the following equation:

$$R_c = \frac{C_i - C_{i-1}}{T_i - T_{i-1}}$$

In some embodiments, the rate $R_c$ can be calculated from the currently estimated concentration of the analyte $C_i$ at time $T_i$ and several previously determined values for the concentration of the analyte stored in the database or memory location. In the method 3000, the treatment dose is determined using a glycemic control protocol based at least in part on the rate of change $R_c$ of the concentration of the analyte as shown in block 3070. In some embodiments, determining the treatment dose based on the rate of change $R_c$ of the concentration of the analyte can ensure that the treatment dosing protocol responds to certain extreme conditions such as rapid change in the concentration of the analyte (e.g. glucose). In some embodiments, such rapid change in the concentration of the analyte can indicate that the patient's medical condition is unstable or critical. In some embodiments, the rapid change in the concentration can be an indicator of a failure of the measurement system or a part thereof.

Figure 31A:
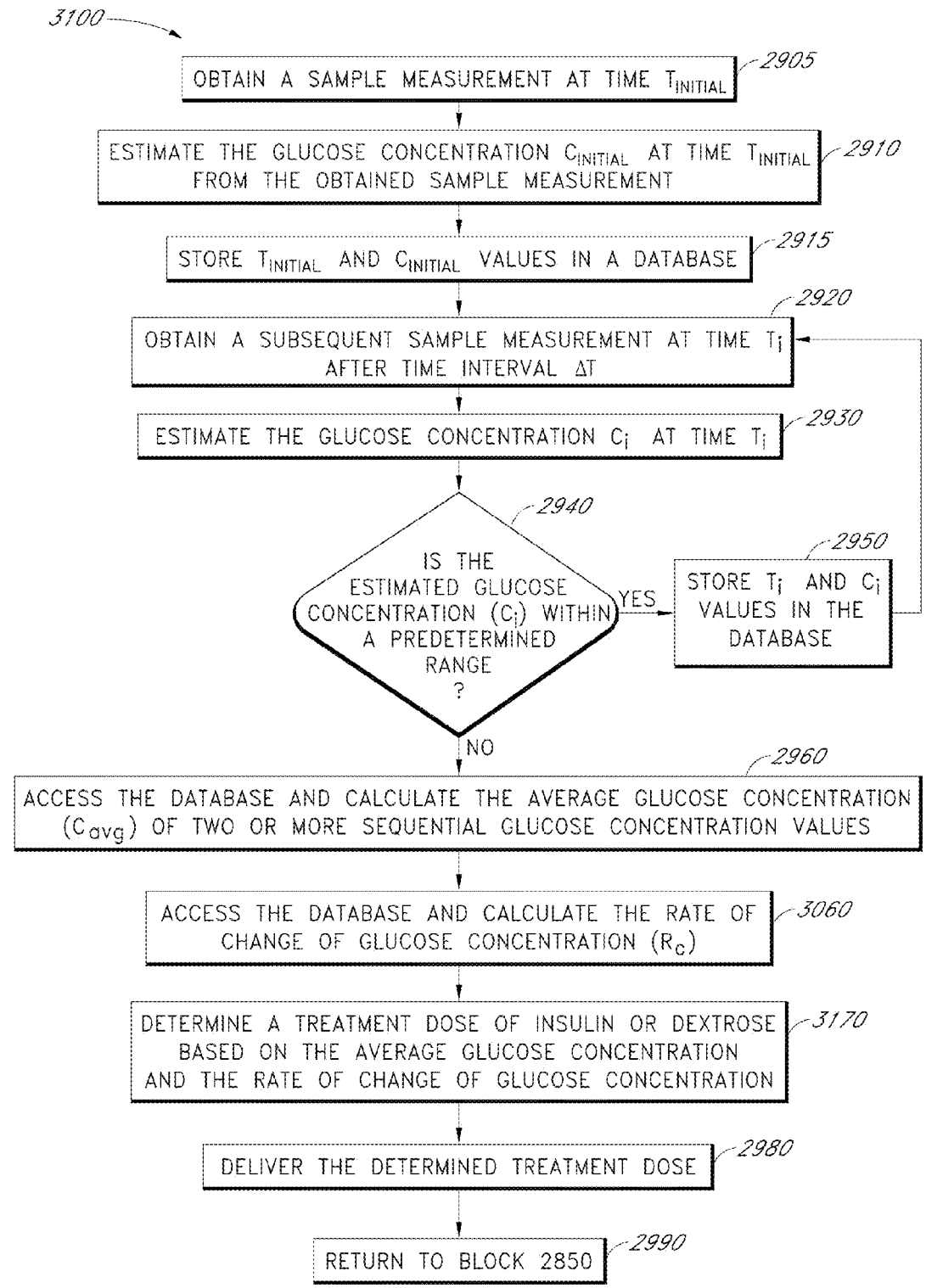
FIG. 31A is a flowchart that schematically illustrates an embodiment of a method of determining a treatment dose based on the average concentration of an analyte and the rate of change of the concentration of the analyte.
Figure 31B:
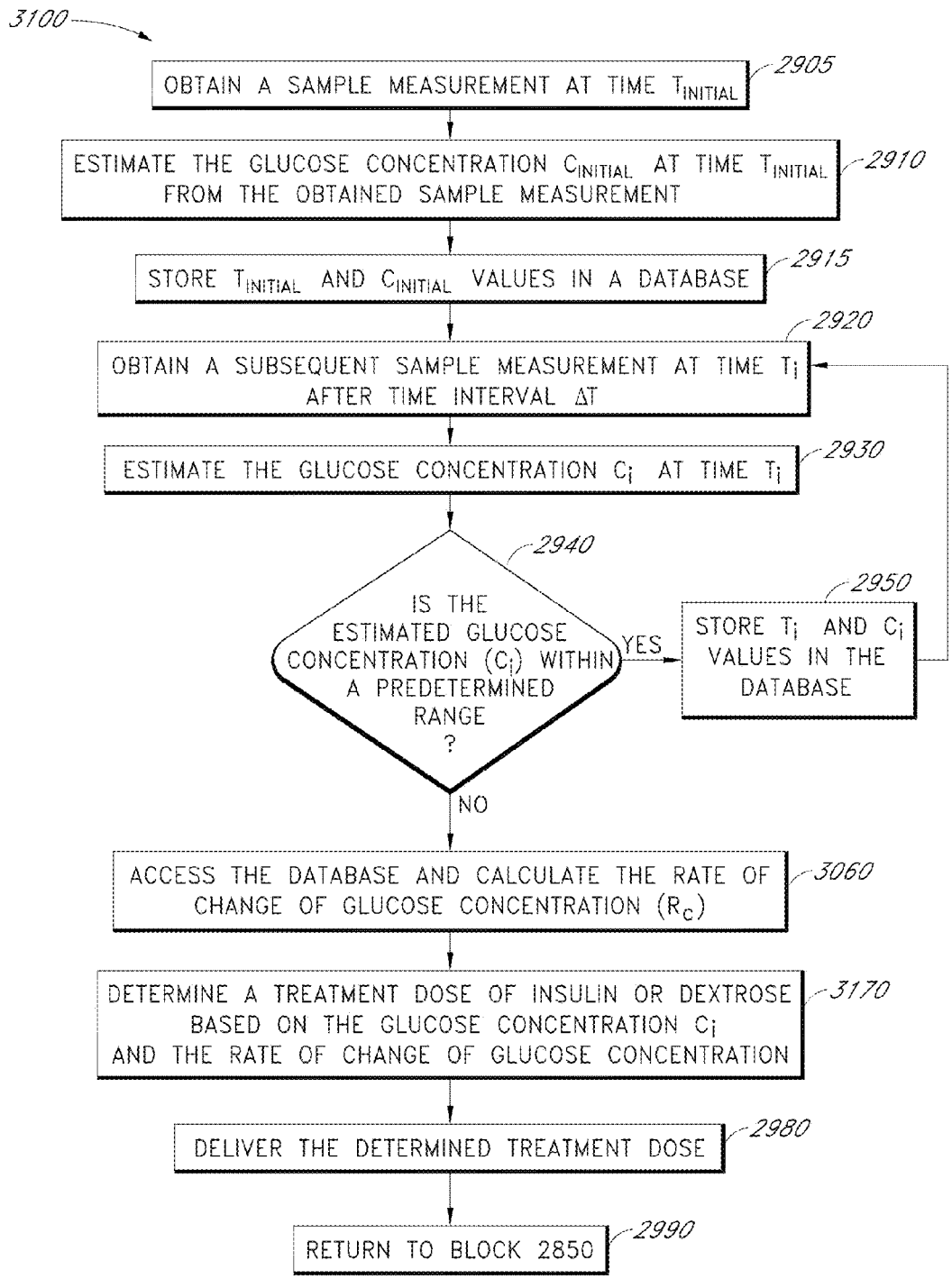
FIG. 31B is a flowchart that schematically illustrates an embodiment of a method of determining a treatment dose based on the current concentration of an analyte and the rate of change of the concentration of the analyte.

FIG. 31A is a flowchart that schematically illustrates an embodiment of a method 3100 of determining the treatment dose based on the current estimated concentration or the average concentration of an analyte (e.g. glucose) and the rate of change of the concentration of the analyte. The method 3100 determines the treatment dose using a glycemic control protocol based at least in part on the average concentration $C_{avg}$ of the analyte and the rate of change of the concentration $R_c$ of the analyte as shown in block 3170. The average concentration $C_{avg}$ and the rate of change of the concentration $R_c$ can be calculated by one or more of the methods described above. In some embodiments, as illustrated in FIG. 31B, the treatment dose can be determined using a glycemic control protocol based at least in part on the currently estimated concentration $C_i$ and the rate of change of the concentration $R_c$ of the analyte.

Treatment Dose Feedback System

As described above, in some embodiments, the analyte monitoring system can be configured to control the concentration of one or more analyte by infusing a treatment dose calculated by a treatment dosing protocol. However, the analyte monitoring system or the healthcare provider may not have feedback regarding the effectiveness of the treatment dose suggested by the treatment dosing protocol. Thus it may be advantageous to have a system that can both: (i) predict the concentration of an analyte (e.g. glucose) at a future time based on the treatment dose suggested by the treatment dosing protocol; and (ii) provide feedback to the healthcare provider.

As described above, an analyte monitoring apparatus comprising a fluidic system (e.g. the fluid system kit 2634 of FIG. 26) can obtain a sample of bodily fluid (e.g., a blood or blood plasma sample) from a source of bodily fluid (e.g., a patient) and estimate the concentration of one or more analytes in the sample several times during an hour. The concentration of the one or more analytes can be stored in a measurement history that can be accessed later. The measurement history may comprise one or more stored databases or memory locations.

Figure 32:
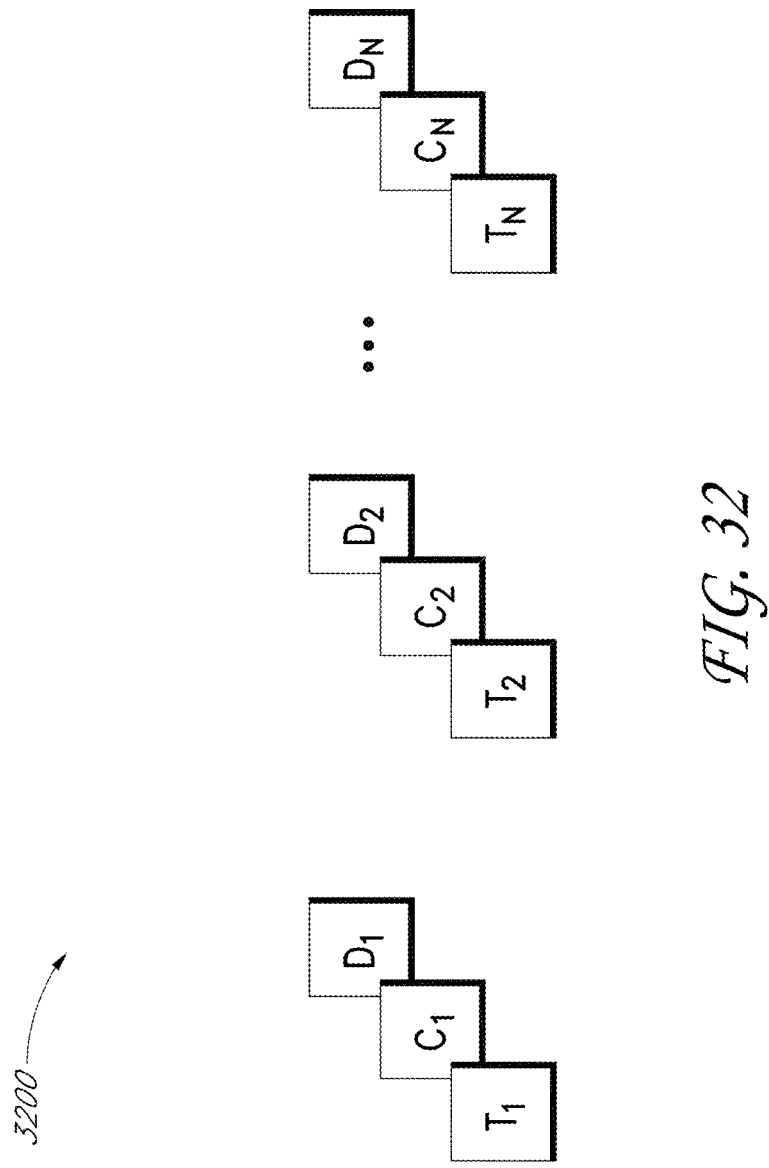
FIG. 32 schematically illustrates an embodiment of a history that stores the previously determined values for the concentration of an analyte and the values for a treatment dose previously administered.

In some embodiments, the measurement history can be located in a processing system (e.g. a computer system 2646 of FIG. 26) in electrical communication with the monitoring system. In some embodiments, the concentration of the one or more analytes can be stored in a memory location of a memory device. The memory device can be located in the monitoring system or the processing system. In some embodiments, the memory device can be located external to the monitoring system and be in electrical communication with the monitoring system. FIG. 32 illustrates an embodiment of a measurement history 3200 that stores the time of measurement $T_i$, the estimated or measured concentration of an analyte (e.g. glucose) $C_i$ and the treatment dose $D_i$ (of insulin or sugar, for example) administered to the patient. In some embodiments, the measurement history 3200 may store information regarding estimated or measured concentration of other analytes. Other embodiments of the measurement history are also possible.

Figure 33:
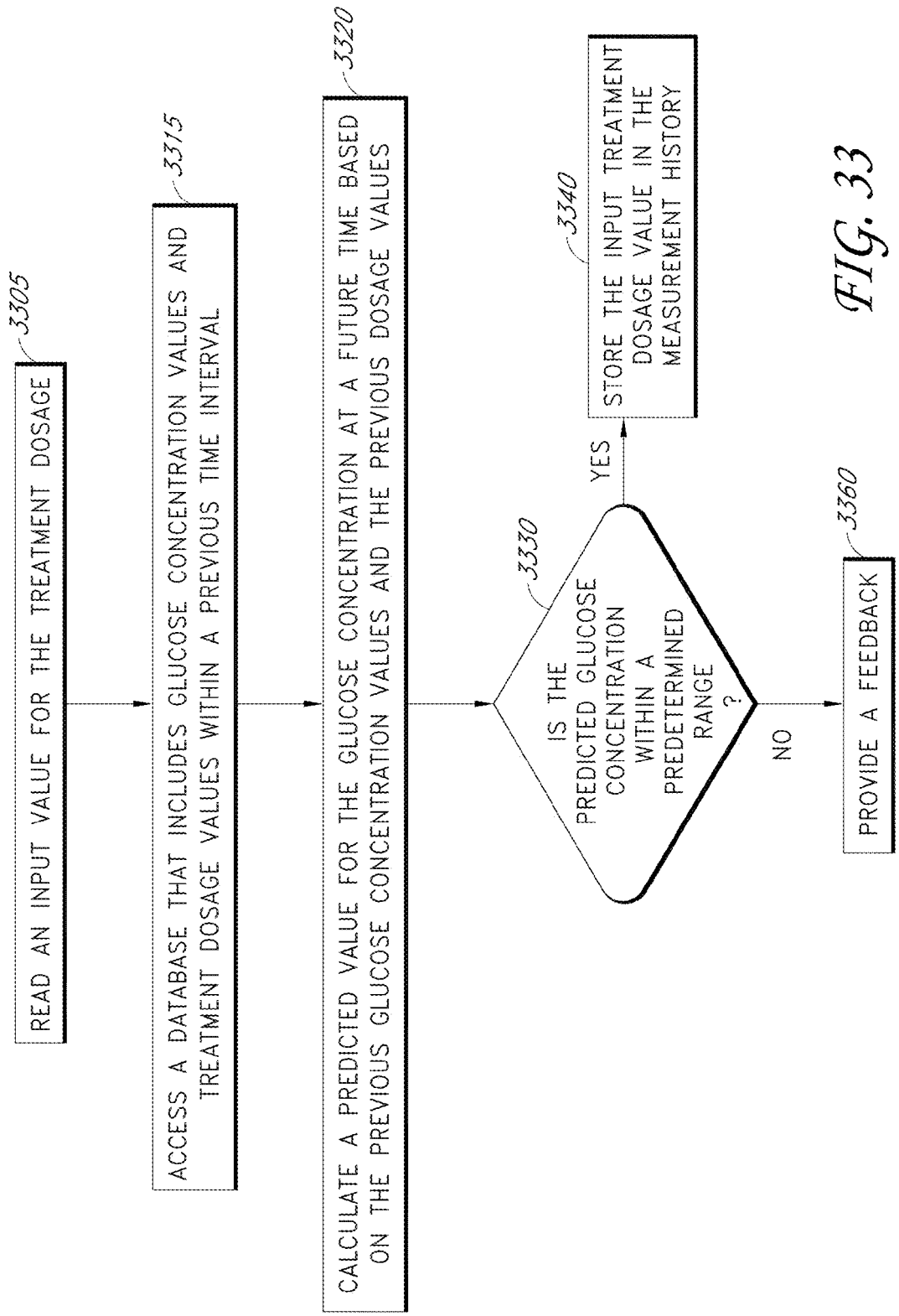
FIG. 33 is a flowchart that schematically illustrates steps in a method of providing feedback regarding a treatment dose.
Figure 34:
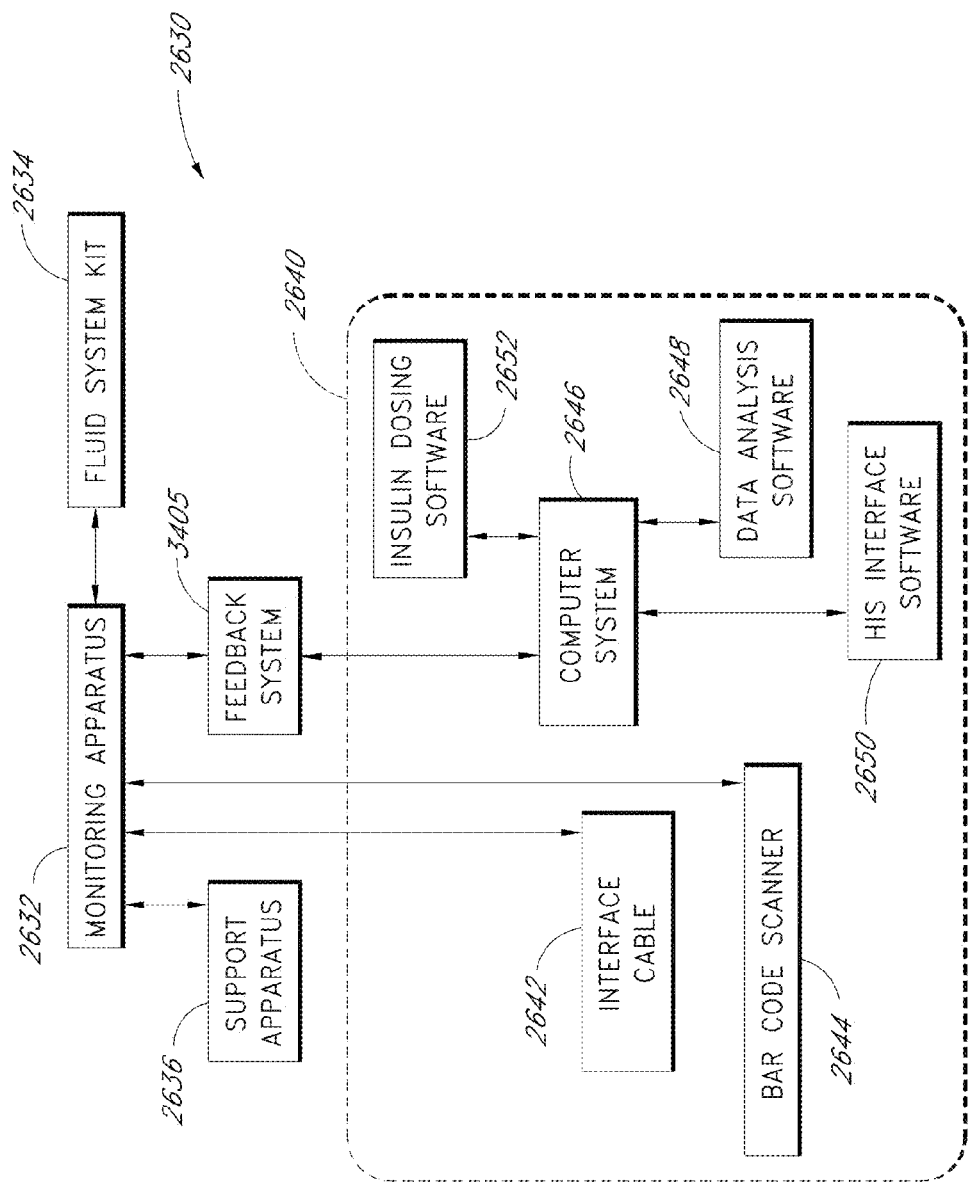
FIG. 34 schematically depicts a feedback system and the relationship between the feedback system and the other components and/or aspects of the patient monitoring system.

If the estimated or measured concentration of an analyte (e.g. glucose) is not within an acceptable range, then a healthcare provider may administer a treatment dose based on a treatment dosing protocol to bring the concentration of the analyte within the acceptable range. FIG. 33 schematically illustrates steps in a method to provide feedback to the monitoring and/or dosing system (and, e.g., the healthcare provider) regarding the effectiveness of the treatment dose suggested by the treatment dosing protocol. Feedback can be provided by a feedback system 3405 illustrated in FIG. 34 which is in electronic communication with the analyte monitoring apparatus 2632 and/or the computer system 2646 of FIG. 34. Referring to FIG. 33, in block 3305 the feedback system 3405 reads the treatment dose input by the healthcare provider or determined by the treatment dosing software. The treatment dose can be put in to the system in a variety of ways. For example, in one embodiment, the healthcare provider may input the treatment dose using a keyboard. In some embodiments, the healthcare provider may input the treatment dose using a touch screen. In some embodiments, the treatment dose can be provided automatically (e.g. by computer).

In block 3315 the feedback system 3405 accesses the measurement history (e.g. the measurement history 3200 illustrated in FIG. 32) that stores the previously determined values for the concentration of the analyte and the values for a treatment dose previously administered. The method 3300 then proceeds to block 3320 where the feedback system 3405 calculates a predicted value for the concentration of the analyte at a future time (e.g. in the next hour) based on the previously determined values for the concentration of the analyte and the treatment dosing history. In some embodiments, the calculation may predict the value for the concentration of the analyte at a future time by extrapolating the concentration of the analyte assuming that the patient's sensitivity to the treatment drug (e.g. insulin) remains the same and by further assuming that the amount of medications and drugs being administered to the patient remain the same. For example, in some embodiments, the feedback system 3405 may assume that treatment dose input by the healthcare provider will not change over the next several time durations.

In block 3330, the predicted value for the concentration of the analyte is compared with a predetermined range. The predetermined range can be determined by taking into account various factors such as a patient's medical condition, the medications and drugs being administered to the patient, etc. In some embodiments, the predetermined range may be a glucose concentration in a range from about 70 mg/dL to about 110 mg/dL. If in block 3330, the predicted concentration of the analyte is determined to be within the predetermined range, then the method 3300 moves to block 3340 where the treatment dose input by the healthcare provider is stored in the measurement history.

However, if in block 3330, the predicted concentration of the analyte is determined to be not within the predetermined range, then the method 3300 proceeds to block 3360 where feedback is provided (e.g. to the healthcare provider or analyte monitoring system) that the predicted concentration of the analyte at a future time may be outside the predetermined range if the treatment dose input to the system is delivered to the patient. The system or the healthcare provider may change the treatment dose based on the feedback. In some embodiments, the feedback system 3405 can be configured to automatically stop the flow of the infusion fluid (e.g. glucose or insulin) based on the trend or a value of the concentration of one or more analytes. For example, in the case where the analyte of interest is glucose and the infusion fluid is insulin, the feedback system 3405 may stop the flow of insulin if the concentration of glucose is low enough to be life threatening or if the trend of successive glucose measurements indicated that the concentration of glucose may drop to levels that may to harmful to the patient.

In some embodiments, the feedback system 3405 can provide feedback regarding one or more drugs being administered to the patient without requiring an input from the healthcare provider. In some embodiments the feedback system 3405 can spectroscopically analyze the infusion fluid as it flows out of the infusion pump and/or source of infusion fluid (e.g. 518, 520 or 2782 of FIG. 5) through the infusion fluid tubes (e.g. 514, 516 or 2784 of FIG. 5) to determine the contents of the infusion fluid. For example, in some embodiments the feedback system 3405 may irradiate the infusion fluid with three or more wavelengths. In some embodiments, the wavelengths can be selected from the wavelength range of approximately 275 nm to 310 nm. In some embodiments, the wavelengths can be selected from the near infrared or infrared range of wavelengths. The feedback system 3405 can then obtain one or more spectra from the radiation reflected, transmitted and/or scattered by the infusion fluid to determine the contents of the infusion fluid. The spectra obtained by the feedback system 3405 can be compared with a catalog of drug or chemical spectra to identify the contents of the infusion fluid. In some embodiments, the spectra can be further analyzed to determine the concentration of the various contents of the infusion fluid.

The feedback system 3405 can comprise a watch list including the drugs or chemicals that may be detrimental to the health of the patient. The identified contents of the infusion fluid can be compared with the watch list. If a particular drug or chemical present in the watch list is detected in the infusion fluid, then the feedback system 3405 can be configured to shut off the infusion system delivering that particular drug or chemical to the patient. In addition, the feedback system 3405 may provide alerts or warnings to the healthcare provider and request confirmation from the healthcare provider before resuming the flow of that particular drug or chemical. In some embodiments, the feedback system 3405 can be configured to prevent the flow of a drug or chemical if the concentration of that drug or chemical in the infusion fluid is determined to be outside an acceptable range. For example, the system can issue an alert or warning to the healthcare provider.

Dilution Calibration

As described above, in certain embodiments, the systems and methods determine a concentration of an analyte such as, for example, glucose, in a bodily fluid sample such as, for example, whole blood or blood plasma. In some cases, the concentration of a blood plasma analyte can be affected by dilution of the whole blood sample from which the plasma is obtained. Dilution of a sample may occur during processing of the sample (e.g., by addition of a diluent to the sample), during operation of the sampling apparatus (e.g., by mixing of the sample with diluents in the apparatus), and so forth. For example, dilution may occur if an anticoagulant (e.g., heparin) is added to a blood sample to prevent clotting. Also, dilution may occur as a fluid sample travels through the apparatus, for example, through accumulation of residual diluent fluids (e.g., saline solution) in tubing.

Generally, dilution of a bodily fluid sample will result in the analyte concentration measured from the diluted sample being less than the analyte concentration present in the patient's body. Because diluents are more likely to reside in the plasma portion of the blood, dilution effects may be greater for analyte concentrations measured in blood plasma. Accordingly, it may be advantageous to calibrate a measured analyte concentration for some or all of the effects of dilution. In some embodiments, a measured analyte concentration is corrected for dilution to provide an estimate of analyte concentration that is more representative of the concentration in the patient's body.

As described above, certain embodiments of the disclosed systems and methods are directed to the measurement of blood plasma analytes in samples of whole blood. Since fluid diluents typically reside in blood plasma rather than in non-plasma components, it may be advantageous to determine the relative amounts of plasma and non-plasma components in a whole blood sample.

Whole blood includes fluid components (e.g., blood plasma) and non-fluid components (e.g., red blood cells, white blood cells, platelets, etc.). In a typical sample of whole human blood, red blood cells constitute approximately 45% of the blood volume, and white blood cells constitute approximately 1% of the blood of the blood volume. Platelets are small, non-fluid blood components that typically remain in the plasma, even after the plasma is separated (e.g., via centrifuging). Consequently, blood plasma typically constitutes approximately 54% of the blood volume.

The relative amounts of plasma and corpuscles in a whole blood sample can be determined in many ways, for example, by using an instrument that separates a blood sample by centrifugation. The hematocrit value (commonly referred to as "Ht" or "HCT") is the percentage of red blood cells in whole blood. The hematocrit value can be determined by centrifuging a sample of whole blood in a graduated tube, a process which packs the red blood cells into the bottom of the tube. Values of the volume of packed red blood cells and the total volume of the blood sample are measured, and the percentage of red blood cells in the total sample, Ht, is calculated as the ratio of these values. As noted above, red blood cells form the bulk of the non-plasma component of blood. Accordingly, the fraction of blood plasma in whole blood is approximately 1−Ht.

The hematocrit value can be estimated without separating red blood cells from whole blood in a centrifuge. One method for estimating Ht uses the fact that hemoglobin predominantly resides in the red blood cells. The concentration of hemoglobin in whole blood can be determined, for example, by optical spectroscopy of the blood sample. Apparatus and methods for optical measurements of blood are described, for example, in U.S. Pat. No. 5,385,539, issued Jan. 31, 1995, entitled "APPARATUS FOR MONITORING HEMATOCRIT LEVELS OF BLOOD," the entire disclosure of which is hereby incorporated by reference herein. The hematocrit, Ht, has been found to be approximately related to the concentration of hemoglobin in whole blood, Hb, as follows:

$$Ht(\%) = 3 \, Hb/(g/dL) \quad (1)$$

Accordingly, a measurement of hemoglobin concentration, Hb, can be converted into an approximation of hematocrit, Ht, (and vice versa) by application of Equation (1). Therefore, embodiments of analyte detection systems can be configured with hematocrit sensors, hemoglobin sensors, or a combination thereof to determine, as appropriate, hematocrit and/or hemoglobin concentration.

Hematocrit (and/or hemoglobin concentration) can be measured via other techniques as well. For example, one example method for estimating Ht uses changes in the electrical conductivity through whole blood, where blood cells act as electrical insulators. Electrical conductivity apparatus and methods are described, for example, in U.S. Pat. No. 6,058,934, issued May 9, 2000, entitled "PLANAR HEMATOCRIT SENSOR INCORPORATING A SEVEN-ELECTRODE CONDUCTIVITY MEASUREMENT CELL," the entire disclosure of which is hereby incorporated by reference herein. Another example method for estimating Ht uses acoustic ultrasound measurements to determine Ht, for example, as described in U.S. Pat. No. 4,854,170, issued Aug. 8, 1989, entitled "APPARATUS AND METHOD FOR USING ULTRASOUND TO DETERMINE HEMATOCRIT," the entire disclosure of which is hereby incorporated by reference herein. In other techniques, hematocrit and/or hemoglobin concentration can be measured using a combination of approaches such as, for example, optical and acoustic techniques as described in U.S. Pat. No. 6,751,490, issued Jun. 15, 2004, entitled "CONTINUOUS OPTOACOUSTIC MONITORING OF HEMOGLOBIN CONCENTRATION AND HEMATOCRIT," the entire disclosure of which is hereby incorporated by reference herein. Embodiments of the systems and methods disclosed herein may use one or more of the above-described example approaches (or other approaches) to measure hematocrit and/or hemoglobin concentration in a fluid sample.

In certain embodiments, an analyte concentration, g, is calibrated for the effects of dilution by determining or inferring a volume of diluent fluid added to the bodily fluid sample during processing of the sample, operation of the analyte detection system, and so forth. The estimated analyte concentration can be calibrated to account for the added diluent volume. For example, in some embodiments, one or more measurements of hematocrit (and/or hemoglobin concentration) in the fluid sample are made before and after dilution, and these measurements are used to at least partially correct an estimated analyte concentration for the effects of dilution. Examples of dilution calibration methods and systems will now be described.

Example Dilution Calibration Systems

Figure 35:
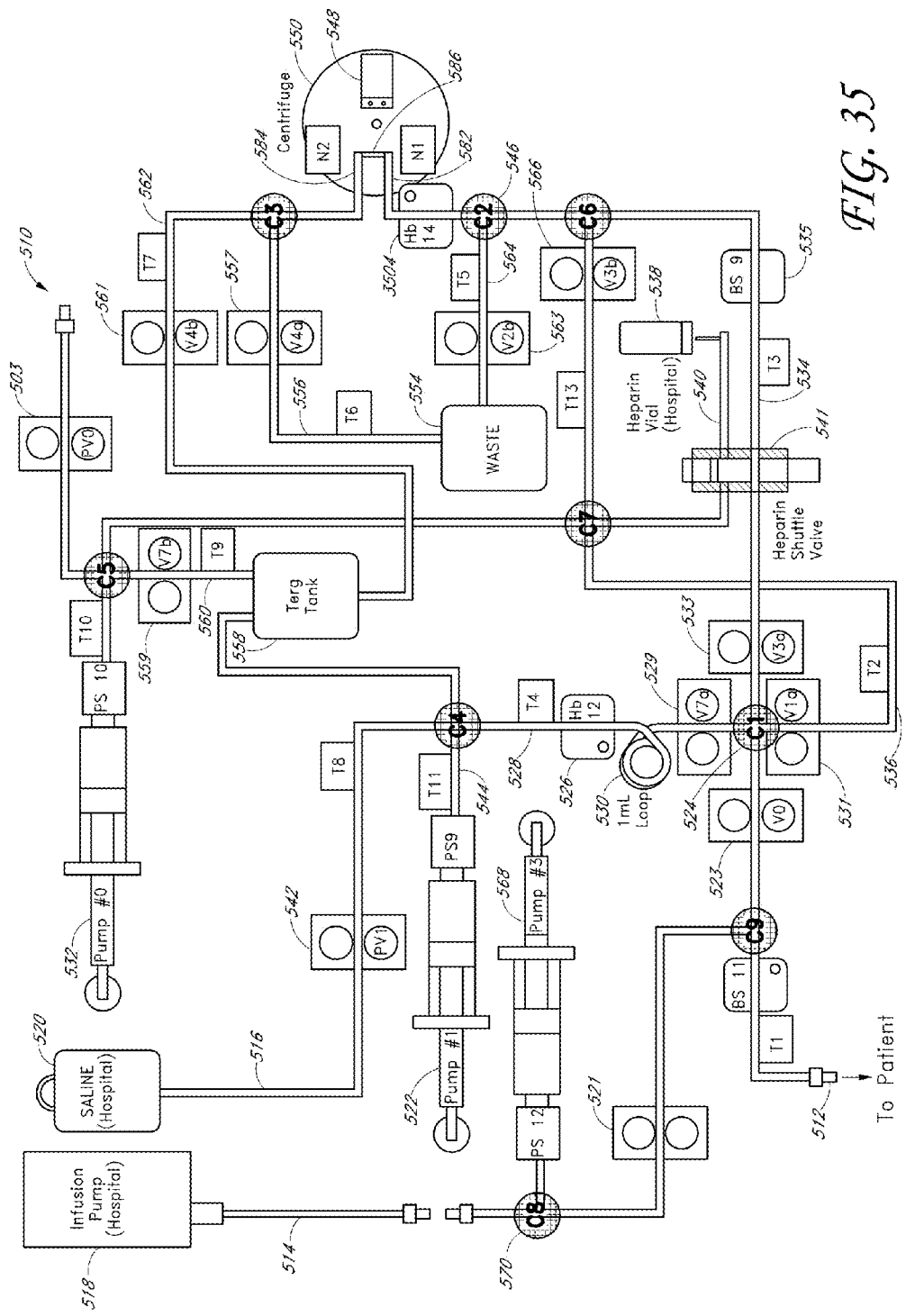
FIG. 35 schematically illustrates an embodiment of a fluid system that can be part of a system for withdrawing and analyzing fluid samples and calibrating the analyzed samples for sample dilution.
Figure 36:
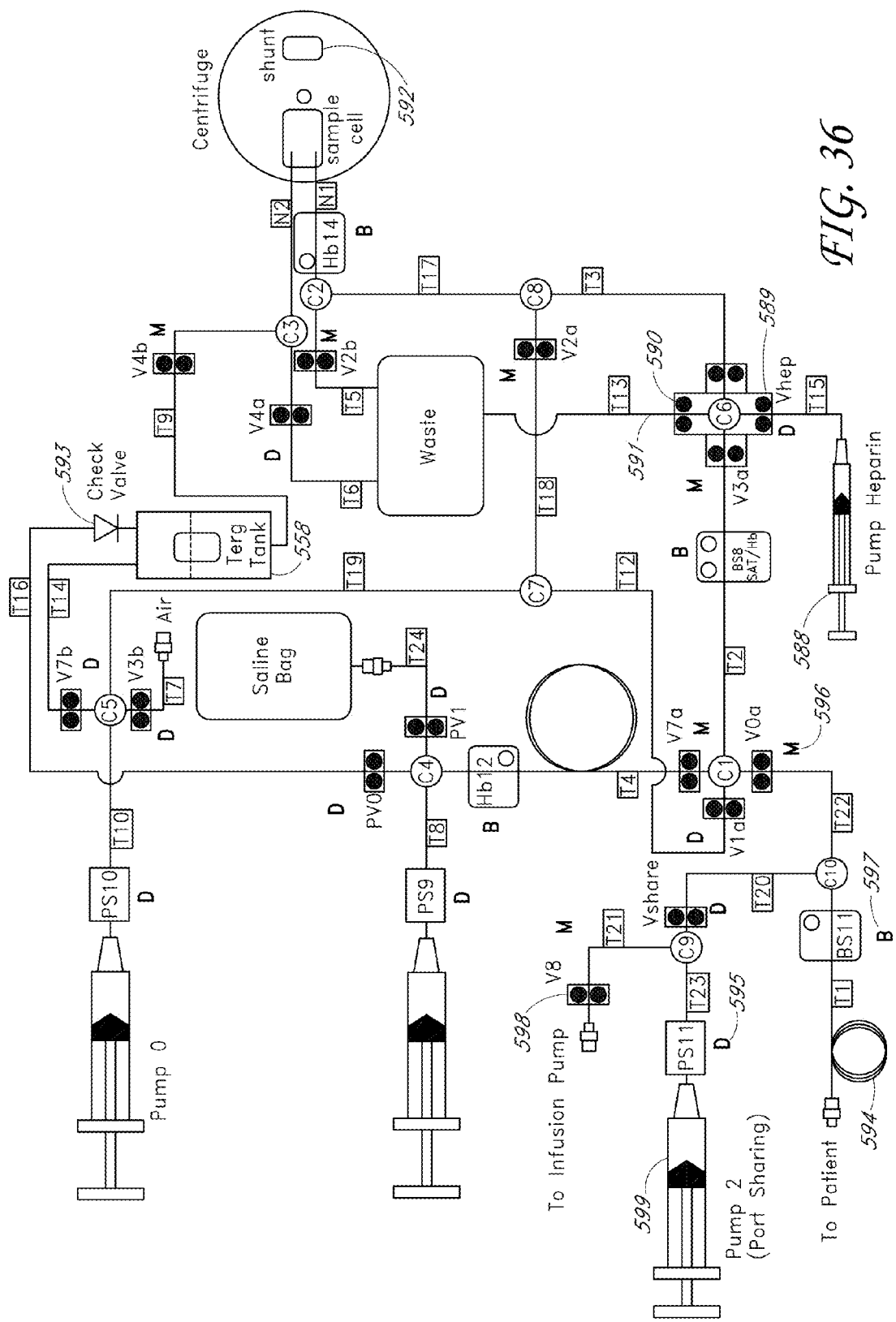
FIG. 36 schematically illustrates another embodiment of a fluid system that can be part of a system for withdrawing and analyzing fluid samples and calibrating the analyzed samples for sample dilution.

Any of the example analyte detection systems (and/or fluid handling systems) described herein can be used to provide dilution calibration. For example, FIGS. 35 and 36 schematically illustrate embodiments suitable for using hematocrit and/or hemoglobin concentration measurements to at least partially correct for dilution. Many of the components shown in FIGS. 35 and 36 have been described above with reference to FIGS. 5 and 6. In the embodiments depicted in FIGS. 35 and 36, the bubble sensor BS14 shown in FIG. 5 (reference numeral 552) and FIG. 6 has been interchanged with a hemoglobin sensor Hb14 (reference numeral 3504 in FIG. 35). In some embodiments, the hemoglobin sensor Hb14 is generally similar to the hemoglobin sensor 526 (Hb12) described above with reference to FIGS. 5 and 6. As will be described below, in these embodiments, the hemoglobin sensor Hb12 is used to measure hemoglobin concentration of the fluid sample after drawing from the body (and before substantial dilution has occurred). The hemoglobin sensor Hb14 is used to measure hemoglobin concentration after the fluid sample has traveled through the tubing to the vicinity of the centrifuge (and therefore after dilution may have occurred). These "before dilution" and "after dilution" measurements of hemoglobin concentration can be used to at least partially correct for the effects, if present, of dilution.

Although the embodiments shown in FIGS. 35 and 36 utilize a hemoglobin concentration sensor Hb14, in other embodiments either (or both) of the hemoglobin concentration sensors Hb12 and Hb14 may be hematocrit sensors.

Further, although the bubble sensor BS14 (shown in FIGS. 5 and 6) has been interchanged with the hematocrit sensor Hb14 in the embodiments shown in FIGS. 35 and 36, in other embodiments, the hematocrit sensor Hb14 is provided in addition to the bubble sensor BS 14. Also, in other embodiments the sensors Hb12 and Hb14 can be disposed at locations in the fluid handling network that are different than shown in FIGS. 5, 6, 35, and 36. For example, the sensor Hb12 can be located closer to the patient tube 512 (T1), and the sensor Hb14 can be located closer to (but downstream of) the anticoagulant valve 541. It is advantageous for the sensors Hb12 and Hb14 to be disposed at locations in the fluid handling network such that substantially all the dilution of the fluid sample can be accounted for. Although two sensors Hb12 and Hb14 are shown in FIGS. 35 and 36, in other embodiments three, four, five, six, or more sensors can be used to measure dilution of the fluid sample. For example, in some embodiments, sensors are positioned upstream and downstream of the location where an anticoagulant (e.g., heparin) is added to the fluid sample. Such embodiments advantageously can be used to calibrate for dilution by the anticoagulant.

An example of collection of a fluid sample will now be described with reference to FIG. 35. With the valves 542 (PV1), 559 (V7b), and 561 (V4b) closed, a first pump 522 (pump #1) is actuated to draw sample fluid to be analyzed (e.g. blood) from a fluid source (e.g., a laboratory sample container, a living patient, etc.) up into the patient tube 512 (T1), through the tube past the two flanking portions of the open pinch-valve 523 (V0), through the first connector 524 (C1), into the looped tube 530, past the hemoglobin sensor 526 (Hb12), and into the Hb sensor tube 528 (T4). During this process, the valve 529 (V7a) and 523 (V0) are open to fluid flow, and the valves 531 (V1a), 533 (V3a), 542 (PV1), 559 (V7b), and 561 (V4b) can be closed and therefore block (or substantially block) fluid flow by pinching the tube.

Before drawing the sample, the tubes 512 (T1) and 528 (T4) are filled with saline and the hemoglobin (Hb) level is zero. The tubes that are filled with saline are in fluid communication with the sample source (e.g., the fluid source 402). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually a nondiluted sample fluid.

The hemoglobin sensor 526 (Hb12) detects the concentration of hemoglobin in the sample fluid. As blood starts to arrive at the hemoglobin sensor 526 (Hb12), the hemoglobin level rises. A hemoglobin level can be selected, and the system can be pre-set to determine when that level is reached. A controller such as the fluid system controller 405 of FIG. 4 can be used to set and react to the pre-set value, for example. In some embodiments, when the sensed hemoglobin level reaches the pre-set value, a substantially undiluted sample is present at the first connector 524 (C1). The preset value can depend, in part, on the length and diameter of any tubes and/or passages traversed by the sample. A nondiluted sample can be, for example, a blood sample that is not diluted with saline solution, but instead has the characteristics of the rest of the blood flowing through a patient's body. The hemoglobin sensor 526 (Hb12) can measure the hemoglobin concentration of this "before dilution" blood sample. A loop of tubing 530 (e.g., a 1-mL loop) can be advantageously positioned as illustrated to help insure that undiluted fluid (e.g., undiluted blood) is present at the first connector 524 (C1) when the hemoglobin sensor 526 (Hb12) registers that the preset Hb threshold is crossed. The loop of tubing 530 provides additional length to the Hb sensor tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1). Accordingly, a possible advantage of embodiments using the loop of tubing 530 is that the "before dilution" hemoglobin concentration measured by the sensor 526 (Hb12) is representative of the (non-diluted) hemoglobin concentration of the patient's body.

When sufficiently nondiluted blood is present at the first connector 524 (C1), the fluid sample can be directed through the tube 534 (T3), past the connectors C6 and C2, and to the sample cell 548 for analysis. While traveling through this tubing, the fluid sample can be diluted by accumulation of saline solution, cleaning solution, etc. that has been left behind on the tube walls after cleaning or purging. Additionally, in some embodiments, an amount of anticoagulant (e.g., heparin) can be introduced into the tube 534 (T3), and then the fluid sample is mixed with the anticoagulant. As described above, the anticoagulant can be shuttled from the tube 540 into the anticoagulant valve tube 534 (T3) to provide a controlled amount of anticoagulant into the tube 534 (T3), which thereby additionally dilutes the fluid sample. After addition of the anticoagulant (if desired), the fluid sample is pushed up the anticoagulant valve tube 534 (T3), through the connector C6, and through the second connector 546 (C2). Along this path, the fluid sample may experience further dilution from accumulation of fluids on the tube walls. After passing the connector C2, the sample comes into sensing contact with the hemoglobin sensor 3404 (Hb14), which determines an "after-dilution" hemoglobin concentration of the sample. The sample is then pushed into the sample cell 548, which can be located on the centrifuge rotor 550. The fluid in the sample cell is centrifuged, which separates blood corpuscles from the blood plasma and any diluents present in the plasma (e.g., heparin, saline, cleaning fluid, etc.). Concentration of analytes in the diluted blood plasma can be measured as described above.

An example of the collection of a fluid sample in the fluid handling embodiment schematically illustrated in FIG. 36 will be described. Collection of the fluid sample may be generally similar to the collection described above with reference to FIG. 35. For example, blood is drawn from a patient (or from a suitable extracorporeal conduit), through the tubes T1, T22, and T4 and into the loop. When the hemoglobin sensor Hb12 determines, via a "before dilution" hemoglobin measurement, that the loop contains undiluted blood, the blood sample is directed to connector C1 and into line T2. If desired, as the blood sample passes the connector C6 an anticoagulant (e.g., heparin) can be injected, which dilutes the blood sample. The blood sample is then directed through the tubes T3 and T17 and passes the connector C2, where the hemoglobin sensor Hb14 performs an "after dilution" hemoglobin measurement. The blood sample is then directed into the sample cell of the centrifuge, where the blood corpuscles are separated from a diluted volume of blood plasma. A measurement of analyte concentration may then be performed on the diluted plasma sample. As discussed above, as the blood sample travels from the sensor Hb12 to the sensor Hb14, the blood sample can be diluted due to 1) accumulation of fluids (e.g., saline, cleaning solution, etc.) left behind on the tube walls from a previous tube purging/cleaning, and/or 2) injection, if desired, of an amount of a anticoagulant at the connector C6.

Example Dilution Calibration Methods

Figure 37:
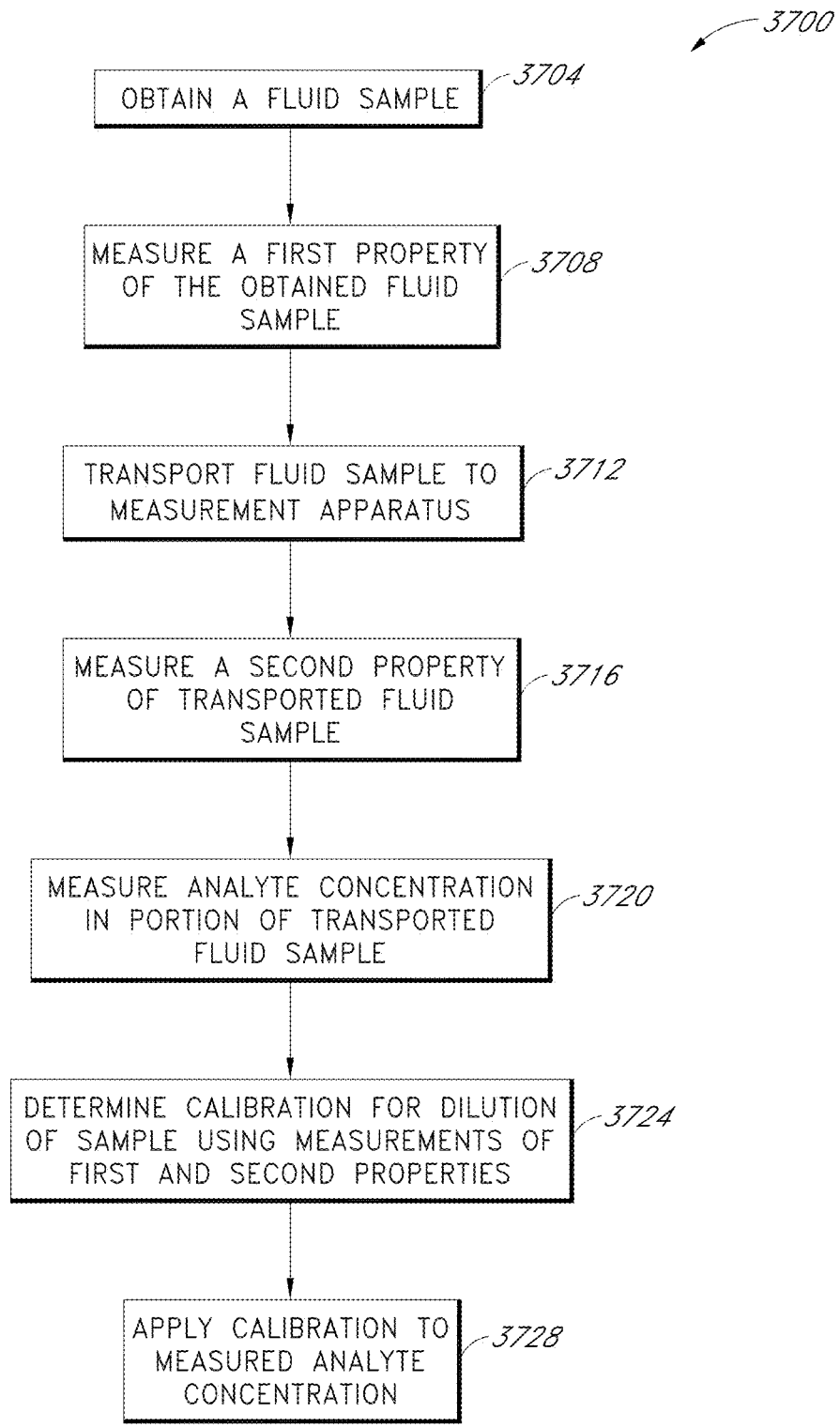
FIG. 37 is a flowchart that schematically illustrates an embodiment of a method for calibrating an analyte measurement in a fluid sample for effects of dilution of the fluid sample.

FIG. 37 is a flowchart illustrating an example method 3700 for calibrating an analyte measurement in a fluid sample for dilution of the fluid sample. In block 3704, a fluid sample is obtained for measurement. The fluid sample may comprise whole blood, blood plasma, interstitial body fluid, and so forth. The fluid sample can be obtained from a suitable fluid source (e.g., a laboratory sample container, a living patient, etc.). In many of the illustrative examples described herein, the fluid sample is a whole blood sample drawn from a patient, but this is not intended to be a limitation to embodiments of the calibration methods.

In block 3708, a first property of the fluid sample is measured. Advantageously, the first property may be sensitive to dilution of the sample. For example, in some embodiments the first property is hematocrit and/or hemoglobin concentration, and the first property is measured by a blood sensor such as, e.g., a hematocrit sensor and/or a hemoglobin sensor. In other embodiments, the first property may be a concentration of a particular component, analyte, or species in the fluid sample. Properties such as, for example, density and/or volume of the fluid sample can be measured. The first property may be a measurement of a single parameter or characteristic of the fluid sample or may include a group of measurements.

In block 3712, the obtained fluid sample is transported to a measurement site capable of providing a measurement of an analyte in the fluid sample. For example, the obtained fluid sample can be transported by a fluid handling network in an analyte detection system, such as, e.g., the fluid handling networks schematically depicted in FIGS. 35 and 36. While being transported, the fluid sample may experience dilution caused by, for example, processing of the fluid sample (e.g., addition of one or more diluents) and/or through routine operation of the fluid transport network (e.g., accumulation in the sample of diluents present in tubing in the fluid handling network). The amount of dilution can be known and/or unknown. For example, the amount (e.g., volume) of an anticoagulant added to the sample can be known (or determinable), while the amount of diluent accumulated from the fluid handling network can be unknown (and dependent on how the system has been operated prior to transport of the sample).

In block 3716, a second property of the fluid sample is measured. Advantageously, the second property may be sensitive to dilution of the sample such that the amount of dilution can be determined from comparison of the first property and the second property. As discussed above for the first property, the second property may include hematocrit, hemoglobin concentration, concentration of a particular component, analyte, or species in the fluid sample, density, and/or volume of the fluid sample. The second property may be a measurement of a single parameter or characteristic of the fluid sample or may include a group of measurements. The second property may be the same as the first property (e.g., both the first and the second property may be hematocrit), or the second property may be different from the first property (e.g., the first property may be hematocrit and the second property may be hemoglobin concentration).

In block 3720, a measuring apparatus performs a measurement of an analyte concentration in a portion of the fluid sample. For example, the measuring apparatus may comprise a spectroscopic analyte detection system configured to measure the concentration of an analyte (e.g., glucose) in plasma separated from a blood sample. The measuring apparatus may perform the analyte measurement on the fluid sample (e.g., a whole blood sample) and/or a component of the fluid sample (e.g., blood plasma separated from whole blood). Because of the possible effects of dilution of the fluid sample during transport in block 3712, the measured analyte concentration may not represent the analyte concentration in the nondiluted fluid sample obtained in block 3704. Accordingly, in blocks 3724 and 3728, the measured analyte concentration is calibrated for dilution of the fluid during transport. In some embodiments, the calibration at least partially corrects the measured analyte concentration for the dilution. For example, in block 3724 a calibration is determined based at least in part on the first property and the second property. Illustrative, non-limiting examples of the calculation of the calibration will be presented below. In block 3728, the calibration is applied to the analyte concentration measured in block 3720 to provide an at least partially dilution-calibrated estimate for analyte concentration.

In some embodiments, one or more general purpose and/or special purpose computers can be used to implement embodiments of the method 3700. Embodiments of the method 3700 can be represented as computer-executable instructions on a computer-readable medium. For example, the fluid system controller 405 may control the measurements of the first and second properties in blocks 3708 and 3716 (e.g., using measurement of hematocrit and/or hemoglobin concentration), and the algorithm processor 416 may control the measurement and calibration of the analyte concentration in blocks 3720-3728. In other embodiments, portions of the method 3700 can be executed by processors that are remote from analyte detection system. In certain embodiments, some (or all) of the blocks 3604-3728 can be combined or can be performed differently (or in different orders) than shown in the example method 3700 shown in FIG. 37. Many variations are possible.

An example procedure for calibrating an analyte measurement for the effects of dilution will now be described. This example is intended to be illustrative and not to limit the scope of the dilution calibration methods. In this example, a measurement of hematocrit and/or hemoglobin in a blood sample is performed "before dilution" (e.g., in block 3708) and another hematocrit and/or hemoglobin measurement is performed "after dilution" (e.g., in block 3716). For example, in the fluid system embodiments shown in FIGS. 35 and 36, the "before dilution" measurement can be provided by the hemoglobin sensor Hb12 and the "after dilution" measurement can be provided by the hemoglobin sensor Hb14. As described above, in other embodiments, additional hematocrit and/or hemoglobin measurements can be obtained. In such embodiments, the additional measurements can be used to improve accuracy and/or precision of the dilution calibration according to any suitable statistical techniques (e.g., regression, least squares, maximum likelihood, outlier analysis, etc.).

In this example procedure, "before dilution" measurements are indicated with a subscript "0," and "after dilution" measurements are indicated with a subscript "1." Further, in this example, the blood sample will be considered to include corpuscles, e.g., red and white blood cells, (subscript "c") and plasma (subscript "p"). In a volume of blood denoted by V, a volume $V_c$ contains corpuscles, and the remaining volume $V_p = V - V_c$ contains plasma. Thus, hematocrit, Ht, can be written as $$Ht = \frac{V_c}{V} = 1 - \frac{V_p}{V} \qquad (2)$$

If hemoglobin concentration, Hb, is used to estimate Ht, Equation (1) can be used to convert Hb to Ht (or vice versa).

The total amount of glucose in the plasma is denoted by G, and equals the plasma glucose concentration, g, multiplied by the plasma volume $$G = g V_p \qquad (3)$$

In this example, assume that as the blood sample is transported, it is diluted with a volume $\Delta V$ of fluid having no glucose and no solids. For example, $\Delta V$ may represent the controlled amount of anticoagulant mixed with the blood sample at the tube 534 (T3, shown in FIG. 35). Because no glucose and no solids are assumed to be added to the blood sample, the values of G and $V_c$ do not change during dilution. Consequently, $$G_0 = G_1 = G \qquad (4)$$

$$V_{c0} = V_{c1} = V_c. \qquad (5)$$

The total blood volume and the plasma volume after dilution are related to the volumes before dilution and the dilution volume $\Delta V$ by $$V_1 = V_0 + \Delta V \qquad (6)$$

$$V_{p1} = V_{p0} + \Delta V. \qquad (7)$$

The plasma glucose concentration after dilution, $g_1$, is determined by the analyte detection system (e.g., in block 3720 of FIG. 37) and is thus a measured (known) quantity. Because the total amount of glucose, G, in the blood sample is assumed to be constant (no glucose is added by the diluent fluid), the value of the plasma glucose concentration before dilution, $g_0$, is unknown but may be related to $g_1$ from Equations (3) and (4): $G = g_0 V_{p0} = g_1 V_{p1}$. Combining this relationship with Equation (7) yields $$\frac{g_0}{g_1} - 1 = \frac{\Delta V}{V_{p0}}, \qquad (8)$$

hence, the calibration of the plasma glucose measurement is related to the amount of dilution, $\Delta V$, of the blood sample. The "before dilution" plasma volume $V_{p0}$ can be replaced with the "before dilution" hematocrit, $Ht_0$, by using Equation (2), which yields $$\frac{g_0}{g_1} - 1 = \frac{\Delta V / V_0}{1 - Ht_0}, \qquad (9)$$

where $V_0$ is the total blood volume before dilution.

In embodiments in which hemoglobin concentration, Hb, is measured instead of hematocrit, Ht, Equation (1) can be used in Equation (9) to yield $$\frac{g_0}{g_1} - 1 = \frac{\Delta V / V_0}{1 - 3 Hb_0}, \qquad (10)$$

where $Hb_0$ is measured in g/dL.

In some embodiments, the volumes $\Delta V$ and $V_0$ (or the ratio $\Delta V / V_0$) and the value $Hb_0$ are measured, and Equation (10) is used to adjust the measured plasma glucose concentration, $g_1$, to yield an estimate of the undiluted plasma glucose concentration, $g_0$. For example, in implementations where addition of an anticoagulant predominates dilution of the sample, the amount $\Delta V$ of the added anticoagulant can be measured (or otherwise know) and used in Equation (10) to calibrate the analyte concentration measurement.

In other embodiments, the diluted hematocrit, $Ht_1$ (and/or the diluted hemoglobin concentration $Hb_1$) is measured, and the volumes in Equation (10) are replaced with measured blood sample values. For example, because no solids are assumed to be added by the fluid diluent, the volume of corpuscles in the sample, $V_c$, is constant, and Equations (2) and (5) can be combined as $V_c = V_0 Ht_0 = V_1 Ht_1$. Equation (6) can be used eliminate $V_1$ to yield $$\frac{\Delta V}{V_0} = \frac{Ht_0}{Ht_1} - 1. \qquad (11)$$

Consequently, measurements of hematocrit (and/or hemoglobin concentration) "before dilution" and "after dilution" can be used to provide an estimate of fractional sample dilution, $\Delta V / V_0$.

Substituting Equation (11) into Equation (9) provides another relationship that can be used to calibrate an "after dilution" glucose measurement to yield an estimate for the "before dilution" glucose measurement:

$$\frac{g_0}{g_1} - 1 = \frac{Ht_0 / Ht_1 - 1}{1 - Ht_0}, \qquad (12)$$

or if hemoglobin concentration Hb is measured (see, Eq. (1)), $$\frac{g_0}{g_1} - 1 = \frac{Hb_0 / Hb_1 - 1}{1 - 3 Hb_0}. \qquad (13)$$

Equations (12) and (13) can be rewritten to show how the estimate for the "before dilution" analyte concentration $g_0$ is related to the measured "after dilution" analyte concentration $g_1$:

$$g_0 = g_1 \left[ \frac{Ht_0}{Ht_1} \frac{(1 - Ht_1)}{(1 - Ht_0)} \right], \qquad (14)$$

$$g_0 = g_1 \left[ \frac{Hb_0}{Hb_1} \frac{(1 - 3 Hb_1)}{(1 - 3 Hb_0)} \right]. \qquad (15)$$

If there is no measurable dilution of the sample, the "before dilution" and the "after dilution" Ht and/or Hb measurements will be substantially the same (e.g., the factors in square brackets will be approximately equal to one), and Equations (14) and (15) demonstrate that, as expected, $g_0 \approx g_1$. In some embodiments, the calibration shown in Equation (14) or (15) is not applied if the change between $Ht_1$ and $Ht_0$ (or $Hb_1$ and $Hb_0$) is more representative of measurement errors by hematocrit (and/or hemoglobin) sensors than dilution of the sample. If measurable dilution of the sample occurs, the "before dilution" and "after dilution" values for Ht (and/or Hb) will be different, and the factors in square brackets in Equations (14) and (15) provide an approximate correction factor that at least partially accounts for the dilution.

Thus, for example, in an embodiment in which $Hb_0$, $Hb_1$, and $g_1$ are measured (e.g., the embodiments shown in FIGS. 35 and 36), Equation (13) (or Eq. (15)) provides a relationship that can be used to estimate the "before dilution" analyte concentration $g_0$. Although the above example has been described in terms of glucose concentration, this is not a limitation, and the example procedure described herein can be used to calibrate concentration of any analyte measured in blood plasma. Further, Equations (2)-(15) can be readily modified if various assumptions that went into their derivation are relaxed. For example, an appropriate calibration for an analyte concentration can be derived if the diluent fluid added to the blood sample contains a known amount (or concentration) of the analyte of interest and/or blood solids. Also, Equations (12)-(15) can be modified if more than two hematocrit (and/or hemoglobin concentration) measurements are made while the blood sample is being transported between the patient (or an extracorporeal fluid container) and the analyte measurement apparatus (e.g., the centrifuge and spectroscopic analyzer). Many variations are contemplated, and an appropriate calibration may readily be determined for each such variation using the teachings herein. For example, in many implementations, the calibration will be a linear (e.g., affine) relationship, thus the "before dilution" concentration estimate will be related to the "after dilution" concentration measurement according to $g_0 = C\, g_1 + D$, where C is a calibration factor and D is a calibration offset. In the example calibration procedure described above, the calibration offset D=0, and the calibration factor C is the quantity in the square brackets in Equation (14) (if hematocrit is measured) or Equation (15) (if hemoglobin concentration is measured). In other embodiments, the calibration offset is non-zero. For example, the calibration offset may at least partially correct for a diluent fluid that also includes the analyte of interest.

Integrated Insulin Delivery

Disclosed herein is a glucose monitoring and insulin control system capable of automatically, frequently, and accurately measuring a patient's blood glucose concentration and automatically adjusting the patient's insulin dosage according to the measurements. The system can cut off the infusion of insulin altogether if continued infusion would be harmful to the patient. The glucose monitoring system can deliver insulin to the patient through the same line that draws bodily fluid samples for glucose monitoring. The patient is thus connected to fewer access points and has less exposure for infections. The glucose monitoring system can have a downloadable insulin dosing protocol stored in its memory, enabling the monitoring system to calculate the proper dosage of insulin based on the patient's measured glucose concentration. Because the protocol is downloadable, the user can modify or substitute the dosing protocol. Also, the glucose monitoring device can control the actual infusion of insulin directly or indirectly, thus providing automatic adjustments to insulin dosage and minimizing the chances for dosing errors caused by human error. The monitoring device can cut off insulin delivery when continued insulin infusion would be hazardous to the patient's health (e.g., at a user-settable threshold which can have a lower limit of 40 mg/dl, for example). The monitoring device can turn off insulin delivery after it measures one or more values below the threshold. Details of these features have been described above, and additional details are provided below.

Insulin Cutoff

Diabetic patients may require regular doses of insulin to control their blood glucose levels. These patients are often unable to self-administer the required insulin when admitted to a hospital or ICU. A majority of patients admitted to the ICU experience hyperglycemia even without having diabetes. Therefore, it has been increasingly important to monitor a patient's blood glucose levels and administer regular doses of insulin in the ICU setting. However, insulin administered to patients in the ICU to treat hyperglycemia can lead to increased cases of hypoglycemia and even severe hypoglycemia. Severe hypoglycemia can be defined as a single glucose value measurement of approximately 40 g/dl (or 2.2 mmol) or less. This is especially true when IV insulin is used because it is infused directly into the patient's blood stream and it can be very fast-acting and potent. Recent studies have shown that even a single episode of severe hypoglycemia greatly increases a patient's risk of mortality. The findings of one such study (The Normorglycaemia in Intensive Care Evaluation and Survival Using Glucose Algorithm Regulation (NICE-SUGAR) study) are discussed below. The primary aim of the NICE-SUGAR study was to compare the effects of two blood glucose targets on all-cause mortality in intensive care patients who are predicted, on admission to the ICU, to stay in the ICU for at least 48 hours. In this study, over 6000 patients were recruited in over 35 Intensive Care Units. The treatment groups were assigned one of two targets for blood glucose, either the lower range target of 4.5-6.0 mmol/L (81-108 mg/dl) or the higher range target of 8.0-10.0 mmol/L (144-180 mg/dl). A treatment group can also be assigned a target comprising 80-140 mg/dl.

The NICE-SUGAR study characterized all episodes of hypoglycemia (e.g. blood glucose concentration ~2.2 mmol/L) as serious adverse events (SAEs). The incidence and timing of the first 100 SAEs were extracted from the study database. Two assessors independently reviewed the SAEs to determine the cause of hypoglycaemia and the differences were resolved by consensus. Patients' baseline characteristics were extracted from the study database to investigate risk factors for hypoglycemia. Clinical sequelae were recorded. It was found that there is an increase in sever hypoglycemia events in the lower target group. For example, 8% of the patients in the lower target group had hypoglycemia versus 0.3% of the patients in the higher target group. Initial multivariate analysis of baseline characteristics did not yield a useful model for predicting hypoglycemia although patients with hypoglycemia were older and had higher APACHE II and SOFA renal scores. In approximately 37% of cases, the adjudicated cause for hypoglycemia was clinical error (e.g. failure to follow the computerized treatment algorithm and infrequent blood glucose monitoring). In approximately 24% of cases, the adjudicated cause for hypoglycemia was decreased nutritional intake. In approximately 8% of the cases, the cause for hypoglycemia was pre-terminal. In approximately 16% of the cases, the cause for hypoglycemia was spurious (e.g. measurement error) and in approximately 15% of the cases, the cause of hypoglycemia was none of the above (miscellaneous reasons). It was also observed that most cases of hypoglycemia occurred within 55 days after randomization with 56% of episodes of hypoglycemia occurring within 5 days of randomization and 26% within 48 hours of randomization. No adverse clinical sequelae were detected. This study demonstrates the need for improved control of glucose, especially in the ICU. Also demonstrated is the need for automated glucose monitoring and a system for helping guarantee that hypoglycemia will not occur. The systems, features, and methods described herein help meet these needs.

Hypoglycemia often goes undetected in patients in the ICU for several reasons. First, many of the symptoms of hypoglycemia (e.g., headache, fatigue, confusion, dysarthiria, and impaired judgment) are difficult to measure and difficult for an ICU patient to report. Second, a recent study shows that blood glucose meters that use capillary blood are only accurate in measuring severe hypoglycemia 26% percent of the time. Third, because monitoring glucose on a regular basis is time consuming, medical professional are often unable to comply with glucose measurement protocols. Therefore, it is desirable to have a glucose monitoring system that is capable of automatically preventing hypoglycemia in a patient.

Thus systems and methods that can automatically monitor and control the blood glucose level at periodic intervals so as to prevent incidents of hypoglycemia will be advantageous. Accordingly, some embodiments are configured to prevent hypoglycemia by periodically measuring a patient's blood glucose concentration at predefined time intervals and cutting off the infusion of insulin to the patient if the blood glucose concentration falls below a certain level, or if the trend of blood glucose concentration indicates that the blood glucose concentration will fall below a certain level at a future time. Although embodiments are described here in the context of preventing hypoglycemia, other embodiments can be applied to prevent other harmful conditions. For example, some embodiments may be configured to prevent hyperglycemia by measuring blood glucose concentration and cutting off infusion of dextrose. Some embodiments may be configured to measure other physiological parameters in a patient and cut off infusion of other infusion fluids.

Figure 38:
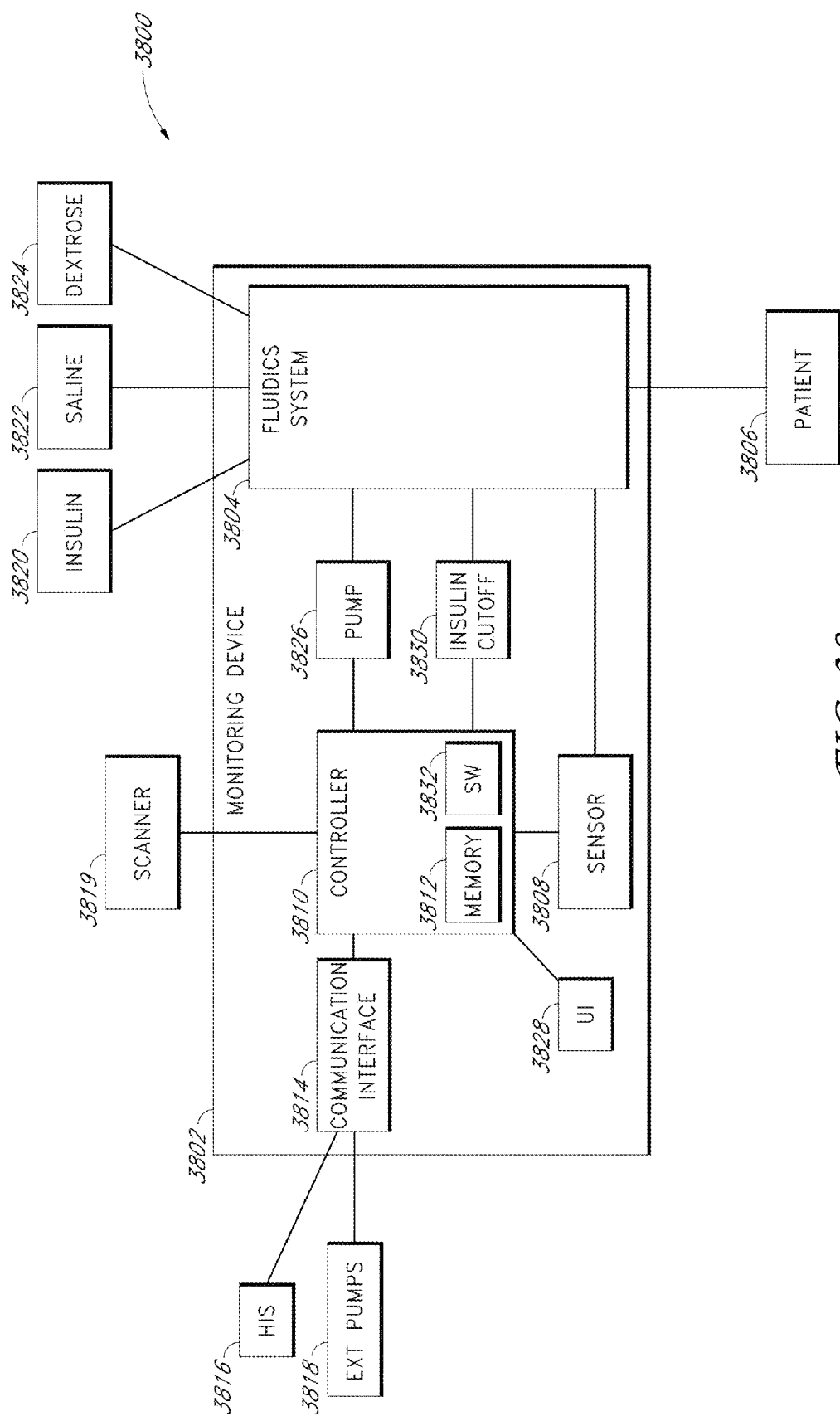
FIG. 38 schematically depicts various components and/or aspects of a patient monitoring system and the relationships among the components and/or aspects.

FIG. 38 schematically shows various components of a patient monitoring system 3800 and how those components relate to each other. Some of the depicted components can be included in a kit containing a plurality of components. Some of the depicted components are optional. Many aspects of patient monitoring system 3800 are similar to embodiments described above and need not be discussed in detail here. The patient monitoring system includes a monitoring device 3802. In some embodiments the monitoring device 3802 can be the monitoring device 102 of FIG. 1, the system 400 of FIG. 4, and/or the monitoring apparatus 2632 of FIG. 26. Patient monitoring device 3802 includes a fluidics system 3804 that is connected to a patient 3806. Fluidics system 3804 may be connected to patient 3806 by a single lumen catheter, a double lumen catheter, two or more catheters or any other manner described above that provides a fluid connection between patient 3806 and monitoring device 3802.

In some embodiments, a sample of a bodily fluid is drawn from patient 3806 and delivered by fluidics system 3804 to a sensor 3808. Sensor 3808 measures a physiological parameter of the bodily fluid. For example, the sensor 3808 can measure the concentration of an analyte (e.g., glucose) in the bodily fluid. The details of the sensor 3808 and methods for measuring the concentration of an analyte are discussed above. The sensor 3808 communicates the measurements to a controller 1810. The controller 3810 can contain a memory 3812 for storing measurements. The memory 1812 may also store patient information such as a patient's weight, age, diet, medication schedule, etc. In some embodiments, the memory 3812 contains protocols and algorithms as discussed in more detail below.

In some embodiments, monitoring device 3802 can be calibrated with a glucose control solution (not shown) to improve accuracy. The control solution can contain a known concentration glucose, and may also contain known amounts of interferents. In some embodiments, more than one control solution can be used. The control solution can be measured as though it was body fluid and the measured glucose concentration is compared to the known concentration. Adjustments to the sensor 3808, or other parts of monitoring device 3802, can be then be made to compensate for discrepancies.

In some embodiments, it is desirable for a system to be reliably stable and not inherently prone to instrumental drift and/or other inaccuracies so that intervals between glucose control solution calibrations can be long. In some embodiments, the monitoring device 3802 is capable of maintaining accuracy between long glucose control solution calibration intervals. For example, sensor 3808 can be a nondisposable sensor, such as an optical sensor that spectroscopically measures for glucose, as discussed above. Thus, some embodiments of sensor 3808 do not require glucose control solution calibrations at such frequent intervals as those needed to maintain consistency between frequently changed disposable sensors. In some embodiments, the monitoring device 3802 can make self-adjustments between glucose control solution calibrations, according to known or predictable patterns, to provide for accuracy over a longer period, thus extending the time between calibration intervals. For example, monitoring device 3802 can check the accuracy of the optical sensor after each glucose measurement by performing a spectroscopic analysis of saline or some other flush solution. By comparing the measured spectroscopic readings against the known spectra of saline, the system can confirm that the optical sensor is operating accurately. Because the spectroscopic reading of saline is similar in some ways to the spectroscopic reading of glucose, saline provides a good proxy solution that can be used for frequent calibration (e.g., after each glucose measurement). If the spectroscopic analysis of the saline solution indicates that the accuracy of the optical sensor is outside of an acceptable range, the monitoring system can alert a user (medical personnel) that adjustments should be made, or the monitoring system can perform self-adjustments to compensate. The monitoring device 3802 can be configured for glucose control solution calibration of less than than twice per day, twice per day, once per day, once every 36 hours, once every two days, once every three days, once each week, once each month, once each year, or even less frequently.

The patient monitoring device 3802 may also contain a communication interface 3814. Communication interface 3814 can provide a connection to a hospital information system (HIS) 3816, allowing the patient monitoring device 3802 to report measurements and other data to HIS 3816 and allowing the patient monitoring device 3802 to retrieve patient information or other data from HIS 3816. Communication interface 3814 can provide communication between patient monitoring device 3802 and other monitoring devices (not shown) or to external infusion pump(s) 3818 that are also associated with patient 3806. The communication interface 3814 can be a wired connection or a wireless connection or a combination thereof. For example, patient monitoring device can communicate with HIS 3816 through a wired connection while communicating with external infusion pumps 3818 through a wireless connection. Alternatively, patient monitoring device may communicate with external infusion pumps 3818 through HIS 3816. In some embodiments, monitoring device 3802 retrieves information from external infusion pumps 3818. In some embodiments, monitoring device 3802 sends information to external infusion pumps 3818. In some embodiments, the monitoring device 3802 sends commands to and controls the external infusion pumps 3818.

Figure 39:
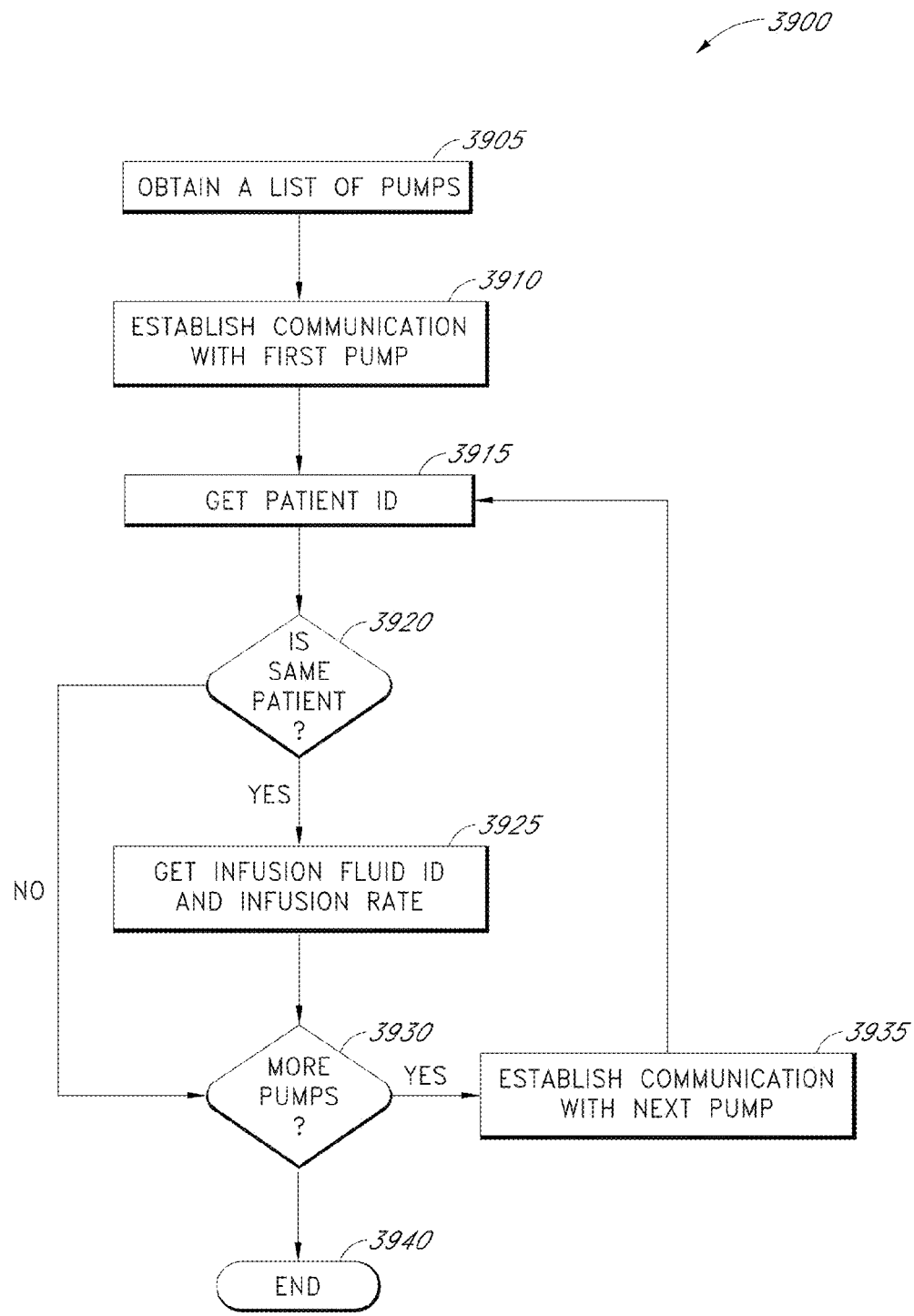
FIG. 39 is a flowchart that schematically illustrates an embodiment of a method for acquiring information from an external infusion pump.

FIG. 39 is a flow chart that shows an exemplary process 3900 by which communication interface 3814 can obtain information from external infusion pumps. Process 3900 begins at block 3905 where communication interface 3814 obtains a list of external pumps to which it can communicate. In block 3910 communication interface 3814 establishes communication with a first external pump. In block 3915 communication interface 3814 obtains the patient identify associated with the external pump. The patient identity can be stored in a memory on the external pump, and may be inputted by a user (e.g., a nurse) by a user interface or a scanner. In block 3920, the external pump's patient identifier is compared to the patient identifier associated with monitoring device 3802. If the patient identifiers do not match, the process proceeds to block 3930. If the patient identifiers do match then communication interface retrieves additional information from the external pump at block 3925. The additional information may include the identity of the fluid being infused by the external pump and the infusion rate. In some embodiments the infusion rate is only requested if the infusion substance is determined to be of interest. For example, a rate at which saline is being infused may be irrelevant and need not be received, while a rate at which insulin is being infused is important and would be requested. In block 3930, the process determines if there is at least one additional pump to be queried. If no additional external pumps are on the list, the process ends at block 3940. If additional pumps are on the list, the process proceeds to block 3935 where communication interface 3814 establishes communication with the next external infusion pump. The process then returns to block 3915 and repeats.

Memory 3812 can store the identities of the external pumps that are associated with the same patient as monitoring device 3802. Thus, communication interface 3814 would not need to repeatedly communicate with pumps not associated with patient 3806. The external pump identities can be input through user the interface 3828 or through the scanner 3819 (e.g., the bar code scanner 2644). In some embodiments, the external infusion pumps may initiate communication with the communication interface 3814 when information associated with the external pump changes. Thus, less communication may be needed in situations where a pump's infusion rate does not change frequently.

Returning now to FIG. 38, the patient monitoring system 3800 can include a source of insulin 3820 (or other glycemic control medication) connected to a fluidics system 3804. In some embodiments, patient monitoring system 3800 also includes additional sources of infusion fluids. For example, patient monitoring system 3800 may include a source of saline 3822 and a source of dextrose (or other sugar) 3824. Different types of insulin can be used depending on the particular circumstances. In some embodiments, IV insulin can be used. As discussed above, different types of insulin have different activation properties and remain active in the body for different amounts of time. In some embodiments, multiple sources of insulin are used. For example, one type of insulin can be used for continuous basal insulin infusion while another, faster-acting insulin can be used for periodic bolus infusion. In some embodiments, the source of insulin 3820 is a non-dedicated reservoir such as a free hanging IV bag filled with the medicament (e.g., insulin). In some embodiments, the system 3800 can be compatible with various sizes and types of non-dedicated reservoirs, so that a user is able to use a container with which the user is familiar and accustomed to using and which can be compounded by a pharmacy without a need for specialized equipment specific to the specialized container type. The source of insulin 3820 can be an insulin IV bag hung within close proximity to the patient such as on one or more hooks (e.g., hooks 112) associated with the system 3800. In some embodiments, the source of insulin 3820 is a dedicated insulin reservoir, such as a cartridge which is contained within the housing of the monitoring device 3802, reducing the risk that medical personnel attach the incorrect type of insulin, or the wrong drug altogether, to the patient 3806.

The source of insulin 3820 can provide insulin that is infused into the patient 3806 through the same line used to draw samples of bodily fluid. In some embodiments, the source of insulin 3820 is connected to the patient 3806 through a separate line and may be controlled by one of the external infusion pumps 3818. The draw line and the infusion line may both be parts of a multi-lumen catheter and/or they may connect to patient 3806 at distinct locations. In some embodiments, the draw line and infusion line connect at distinct locations, but relatively close to each other. For example, both lines can connect to the patient on the same side or on the same arm, or they can both connect to the same vein or artery but at different locations. In some embodiments, insulin (or other medication) can be delivered to the patient at intervals (boluses) instead of by strictly continuous infusion. Bolus dosing can be used in embodiments comprising a shared line or having relatively close connection points, to allow the insulin to be properly assimilated into the body before the next sample is drawn, thus reducing the risk that the infusion fluid skews analysis readings. (Note, however, that relatively frequent dosing can be referred to as "continuous" when compared to less frequent dosing). In some embodiments basal dosing of insulin can be used, and the basal infusion can be interrupted at a predetermined time (e.g., 5 minutes or 10 minutes) before the next sample is scheduled to be drawn, thereby reducing the risk that the infused insulin will skew the next sample reading. In some embodiments, insulin can be infused into the patient (e.g., via basal dosing) during a period from after a sample measurement up until a time about midway between sample measurements.

Insulin (or other medication) can be delivered to the patient in bolus doses. Each bolus of insulin can be delivered to the patient 3806 just before unused blood is returned to the patient 3806. In some embodiments, the bolus of insulin can be combined with the unused blood so that they are delivered together. Thus, depending on the timing of the measurement cycles, the bolus of insulin can be delivered to the patient at least 5 minutes before the next sample is drawn, or at least 10 minutes before the next sample is drawn, or at least 15 minutes before the next sample is drawn, etc. In some implementations, a bolus of insulin is delivered midway between sample draws (e.g., 7.5 minutes after sampling if samples are drawn every 15 minutes). In some embodiments, the monitoring system can calculate a recommended bolus dose of insulin in response to each glucose measurement or timed to coincide with a glucose measurement or series of measurements. In some embodiments, the system may administer more than one bolus of insulin per glucose measurement (e.g., the recommended dose may be administered in designated proportions (e.g., equal halves or fourths) at different times between measurements). In some embodiments, the system can calculate a recommended insulin dose less often than once per glucose measurement. For example, the system can calculate a recommended insulin dose after every two, three, or four (etc.) glucose measurements. In some embodiments, the monitoring system measures glucose every 15 minutes and calculates a recommended insulin dose every 30 minutes. Taking multiple glucose measurements per dose of insulin can provide additional data points for the insulin dosing system to analyze when calculating a recommended dose of insulin, resulting in insulin dosing that is better tailored to the patient's needs. Although some embodiments disclosed herein discuss calculating and administering a recommended dose of insulin at a rate of one dose per glucose measurement, other calculation and/or dosing rates can be used, as discussed above.

In some embodiments, the insulin infusion rate is controlled by a medical professional independently of patient monitoring device 3802 through operation of a drip chamber or an external infusion pump connected to the source of insulin 3820. In some embodiments, the insulin infusion rate is controlled through the patient monitoring device 3802. The controller 3810 can be configured to provide instructions to an infusion pump 3826 positioned on the fluidics system 3804 to adjust the rate of insulin infusion. Alternatively, the rate of insulin infusion may be controlled by one of external infusion pumps 3818. The controller 3810 can send commands to the external infusion pump 3818 via communication interface 3814 to adjust the rate of insulin infusion. The communication interface 3814 can be a wireless link and/or involve telemetry of some sort.

In some embodiments, patient monitoring device 3802 controls the rate of insulin infusion automatically. Controller 3810 can include insulin dosing software stored in a memory 3812 which calculates insulin dosage to be infused into patient 3806. Additional details regarding insulin dosing software and automatic insulin dosage calculation and infusion are provided above.

Figure 40A:
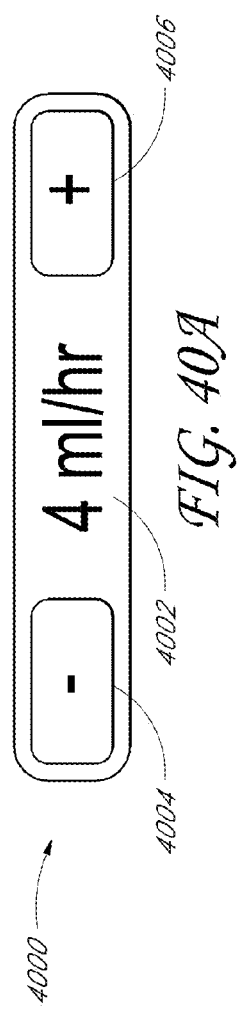
FIG. 40A-40B schematically illustrate the visual appearance of embodiments of a user interface for a system for controlling insulin infusion.

In some embodiments, the monitoring device 3802 includes a user interface 3828 that is configured to receive user input, and the controller 3810 adjusts the rate of insulin infusion based on that user input. FIG. 40A shows an example user interface 4000 for controlling the insulin infusion rate that can be used for the user interface 3828. The user interface 4000 may be a touchscreen display that allows the user to view information and push control buttons on a single display screen. The user interface 4000 includes an infusion rate display 4002 displaying the rate that insulin is being infused into the patient 3806. The user interface 4000 also includes a rate decrement button 4004 and a rate increment button 4006 for adjusting the infusion rate.

Figure 40B:
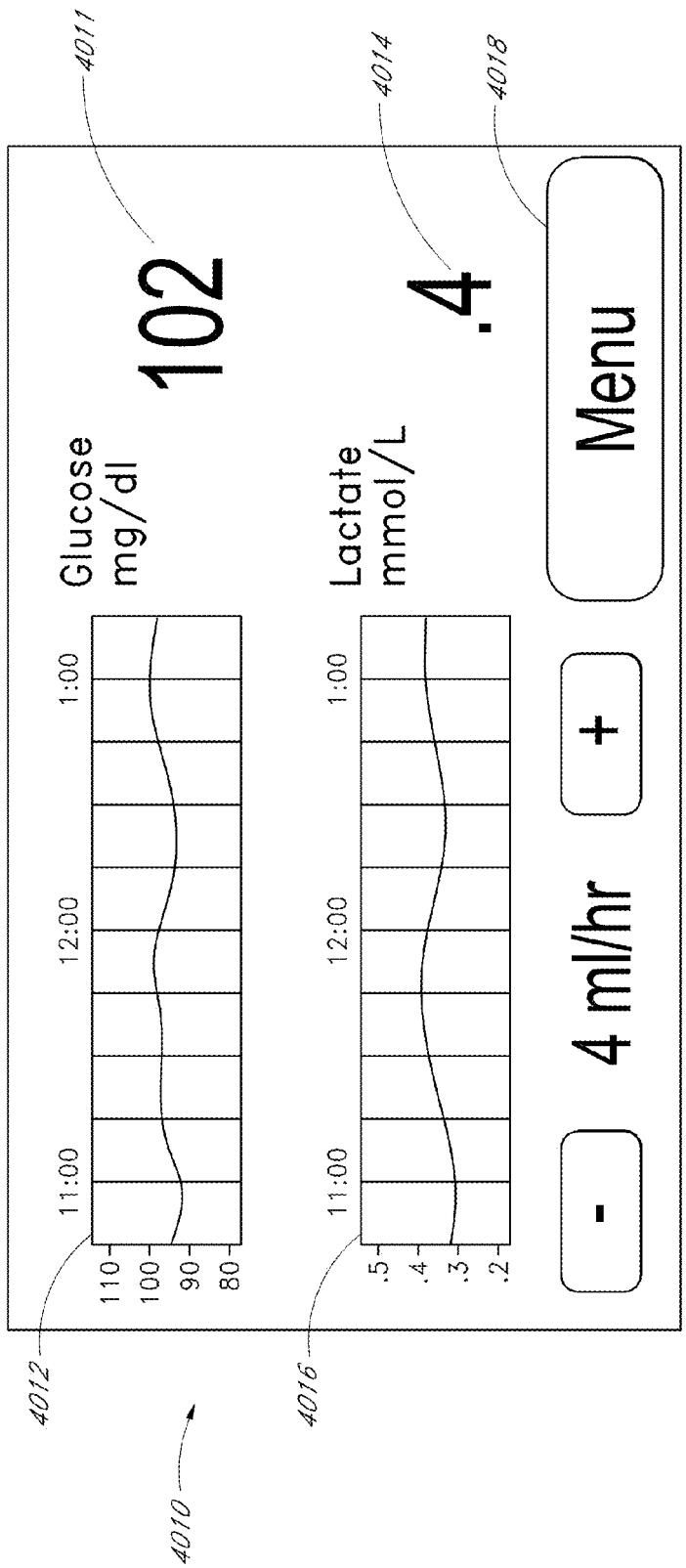

FIG. 40B shows an alternative user interface 4010 that can be used for user interface 3828. User interfaces 4000 and 4010 are similar except that user interface 4010 includes additional information to assist the user in selecting an appropriate insulin infusion rate. For example, a user interface 4010 can include a blood glucose concentration display 4011, a trend graph 4012 showing a history of past blood glucose concentration measurements, as well as additional physiological parameter displays such as lactate display 4014 and trend graph 4016. Also, user interface 4010 can include a menu button 4018 that allows the user to look up additional patient information from memory 3812 or HIS 3816 and change the selection of data being displayed on user interface 4010. In some embodiments, user interface 4010 can also include a recommended dosage display (not shown) that displays a recommended insulin infusion rate calculated using the insulin dosage software.

In some embodiments, the user interface 3828 is part of monitoring device 3802 and it controls a pump inside monitoring device 3802, such as infusion pump 3826. In some embodiments, the user interface 3828 is external to monitoring device 3802 and the interface controls an external pump. If the user interface 3828 is external, it may communicate with monitoring device 3802 via communication interface 3814 to receive information such as the measured blood glucose concentration for display, or it may be a simple user interface, such as user interface 4000.

The monitoring device 3802 can be configured to cut off the infusion of insulin to the patient 3806 when continued insulin infusion would be harmful to the patient 3806. If the monitoring device 3802 includes an infusion pump 3826 that controls insulin infusion, cutting off insulin may be achieved by sending a signal to the infusion pump 3826 to stop pumping. Alternatively, monitoring device 3802 can include an insulin cutoff module 3830. Insulin cutoff module 3830 can be a pinch valve, a rotary valve, or any other element that cuts off the fluid connection between source of insulin 3820 and patient 3806. In some embodiments, insulin cutoff module 3830 may include multiple pinch valves, rotary valves, and/or other elements. When a monitoring device cuts off insulin infusion, it can also cut off any and all infusion into patient 3806, or it may allow one or more other infusion fluids to continue infusing while insulin is cut off. It is sometimes desirable to allow continued infusion during insulin cutoff in order to keep the blood vessel in the patient 3806 from collapsing, or to allow for continued infusion of other medical fluids (e.g., dextrose, TPN, Heparin, or other medicines). The insulin cutoff module 3830 may be configured so that it cuts off more fluids than just insulin, but allows infusion of at least one fluid. For example, the insulin cutoff module 3830 can cut off insulin and dextrose but allow saline to continue infusing into patient 3806. In this scenario, the patient 3806 is allowed to coast toward a blood glucose concentration uninfluenced by external insulin or dextrose.

Figure 41A:
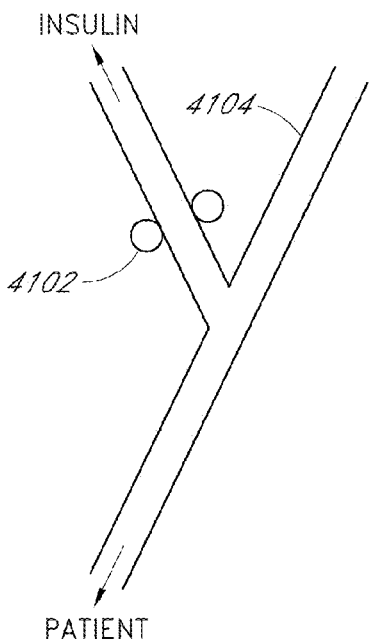
FIG. 41A-41B schematically illustrate an embodiment of an insulin cutoff module that includes a pinch valve.
Figure 41B:
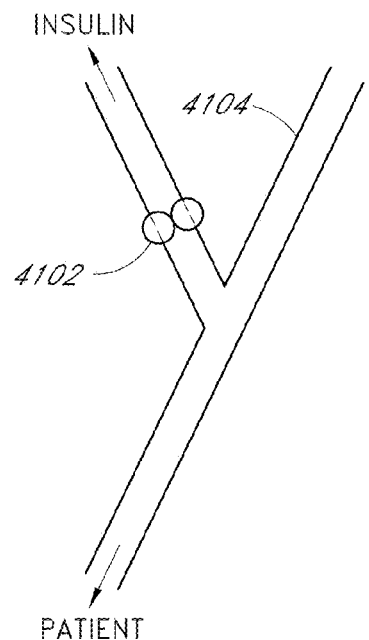

FIGS. 41A and 41B schematically show an embodiment of insulin cutoff module 3830 that includes a pinch valve 4102. FIG. 41A shows pinch valve 4102 in an open position, allowing insulin to infuse pass through and infuse into patient 3806. FIG. 41B shows pinch valve 4102 in a closed position, preventing insulin from passing through and cutting off insulin infusion into patient 3806. In the embodiment shown by FIGS. 41A and 41B, infusion through line 4104 is allowed to continue even when insulin is cut off. Any combination of saline, dextrose, or other fluids can be infused through the line 4104. The line 4104 can be replaced with several lines, each carrying a different fluid. A variety of other configurations are possible. For example, pinch valve 4102 can be positioned so that it stops any and all infusion into patient 3806 when closed, or so that it stops infusion of both insulin and dextrose, but allows continued saline infusion.

Figure 42A:
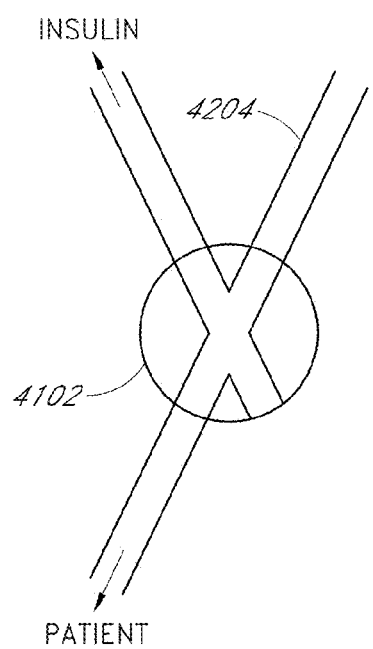
FIG. 42A-42B schematically illustrate an embodiment of an insulin cutoff module that includes a rotary valve.
Figure 42B:
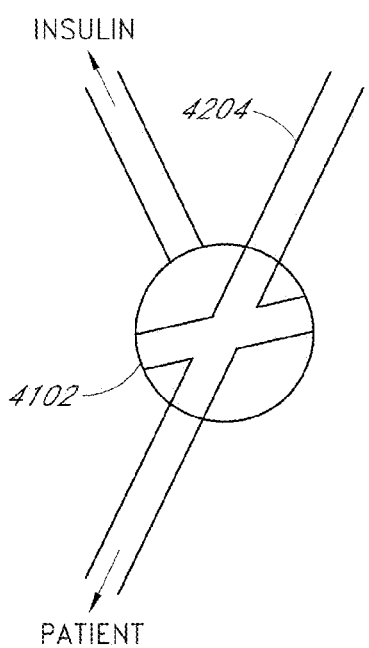

FIGS. 42A and 42B schematically show an embodiment of insulin cutoff module 3830 that includes a rotary valve 4202. FIG. 41A shows rotary valve 4202 in a first position, allowing insulin to infuse pass through and infuse into patient 3806. FIG. 41B shows rotary valve 4202 in a second position, preventing insulin from passing through and cutting off insulin infusion into patient 3806. In the embodiment shown by FIGS. 42A and 42B, infusion through line 4204 is allowed to continue even when insulin is cut off. Any combination of saline, dextrose, or other fluids can be infused through the line 4204. The line 4204 can be replaced with several lines each carrying a different fluid. A variety of other configurations are possible. For example, rotary valve 4202 can be configured so that it stops any and all infusion into patient 3806 when closed, or so that it stops infusion of both insulin and dextrose but allows continued saline infusion.

When insulin infusion is stopped, an amount of insulin may remain in the line between insulin source 3820 and patient 3806. If infusion of other fluids is allowed to continue, that amount of insulin would be infused into patient 3806 at a time when additional insulin may be harmful to patient 3806. To prevent this, the insulin cutoff module 3830 may be positioned as close to patient 3806 as possible, minimizing the amount of insulin remaining in the line after insulin cutoff. The insulin cutoff module 3830 can be external to the monitoring device 3802 allowing the insulin cutoff module 3830 to be placed extremely close to the patient 3806. For example, insulin cutoff module may be wearable or directly attached to the patient 3806. The insulin cutoff module 3830 can be place relatively far from the patient, but if the insulin line intersects with the other fluids at a point close to the patient, much of the insulin remaining in the line will not be infused into patient 3806. Alternatively, insulin can be supplied to patient 3806 through a dedicated insulin line (or a dedicated passageway in a multiple-passageway line) that can be stopped without halting the infusion of other fluids.

In some embodiments the monitoring device 3802 can employ communication interface 3814 to cut off insulin infusion. If the insulin cutoff module 3830 is external to monitoring device 3802, the communication interface 3814 can send a command to insulin cutoff module 3830 to stop infusion of insulin (e.g., by actuating a pinch valve or rotary valve). An external insulin cutoff module may be positioned close to patient 3806 as discussed above or may be placed elsewhere between insulin source 3820 and patient 3806. The connection between communication interface 3814 and the external insulin cutoff module can be wired or wireless. The identity of the external insulin cutoff module can be stored in memory 3812 and can be entered into memory 3812 by a medical professional by use of scanner 3819 or through user interface 3828. Alternatively, the external insulin cutoff module can store the identity of the patient 3806, and the monitoring device 3802 can be configured to search for the external insulin cutoff module assigned to patient 3806.

Figure 43A:
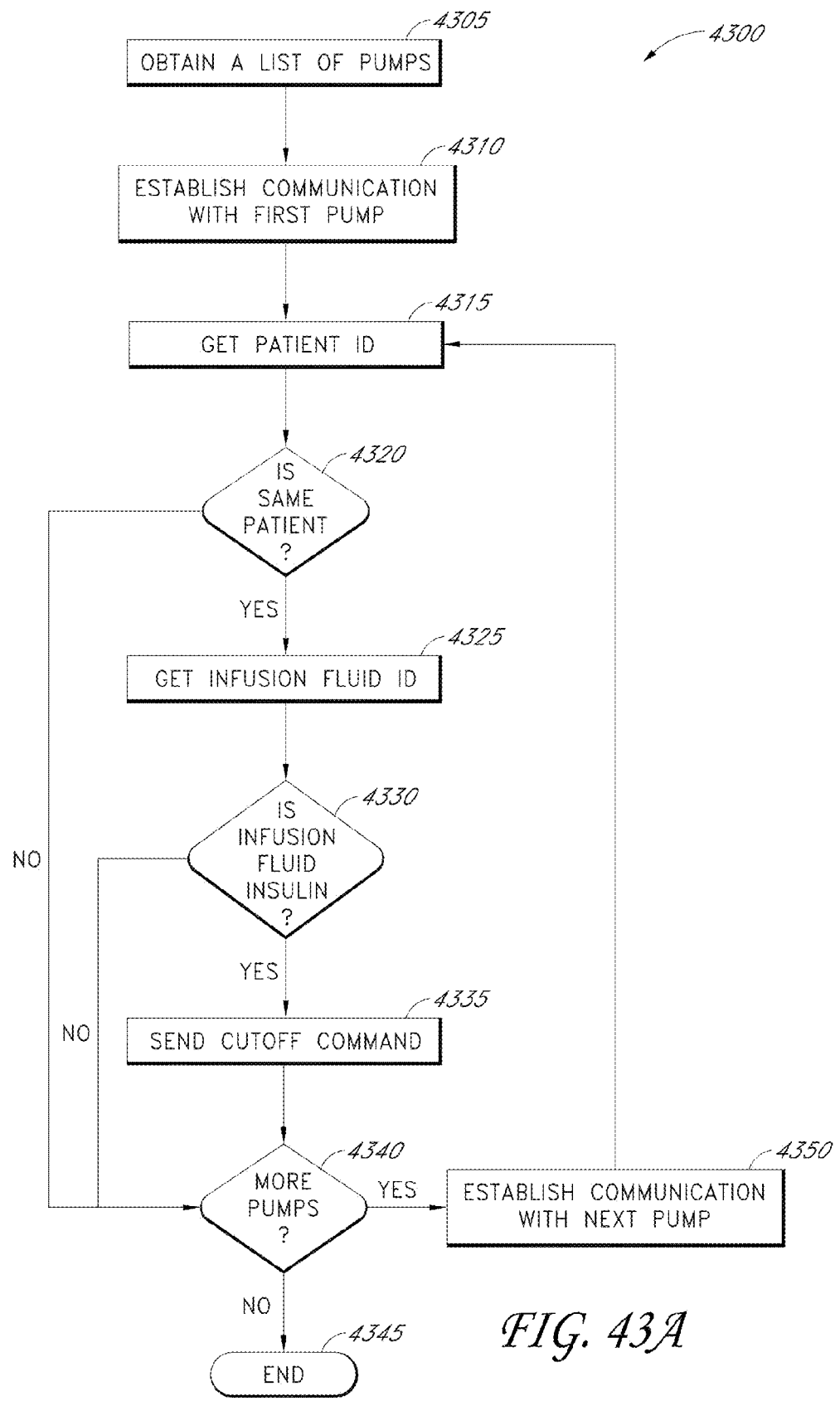
FIG. 43A is a flowchart that schematically illustrates an embodiment of a method for sending an insulin cutoff command to an external infusion pump.
Figure 43B:
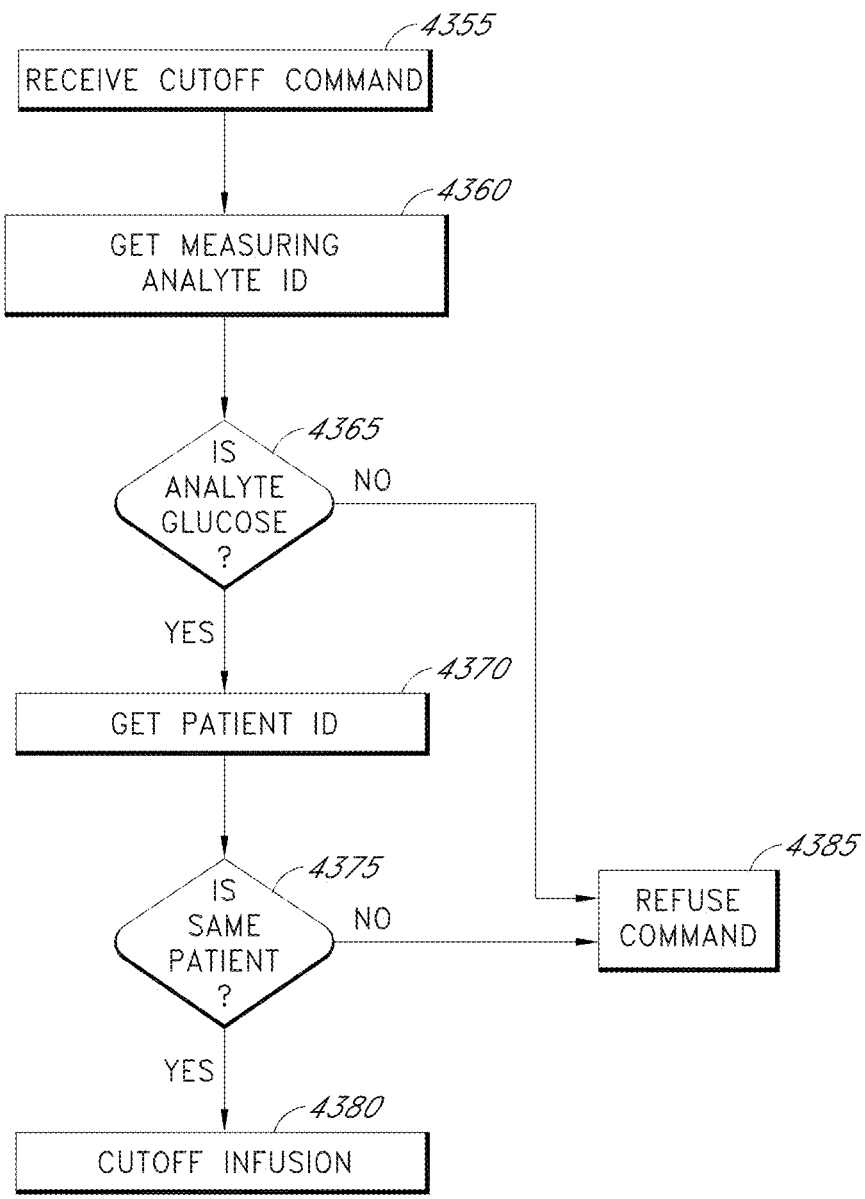
FIG. 43B is a flowchart that schematically illustrates an embodiment of a method for an external infusion pump to accept or reject an insulin cutoff command.

If the insulin infusion rate is controlled by an external infusion pump 3818, the communication interface 3814 can send a command to the external infusion pump 3818 to cause it to stop pumping. In some embodiments, communication interface 3814 can employ a double handshake protocol to reduce the risk of error. FIGS. 43A and 43B show an exemplary process by which the communication interface 3814 can send a command to an external insulin pump using a double handshake protocol.

Turning first to FIG. 43A, process 4300 begins at block 4305 where communication interface 3814 obtains a list of external pumps to which it can communicate. In block 4310 communication interface 3814 establishes communication with a first external pump. In block 4315 communication interface 3814 obtains the patient identify associated with the external pump. The patient identify can be stored in a memory on the external pump, and may be inputted by a user (e.g., a nurse) by a user interface or a scanner. In block 4320, the external pump's patient identifier is compared to the patient identifier associated with monitoring device 3802. If the patient identifiers do not match, the process proceeds to block 4340. If the patient identifiers do match then communication interface retrieves the infusion fluid identifier the external pump at block 4325. In block 4330, the process determines if the infusion fluid is insulin. If the infusion fluid is not insulin, the process proceeds to block 4340. If the infusion fluid is insulin, the process sends a command to the external pump to cut off insulin infusion at block 4335. In some embodiments (not shown) the process can end after the insulin cutoff command has been sent. However, in some embodiments, the process can continue to ensure that any other pumps infusion insulin are also stopped. The process proceeds to block 4340, where the process determines if there is at least one additional pump to be queried. If no additional external pumps are on the list, the process ends at block 4345. If additional pumps are on the list, the process proceeds to block 4350 where communication interface 3814 establishes communication with the next external infusion pump. The process then returns to block 4315 and repeats.

FIG. 43B shows the process performed by the external pump when it receives a command to stop infusion. At block 4355, the external pump receives a command to cut off infusion. At block 4360, the external pump queries the source of the command (here, the monitoring device 3802) and receives an identifier of the analyte the device is monitoring. In block 4365, the external pump determine whether the analyte being monitored is glucose. If the analyte is not glucose, the process proceeds to block 4385 where the external pump refuses the cutoff command. In some embodiments (not shown), if the analyte is glucose, the external pump cuts off insulin without additional safety checks. In the embodiment shown in FIG. 43B, if the analyte is glucose, the process proceeds to block 4370 where the external pump queries the source of the command for its patient identifier. In block 4375 the external pump compares the patient identifier with the patient identifier associated with the external pump. If the patient identifiers are not the same, the process proceeds to block 4385 where the external pump refuses the cutoff command. If the patient identifiers are the same the process proceeds to block 4380 and the external pump stops infusion. Thus, the external pump is able to protect against an error where the external pump receives a cutoff command from a device unable to monitor glucose or assigned to a different patient. In some embodiments, when the external pump refuses a cutoff command it also triggers an alarm or sends a message back to the source of the command to inform the source that the command was refused.

In the embodiment described in FIGS. 43A and 43B, both the monitoring device 3802 and the external pump execute a portion of the double handshake protocol. In some embodiments, the communication protocol is entirely contained in the monitoring device. In some embodiments, the entire communication protocol can be contained in the external pump. The external pump can initiate communication with the monitoring device, query the monitoring device to establish that it is monitoring glucose in the same patient connected to the external pump, and query the monitoring device whether insulin infusion should continue or be cut off Although the double handshake protocol is described in FIGS. 43A and 43B in the context of an insulin cutoff command, the monitoring device 3802 can use a similar double handshake protocol to send other commands to an external pump, such as a command to start infusion, or to increase the infusion rate, or to decrease the infusion rate, etc.

Memory 3812 can store the identities of the external pumps that infuse insulin and are associated with the same patient as monitoring device 3802. Thus, communication interface 3814 would not need to repeatedly communicate with pumps not associated with patient 3806 or not infusing insulin. The external pump identities can be inputted through user interface 3828 or through scanner 3819 (e.g., bar code scanner 2644). In some embodiments, the external infusion pump receives the command to cut off insulin and sends a reply to communication interface 3814 when insulin infusion has been cut off. Thus, monitoring system 3802 can monitor the compliance of external infusion pumps.

The monitoring device 3802 can take additional actions when it cuts off insulin. For example, communication interface 3814 can send information to HIS 3816, such as the time of the cutoff, the patient's blood glucose concentration at the time of cutoff, a history of past blood glucose concentration measurements, etc. Also, monitoring device 3802 may trigger an alarm if insulin is cut off, or if monitoring device 3802 attempts to cut off insulin but is unable to do so (e.g., due to a mechanical malfunction or failure in the communication link to an external pump or cutoff module), or if the patient's blood glucose concentration continues to drop after insulin is cutoff. The user interface 3828 can allow a user to configure the alarm settings. The alarm may be an audible alarm emitted from the monitoring device 3802 or a signal sent through the communication interface 3828 to an external alarm.

Controller 3810 can include insulin cutoff software 3832. In some embodiments, insulin cutoff software 3832 can be a part of insulin dosing software 2652. Insulin cutoff software

Figure 44:
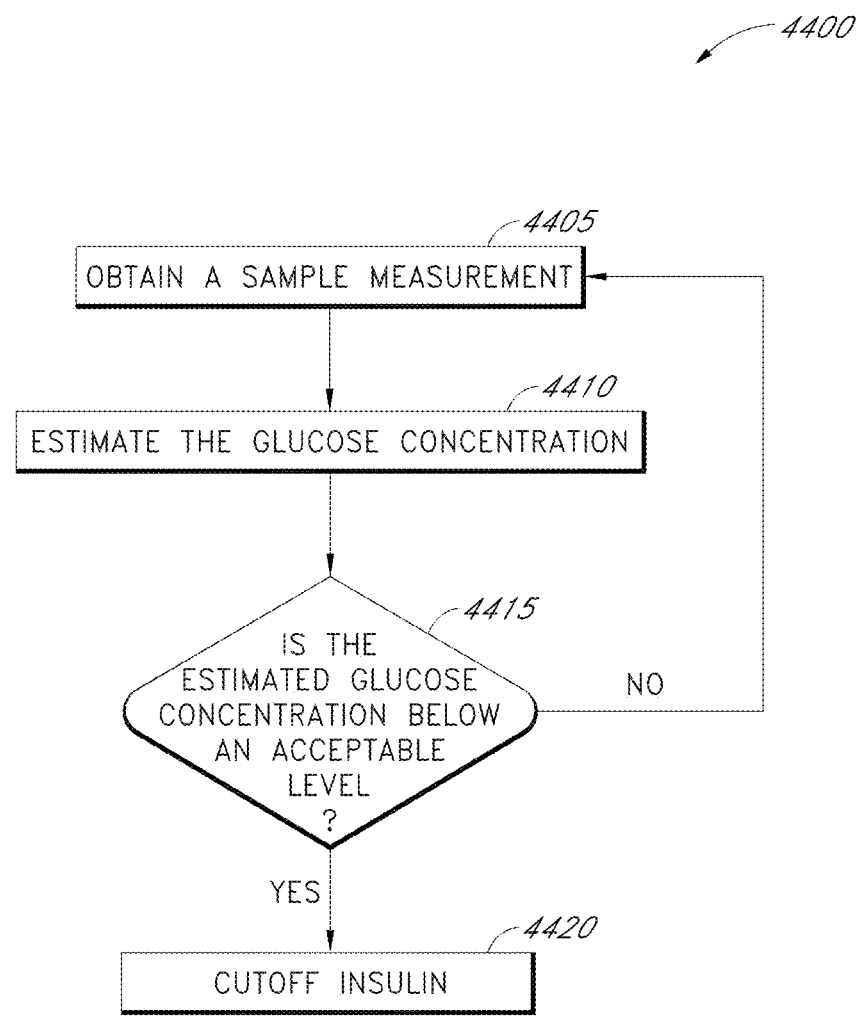
FIG. 44 is a flowchart that schematically illustrates an embodiment of a method for determining whether to cut off insulin infusion based on the measured glucose concentration.

3832 includes an algorithm for determining when to cut off insulin. FIG. 44 is a flow chart showing one exemplary algorithm 4400 that may be used by insulin cutoff software 3832 to determine when to cut off insulin. In block 4405, a glucose monitoring apparatus (e.g., the monitoring device 3802) draws a sample (e.g., a blood or blood plasma sample) from a sample source (e.g., a patient) and obtains a measurement from the sample (e.g., a portion of the drawn sample). The measurement may comprise an optical measurement such as, for example, an infrared spectrum of the sample. In block 4410, the concentration of an analyte (e.g. glucose) in the sample is estimated from the measurement by using any of the methods described above.

In block 4415, the estimated glucose concentration is compared to an acceptable level. The acceptable level can be determined by a hospital protocol (which can be uploaded to the system by a hospital administrator, for example). For example, the acceptable level may be the glucose concentration at the upper limit where the patient is determined to be severely hypoglycemic (e.g., at 40 mg/dL or 45 mg/dL), or the acceptable level may be a higher blood glucose concentration that is determined to indicate that a patient is dangerously close to becoming hypoglycemic. The user interface 3828 can allow the user to adjust the acceptable level, or an acceptable level may be received through communication interface 3814 and stored in memory 3812. The acceptable level may be patient specific and depend upon patient information such as patient age, weight, medication schedule, diet, or a calculated insulin sensitivity. In some embodiments, communication interface 3828 can receive updates to the patient info and the acceptable level can be automatically adjusted according to those updates. The acceptable level can also depend on the current insulin infusion rate. For example, if insulin is being infused at a high rate, the acceptable level of glucose concentration may be higher. In some embodiments, the acceptable level is based in part on the type of insulin being infused and the amount of time it remains active in the body.

If the estimated glucose concentration is above the acceptable level, process 4400 proceeds back to block 4405 where another sample is obtained at a later time and the process repeats. If the estimated glucose concentration is below the acceptable level, process 4400 proceeds to block 4420 and insulin is cutoff by any of the methods discussed above.

Figure 45:
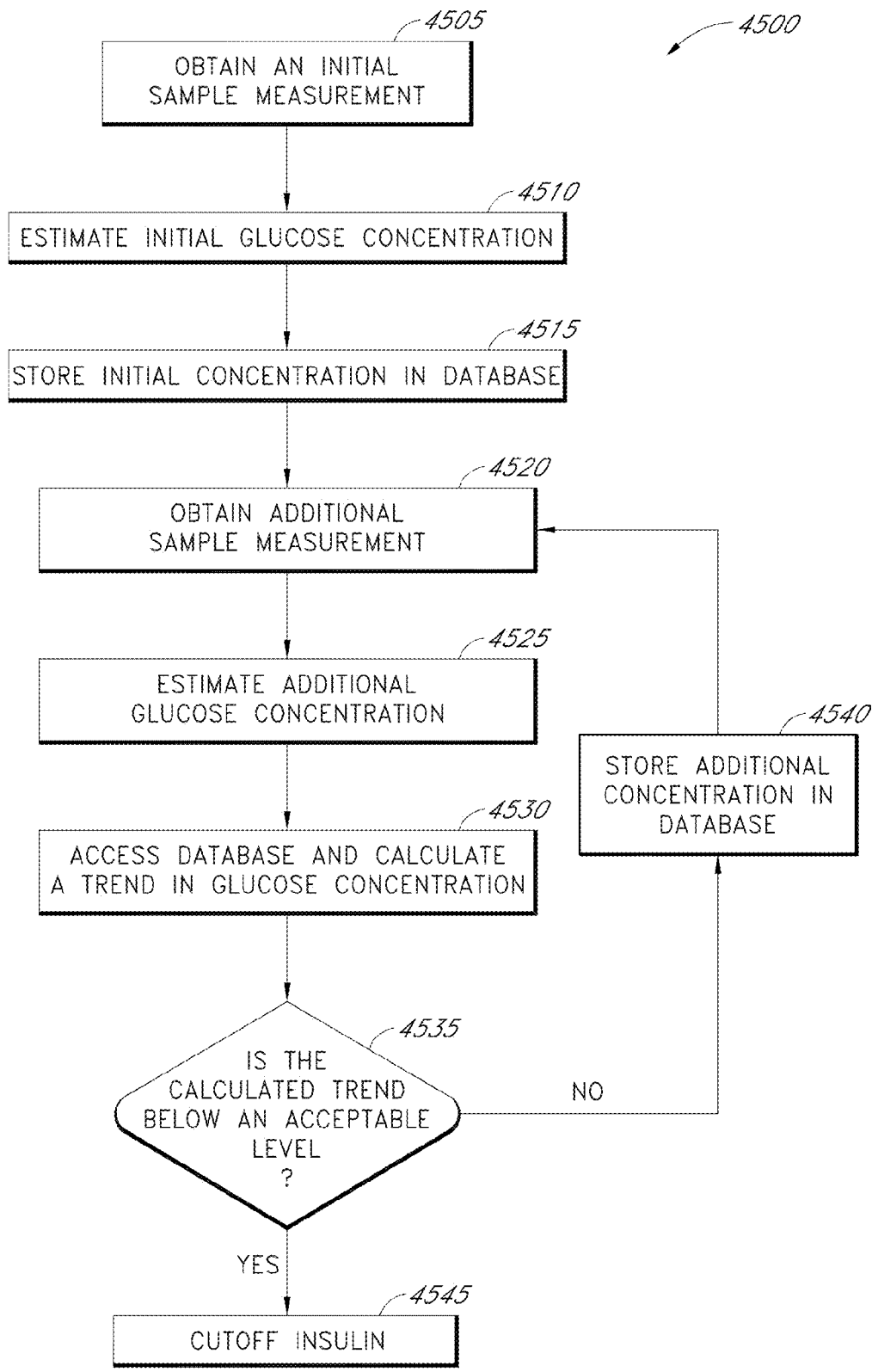
FIG. 45 is a flowchart that schematically illustrates an embodiment of a method for determining whether to cut off insulin infusion based on a calculated trend in glucose concentration.

FIG. 45 is a flow chart showing another exemplary algorithm 4500 that may be used by insulin cutoff software 3832 to determine when to cut off insulin. In block 4505, a glucose monitoring apparatus (e.g., the monitoring device 3802) draws an initial sample (e.g., a blood or blood plasma sample) from a sample source (e.g., a patient) and obtains an initial measurement from the sample (e.g., a portion of the drawn sample). The initial measurement may comprise an optical measurement such as, for example, an infrared spectrum of the sample. In block 4510, the initial concentration of an analyte (e.g. glucose) in the sample is estimated from the measurement by using any of the methods described above. In block 4515, the initial concentration is stored in a database. The database can be in memory 3812 or can be external (e.g., part of HIS 3816).

In block 4520, the glucose monitoring apparatus draws another sample from the sample source and obtains another measurement from the sample. In block 4525, another glucose concentration is estimated from the measurement. In block 4530, the process accesses the database and reads one or more past glucose concentrations and calculates a trend in glucose concentration. In block 4535, the trend is compared to an acceptable trend. The acceptable trend can be determined by hospital protocol. User interface 3828 can allow the user to adjust the acceptable trend, or an acceptable trend may be received through communication interface 3814 and stored in memory 3812. The acceptable trend may be patient specific and depend upon patient information such as patient age, weight, medication schedule, diet, or a calculated insulin sensitivity. In some embodiments, communication interface 3828 can receive updates to the patient info and the acceptable trend can be automatically adjusted according to those updates. The acceptable trend can also depend on the current insulin infusion rate, the current estimated glucose concentration, or the type of insulin being infused.

If the trend is above the acceptable trend, process 4500 proceeds back to block 4540 where the most recent estimated glucose concentration is stored in the database, after which the process returns to block 4520 where another sample is obtained at a later time and the process repeats. If the trend is below the acceptable trend, process 4500 proceeds to block 4545, where insulin is cutoff by any of the methods discussed above.

Other methods can be used to determine when insulin infusion should be cut off. The determination may be time dependent, so that insulin cutoff software 3832 stops insulin infusion if the glucose concentration has been below a predetermined level for a predetermined amount of time. For example, some protocols define severe hypoglycemia as prolonged exposure to a blood glucose concentration of 72 mg/dl or less. Accordingly, in some embodiments the insulin cutoff software 3832 can cutoff insulin if the measured blood glucose concentration is below a predetermined level (e.g., 72 mg/dl) for a predetermined time (e.g., for more than 15 minutes, 30 minutes, 1 hour, 2 hours, or longer).

In some embodiments, the insulin cutoff software 3832 calculates a predicted future glucose concentration using at least some of the following information (current estimated glucose concentration, one or more past glucose concentrations, the current rate of insulin infusion, the history of past insulin infusion rates, type of insulin being used, and patient specific data). This future predicted glucose concentration is then compared to an acceptable level. If the future predicted glucose concentration is above the acceptable level, insulin infusion continues and the process repeats after the next sample measurement. If the future predicted glucose concentration is below the acceptable level, insulin infusion is cut off by any of the methods discussed above.

In some embodiments where multiple sources of insulin are used, the insulin cutoff software 3832 can be configured to cut off one source of insulin while allowing infusion of the other source to continue. For example, insulin cut off software 3832 may cut off infusion of bolus insulin infusions but allow basal insulin infusion to continue. In some embodiments, the insulin cutoff software 3832 is configured to cut off the different sources of insulin when different conditions are met. For example, insulin cutoff software 3832 can cut off bolus insulin infusion at a first glucose concentration (or trend or predicted value) and cut off basal insulin infusion at a second, more threatening glucose concentration (or trend or predicted value).

The monitoring device 3802 can be configured to restart insulin infusion after insulin has been cut off. For example, insulin infusion can be restarted automatically once the estimated glucose concentration, trend, or future predicted glucose concentration has raised sufficiently. Alternatively, insulin infusion can be restarted based on user input received through user interface 3828. User interface 3828 can provide the user with a warning, or require a password, when the user attempts to override the insulin cutoff to restart insulin infusion. In some embodiments, monitoring device 3802 will not allow the user to override the insulin cutoff, or will allow user override in some conditions, but not when the glucose concentration is below a certain level.

Patient Specific Insulin Sensitivity

While some ICU patients experience hypoglycemia and/or hyperglycemia and receive regular doses of dextrose and/or insulin, others are able to maintain safe blood glucose levels without supplemental medication. Even among ICU patients that are medicated to control glucose levels, determining the proper treatment doses of insulin and/or dextrose can be challenging because some ICU patients are more sensitive to insulin and/or dextrose than others. Moreover, a single ICU patient's insulin sensitivity can change significantly within a relatively short period of time. Further complicating diagnosis and control of ICU patients is the fact that it may not be immediately known whether an ICU patient has diabetes because approximately 80% of ICU patients exhibiting hyperglycemia to not have diabetes. Insulin dosing protocols designed to be used by a diabetic person to control blood glucose levels can be harmful if applied to some ICU patients (for example, those that are not diabetic). For example, a type I diabetic may take 0.7 units of insulin per kilogram of body weight each day. Under this metric, a 70 kg person would take about 50 units of insulin in a given 24 hour period. This same dosage of insulin may be harmful if given to an ICU patient who is able to maintain safe glucose levels without supplemental insulin. Not only is there a difference in a diabetic person's and a non-diabetic person's sensitivity to insulin, but there can be important differences between each individual ICU patient's sensitivity to insulin, and that sensitivity can change over time. Thus, it is desirable to calculate a particular patient's insulin sensitivity and update that calculation frequently so that insulin and/or dextrose dosages can be determined to meet a particular patient's specific needs at any given time.

Medical professionals are often unable to calculate and frequently update a patient's insulin sensitivity. Although some hospital protocols direct medical professionals to measure a patient's blood glucose concentration once every hour, studies have shown that medical professionals are often unable to comply, resulting in infrequent and irregular measurements. Also, medical professionals commonly measure a patient's blood glucose concentration using the finger prick method, which is not only uncomfortable for the patient but also relatively inaccurate, especially in patients experiencing shock. Furthermore, calculating a patient's insulin sensitivity can involve complicated calculations, becoming more and more complicated as more factors and more data points are considered. For these reasons, medical professionals are often unable to accurately calculate their patients' insulin sensitivities and instead apply the same dosing protocol to many patients. A conservative dosing protocol, such as the "Atlanta Protocol" described above, is often used to allow for compatibility across a wide range of insulin sensitivities, but such a conservative dosing protocol is not designed to meet the specific needs of each patient. The Atlanta Protocol directs the medical professional to make merely directional changes such as "move one column to the right."

Many dosing protocols do not account for changes in the patient's food intake, medication, exercise, etc. In traditional dosing protocols, changes in insulin/dextrose dosages to compensate for changes in these factors are only made after they have caused the patient's blood glucose level to change, which can be harmful to the patient, especially for changes in the patient's circumstances that can cause a significant change in glucose over a short period of time. Thus, it is desirable to anticipate changes in the patient's insulin needs and adjust the patient's dosages before the patient's glucose level is significantly affected by the changes.

An external dosage calculating program can allow a user to input the factors to be considered and the program can provide a recommended insulin and/or dextrose dosage. However, because the manual data input process is time consuming and the measurements that are taken by hand are often inaccurate and infrequent, such a dosing program may not have enough data to reliably calculate a patient's insulin sensitivity. Thus, in many cases, available external dosage calculating programs also apply conservative dosing protocols that are not tailored to the patient's specific circumstances.

In some embodiments, the insulin dosing software (e.g., insulin dosing software 2652) calculates a patient's insulin sensitivity and determines a recommended dose of insulin based at least in part on the patient's insulin sensitivity. Although the discussion below describes the calculation of insulin sensitivity to be used in determining a recommended insulin dose, similar methods can be used to determine patient sensitivities and to calculate recommended doses for other medications as well. For example, the monitoring system can include software for calculating a patient's dextrose sensitivity and determining a recommended dextrose dose. In embodiments where analytes other than glucose are measured by the monitoring system, the sensitivity of other medications that relate to those analytes can be calculated and used to provide recommended doses for those other medications.

Figure 46:
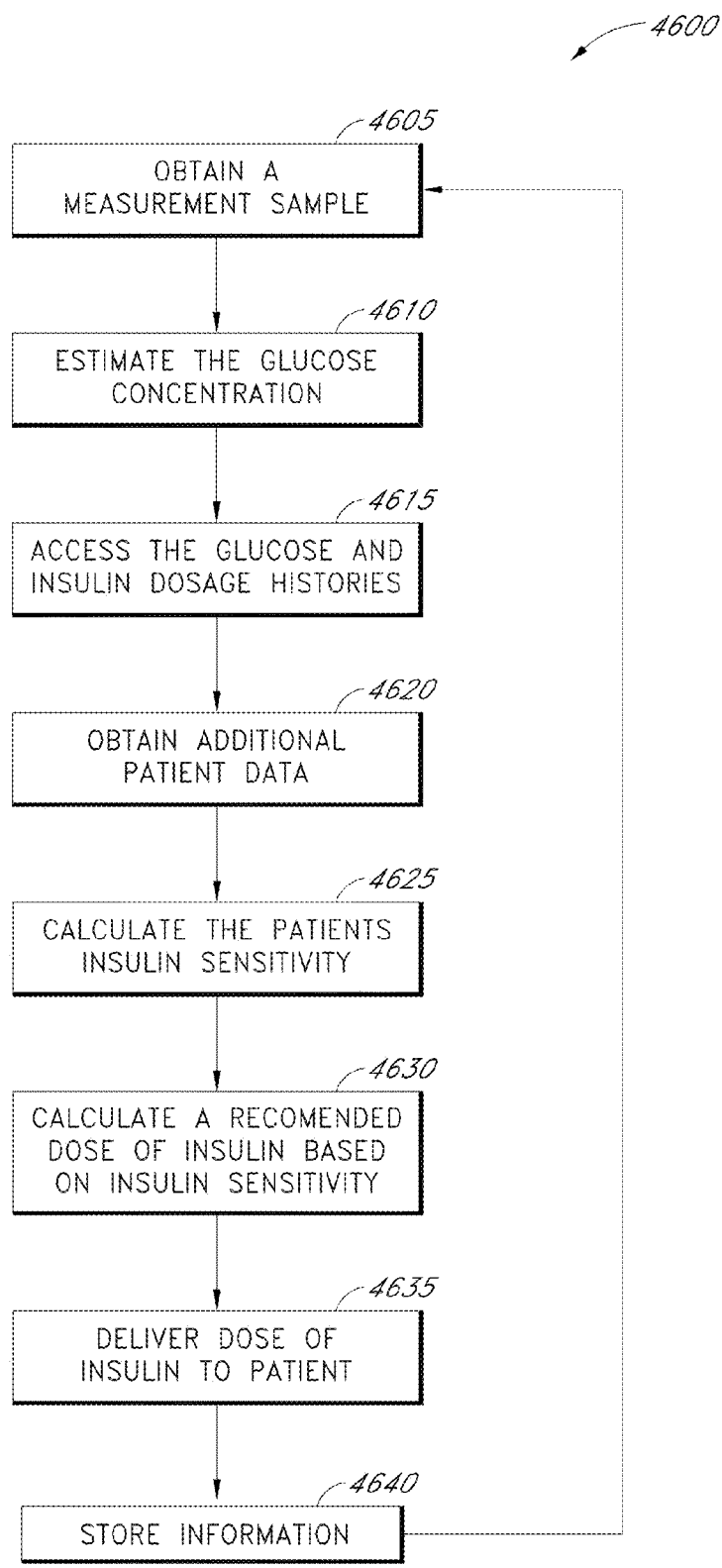
FIG. 46 is a flowchart that schematically illustrates an embodiment of a method for providing glycemic control based on a patient's insulin sensitivity.

FIG. 46 is a flowchart that schematically shows an embodiment of a method 4600 for providing glycemic control based on a patient's insulin sensitivity. At block 4605, an analyte monitoring apparatus (e.g., the monitoring apparatus 2632 of FIG. 26) comprising a fluidic system (e.g. the fluid system kit 2634 of FIG. 26) obtains a sample of bodily fluid (e.g., a blood or blood plasma sample) from a source of bodily fluid (e.g., a patient). In some embodiments, the analyte monitoring system may further comprise an analyte detection system that spectroscopically analyzes the sample and obtains a measurement from the sample. The measurement may comprise an optical measurement such as, for example, an infrared spectrum of the sample. In block 4610, the concentration glucose in the sample is estimated from the measurement by using any of the methods described above.

In block 4615, the monitoring system accesses the patient's glucose concentration history and insulin dosage history. In some embodiments, the history information can be retrieved from a database, which can be stored in the monitoring system's memory or in a location external to the monitoring system (e.g., the hospital information system, or "HIS"). In block 4620, the monitoring system obtains additional patient data that can affect the patient's insulin sensitivity, such as the type and amount of the patient's food intake, medications administered to the patient, patient exercise, diagnosed illnesses, etc. For example, changes in the patient's feeding method (e.g., a change from IV parental nutrition to stomach enteral nutrition) and changes in the number of calories consumed can dramatically change the patient's insulin needs. Likewise, changes in the patient's medication (e.g., starting a patient on steroids) can also change the patient's insulin needs. The additional patient data can be obtained from a number of different sources such as the monitoring system itself, the HIS, user input from the user interface, or external infusion pumps. In some embodiments, the monitoring system includes a communication interface that provides a communication link to the external infusion pumps. The communication interface may include, but is not limited to, optical interfaces, electrical interfaces, and/or wireless interfaces. In some embodiments, the monitoring device received insulin infusion information from an external infusion pump and updates the insulin dosing history obtained from the database with information received from the external insulin infusion pump.

In block 4625 the monitoring system calculates the patient's insulin sensitivity based on how the patient's blood glucose concentration has reacted to previously administered doses of insulin. In some embodiments, the monitoring system calculates the patient's insulin sensitivity using a formula. The formula can be determined by empirical study and agreed upon by doctors and researchers. For example, the formula can resemble the following formula and be derived similarly to the way that formula was determined. For diabetic patients, the following formula provides an estimate of how much one unit of insulin will lower blood glucose: (Blood Glucose−120)/(Correction Factor), where the Correction Factor is either 1500/(Total Daily Glucose) under an older rule, or 1700/(Total Daily Glucose) under a newer rule proposed by Paul C. Davidson, Md. in 2003. Rules are known in the art that allow for calculation of how much insulin a diabetic patient should take for a given amount (often in grams) of carbohydrate and for blood glucose correction when readings are too high or too low. Some rules indicate that the carbohydrate-to-insulin ration should be (2.8×body weight in pounds)/total dose of insulin per day. With regard to correcting lows, some rules recommend using the formula (100−blood glucose)×0.2=grams of carbohydrate for blood glucose corrections. Therefore, for a reading of 50, the formula would be 50×0.2=10 grams. This amount is less than the recommended dose by other alternative methods and authorities.

The formulae discussed above were not derived, however, in the context of patients that do not have diabetes. Indeed, as discussed above, existing methods do not calculate the insulin sensitivity of an ICU patient who does not have diabetes, and existing studies have not provided an empirically-derived rule. A complicating factor for non-diabetic ICU patients is that while in the ICU, their body systems are under a great deal of stress, which can have the effect of elevating their glucose values in the short term. Thus, it is advantageous to determine on a patient-by-patient basis, in a constantly updated manner, patients' specific, recent response to insulin. Accordingly, and as set forth more fully below, ongoing analysis of the fifteen, thirty, and forty-five minute response by a patient to the given amounts of IV insulin can be highly advantageous, especially when that information is fed back in to an algorithm that adjusts dosing recommendations and/or decisions based on that changing response. As a patient's health improves, there is less stress on body systems and the patient's response to glucose doses will likely change and glucose values will likely stabilize. Indeed, an improving patient may have increased sensitivity over time, allowing reduced amounts of insulin to be administered per dose without reducing clinical effect of the doses.

A system for determining near real-time glucose sensitivity on an ongoing basis for each specific ICU patient can take advantage of the analyte monitoring system described in detail herein. Insulin administered in hospitals intravenously (IV insulin) is often fast acting, to the point that IV insulin has almost entirely cleared a patient's system within 30 minutes of delivery into the patient's veins. A concept of "half-life" can be used to describe how quickly insulin clears the blood stream, and that the half-life of IV insulin is only about seven minutes. There is general agreement among researchers that, while a specific "decay" function may not be known for IV insulin in the blood, the half-life is between 5 and 9 minutes. Because most of the IV insulin is no longer active in the blood after less than 15 minutes, only the last few doses need be considered in a rolling insulin sensitivity calculation.

In some embodiments, a multi-compartment model can be used to determine insulin sensitivity. For example, in some embodiments, four compartments are used. The four "compartments" represent the last four insulin doses provided before any given time. Under this example four-compartment model, assuming that the "half-life" of IV insulin is about 7.5 minutes, after fifteen minutes, 75% of a particular dose has cleared out of a human system because in one half-life, 50% of the original dose is cleared, and in the next half-life, 50% of the remaining 50% is cleared. Thus, assuming a half life of 7.5 minutes remains the same throughout the time period for all insulin delivered and assuming insulin doses delivered every fifteen minutes, under the four compartment model (where the immediately preceding compartment is compartment 1, the one preceding that is compartment 2, etc.), at any given time, the following table indicates the contributions of the dosages delivered in each compartment to the overall insulin remaining in the system at that time:

| Compartment | Amount Remaining | Amount Already Used |
|---|---|---|
| 1 (15 min. ago) | 25% | 75% |
| 2 (30 min. ago) | 6.25% | 93.75% |
| 3 (45 min. ago) | 1.5625% | 98.4375% |
| 4 (60 min. ago) | 0.390625% | 99.60938% |

Other models can be used. Indeed, if insulin doses are delivered every 7.5 minutes, the following eight-compartment model may be appropriate (otherwise given the same assumptions as above):

| Compartment | Amount Remaining | Amount Already Used |
|---|---|---|
| 1 (7.5 min. ago) | 50% | 50% |
| 2 (15 min. ago) | 25% | 75% |
| 3 (22.5 min. ago) | 12.5% | 87.5% |
| 4 (30 min. ago) | 6.25% | 93.75% |
| 5 (37.5 min. ago) | 3.125% | 96.875% |
| 6 (45 min. ago) | 1.5625% | 98.4375% |
| 7 (52.5 min. ago) | 0.78125% | 99.21875% |
| 8 (60 min. ago) | 0.390625% | 99.60938% |

As can be seen from the example tables shown above, only about 0.4% of an insulin dose remains active in the bloodstream one hour after the delivery of the dose. Accordingly, in some embodiments of the systems and methods disclosed herein, insulin dosing information for the previous one hour time period is used to determine measurement such as, e.g., insulin sensitivity. Such embodiments advantageously do not need to have access to a record of the insulin dosing history of a patient at times earlier than one hour before a measurement (e.g., insulin sensitivity) is determined.

It can be advantageous to determine the dose of insulin to give to a patient by simply looking at the last few measured glucose value (with readings typically taken every one hour, or in some cases every 15 minutes, e.g., if a patient is diabetic) to see if the glucose trend is approaching the desired range. Such an approach can monitor a rate of change and use a dampening approach to pursue the proper glucose range.

However, in many cases, using frequent automatic measurements and determination of glucose sensitivity as discussed herein can be even more advantageous.

In the example method 4600, a patient's insulin sensitivity is calculated at block 4625. In some embodiments, the patient's insulin sensitivity is updated every time the patient's blood glucose is measured (e.g., every 15, 30, 60, 76, or 90 minutes, or more). In some embodiments, insulin sensitivity (IS) is determined based at least in part on the patient's measured blood glucose values and known insulin dosages over a prior time period. As discussed above, the prior time period may be about one hour in some implementations, because of the relatively short half-life of IV insulin. Other time periods can be used in other embodiments such as, e.g., 30 minutes, 76 minutes, 90 minutes, 2 hours, 12 hours, 1 day, and so forth. In certain embodiments, insulin sensitivity is approximated as the change in the patient's blood glucose, $\Delta G$ (where G equals blood glucose concentration), divided by the insulin concentration, I, responsible for the change in blood glucose: $IS=\Delta G/I$. In certain such embodiments, the monitoring system calculates $\Delta G$ based on a difference between measurements of blood glucose at two different times. For example, in some implementations, the most recent two blood glucose measurements are used. In other embodiments, $\Delta G$ is calculated from a trend in past blood glucose measurements such as, e.g., by estimating a slope from a trend line of blood glucose measurements (e.g., via regression techniques). In various embodiments, 2, 3, 4, 5, 7, 10, 12, or more blood glucose measurements may be used to calculate $\Delta G$.

The value I of insulin concentration used in the calculation of insulin sensitivity may be determined in various ways in various embodiments. For example, in one embodiment I is estimated as the most recent insulin dose (bolus or basal). In certain advantageous embodiments, a multi-compartment model is used to estimate insulin concentration. As one possible non-limiting example, a four-compartment model can be used to estimate the insulin concentration at a time t based on the previous four insulin doses (assumed to be separated in time by about 15 minutes). The insulin concentration can be estimated by multiplying each insulin dose by an "Amount Remaining" factor (e.g., from the first table shown above) appropriate for the time elapsed since the dose was injected and then adding the four weighted insulin contributions. Use of the "Amount Remaining" as a multiplicative factor assumes that it is the insulin (or some percentage thereof) that is still present in the bloodstream that has contributed most to any change in glucose that has already occurred and been measured over the relevant time interval.

Some embodiments may use a multi-compartment model such as the one described above, but rather than estimating the insulin concentration by multiplying each insulin dose by an "Amount Remaining," the insulin doses can be multiplied by an "Amount Already Used" factor (e.g., from the tables shown above) as appropriate for the time elapsed since the dose was injected and then adding the weighted insulin contributions (e.g, four or eight contributions if a four or eight compartment model, respectively, is used). Such an approach assumes that it is the insulin (or some percentage thereof) that is no longer in the bloodstream that contributed to any change in glucose that has already occurred and been measured. In some embodiments, it can be determined (e.g., empirically or theoretically from physiological principles) that some of the "Amount Remaining" and some of the "Amount Already Used" both contribute to the relevant clinical effect and a combination of at least a portion of each can be used.

An advantage of using a multi-component model (such as, e.g., a four-component model) is that the short half-life of insulin is accounted for. In other embodiments, the number of compartments may be 2, 3, 5, 7, 8, or more. In other embodiments, a mathematical formula or algorithm may be used to reflect the clearance rate (e.g., a rate approximating exponential decay) of each dosage of insulin. For example, some formulas or algorithms can include an assumption that insulin has a particular half-life (e.g., about 7 minutes, between 5 and 9 minutes, etc). In some embodiments, the half-life may be different for different doses of insulin (e.g., a short half-life for insulin types that are rapidly removed from the bloodstream).

In certain embodiments, statistical techniques are used to calculate the evolving insulin sensitivity of a patient as a function of time. For example, in some implementations, correlation techniques are used to estimate IS based on time history of blood glucose measurements and insulin doses provided to the patient. In some such implementations, one or more insulin doses can be adjusted (e.g., via a multi-compartment model) to account for the half-life of insulin in the bloodstream. In some embodiments, statistical techniques including but not limited to smoothing, filtering, extrapolation, interpolation, and so forth can be applied to estimated values of insulin sensitivity to determine a suitable IS value at a given time.

In some embodiments, the additional patient data can be used to calculate or adjust the insulin sensitivity. For example, if a patient's caloric intake is increased, the insulin sensitivity can be adjusted accordingly, indicating that the patient will likely require a larger dose of insulin to maintain a safe blood glucose level. In some embodiments, adjustment of the insulin sensitivity is dependent on the way the patient was affected by similar changes in the past. For example, a patient whose pancreas is functioning properly will be affected differently by an increase in food than a patient whose pancreas is not producing the proper amount of insulin. Thus, an adjustment to the patient's insulin sensitivity based on a change in feeding can be based in part on how the patient reacted to previous feeding adjustments. Patient data relating to medications and other substances administered to the patient, patient exercise, and medical procedures or tests that may influence insulin needs can all be used to adjust the calculated insulin sensitivity. As discussed above, different types of insulin take effect after different amounts of time and remain active for different amounts of time, and the insulin sensitivity can be calculated for the specific type of insulin being delivered to the patient and/or the manner of delivery (e.g., IV insulin).

At block 4630, the monitoring system calculates a recommended dose of insulin based at least in part on the patient's insulin sensitivity. In some embodiments, the recommended dose also depends on the most recent estimated blood glucose concentration, a target glucose range, a maximum rate of change of glucose, or a maximum allowable insulin dose. Other factors like the trend or rate of change in blood glucose can be considered when calculating the recommended dose of insulin. Because the patient's individual insulin sensitivity may be known, a recommended dose that is specifically designed to meet the patient's insulin needs can be calculated, allowing for more aggressive insulin dosing that is able to bring the patient to safe blood glucose levels faster than traditional conservative insulin dosing protocols. In some embodiments, the recommended dose can be calculated using a formula that provides a precise recommended dosage, rather than a directional instruction to be applied to a protocol chart (e.g., move left one column in the "Atlanta Protocol").

In some embodiments, a chart based dosing protocol that considers the patient's insulin sensitivity can be used to generate the recommended dosage.

The recommended dose of insulin can be determined based on, among other factors, the estimated insulin sensitivity of the patient. For example, in some embodiments, a recommended insulin dose, $I_D$, is determined based on a target glucose level, $G_T$, for the patient and an estimated current glucose level, $G_C$, for the patient according to: $I_D=(G_T-G_C)/IS$. In some such embodiments, the estimated current glucose level is determined from one or more of the most recent blood glucose determinations performed by the system, for example, as the most recent determination, as an estimate from a trend in recent glucose determinations, as an average (weighted or unweighted) of recent determinations, and so forth.

Then, at block 4635, the recommended dose of insulin is delivered to the patient. In some embodiments, the monitoring system includes a source of insulin and a pump for controlling the infusion of insulin, so that the monitoring system can directly control the delivery of the dose of insulin. The source of insulin can be a bag of IV insulin hanging from a support apparatus (e.g., support apparatus 2636) or an insulin cartridge inserted into the housing of the monitoring device. In some embodiments, the monitoring system sends a command to an external insulin infusion pump via the communication interface to indirectly control the delivery of the dose of insulin. As discussed above, the communication can use security measures, such as a double handshake protocol, to prevent errors in the transfer of pump control information. These security measures are particularly important in the case of wireless communication. In some embodiments, the monitoring device displays the recommended dose of insulin to a medical professional who then administers the dose by adjusting an external pump or by injecting insulin into an IV line or directly into the patient. In some embodiments, the dose of insulin is delivered continuously as a basal infusion. In some embodiments, the dose of insulin is delivered at one time as a bolus injection. In some embodiments, the both basal and bolus dosing is provided.

At block 4640, the monitoring system stores information in a database, which can then be used for future calculations. For example, the estimated glucose concentration, the amount of insulin delivered to the patient, the additional patient data, and sensitivities can be stored in the database. In some embodiments, the monitoring system can query the external insulin infusion pump to determine the amount of insulin that was delivered. Where the insulin was delivered by a medical professional, the monitoring system can prompt the medical professional to manually input the amount of insulin delivered. The method 4600 then returns to block 4605 to await the start of the next measurement cycle, which can be less than one minute to more than one hour (e.g., every fifteen minutes or less, every 30 minutes or less, every 45 minutes or less, etc.). Frequent measurements of the patient's blood glucose allow for the patient's insulin sensitivity to be calculated with greater accuracy. Moreover, if a patient's blood glucose is measured frequently, a miscalculated dose of insulin or a change in the patient's insulin needs can be identified quickly, allowing for more aggressive, and often more effective, insulin dosing protocols.

Method 4600 can be modified in a variety of ways. Some of the steps described can be skipped, combined, interchanged, or performed in conjunction. For example, block 4620 can be skipped so that the patient's insulin sensitivity is determined by the glucose concentration and insulin dosing histories, but is not adjusted based on additional patient info. Blocks 4625 and 4630 can be combined, so that the recommended dose of insulin is calculated using a single formula or calculation that incorporates the patient's insulin sensitivity. However, as will be discussed below, it is sometime desirable to monitor a patient's insulin sensitivity. Therefore, in some embodiments, the patient's insulin sensitivity is calculated separately from the recommended insulin dose.

At times, the monitoring system may have insufficient information to accurately calculate the patient's insulin sensitivity. For example, when a patient is first admitted the database has no history of how the patient's glucose concentration has reacted to previous doses of insulin. Also, events can occur which have the potential to change the patient's insulin sensitivity in unpredictable ways, such as surgery, being disconnected from the monitoring device for a prolonged period of time for other reasons (e.g., medical tests), or some changes in medication. During times when the patient's insulin sensitivity cannot be accurately determined, it can be risky to apply an aggressive insulin dosing protocol because if the estimated insulin sensitivity is significantly different than the patient's actual insulin sensitivity, the aggressive recommended dose of insulin has the potential to be more harmful to the patient than a conservative recommended dose of insulin. Therefore, in some embodiments, the insulin dosing protocol applies a less aggressive insulin dosing protocol during times when the patient's insulin sensitivity cannot be calculated with enough accuracy for an aggressive insulin dosing protocol to be used safely.

Figure 47:
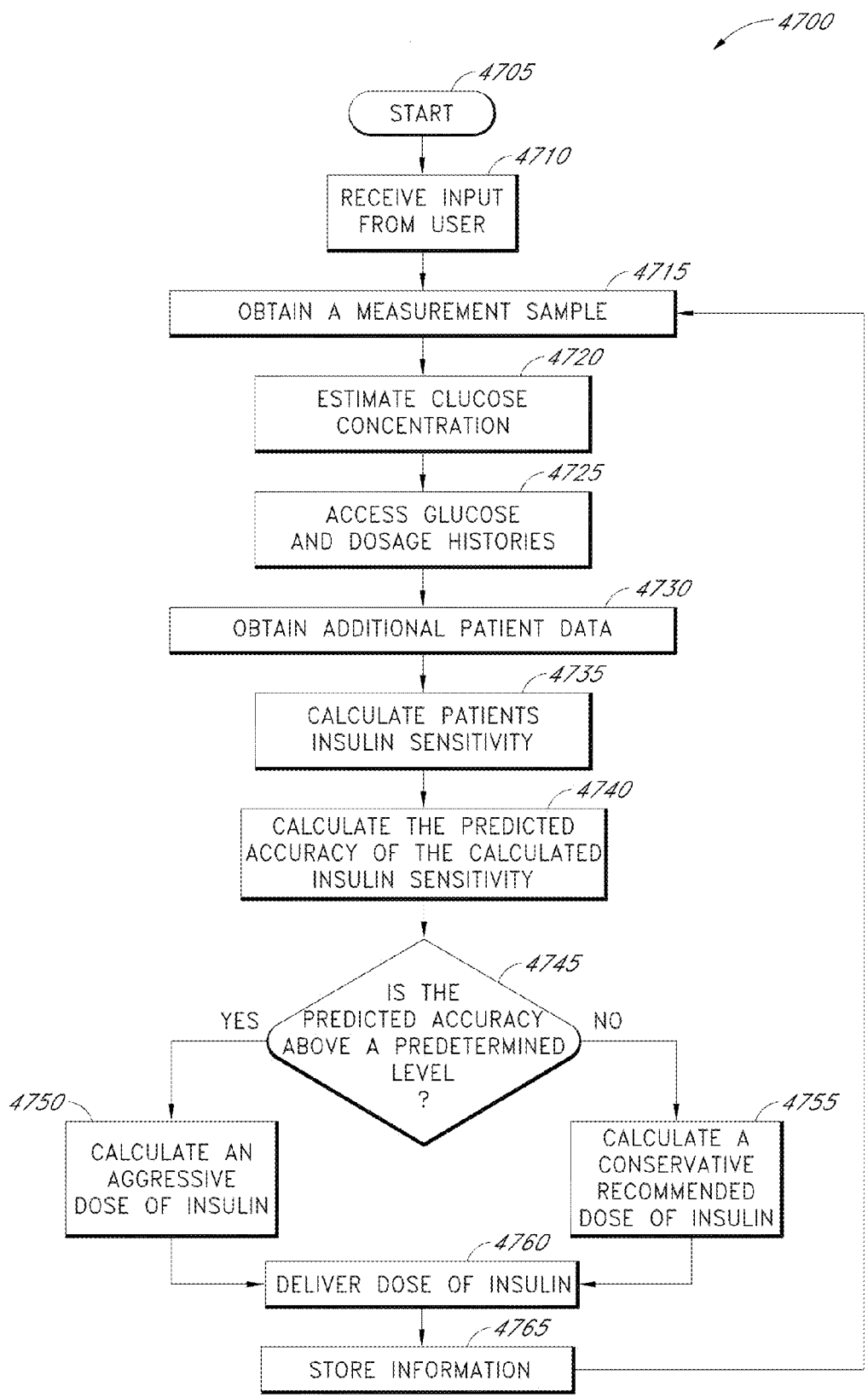
FIG. 47 is a flowchart that schematically shows an embodiment of a method for providing glycemic control by selectively administering either a conservative or an aggressive recommended dose of insulin.

FIG. 47 is a flowchart that schematically shows an embodiment of a method 4700 for providing glycemic control by selectively recommending and administering either a conservative or an aggressive recommended dose of insulin. The method 4700 starts at block 4705, which can be triggered by an event such as a new patient being assigned to the monitoring system, or the patient being reconnected to the monitoring system after a period of absence (e.g., during surgery or medical tests). At block 4710, the monitoring system can receive input from the user. The user can manually input the patient's insulin sensitivity or patient information that can be used by the monitoring system to calculate the patient's insulin sensitivity. Alternatively, the user can provide an instruction for the monitoring system to auto-start without providing any patient information. In some embodiments, the user may provide additional user input at any point of the method 4700 to provide additional information or instructions to the monitoring system.

Similar to method 4600 described above, at block 4715, the monitoring system obtains a sample measurement, and at block 4720, an estimated glucose concentration is calculated. At block 4725, the monitoring system accesses the patient's glucose concentration and insulin dosage histories, and at block 4730 the monitoring system obtains additional patient data, as discussed above. At block 4735, the patient's insulin sensitivity is calculated. In some embodiments, a default insulin sensitivity can be used when insufficient data is available to make the calculation.

Then, at block 4740, the monitoring system calculates a predicted accuracy for the calculated insulin sensitivity. Many factors can influence this calculation such as the number and frequency of past glucose concentration measurements and insulin dosing information, the accuracy of the glucose concentration measurements (some glucose measurement techniques are more accurate than others), and the amount of additional patient data available to the monitoring system. For example, in some embodiments, the monitoring system can be configured to consider an insulin sensitivity calculation to be accurate only if it was able to obtain complete dosing information regarding each medication being administered to the patient. In some embodiments, the monitoring system includes a lookup table to determine which medications are likely to affect the patient's insulin sensitivity and which medications can safely be disregarded. The monitoring system can use its analyte detection capabilities, described in detail above, to determine what medications or other substances may be present in the blood. In some embodiments, the accuracy determination can be based in part on how accurate previous insulin sensitivity calculations have been. For example, in some embodiments, the monitoring system can compare previously calculated insulin sensitivities to the patient's actual glucose reactions to insulin doses. The more accurate the previously calculated insulin sensitivities have been the more accurate the current calculated insulin sensitivity is likely to be, if other changes have not been made.

The process 4700 then proceeds to decision block 4745, where the monitoring system determines whether the predicted accuracy is above a predetermined threshold level. If the predicted accuracy is above the predetermined level, the method 4700 proceeds to block 4750 where an aggressive recommended dose of insulin is calculated based at least in part on the patient's insulin sensitivity. If the predicted accuracy is below the predetermined level, the method 4700 proceeds to block 4755 where a conservative recommended insulin dose is calculated (e.g., by the "Atlanta Protocol") without considering the patient's calculated insulin sensitivity. In some embodiments, the predetermined level of accuracy can be adjusted by the user through a user interface. Although the term "aggressive" recommended dose is used herein to contrast with "conservative" recommended dose, in some embodiments an aggressive dose may actually be less than a conservative dose. The term "aggressive" is used to indicate that the dose is allowed to be more responsive, sensitive and specific to the patient—and not so constrained by averages and generalities.

Once the recommended dose of insulin is calculated the dose is delivered to the patient at block 4760. As discussed above, the monitoring system can control the delivery of insulin directly or indirectly (e.g., through a command to an external infusion pump), or the monitoring system can display the recommended dose to a medical professional, who can deliver the dose of insulin. Then, at block 4765, information is stored in a database so that it can be used for future calculations. The glucose concentration and insulin dosing histories can be updated, and any portion of the additional patient data can be stored for later use. Also, the calculated insulin sensitivity and predicted accuracy can be stored. The method 4700 then returns to block 4715 to await the start of the next cycle.

In some embodiments, the monitoring system calculates the patient's insulin sensitivity only if the monitoring system determines that it can be calculated with enough accuracy to be used. In some embodiments, the insulin sensitivity and predicted accuracy can be calculated together as a single step. In some embodiments, the monitoring system is configured to use a sliding scale of accuracy. Thus, instead of toggling between aggressive and conservative dosing protocols, the system can use a single protocol that can self-adjust smoothly along a continuum between the extremes of fully aggressive and fully conservative, based on the level of predicted accuracy. The monitoring system can provide a user interface to allow a medical professional to adjust the sliding scale protocol's overall level of aggressiveness. In some embodiments, the monitoring system can display both the conservative and the aggressive doses along with the predicted level of accuracy to a medical professional, allowing the medical professional to ultimately choose the dose to be delivered to the patient.

Figure 48:
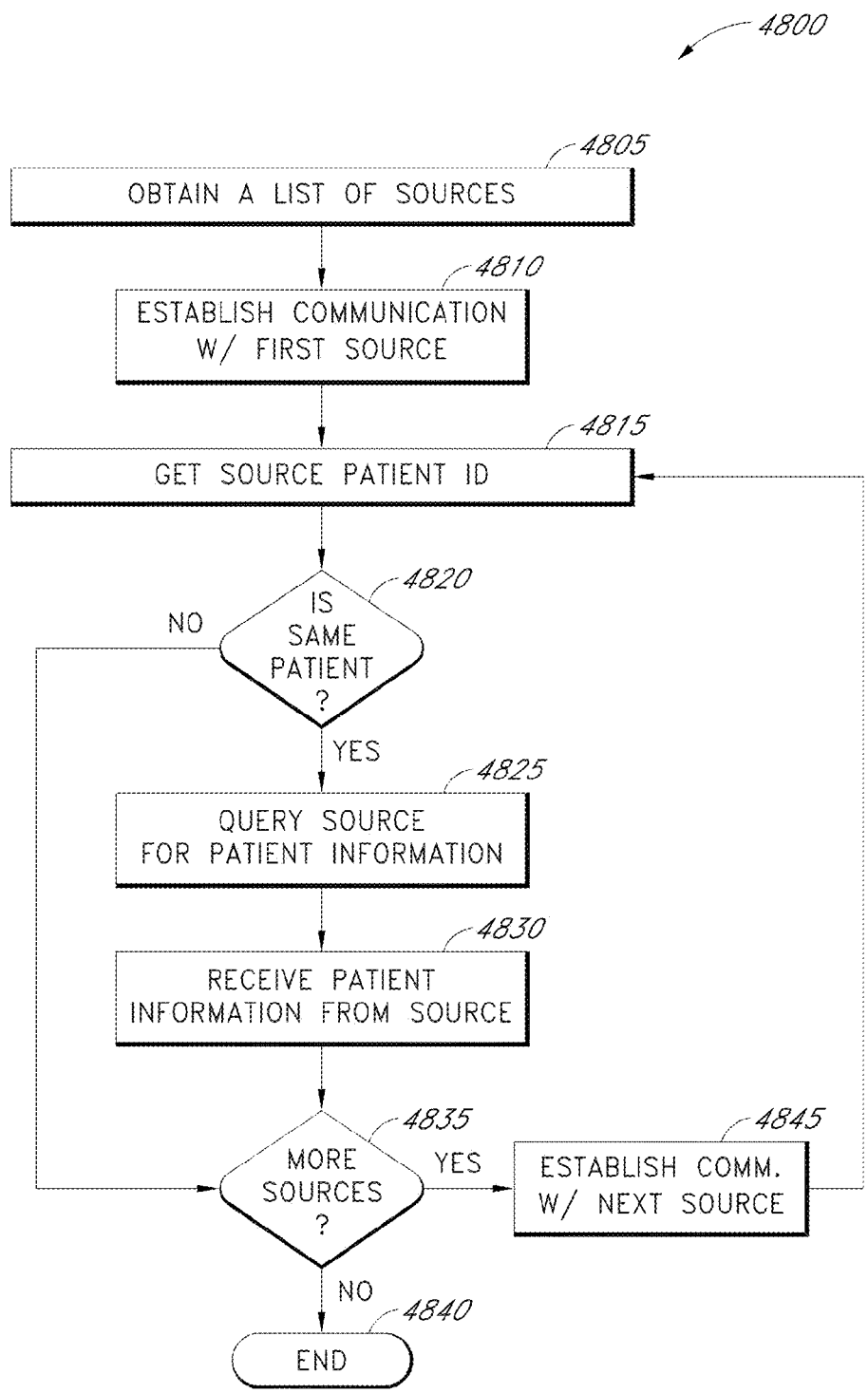
FIG. 48 is flowchart that schematically shows an embodiment of a method for collecting additional patient data.

FIG. 48 is flowchart that schematically shows an embodiment of a method 4800 for collecting additional patient data. The method 4800 begins at block 4805 where the system obtains a list of external sources with which it can communicate. The external sources can be feeding pumps, other infusion pumps, additional monitoring systems, information archives, etc. In block 4810, the communication interface establishes communication with a first external source. In block 4815 communication interface obtains the patient identifier associated with the external source. The patient identifier can be stored in a memory on the external source and may be input by a user (e.g., a nurse) through a user interface or a scanner. In block 4820, the external source's patient identifier is compared to the patient identifier associated with the monitoring system. If the patient identifiers do not match, the process proceeds to block 4835. If the patient identifiers do match then the monitoring system queries the external source for its patient information at block 4825, and receives the patient information at block 4830. The patient data can include various types of information depending on the external source. For example, an external infusion pump can provide patient data that includes an infusion fluid identifier, a current infusion rate, and a history of previous infusion rates. The method 4800 then proceeds to block 4835, where it is determined whether there is at least one additional source to be queried. If no additional sources are on the list, the process ends at block 4840. If additional sources are on the list, the process proceeds to block 4845 where communication interface establishes communication with the next external source. The process then returns to block 4815 and repeats. Some external sources can include multiple patient identifiers if the source is associated with more than one patient (e.g., a patient information archive). In such a case, the monitoring system can query the source for only data that relates to the patient assigned to the monitoring system. In some embodiments, the external sources can report to a single external entity (e.g., the HIS) and the monitoring system can obtain all of the patient data from that single external entity.

Because the information received by the monitoring system from external sources can significantly affect the recommended dose of insulin provided by the monitoring system, errors in the transmitted data can cause an inappropriate dosage calculation resulting in serious harm to the patient. Accordingly, some embodiments employ security measures to prevent data errors. These security measures can be particularly useful when communication is provided through a wireless communication link (e.g., Bluetooth, WIFI, RF, infrared signals, etc.). For example, an external source (e.g., an enteral pump) can be programmed to communicate only with the monitoring system that is assigned to the same patient as the external source. A user can use a scanner to assign a patient to the external source and monitoring system.

Figure 49:
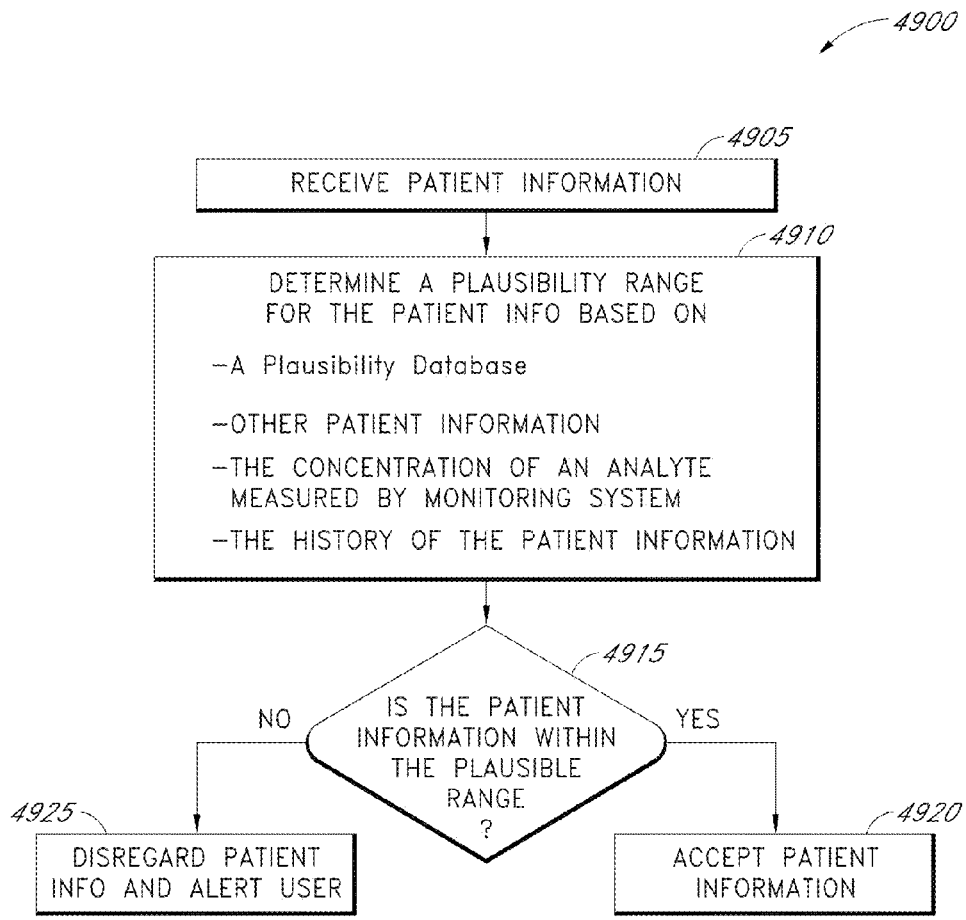
FIG. 49 is a flowchart schematically showing an embodiment of a method for performing a security check on information received from outside sources.

FIG. 49 is a flowchart schematically showing an embodiment of a method for performing a security check on information received from outside sources. At block 4905, the monitoring system receives patient information. Patient data can be, for example, an infusion fluid identifier and an infusion rate (or a history of infusion rates) received from an external infusion pump. At block 4910, the system determines a plausible range for the patient information. The plausibility range can be derived from a combination of difference sources. In some embodiments, the monitoring system includes a database with plausible ranges for various types of patient information. For example, the monitoring system can lookup a range of plausible infusion rates for the infusion fluid identified. In some embodiment, the plausible range is adjusted based on other patient information. For example, a plausible range for the infusion of one medication can vary depending on what other medications are being delivered to the patient. In some embodiments, the plausibility range is adjusted based on the concentration of an analyte measured by the monitoring system. For example, if the monitoring system receives information indicating that the patient's feeding has increased (without a corresponding increase in insulin), the patient's blood glucose concentration would be expected to increase accordingly. Thus, if the monitoring system has measured a drop in the patient's blood glucose level (with no increase in insulin), the plausibility range for feeding information can be adjusted to exclude an increase in feeding. In some embodiments, the plausibility range can be adjusted based on the history of the patient information, which may be stored in the monitoring system's memory. For example, the dosage of some medications is generally adjusted gradually. Thus, the plausible range for the medication can be a relatively narrow range surrounding the previously recorded dosage.

The process 4900 then proceeds to decision block 4915, where the monitoring system determines whether the patient information is within the plausible range. If the patient information is within the plausible range, the monitoring system accepts the patient information at block 4920. The monitoring system can then use the patient information for calculating the patient's insulin sensitivity, or for calculating the recommended insulin dose, or for other purposes. If the patient information falls outside the plausible range, the monitoring system concludes that the information is flawed and disregards the patient information at block 4925. In some embodiments, the monitoring system can alert the user because a suspected data error can be indicative of an equipment malfunction, a significant change in the patient's health, an incorrectly administered dose of medication, or other serious problem. In some embodiments, the monitoring system repeats process 4900 for each piece of patient information received from outside sources.

The monitoring system can perform other kinds of security measures to identify data errors. For example, an external infusion pump can send the monitoring system its current infusion rate as well as a history of previous infusion rates. The monitoring system can store the history of infusion rates in its memory, and each time the monitoring system receives a new set of infusion rates from the pump it can compare the received history with the overlapping portions of the saved history. If the monitoring system finds a discrepancy, it can conclude that the information received from the infusion pump contains errors, disregard the information, and/or alert the user.

Figure 50:
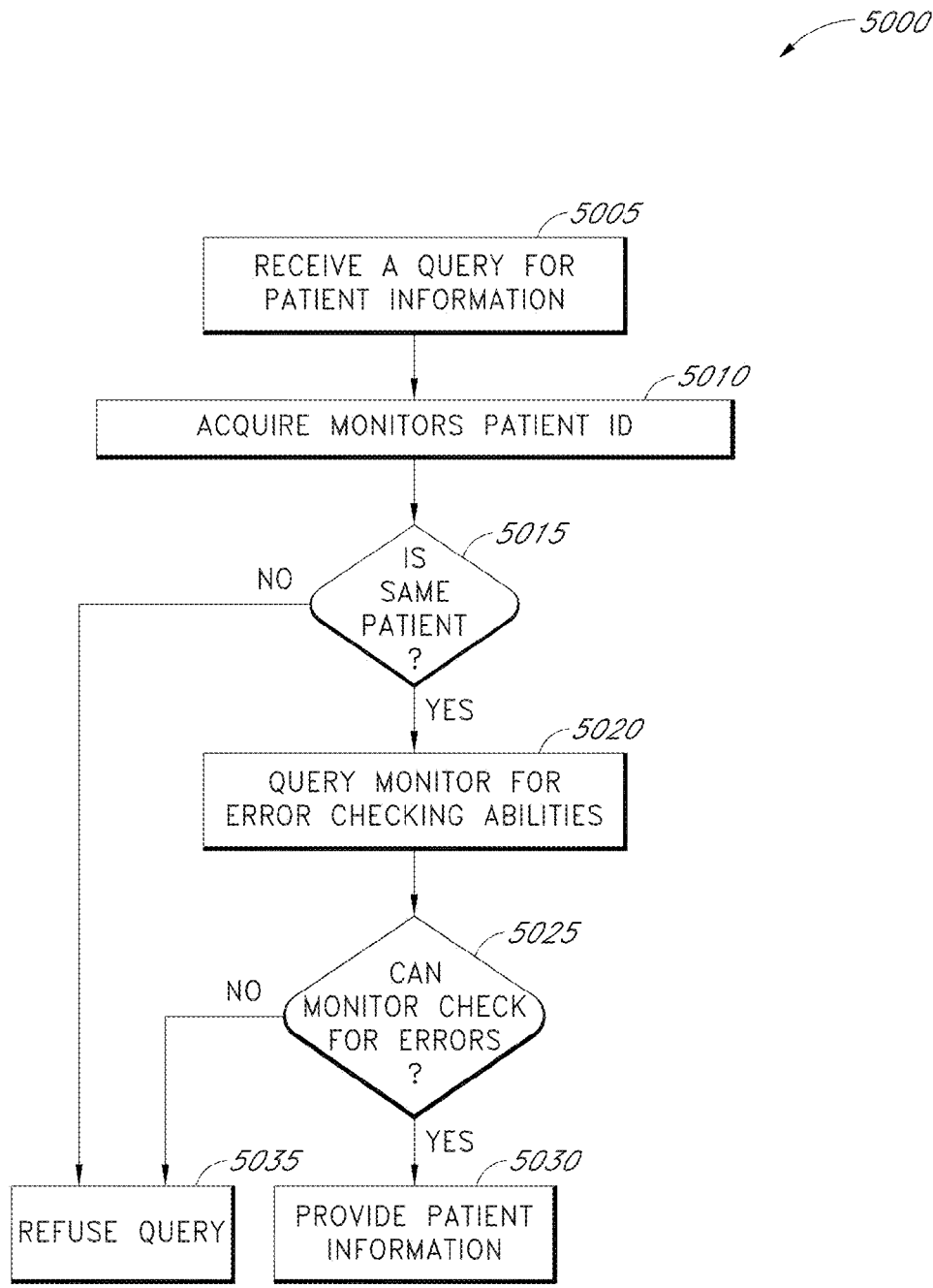
FIG. 50 is a flowchart schematically showing an embodiment of a method for an external source to perform a security check before providing patient data to the monitoring system.

FIG. 50 is a flowchart schematically showing an embodiment of a method for an external source to perform a security check before providing patient data to the monitoring system. The source can be, for example, an external infusion pump or an external monitor. In block 5005, the source receives a query for patient information. In block 5010, the source acquires the monitoring system's patient identifier. In decision block 5015 the source compares the acquired patient identifier against its own patient identifier. If the patients do not match, the process 5000 proceeds to block 5035 where the source refuses at least part of the query for information. If the patients do match, the process 5000 proceeds to block 5020 where the source queries the monitoring system for its error checking abilities. In decision block 5025, the source determines whether the monitoring system is able to check for errors in the information sent to it. In some embodiments, the source is satisfied if the monitoring system is able to lookup a plausibility range in a database. In some embodiments, the source is not satisfied unless the monitoring system is able to measure an analyte that relates to the requested information to check for errors. If the source determines that the monitoring system is able to sufficiently check for errors, it provides the requested patient information to the monitoring system in block 5030. If the source determines that the monitoring system is unable to sufficiently check for errors, it refuses at least part of the query in block 5035. A security check can also or alternatively be performed by the monitoring system with respect to the external source.

Figure 51:
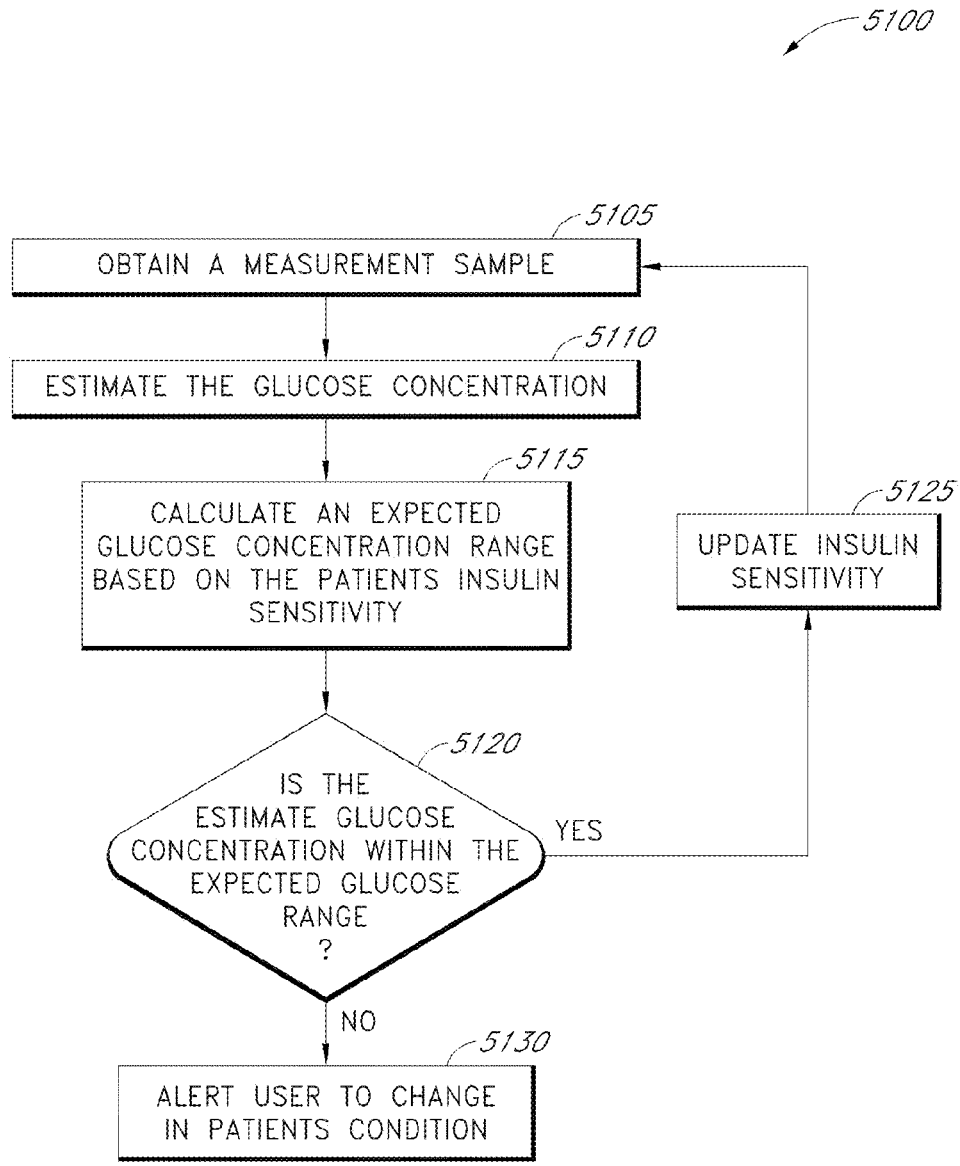
FIG. 51 is a flowchart schematically showing an embodiment of a method for detecting changes in a patient's condition.

FIG. 51 is a flowchart schematically showing an embodiment of a method for detecting changes in a patient's condition. In block 5105 the monitoring system obtains a sample measurement, and in block 5110 the monitoring system estimates the glucose concentration. At block 5115, the monitoring system calculates an expected glucose value based on the patient's insulin sensitivity. In some embodiments, the expected glucose value is based on the amount of recently administered of insulin. In some embodiment, the expected glucose value is based on additional patient info received from external sources, as discussed above. In some embodiments, the expected glucose range is narrowed based upon the predicted accuracy of the insulin sensitivity.

At decision block 5120, the monitoring system compares the estimated glucose concentration with the expected glucose range. If the estimated glucose concentration is within the expected glucose range, the process 5100 proceeds to block 5125 where the monitoring system updates the patient's insulin sensitivity as discussed above. The process 5100 then returns to block 5105 to await the next measurement cycle. If the estimated glucose concentration falls outside the expected glucose range, the process 5100 proceeds to block 5130 where the monitoring system alerts the user to a change in the patient's condition.

In some embodiments, the monitoring system can identify a change in the patient's condition by calculating the patient's insulin sensitivity over a small time interval (e.g., the most recent two measurement cycles). If the patient's recent insulin sensitivity changes significantly, the monitoring system can alert the user to an unexpected change in the patient's condition. In some embodiments, the monitoring system can adjust the patient's overall insulin sensitivity and recommended dosage when the monitoring system determines that the patient's recent insulin sensitivity has changed significantly. For example, if the monitoring system determines that the patient's recent insulin sensitivity has changed significantly the patient's overall insulin sensitivity can be adjusted to give less weight to older measurements.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Embodiments of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in some embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A patient treatment and analysis system, comprising:
   a body fluid analyzer configured to:
      measure a concentration of an analyte in a bodily fluid; and
      access an analyte history database and store the measured concentration of the analyte in the analyte history database; and
   a treatment dosing system in communication with the body fluid analyzer, the treatment dosing system comprising:
      a source of a treatment substance; and
      a treatment dosing algorithm stored in a computer memory;
   wherein the treatment dosing system is configured to:
      use the treatment dosing algorithm to calculate an estimated treatment sensitivity for the patient by accessing the analyte history database and a dosage history database and comparing portions of the analyte history database to portions of the dosage history database;
      use the treatment dosing algorithm to calculate a recommended treatment dosage for the patient based at least in part on the estimated treatment sensitivity;
      administer a dose of the treatment substance to the patient; and
      access a dosage history database and store a record of the administered dose therein;
      wherein the treatment dosing algorithm is configured to calculate a predicted accuracy of the estimated treatment sensitivity, and wherein the treatment dosing algorithm is configured to calculate the recommended treatment dosage based at least in part on the predicted accuracy of the estimated treatment sensitivity.

2. The patient treatment and analysis system of claim 1, further comprising a communication interface configured to communicate with an external infusion pump, wherein the communication interface is configured to receive infusion information from the external infusion pump and the treatment dosing algorithm is configured to calculate the estimated treatment sensitivity based at least in part on the infusion information received from the external infusion pump.

3. The patient treatment and analysis system of claim 1, wherein the analyte is glucose and the treatment substance is insulin.

4. The patient treatment and analysis system of claim 3, wherein the treatment substance is IV insulin.

5. The patient treatment and analysis system of claim 1, wherein the system is configured to perform a measurement cycle more frequency than once per hour.

6. The patient treatment and analysis system of claim 5, wherein the patient treatment and analysis system is configured to perform the measurement cycle at least once every thirty minutes.

7. The patient treatment and analysis system of claim 6, wherein the patient treatment and analysis system is configured to perform the measurement cycle at least once every fifteen minutes.

8. The patient treatment and analysis system of claim 1, further comprising a fluid network that is configured to draw a sample of bodily fluid through a catheter connected to the patient and transport at least a portion of the sample of bodily fluid to the body fluid analyzer, wherein the fluid network is further configured to deliver the treatment dose to the patient using the same catheter used to draw samples of bodily fluid.

9. The patient treatment and analysis system of claim 1, wherein the dose of the treatment fluid administered to the patient is the recommended treatment dosage calculated by the treatment dosing system.

10. The patient treatment and analysis system of claim 1, further comprising a user interface configured to display the recommended treatment dosage to a user and to receive input from the user, and wherein the dose of the treatment fluid administered to the patient is determined at least in part by the input received from the user via the user interface.

11. The patient treatment and analysis system of claim 1, wherein the source of the treatment substance is a non-dedicated reservoir.

12. The patient treatment and analysis system of claim 1, wherein the treatment dosing algorithm is configured to apply a first dosing protocol if the predicted accuracy is above a predetermined level and apply a second dosing protocol if the predicted accuracy is below the predetermined level, wherein the second dosing protocol is more conservative than the first dosing protocol.

13. The patient treatment and analysis system of claim 1, wherein the treatment dosing algorithm comprises a sliding scale dosing protocol having a varying level of aggressiveness that is based at least in part on the predicted accuracy, such that the aggressiveness of the sliding scale dosing protocol increases as the predicted accuracy increases.

14. A patient monitoring and dosing system, comprising:
a body fluid analyzer configured to measure a concentration of an analyte in a sample of bodily fluid from a patient; and
a treatment dosing system in communication with the body fluid analyzer, said treatment dosing system comprising a treatment dosing algorithm stored in a computer memory, the treatment dosing algorithm being configured to automatically calculate:
an estimated treatment sensitivity for the patient based at least in part on the measured concentration of the analyte; and
a recommended treatment dosage for the patient, wherein the automatic calculation of the recommended treatment dosage is based at least in part on the estimated treatment sensitivity;
wherein the treatment dosing algorithm is configured to calculate a predicted accuracy of the estimated treatment sensitivity, and wherein the treatment dosing algorithm is configured to calculate the recommended treatment dosage based at least in part on the predicted accuracy of the estimated treatment sensitivity.

15. The patient monitoring and dosing system of claim 14, wherein the treatment dosing system further comprises a source of treatment fluid, the treatment dosing system being configured to automatically deliver the recommended treatment dosage to the patient.

16. The patient monitoring and dosing system of claim 15, wherein the body fluid analyzer is configured to periodically measure samples of bodily fluid, and the treatment dosing system is configured to deliver the recommended treatment dosage to the patient at least in part as a basal infusion, the treatment dosing system being configured to adjust a basal infusion rate to deliver the recommended treatment dosage to the patient, and wherein the basal infusion is halted at least five minutes before the next measurement is taken.

17. The patient monitoring and dosing system of claim 15, wherein the body fluid analyzer is configured to periodically measure samples of bodily fluid, and the treatment dosing system is configured to deliver the recommended treatment dosage to the patient at least in part as a bolus injection delivered at least five minutes before the next measurement is taken.

18. The patient monitoring and dosing system of claim 15, wherein the body fluid analyzer is configured to periodically measure samples of bodily fluid, and the treatment dosing system is configured to deliver the recommended treatment dosage to the patient at least in part as a bolus injection delivered about midway between sample measurements.

19. The patient monitoring and dosing system of claim 14, further comprising a database in communication with the body fluid analyzer, the database being configured to store a history of measured concentrations of the analyte, wherein the treatment dosing algorithm is configured to access the database and calculate the estimated treatment sensitivity based at least in part on the history of measured concentrations of the analyte.

20. The patient monitoring and dosing system of claim 19, wherein the database is configured to store a history of treatment doses delivered to the patient, and wherein the treatment dosing algorithm is configured to calculate the estimated treatment sensitivity based at least in part on the history of treatment doses.

21. The patient monitoring and dosing system of claim 20, wherein the history of treatment doses comprises a plurality of active dose amounts delivered to the patient at different times, and the treatment dosing algorithm is configured to calculate an amount remaining for each of the plurality of active dose amounts based at least in part on a treatment fluid half-life, and the treatment dosing algorithm is configured to calculate the estimated treatment sensitivity based at least in part on the amount remaining for each of the plurality of active dose amounts.

22. The patient monitoring and dosing system of claim 20, wherein the treatment dosing system further comprises a source of treatment fluid, the treatment dosing system being configured to automatically deliver the recommended treatment dosage to the patient, the treatment dosing system being configured to access the database and update the history of treatment doses.

23. The patient monitoring and dosing system of claim 20, wherein the treatment dosing algorithm is configured to calculate the estimated treatment sensitivity based at least in part on a comparison of at least a portion of the history of measured concentrations of the analyte to at least a portion of the history of treatment doses.

24. The patient monitoring and dosing system of claim 23, wherein the treatment dosing algorithm is configured to calculate the estimated treatment sensitivity using a weighted average, the weighted average giving greater weight to more recent entries in the history of measured concentrations of the analyte and the history of treatment doses.

25. The patient monitoring and dosing system of claim 19, wherein the body fluid analyzer is configured to measure a new concentration of the analyte and update the history of measured concentrations of the analyte at least once every hour, and the treatment dosing algorithm is configured to calculate a new estimated treatment sensitivity and a new recommended treatment dosage at least once every hour.

26. The patient monitoring and dosing system of claim 19, wherein the body fluid analyzer is configured to measure a new concentration of the analyte and update the history of measured concentrations of the analyte at least once every thirty minutes, and the treatment dosing algorithm is configured to calculate a new estimated treatment sensitivity and a new recommended treatment dosage at least once every thirty minutes.

27. The patient monitoring and dosing system of claim 19, wherein the body fluid analyzer is configured to measure a new concentration of the analyte and update the history of measured concentrations of the analyte at least once every fifteen minutes, and the treatment dosing algorithm is configured to calculate a new estimated treatment sensitivity and a new recommended treatment dosage at least once every fifteen minutes.

28. The patient monitoring and dosing system of claim 14, wherein the treatment dosing algorithm is configured to apply a first dosing protocol if the predicted accuracy is above a predetermined level and apply a second dosing protocol if the predicted accuracy is below the predetermined level, wherein the second dosing protocol is more conservative than the first dosing protocol.

29. The patient monitoring and dosing system of claim 14, wherein the treatment dosing algorithm comprises a sliding scale dosing protocol having a varying level of aggressiveness that is based at least in part on the predicted accuracy, such that the aggressiveness of the sliding scale dosing protocol increases as the predicted accuracy increases.

30. The patient monitoring and dosing system of claim 14, wherein the treatment dosing algorithm is configured to calculate an expected analyte concentration range based at least in part on the estimated treatment sensitivity, and the treatment dosing algorithm is configured to trigger an alert if the measured analyte concentration falls outside the expected analyte concentration range.

31. The patient monitoring and dosing system of claim 14, wherein the treatment dosing algorithm is configured to calculate the estimated treatment sensitivity based at least in part on additional patient data, the additional patient data including patient feeding information, patient medication information, or patient exercise information.

32. The patient monitoring and dosing system of claim 14, wherein the body fluid analyzer is configured for glucose control solution calibration no more than once per day.

33. The patient monitoring and dosing system of claim 14, wherein the body fluid analyzer is configured for glucose control solution calibration no more than once each week.

34. The patient monitoring and dosing system of claim 14, further comprising a fluid network connected to the patient and the body fluid analyzer, the fluid network configured to draw a sample of bodily fluid through a catheter connected to the patient and transport at least a portion of the sample of bodily fluid to the body fluid analyzer for measurement.

35. The patient monitoring and dosing system of claim 34, further comprising a source of treatment fluid, and wherein the treatment and dosing system is configured to automatically deliver the recommended treatment dosage to the patient through the same catheter used to draw the sample of bodily fluid.

36. The patient monitoring and dosing system of claim 14, wherein the analyte is glucose and the estimated treatment sensitivity is estimated insulin sensitivity and the recommended treatment dosage is a recommended dose of insulin.

37. The patient monitoring and dosing system of claim 14, wherein the treatment dosing system further comprises a display configured to display the recommended treatment dosage to a user.

\* \* \* \* \*